US011712439B2

(12) United States Patent
Huang et al.

(10) Patent No.: US 11,712,439 B2
(45) Date of Patent: Aug. 1, 2023

(54) METHODS AND MATERIALS FOR IDENTIFYING AND TREATING BET INHIBITOR-RESISTANT CANCERS

(71) Applicants: Mayo Foundation for Medical Education and Research, Rochester, MN (US); Shanghai Changhai Hospital, Shangahi Shi (CN)

(72) Inventors: Haojie Huang, Rochester, MN (US); Yinghao Sun, Shanghai (CN); Shancheng Ren, Shanghai (CN)

(73) Assignees: Mayo Foundation for Medical Education and Research, Rochester, MN (US); Shanghai Changhai Hospital, Shangahi Shi (CN)

( * ) Notice: Subject to any disclaimer, the term of this patent is extended or adjusted under 35 U.S.C. 154(b) by 62 days.

(21) Appl. No.: 16/637,674

(22) PCT Filed: Aug. 9, 2018

(86) PCT No.: PCT/US2018/045976
§ 371 (c)(1),
(2) Date: Feb. 7, 2020

(87) PCT Pub. No.: WO2019/032810
PCT Pub. Date: Feb. 14, 2019

(65) Prior Publication Data
US 2021/0361653 A1 Nov. 25, 2021

Related U.S. Application Data

(60) Provisional application No. 62/543,313, filed on Aug. 9, 2017.

(51) Int. Cl.
| | | |
|---|---|---|
| *A61K 31/517* | (2006.01) | |
| *A61K 31/4375* | (2006.01) | |
| *A61K 31/551* | (2006.01) | |
| *A61P 35/00* | (2006.01) | |
| *C12Q 1/6886* | (2018.01) | |
| *A61K 45/06* | (2006.01) | |

(52) U.S. Cl.
CPC ........ *A61K 31/517* (2013.01); *A61K 31/4375* (2013.01); *A61K 31/551* (2013.01); *A61P 35/00* (2018.01); *C12Q 1/6886* (2013.01); *C12Q 2600/106* (2013.01); *C12Q 2600/156* (2013.01)

(58) Field of Classification Search
CPC .............. A61K 31/517; A61K 31/4375; A61K 31/551; A61K 45/06; A61P 35/00; C12Q 1/6886; C12Q 2600/106; C12Q 2600/156; G01N 2800/52; G01N 33/57434
See application file for complete search history.

(56) References Cited

U.S. PATENT DOCUMENTS

| | | | | |
|---|---|---|---|---|
| 2015/0320754 | A1* | 11/2015 | Kutok | A61K 45/06 424/278.1 |
| 2016/0279141 | A1 | 9/2016 | Bradner et al. | |
| 2017/0304315 | A1 | 10/2017 | Haudenschild et al. | |
| 2022/0016130 | A1 | 1/2022 | Huang et al. | |

FOREIGN PATENT DOCUMENTS

| | | |
|---|---|---|
| CN | 107299133 | 10/2017 |
| WO | WO 2012/115789 | 8/2012 |
| WO | WO 2015/160986 | 10/2015 |
| WO | WO 2016/044694 | 3/2016 |
| WO | WO 2016/201370 | 12/2016 |
| WO | WO 2017/027571 | 2/2017 |
| WO | WO 2018/087401 | 5/2018 |

OTHER PUBLICATIONS

Stratikopoulos et al. Kinase inhibitors Together Clamp Inhibition of PI3K Signaling and Overcome Resistance to Therapy. Cancer Cell. 27, 837-851. 2015 (Year: 2015).*
Chandarlapaty et al. AKT inhibition Relieves Feedback Suppression of Receptor Tyrosine Kinase Expression and Activity. Cancer Cell, 19, 58-71, 2011 (Year: 2011).*
Bradley. Nature Reviews Cancer. 17, 574 2017. (Year: 2017).*
Janouskova et al. Nature Medicine, 23, 1046-1054, 2017 (Year: 2017).*
Dai et al. Nature Medicine, 23, 1063-1071, 2017 (Year: 2017).*
Zhang et al. Nature Medicine, 23, 1055-1062, 2017 (Year: 2017).*
GenBank Accession No. AAB87862.1. "BRDT [*Homo sapiens*]," dated Dec. 1, 1997, 2 pages.
GenBank Accession No. CAA04199.1, "SPOP [*Homo sapiens*]," dated Oct. 7, 2008, 2 pages.
GenBank Accession No. NP_031397.1, "bromodomain-containing protein 3 [*Homo sapiens*]," dated Mar. 9, 2016, 4 pages.
GEO Accession No. GSE88872, "SPOP mutation confers intrinsic BET inhibitor resistance in prostate cancer," dated Jul. 21, 2017, 2 pages.
LeRoy et al., "The double bromodomaiil proteins Brd2 and Brd3 couple histone acetylation to transcription," Mol. Cell, Apr. 11, 2008, 30(1):51-60.
Stanlie et al., "Chromatin reader Brd4 functions in Ig class switching as a repair complex adaptor of nonhomologous end-joining," Mol. Cell., Jul. 2014, 55(1):97-110.
Turnbull et al., "Molecular basis of USP7 inhibition by selective small-molecule inhibitors," Nature, Oct. 2017, 550(7677):481-486.
Wikipedia.org [online], "Biosynthesis," last updated Jul. 5, 2021, retrieved on Jul. 26, 2021, retrieved from URL<https://en.wikipedia.org/wiki/Biosynthesis>, 21 pages.

(Continued)

*Primary Examiner* — Mark L Shibuya
*Assistant Examiner* — Luisalberto Gonzalez
(74) *Attorney, Agent, or Firm* — Fish & Richardson P.C.

(57) ABSTRACT

This document provides methods and materials involved in identifying and treating mammals having a cancer resistant to BET inhibitors. For example, methods and materials for administering one or more AKT inhibitors in combination with one or more BET inhibitors to mammals identified as having a cancer resistant to treatment with one or more BET inhibitors in the absence of AKT inhibitors are provided.

24 Claims, 128 Drawing Sheets

Specification includes a Sequence Listing.

(56) References Cited

OTHER PUBLICATIONS

Wu et al., "The Deubiquitinase USP28 Stabilizes LSD1 and Confers Stem-Cell-like Traits to Breast Cancer Cells," Cell Reports, Oct. 2013, 5(1):224-236.
Yuan et al., "USP10 Regulates p53 Localization and Stability by Deubiquitinating p53," Cell, Feb. 2010. 140(3):384-396.
Zhang et al., "USP49 deubiquitinates histone H2B and regulates cotranscriptional pre-mRNA splicing," Genes Development, Jul. 2013, 27(14): 1581-1595.
Urbanucci et al., "Bromodomain-containing proteins in prostate cancer," Mol. Cell. Endocrinology, Feb. 15, 2018, 462(Pt A):31-40.
Abeshouse et al., "The molecular taxonomy of primary prostate cancer," Cell, Nov. 2015, 163(4):1011-25.
An et al., "Destruction of Full-Length Androgen Receptor by Wild-Type SPOP, but Not Prostate-Cancer-Associated Mutants," Cell Rep, 2014, 6(4):657-669.
An et al., "Truncated ERG Oncoproteins from TMPRSS2-ERG Fusions Are Resistant to SPOP-Mediated Proteasome Degradation," Mol. Cell, 2015, 59(6):904-916.
Asangani et al., "Therapeutic targeting of BET bromodomain proteins in castration-resistant prostate cancer," Nature, 2014, 510(7504):278-282.
Baker et al., "BET Inhibitors Induce Apoptosis Through a MYC Independent Mechanism and Synergise with CDK Inhibitors to Kill Osteosarcoma Cells," Scientific Reports, 2015, 5(10120): 1-14.
Barbieri et al., "Exome sequencing identifies recurrent SPOP, FOXA1 and MED12 mutations in prostate cancer," Nat. Genet., 2012, 44(6):685-689.
Beaver et al., "FDA approval: palbociclib for the treatment of postmenopausal patients with estrogen receptor-positive, HER2-negative metastatic breast cancer," Clinical Cancer Research, Nov. 2015, 21(21):4760-6.
Blattner et al., "SPOP Mutation Drives Prostate Tumorigenesis In Vivo through Coordinate Regulation of PI3K/mTOR and AR Signaling," Cancer Cell, 2017, 31(3):436-451.
Blattner et al., "SPOP Mutations in Prostate Cancer across Demographically Diverse Patient Cohorts 1,2," Neoplasia, 2014, 16(1):14-20.
Blee et al., "BET bromodomain-mediated interaction between ERG and BRD4 promotes prostate cancer cell invasion," Oncotarget, 2016, 7(25):38319-38332.
Bookstein et al., "Suppression of tumorigenicity of human prostate carcinoma cells by replacing a mutated RB gene," Science, Feb. 1990, 247(4943):712-5.
Borbely et al., "Induction of USP17 by combining BET and HDAC inhibitors in breast cancer cells," Oncotarget, Oct. 2015, 6(32):33623.
Boyer et al., "Core transcriptional regulatory circuitry in human embryonic stem cells," Cell, 2005, 122(6):947-956.
Cancer Genome Atlas Research Network, "The Molecular Taxonomy of Primary Prostate Cancer," Cell, Nov. 2015, 163(4):1011-25.
Chan et al., "Targeting chromatin binding regulation of constitutively active AR variants to overcome prostate cancer resistance to endocrine-based therapies," Nucleic Acids Res, 2015, 43(12):5880-5897.
Dai et al., "Prostate cancer-associated SPOP mutations confer resistance to BET inhibitors through stabilization of BRD4," Nature medicine, Sep. 2017, 23(9):1063.
Dali-Youcef et al., "Gene Expression Mapping of Histone Deacetylases and Co-factors, and Correlation with Survival Time and 1 H-HRMAS Metabolomic Profile in Human Gliomas," Scientific reports, Mar. 2015, 5:9087.
Dawson et al., "Inhibition of BET recruitment to chromatin as an effective treatment for MLL-fusion leukaemia," Nature, 2011, 478(7370):529-533.
Delmore et al., "BET Bromodomain Inhibition as a Therapeutic Strategy to Target c-Myc," Cell, 2011, 146(6):904-917.
Deng et al., "Deubiquitination and activation of AMPK by USP10," Molecular cell, Feb. 2016, 61(4):614-24.
Drost et al., "Organoid culture systems for prostate epithelial and cancer tissue," Nat. Protoc., 2016, 11(2):347-358.
Esen et al., "WNT-LRP5 signaling induces Warburg effect through mTORC2 activation during osteoblast differentiation," Cell Metab, 2013, 17(5):745-755.
Filippakopoulos et al., "Selective inhibition of BET bromodomains," Nature, 2010, 468(7327):1067-1073.
Finn et al., "Palbociclib and letrozole in advanced breast cancer," New England Journal of Medicine, Nov. 2016, 375(20):1925-36.
Fischer et al., "Isolation and characterization of a novel class II histone deacetylase, HDAC10," Journal of Biological Chemistry, Feb. 2002, 277(8):6656-66.
Fong et al., "BET inhibitor resistance emerges from leukaemia stem cells," Nature, 2015, 525(7570):538-542.
Fu et al., "Inhibition of BET Bromodomains as a Therapeutic Strategy for Cancer Drug Discovery," Oncotarget, 2015, 6(8):5501-5516.
GenBank Accession No. NP_001106653.1, "bromodomain-containing protein 2 isoform 1 [*Homo sapiens*]," dated Dec. 23, 2018, 4 pages.
GenBank Accession No. NP_490597.1, "bromodomain-containing protein 4 isoform long [*Homo sapiens*]," dated Feb. 3, 2019, 4 pages.
Geng et al., "Prostate cancer-associated mutations in speckle-type POZ protein (SPOP) regulate steroid receptor coactivator 3 protein turnover," Proc. Natl. Acad. Sci. USA, 2013, 110(17):6997-7002.
GEO Accession No. GSE44931, "Selective Inhibition of Tumor Oncogenes by Disruption of Super-Enhancers," dated Mar. 7, 2013, 2 pages.
GEO Accession No. GSE51633, " Brd4 and JMJD6-associated Anti-pause Enhancers in Regulation of Transcriptional Pause Release," dated Jan. 14, 2014, 2 pages.
GEO Accession No. GSE66122, "BET Bromodomain Inhibition Suppresses the Function of Hematopoietic Transcription Factors in Acute Myeloid Leukemia [ChIP-Seq]," dated May 1, 2015, 2 pages.
Grasso et al., "The mutational landscape of lethal castration-resistant prostate cancer," Nature, Jul. 2012, 487(7406):239-43.
Groner et al., "TRIM24 Is an Oncogenic Transcriptional Activator in Prostate Cancer," Cancer Cell, 2016, 29(6):846-858.
Hagen et al., "AM-MLV reverse transcriptase with reduced RNaseH activity allows greater sensitivity of gene expression detection in formalin fixed and paraffin embedded prostate cancer samples," Exp. Mol. Pathol., 2013, 95(1):98-104.
Hayward et al., "Establishment and characterization of an immortalized but non-transformed human prostate epithelial cell line: BPH-1," In Vitro Cell Dev. Biol. Anim,, 1995, 31(1):14-24.
Janouskova et al., "Opposing effects of cancer-type-specific SPOP mutants on BET protein degradation and sensitivity to BET inhibitors," Nature medicine, Sep. 2017, 23(9):1046.
Janouskova et al., "Opposing therapeutic efficacy of BET inhibitors is determined by cancer type-specific SPOP mutants," European Journal of Cancer, Dec. 2016, 69:S2.
Jin et al., "Fructose-1, 6-bisphosphatase inhibits ERK activation and bypasses gemcitabine resistance in pancreatic cancer by blocking IQGAP1-MAPK interaction," Cancer research, Aug. 2017, 77(16):4328-41.
Kurimchak et al., "Resistance to BET bromodomain inhibitors is mediated by kinome reprogramming in ovarian cancer," Cell reports, Aug. 2016, 16(5):1273-86.
Lasserre et al., "Raft nanodomains contribute to Akt/PKB plasma membrane recruitment and activation," Nat Chem Biol., 2008, 4(9):538-547.
Li et al., Fructose-1, 6-bisphosphatase opposes renal carcinoma progression, Nature, Sep. 2014, 513(7517):251-5.
Liu et al., "Brd4 and JMJD6-associated anti-pause enhancers in regulation of transcriptional pause release," Cell, 2013, 155(7):1581-1595.
Liu et al., "CDK4/6-dependent activation of DUB3 regulates cancer metastasis through SNAIL1," Nature communications, Jan. 2017, 8(1):1-2.
Loven et al., "Selective inhibition of tumor oncogenes by disruption of super-enhancers," Cell, 2013, 153(2):320-334.

(56) References Cited

OTHER PUBLICATIONS

Lu et al., "Hijacking the E3 Ubiquitin Ligase Cereblon to Efficiently Target BRD4," Chem. Biol., 2015, 22(6):755-763.

Mertz et al., "Targeting MYC dependence in cancer by inhibiting BET bromodomains," Proc. Natl. Acad. Sci. USA, 2011, 108(40):16669-16674.

Mittempergher et al., "Gene expression profiles from formalin fixed paraffin embedded breast cancer tissue are largely comparable to fresh frozen matched tissue," PLoS One, 2011, 6(2):e17163, 15 pages.

Mortazavi et al., "Mapping and quantifying mammalian transcriptomes by RNA-Seq," Nature Methods, 2008, 5(7):621-628.

Nicodeme et al., "Suppression of inflammation by a synthetic histone mimic," Nature, 2010, 468(7327):1119-1123.

O'leary et al., "Treating cancer with selective CDR4/6 inhibitors," Nature reviews Clinical oncology, Jul. 2016, 13(7):417-30.

Patel et al., "BET bromodomain inhibition triggers apoptosis of NF1-associated malignant peripheral nerve sheath tumors through Bim induction," Cell Rep., 2014, 6(1):81-92.

PCT International Preliminary Report on Patentability in International Appln. No. PCT/US2018/045976, dated May 2, 2019, 9 pages.

PCT International Search Report and Written Opinion in International Appln. No. PCT/US2018/045976, dated May 2, 2019, 12 pages.

Rathert et al., "Transcriptional plasticity promotes primary and acquired resistance to BET inhibition," Nature, 2015, 525(7570):543-547.

Renwick et al., "Multicolor microRNA FISH effectively differentiates tumor types," J. Clin. Invest., 2013, 123(6):2694-2702.

Robinson et al., "A scaling normalization method for differential expression analysis of RNA-seq data," Genome Biol., 2010, 11(3):R25, 9 pages.

Robinson et al., "Integrative clinical genomics of advanced prostate cancer," Cell, May 2015, 161(5):1215-28.

Roe et al., "BET Bromodomain Inhibition Suppresses the Function of Hematopoietic Transcription Factors in Acute Myeloid Leukemia," Mol. Cell, 2015, 58(6):1028-1039.

Saci et al., "Rael regulates the activity of mTORC1 and mTORC2 and controls cellular size," Mol Cell, 2011, 42(1):50-61.

Saura et al., "A First-in-Human Phase I Study of the ATP-Competitive ART Inhibitor Ipatasertib Demonstrates Robust and Safe Targeting of ART in Patients with Solid Tumors," Cancer Discov., 2017, 7(1):102-113.

Shi et al., "Disrupting the interaction of BRD4 with diacetylated Twist suppresses tumorigenesis in basal-like breast cancer," Cancer cell, Feb. 2014, 10;25(2):210-25.

Shu et al., "Response and resistance to BET bromodomain inhibitors in triple negative breast cancer," Nature, 2016, 529(7586):413-417.

Stratikopoulos et al., "Kinase and BET Inhibitors Together Clamp Inhibition of PI3K Signaling and Overcome Resistance to Therapy," Cancer Cell, 2015, 27(6):837-851.

The Cancer Genome Atlas Research Network, "The Molecular Taxonomy of Primary Prostate Cancer," Cell, 2015, 163(4):1011-1025.

Theurillat et al., "Ubiquitylome analysis identifies dysregulation of effector substrates in SPOP-mutant prostate cancer," Science, 2014, 346(6205):85-89.

Trapnell et al., "TopHat: discovering splice junctions with RNA-Seq," Bioinformatics, 2009, 25(9):1105-1111.

Urbanucci et al., "Androgen receptor deregulation drives bromodomain-mediated chromatin alterations in prostate cancer," Cell reports, Jun. 2017, 19(10):2045-59.

Wang et al., "BRCA1 is a negative modulator of the PRC2 complex," Embo. J., 2013, 32(11):1584-1597.

Wang et al., "Reprogramming transcription by distinct classes of enhancers functionally defined by eRNA," Nature, 2011, 474(7351):390-394.

Wang et al., "RSeQC: quality control of RNA-seq experiments," Bioinformatics, 2012, 28(16):2184-2185.

Wu et al., "Dub3 inhibition suppresses breast cancer invasion and metastasis by promoting Snaill degradation," Nature communications, Feb. 2017, 8(1):1-6.

Yue et al., "Cholesteryl ester accumulation induced by PTEN loss and PI3K/AKT activation underlies human prostate cancer aggressiveness," Cell Metab, 2014, 19(3):393-406.

Zhang et al., "Intrinsic BET inhibitor resistance in SPOP-mutated prostate cancer is mediated by BET protein stabilization and AKT-mTORC1 activation," Nature medicine, Sep. 2017, 23(9):1055.

Zhang et al., "Model-based analysis of ChTP-Seq (MACS)," Genome Biol., 2008, 9(9):R137, 9 pages.

Zhao et al., "Activation of P-TEFb by Androgen Receptor-Regulated Enhancer RNAs in Castration-Resistant Prostate Cancer," Cell Rep., 2016, 15(3):599-610.

Zhao et al., "CrossMap: a versatile tool for coordinate conversion between genome assemblies," Bioinformatics, 2014, 30(7):1006-1007.

Zhuang et al., "Cholesterol targeting alters lipid raft composition and cell survival in prostate cancer cells and xenografts," J. Clin, Invest., 2005, 115(4):959-968.

Zhuang et al., "Cholesterol-rich lipid rafts mediate akt-regulated survival in prostate cancer cells," Cancer Res, 2002, 62(8):2227-2231.

Zhuang et al., "Structures of SPOP-substrate complexes: insights into molecular architectures of BTB-Cul3 ubiquitin ligases," Mol. Cell, 2009, 36(1):39-50.

Zuber et al., "RNAi screen identifies Brd4 as a therapeutic target in acute myeloid leukaemia," Nature, 2011, 478(7370):524-528.

GenBank Accession No. NG_041815.1, "*Homo sapiens* speckle type BTB/POZ protein (SPOP), RefSeqGene on chromosome 17," dated Feb. 13, 2016, 22 pages.

U.S. Appl. No. 17/263,010, filed Jan. 25, 2021, Haojie Huang, Pending.

* cited by examiner

| SBC motif | φ π S/T S/T S/T | | |
|---|---|---|---|
| BRD2 | (273) LAKKKGVKRKADTTTPPTPTAILA | (295 aa) |
| BRD3 | (236) VVKKKGVKRKADTTTPPTTSAITA | (258 aa) |
| BRD4 | (282) VKTKKGVKRKADTTTPPTTIDPIH | (304 aa) |
| MacroH2A | (161) KQGEVSKAASADSTTEGTPADGF | (231 aa) |
| DEK | (275) KSVKSANVKKADSSTTKKNQNSS | (297 aa) |

Figure 3a

METHODS AND MATERIALS FOR IDENTIFYING AND TREATING BET INHIBITOR-RESISTANT CANCERS

CROSS-REFERENCE TO RELATED APPLICATIONS

This application is a National Stage application under 35 U.S.C. § 371 of International Application No. PCT/US2018/045976, having an International Filing Date of Aug. 9, 2018, which claims priority to U.S. Application Ser. No. 62/543,313, filed on Aug. 9, 2017. The disclosure of the prior application is considered part of the disclosure of this application, and is incorporated in its entirety into this application.

STATEMENT AS TO FEDERALLY SPONSORED RESEARCH

This invention was made with government support under CA134514 and CA193239 awarded by the National Institutes of Health. The government has certain rights in the invention.

SEQUENCE LISTING

This document contains a sequence listing that has been submitted electronically as an ASCII text file named 070391723US1_ST25.txt. The ASCII text file, created on Aug. 1, 2022, is 25 kilobytes in size. The material in the ASCII text file is hereby incorporated by reference in its entirety.

BACKGROUND

1. Technical Field

This document relates to methods and materials involved in identifying and treating mammals having a cancer resistant to BET inhibitors (bromodomain and extra-terminal domain (BET) protein inhibitors). For example, this document provides methods and materials for administering one or more AKT inhibitors (also known as Protein Kinase B (PKB) inhibitors) in combination with one or more BET inhibitors to mammals identified as having a cancer resistant to treatment with one or more BET inhibitors alone.

2. Background Information

BET inhibitors are anti-cancer agents currently in clinical trials. These agents can bind to the bromodomains of BET proteins such as BRD2, BRD3, and BRD4, and interfere with protein-protein interactions between the BET proteins and acetylated histones and transcription factors.

SUMMARY

This document provides methods and materials involved in identifying mammals having a cancer with at least some resistance to treatment with a BET inhibitor. For example, this document provides methods and materials for detecting the presence of cancer cells having a mutant SPOP polypeptide (the E3 ubiquitin ligase substrate-binding adaptor speckle-type POZ polypeptide) and/or an elevated level of BET polypeptide (e.g., BRD2, BRD3, and/or BRD4 polypeptide) expression to identify that cancer as being at least partially resistance to treatment with a BET inhibitor. As described herein, cancers (e.g., prostate cancers) having a mutant SPOP polypeptide or an elevated level of BET polypeptide expression can exhibit a resistance to BET inhibitors. Identifying cancers (e.g., prostate cancers) as being at least partially resistant to BET inhibitor treatment as described herein can allow clinicians to proceed with proper treatment options for cancer patients.

This document also provides methods and materials involved in treating mammals identified as having a cancer with at least some resistance to treatment with a BET inhibitor. For example, this document provides methods and materials for administering one or more AKT inhibitors in combination with one or more BET inhibitors to mammals identified as having a cancer resistant to treatment with one or more BET inhibitors alone. AKT (also known as PKB) is a serine/threonine-specific protein kinase. As described herein, mammals having a cancer at least partially resistant to BET inhibitor treatment can be administered one or more AKT inhibitors to reduce the level of BET inhibitor resistance of the cancer, thereby making the cancer more susceptible to treatment with one or more BET inhibitors. Having the ability to use one or more AKT inhibitors to reduce the level of BET inhibitor resistance of a cancer can allow clinicians and patients to proceed with treatment options that include the effective use of one or more BET inhibitors when such BET inhibitors would have been less effective in the absence of AKT inhibitor treatment.

In general, one aspect of this document features a method for identifying a mammal as having a cancer at least partially resistant to BET inhibitor treatment. The method comprises, or consists essentially of, (a) determining that the mammal has cancer cells comprising a mutant SPOP polypeptide, and (b) classifying the mammal as having the cancer. The mammal can be a human. The cancer can be a prostate cancer. The mutant SPOP polypeptide can be a SPOP polypeptide having a mutation located in a MATH domain. The mutant SPOP polypeptide can be a mutant human SPOP polypeptide. The mutant SPOP polypeptide can be a F133V, F133L, F102C, Y87C, Y87N, S119N, F125V, K129E, W131C, W131G, K134N, or Q165P mutant SPOP polypeptide. The method can comprise sequencing nucleic acid obtained from cancer cells of the mammal to detect the presence of nucleic acid encoding the mutant SPOP polypeptide, thereby determining that the mammal has the cancer cells comprising the mutant SPOP polypeptide. The method can comprise hybridizing a nucleic acid probe specific for a mutant SPOP nucleic acid sequence to a nucleic acid sample obtained from cancer cells of the mammal to detect the presence of nucleic acid encoding the mutant SPOP polypeptide, thereby determining that the mammal has the cancer cells comprising the mutant SPOP polypeptide. The nucleic acid probe can comprise 5'-AGACTGGGGAGTCAAGAA-3' (SEQ ID NO:75) for detecting a F133V mutant SPOP polypeptide, 5'-TCGGGCAAAATGCAAATT-3' (SEQ ID NO:76) for detecting a F102C mutant SPOP polypeptide, or 5'-TCGGGCAAAATCCAAATT-3' SEQ ID NO:77) for detecting a F102S mutant SPOP polypeptide.

In another aspect, this document features a method for identifying a mammal as having a cancer at least partially resistant to BET inhibitor treatment. The method comprises, or consists essentially of, (a) determining that the mammal has cancer cells comprising an elevated level of BET polypeptide expression, and (b) classifying the mammal as having the cancer. The mammal can be a human. The cancer can be a prostate cancer. The elevated level of BET polypeptide expression can be an elevated level of BRD2, BRD3, BRD4, or BRDT polypeptide expression. The elevated level of BET polypeptide expression can be an elevated level as compared to the level of expression present in comparable cancer cells lacking mutant SPOP polypeptides. The method can comprise determining that the mammal has cancer cells comprising a mutant SPOP polypeptide. The mutant SPOP polypeptide can be a SPOP polypeptide having a mutation located in a MATH domain. The mutant SPOP polypeptide can be a mutant human SPOP polypeptide. The mutant SPOP polypeptide can be a F133V, F133L, F102C, Y87C, Y87N, S119N, F125V, K129E, W131C, W131G, K134N, or Q165P mutant SPOP polypeptide. The method can comprise sequencing nucleic acid obtained from cancer cells of the mammal to detect the presence of nucleic acid encoding the mutant SPOP polypeptide, thereby determining that the mammal has the cancer cells comprising the mutant SPOP polypeptide. The method can comprise hybridizing a nucleic acid probe specific for a mutant SPOP nucleic acid sequence to a nucleic acid sample obtained from cancer cells of the mammal to detect the presence of nucleic acid encoding the mutant SPOP polypeptide, thereby determining that the mammal has the cancer cells comprising the mutant SPOP polypeptide. The nucleic acid probe can comprise 5'-AGACTGGGGAGTCAAGAA-3' (SEQ ID NO:75) for detecting a F133V mutant SPOP polypeptide, 5'-TCGGGCAAAATGCAAATT-3' (SEQ ID NO:76) for detecting a F102C mutant SPOP polypeptide, or 5'-TCGGGCAAAATCCAAATT-3' (SEQ ID NO:77) for detecting a F102S mutant SPOP polypeptide.

In another aspect, this document features a method for increasing the susceptibility of a cancer to treatment with a BET inhibitor. The method comprises, or consists essentially of, (a) identifying a mammal as having a cancer at least partially resistant to BET inhibitor treatment, and (b) administering an AKT inhibitor to the mammal, thereby increasing the susceptibility of the cancer to the treatment with the BET inhibitor. The mammal can be a human. The cancer can be a prostate cancer. The BET inhibitor can be JQ1, I-BET 151 (GSK1210151A), I-BET 762 (GSK525762), OTX-015, TEN-010, CPI-203, CPI-0610, olinone, or RVX-208. The AKT inhibitor can be VQD-002, MK-2206 2HCl, Perifosine (KRX-0401), GSK690693 Ipatasertib (GDC-0068), AZD5363, Miransertib HCl (ARQ 092 HCl), Deguelin, PF-04691502, AT7867, Triciribine, CCT128930, A-674563, PHT-427, Miltefosine, Honokiol, TIC10 Analogue, Uprosertib (GSK2141795), TIC10, Akti-1/2, Afuresertib (GSK2110183), AT13148, or SC79. The identifying step can comprise a method of either of the following two paragraphs.

In some cases, the identifying step can comprise a method for identifying a mammal as having a cancer at least partially resistant to BET inhibitor treatment. Such a method can comprise, or consist essentially of, (a) determining that the mammal has cancer cells comprising a mutant SPOP polypeptide, and (b) classifying the mammal as having the cancer. The mammal can be a human. The cancer can be a prostate cancer. The mutant SPOP polypeptide can be a SPOP polypeptide having a mutation located in a MATH domain. The mutant SPOP polypeptide can be a mutant human SPOP polypeptide. The mutant SPOP polypeptide can be a F133V, F133L, F102C, Y87C, Y87N, S119N, F125V, K129E, W131C, W131G, K134N, or Q165P mutant SPOP polypeptide. The method can comprise sequencing nucleic acid obtained from cancer cells of the mammal to detect the presence of nucleic acid encoding the mutant SPOP polypeptide, thereby determining that the mammal has the cancer cells comprising the mutant SPOP polypeptide. The method can comprise hybridizing a nucleic acid probe specific for a mutant SPOP nucleic acid sequence to a nucleic acid sample obtained from cancer cells of the mammal to detect the presence of nucleic acid encoding the mutant SPOP polypeptide, thereby determining that the mammal has the cancer cells comprising the mutant SPOP polypeptide. The nucleic acid probe can comprise 5'-AGACTGGGGAGTCAAGAA-3' (SEQ ID NO:75) for detecting a F133V mutant SPOP polypeptide, 5'-TCGGGCAAAATGCAAATT-3' (SEQ ID NO:76) for detecting a F102C mutant SPOP polypeptide, or 5'-TCGGGCAAAATCCAAATT-3' (SEQ ID NO:77) for detecting a F102S mutant SPOP polypeptide.

In some cases, the identifying step can comprise a method for identifying a mammal as having a cancer at least partially resistant to BET inhibitor treatment. The method comprises, or consists essentially of, (a) determining that the mammal has cancer cells comprising an elevated level of BET polypeptide expression, and (b) classifying the mammal as having the cancer. The mammal can be a human. The cancer can be a prostate cancer. The elevated level of BET polypeptide expression can be an elevated level of BRD2, BRD3, BRD4, or BRDT polypeptide expression. The elevated level of BET polypeptide expression can be an elevated level as compared to the level of expression present in comparable cancer cells lacking mutant SPOP polypeptides. The method can comprise determining that the mammal has cancer cells comprising a mutant SPOP polypeptide. The mutant SPOP polypeptide can be a SPOP polypeptide having a mutation located in a MATH domain. The mutant SPOP polypeptide can be a mutant human SPOP polypeptide. The mutant SPOP polypeptide can be a F133V, F133L, F102C, Y87C, Y87N, S119N, F125V, K129E, W131C, W131G, K134N, or Q165P mutant SPOP polypeptide. The method can comprise sequencing nucleic acid obtained from cancer cells of the mammal to detect the presence of nucleic acid encoding the mutant SPOP polypeptide, thereby determining that the mammal has the cancer cells comprising the mutant SPOP polypeptide. The method can comprise hybridizing a nucleic acid probe specific for a mutant SPOP nucleic acid sequence to a nucleic acid sample obtained from cancer cells of the mammal to detect the presence of nucleic acid encoding the mutant SPOP polypeptide, thereby determining that the mammal has the cancer cells comprising the mutant SPOP polypeptide. The nucleic acid probe can comprise 5'-AGACTGGGGAGTCAAGAA-3' (SEQ ID NO:75) for detecting a F133V mutant SPOP polypeptide, 5'-TCGGGCAAAATGCAAATT-3' (SEQ ID NO:76) for detecting a F102C mutant SPOP polypeptide, or 5'-TCGGGCAAAATCCAAATT-3' (SEQ ID NO:77) for detecting a F102S mutant SPOP polypeptide.

In another aspect, this document features a method for increasing the susceptibility of a cancer to treatment with a BET inhibitor. The method comprises, or consists essentially of, administering an AKT inhibitor to a mammal identified as having a cancer at least partially resistant to BET inhibitor treatment. The mammal can be a human. The cancer can be a prostate cancer. The BET inhibitor can be JQ1, I-BET 151 (GSK1210151A), I-BET 762 (GSK525762), OTX-015, TEN-010, CPI-203, CPI-0610, olinone, or RVX-208. The AKT inhibitor can be VQD-002, MK-2206 2HCl, Perifosine (KRX-0401), GSK690693 Ipatasertib (GDC-0068), AZD5363, Miransertib HCl (ARQ 092 HCl), Deguelin, PF-04691502, AT7867, Triciribine, CCT128930, A-674563, PHT-427, Miltefosine, Honokiol, TIC10 Analogue, Uprosertib (GSK2141795), TIC10, Akti-1/2, Afuresertib (GSK2110183), AT13148, or SC79. The identifying step can comprise a method of either of the following two paragraphs.

In some cases, the identifying step can comprise a method for identifying a mammal as having a cancer at least partially resistant to BET inhibitor treatment. Such a method can comprise, or consist essentially of, (a) determining that the mammal has cancer cells comprising a mutant SPOP polypeptide, and (b) classifying the mammal as having the cancer. The mammal can be a human. The cancer can be a prostate cancer. The mutant SPOP polypeptide can be a SPOP polypeptide having a mutation located in a MATH domain. The mutant SPOP polypeptide can be a mutant human SPOP polypeptide. The mutant SPOP polypeptide can be a F133V, F133L, F102C, Y87C, Y87N, S119N, F125V, K129E, W131C, W131G, K134N, or Q165P mutant SPOP polypeptide. The method can comprise sequencing nucleic acid obtained from cancer cells of the mammal to detect the presence of nucleic acid encoding the mutant SPOP polypeptide, thereby determining that the mammal has the cancer cells comprising the mutant SPOP polypeptide. The method can comprise hybridizing a nucleic acid probe specific for a mutant SPOP nucleic acid sequence to a nucleic acid sample obtained from cancer cells of the mammal to detect the presence of nucleic acid encoding the mutant SPOP polypeptide, thereby determining that the mammal has the cancer cells comprising the mutant SPOP polypeptide. The nucleic acid probe can comprise 5'-AGACTGGGGAGTCAAGAA-3' (SEQ ID NO:75) for detecting a F133V mutant SPOP polypeptide, 5'-TCGGGCAAAATGCAAATT-3' (SEQ ID NO:76) for detecting a F102C mutant SPOP polypeptide, or 5'-TCGGGCAAAATCCAAATT-3' (SEQ ID NO:77) for detecting a F102S mutant SPOP polypeptide.

In some cases, the identifying step can comprise a method for identifying a mammal as having a cancer at least partially resistant to BET inhibitor treatment. The method comprises, or consists essentially of, (a) determining that the mammal has cancer cells comprising an elevated level of BET polypeptide expression, and (b) classifying the mammal as having the cancer. The mammal can be a human. The cancer can be a prostate cancer. The elevated level of BET polypeptide expression can be an elevated level of BRD2, BRD3, BRD4, or BRDT polypeptide expression. The elevated level of BET polypeptide expression can be an elevated level as compared to the level of expression present in comparable cancer cells lacking mutant SPOP polypeptides. The method can comprise determining that the mammal has cancer cells comprising a mutant SPOP polypeptide. The mutant SPOP polypeptide can be a SPOP polypeptide having a mutation located in a MATH domain. The mutant SPOP polypeptide can be a mutant human SPOP polypeptide. The mutant SPOP polypeptide can be a F133V, F133L, F102C, Y87C, Y87N, S119N, F125V, K129E, W131C, W131G, K134N, or Q165P mutant SPOP polypeptide. The method can comprise sequencing nucleic acid obtained from cancer cells of the mammal to detect the presence of nucleic acid encoding the mutant SPOP polypeptide, thereby determining that the mammal has the cancer cells comprising the mutant SPOP polypeptide. The method can comprise hybridizing a nucleic acid probe specific for a mutant SPOP nucleic acid sequence to a nucleic acid sample obtained from cancer cells of the mammal to detect the presence of nucleic acid encoding the mutant SPOP polypeptide, thereby determining that the mammal has the cancer cells comprising the mutant SPOP polypeptide. The nucleic acid probe can comprise 5'-AGACTGGGGAGTCAAGAA-3' (SEQ ID NO:75) for detecting a F133V mutant SPOP polypeptide, 5'-TCGGGCAAAATGCAAATT-3' (SEQ ID NO:76) for detecting a F102C mutant SPOP polypeptide, or 5'-TCGGGCAAAATCCAAATT-3' (SEQ ID NO:77) for detecting a F102S mutant SPOP polypeptide.

In another aspect, this document features a method for treating cancer. The method comprises, or consists essentially of, (a) identifying a mammal as having a cancer at least partially resistant to BET inhibitor treatment, (b) administering an AKT inhibitor to the mammal to increase the susceptibility of the cancer to a BET inhibitor, and (c) administering a BET inhibitor to the mammal. The mammal can be a human. The cancer can be a prostate cancer. The BET inhibitor can be JQ1, I-BET 151 (GSK1210151A), I-BET 762 (GSK525762), OTX-015, TEN-010, CPI-203, CPI-0610, olinone, or RVX-208. The AKT inhibitor can be VQD-002, MK-2206 2HCl, Perifosine (KRX-0401), GSK690693 Ipatasertib (GDC-0068), AZD5363, Miransertib HCl (ARQ 092 HCl), Deguelin, PF-04691502, AT7867, Triciribine, CCT128930, A-674563, PHT-427, Miltefosine, Honokiol, TIC10 Analogue, Uprosertib (GSK2141795), TIC10, Akti-1/2, Afuresertib (GSK2110183), AT13148, or SC79. The identifying step can comprise a method of either of the following two paragraphs.

In some cases, the identifying step can comprise a method for identifying a mammal as having a cancer at least partially resistant to BET inhibitor treatment. Such a method can comprise, or consist essentially of, (a) determining that the mammal has cancer cells comprising a mutant SPOP polypeptide, and (b) classifying the mammal as having the cancer. The mammal can be a human. The cancer can be a prostate cancer. The mutant SPOP polypeptide can be a SPOP polypeptide having a mutation located in a MATH domain. The mutant SPOP polypeptide can be a mutant human SPOP polypeptide. The mutant SPOP polypeptide can be a F133V, F133L, F102C, Y87C, Y87N, S119N, F125V, K129E, W131C, W131G, K134N, or Q165P mutant SPOP polypeptide. The method can comprise sequencing nucleic acid obtained from cancer cells of the mammal to detect the presence of nucleic acid encoding the mutant SPOP polypeptide, thereby determining that the mammal has the cancer cells comprising the mutant SPOP polypeptide. The method can comprise hybridizing a nucleic acid probe specific for a mutant SPOP nucleic acid sequence to a nucleic acid sample obtained from cancer cells of the mammal to detect the presence of nucleic acid encoding the mutant SPOP polypeptide, thereby determining that the mammal has the cancer cells comprising the mutant SPOP polypeptide. The nucleic acid probe can comprise 5'-AGACTGGGGAGTCAAGAA-3' (SEQ ID NO:75) for detecting a F133V mutant SPOP polypeptide, 5'-TCGGGCAAAATGCAAATT-3' (SEQ ID NO:76) for detecting a F102C mutant SPOP polypeptide, or 5'-TCGGGCAAAATCCAAATT-3' (SEQ ID NO:77) for detecting a F102S mutant SPOP polypeptide.

In some cases, the identifying step can comprise a method for identifying a mammal as having a cancer at least partially resistant to BET inhibitor treatment. The method comprises, or consists essentially of, (a) determining that the mammal has cancer cells comprising an elevated level of BET polypeptide expression, and (b) classifying the mammal as having the cancer. The mammal can be a human. The cancer can be a prostate cancer. The elevated level of BET polypeptide expression can be an elevated level of BRD2, BRD3, BRD4, or BRDT polypeptide expression. The elevated level of BET polypeptide expression can be an elevated level as compared to the level of expression present in comparable cancer cells lacking mutant SPOP polypeptides. The method can comprise determining that the mammal has cancer cells comprising a mutant SPOP polypeptide. The mutant SPOP polypeptide can be a SPOP polypeptide having a mutation located in a MATH domain. The mutant SPOP polypeptide can be a mutant human SPOP polypeptide. The mutant SPOP polypeptide can be a F133V, F133L, F102C, Y87C, Y87N, S119N, F125V, K129E, W131C, W131G, K134N, or Q165P mutant SPOP polypeptide. The method can comprise sequencing nucleic acid obtained from cancer cells of the mammal to detect the presence of nucleic acid encoding the mutant SPOP polypeptide, thereby determining that the mammal has the cancer cells comprising the mutant SPOP polypeptide. The method can comprise hybridizing a nucleic acid probe specific for a mutant SPOP nucleic acid sequence to a nucleic acid sample obtained from cancer cells of the mammal to detect the presence of nucleic acid encoding the mutant SPOP polypeptide, thereby determining that the mammal has the cancer cells comprising the mutant SPOP polypeptide. The nucleic acid probe can comprise 5'-AGACTGGGGAGTCAAGAA-3' (SEQ ID NO:75) for detecting a F133V mutant SPOP polypeptide, 5'-TCGGGCAAAATGCAAATT-3' (SEQ ID NO:76) for detecting a F102C mutant SPOP polypeptide, or 5'-TCGGGCAAAATCCAAATT-3' (SEQ ID NO:77) for detecting a F102S mutant SPOP polypeptide.

In another aspect, this document features a method for treating cancer. The method comprises, or consists essentially of, (a) administering an AKT inhibitor to a mammal identified as having a cancer at least partially resistant to BET inhibitor treatment to increase the susceptibility of the cancer to a BET inhibitor, and (b) administering a BET inhibitor to the mammal to reduce the number of cancer cells within the mammal. The mammal can be a human. The cancer can be a prostate cancer. The BET inhibitor can be JQ1, I-BET 151 (GSK1210151A), I-BET 762 (GSK525762), OTX-015, TEN-010, CPI-203, CPI-0610, olinone, or RVX-208. The AKT inhibitor can be VQD-002, MK-2206 2HCl, Perifosine (KRX-0401), GSK690693 Ipatasertib (GDC-0068), AZD5363, Miransertib HCl (ARQ 092 HCl), Deguelin, PF-04691502, AT7867, Triciribine, CCT128930, A-674563, PHT-427, Miltefosine, Honokiol, TIC10 Analogue, Uprosertib (GSK2141795), TIC10, Akti-1/2, Afuresertib (GSK2110183), AT13148, or SC79. The identifying step can comprise a method of either of the following two paragraphs.

In some cases, the identifying step can comprise a method for identifying a mammal as having a cancer at least partially resistant to BET inhibitor treatment. Such a method can comprise, or consist essentially of, (a) determining that the mammal has cancer cells comprising a mutant SPOP polypeptide, and (b) classifying the mammal as having the cancer. The mammal can be a human. The cancer can be a prostate cancer. The mutant SPOP polypeptide can be a SPOP polypeptide having a mutation located in a MATH domain. The mutant SPOP polypeptide can be a mutant human SPOP polypeptide. The mutant SPOP polypeptide can be a F133V, F133L, F102C, Y87C, Y87N, S119N, F125V, K129E, W131C, W131G, K134N, or Q165P mutant SPOP polypeptide. The method can comprise sequencing nucleic acid obtained from cancer cells of the mammal to detect the presence of nucleic acid encoding the mutant SPOP polypeptide, thereby determining that the mammal has the cancer cells comprising the mutant SPOP polypeptide. The method can comprise hybridizing a nucleic acid probe specific for a mutant SPOP nucleic acid sequence to a nucleic acid sample obtained from cancer cells of the mammal to detect the presence of nucleic acid encoding the mutant SPOP polypeptide, thereby determining that the mammal has the cancer cells comprising the mutant SPOP polypeptide. The nucleic acid probe can comprise 5'-AGACTGGGGAGTCAAGAA-3' (SEQ ID NO:75) for detecting a F133V mutant SPOP polypeptide, 5'-TCGGGCAAAATGCAAATT-3' (SEQ ID NO:76) for detecting a F102C mutant SPOP polypeptide, or 5'-TCGGGCAAAATCCAAATT-3' (SEQ ID NO:77) for detecting a F102S mutant SPOP polypeptide.

In some cases, the identifying step can comprise a method for identifying a mammal as having a cancer at least partially resistant to BET inhibitor treatment. The method comprises, or consists essentially of, (a) determining that the mammal has cancer cells comprising an elevated level of BET polypeptide expression, and (b) classifying the mammal as having the cancer. The mammal can be a human. The cancer can be a prostate cancer. The elevated level of BET polypeptide expression can be an elevated level of BRD2, BRD3, BRD4, or BRDT polypeptide expression. The elevated level of BET polypeptide expression can be an elevated level as compared to the level of expression present in comparable cancer cells lacking mutant SPOP polypeptides. The method can comprise determining that the mammal has cancer cells comprising a mutant SPOP polypeptide. The mutant SPOP polypeptide can be a SPOP polypeptide having a mutation located in a MATH domain. The mutant SPOP polypeptide can be a mutant human SPOP polypeptide. The mutant SPOP polypeptide can be a F133V, F133L, F102C, Y87C, Y87N, S119N, F125V, K129E, W131C, W131G, K134N, or Q165P mutant SPOP polypeptide. The method can comprise sequencing nucleic acid obtained from cancer cells of the mammal to detect the presence of nucleic acid encoding the mutant SPOP polypeptide, thereby determining that the mammal has the cancer cells comprising the mutant SPOP polypeptide. The method can comprise hybridizing a nucleic acid probe specific for a mutant SPOP nucleic acid sequence to a nucleic acid sample obtained from cancer cells of the mammal to detect the presence of nucleic acid encoding the mutant SPOP polypeptide, thereby determining that the mammal has the cancer cells comprising the mutant SPOP polypeptide. The nucleic acid probe can comprise 5'-AGACTGGGGAGTCAAGAA-3' (SEQ ID NO:75) for detecting a F133V mutant SPOP polypeptide, 5'-TCGGGCAAAATGCAAATT-3' (SEQ ID NO:76) for detecting a F102C mutant SPOP polypeptide, or 5'-TCGGGCAAAATCCAAATT-3' (SEQ ID NO:77) for detecting a F102S mutant SPOP polypeptide.

In another aspect, this document features a method for treating cancer. The method comprises, or consists essentially of, administering an AKT inhibitor and a BET inhibitor to a mammal identified as having a cancer at least partially resistant to BET inhibitor treatment. The mammal can be a human. The cancer can be a prostate cancer. The BET inhibitor can be JQ1, I-BET 151 (GSK1210151A), I-BET 762 (GSK525762), OTX-015, TEN-010, CPI-203, CPI-0610, olinone, or RVX-208. The AKT inhibitor can be VQD-002, MK-2206 2HCl, Perifosine (KRX-0401), GSK690693 Ipatasertib (GDC-0068), AZD5363, Miransertib HCl (ARQ 092 HCl), Deguelin, PF-04691502, AT7867, Triciribine, CCT128930, A-674563, PHT-427, Miltefosine, Honokiol, TIC10 Analogue, Uprosertib (GSK2141795), TIC10, Akti-1/2, Afuresertib (GSK2110183), AT13148, or SC79. The identifying step can comprise a method of either of the following two paragraphs.

In some cases, the identifying step can comprise a method for identifying a mammal as having a cancer at least partially resistant to BET inhibitor treatment. Such a method can comprise, or consist essentially of, (a) determining that the mammal has cancer cells comprising a mutant SPOP polypeptide, and (b) classifying the mammal as having the cancer. The mammal can be a human. The cancer can be a prostate cancer. The mutant SPOP polypeptide can be a SPOP polypeptide having a mutation located in a MATH domain. The mutant SPOP polypeptide can be a mutant human SPOP polypeptide. The mutant SPOP polypeptide can be a F133V, F133L, F102C, Y87C, Y87N, S119N, F125V, K129E, W131C, W131G, K134N, or Q165P mutant SPOP polypeptide. The method can comprise sequencing nucleic acid obtained from cancer cells of the mammal to detect the presence of nucleic acid encoding the mutant SPOP polypeptide, thereby determining that the mammal has the cancer cells comprising the mutant SPOP polypeptide. The method can comprise hybridizing a nucleic acid probe specific for a mutant SPOP nucleic acid sequence to a nucleic acid sample obtained from cancer cells of the mammal to detect the presence of nucleic acid encoding the mutant SPOP polypeptide, thereby determining that the mammal has the cancer cells comprising the mutant SPOP polypeptide. The nucleic acid probe can comprise 5'-AGACTGGGGAGTCAAGAA-3' (SEQ ID NO:75) for detecting a F133V mutant SPOP polypeptide, 5'-TCGGGCAAAATGCAAATT-3' (SEQ ID NO:76) for detecting a F102C mutant SPOP polypeptide, or 5'-TCGGGCAAAATCCAAATT-3' (SEQ ID NO:77) for detecting a F102S mutant SPOP polypeptide.

In some cases, the identifying step can comprise a method for identifying a mammal as having a cancer at least partially resistant to BET inhibitor treatment. The method comprises, or consists essentially of, (a) determining that the mammal has cancer cells comprising an elevated level of BET polypeptide expression, and (b) classifying the mammal as having the cancer. The mammal can be a human. The cancer can be a prostate cancer. The elevated level of BET polypeptide expression can be an elevated level of BRD2, BRD3, BRD4, or BRDT polypeptide expression. The elevated level of BET polypeptide expression can be an elevated level as compared to the level of expression present in comparable cancer cells lacking mutant SPOP polypeptides. The method can comprise determining that the mammal has cancer cells comprising a mutant SPOP polypeptide. The mutant SPOP polypeptide can be a SPOP polypeptide having a mutation located in a MATH domain. The mutant SPOP polypeptide can be a mutant human SPOP polypeptide. The mutant SPOP polypeptide can be a F133V, F133L, F102C, Y87C, Y87N, S119N, F125V, K129E, W131C, W131G, K134N, or Q165P mutant SPOP polypeptide. The method can comprise sequencing nucleic acid obtained from cancer cells of the mammal to detect the presence of nucleic acid encoding the mutant SPOP polypeptide, thereby determining that the mammal has the cancer cells comprising the mutant SPOP polypeptide. The method can comprise hybridizing a nucleic acid probe specific for a mutant SPOP nucleic acid sequence to a nucleic acid sample obtained from cancer cells of the mammal to detect the presence of nucleic acid encoding the mutant SPOP polypeptide, thereby determining that the mammal has the cancer cells comprising the mutant SPOP polypeptide. The nucleic acid probe can comprise 5'-AGACTGGGGAGTCAAGAA-3' (SEQ ID NO:75) for detecting a F133V mutant SPOP polypeptide, 5'-TCGGGCAAAATGCAAATT-3' (SEQ ID NO:76) for detecting a F102C mutant SPOP polypeptide, or 5'-TCGGGCAAAATCCAAATT-3' (SEQ ID NO:77) for detecting a F102S mutant SPOP polypeptide.

Unless otherwise defined, all technical and scientific terms used herein have the same meaning as commonly understood by one of ordinary skill in the art to which this invention pertains. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

Figure 1A:
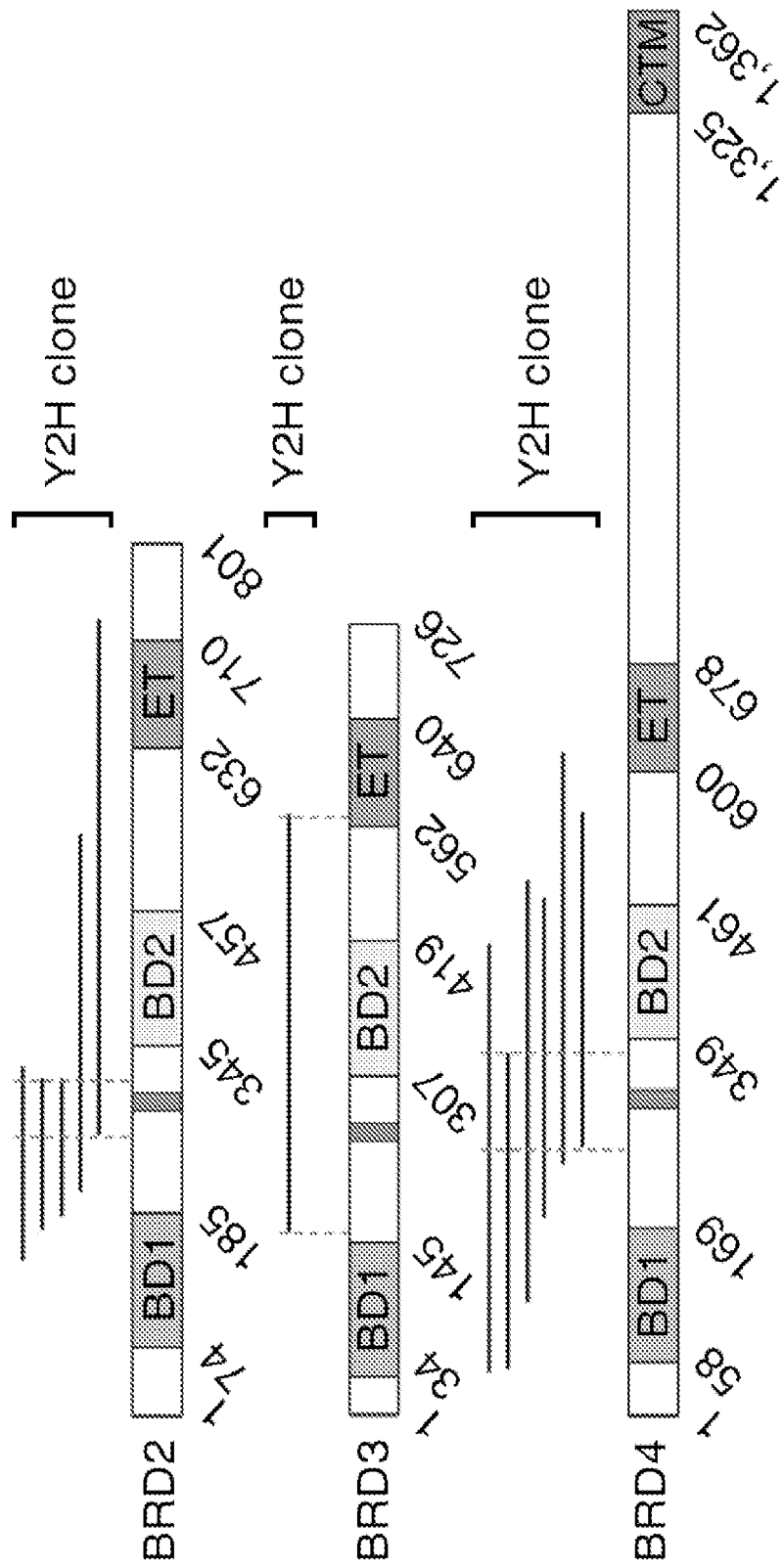
FIG. 1. SPOP interacts with and promotes BRD2/3/4 protein ubiquitination and degradation. a, Diagram showing portions of BRD2/3/4 proteins identified by yeast two-hybrid screen in a human fetal brain cDNA library using the full-length SPOP as bait. The region between two dashed red lines is the minimal interaction region shared by positive clones, and the bolded red vertical line represents the substrate-binding consensus (SBC) motif. BD1, bromodomain 1; BD2, bromodomain 2; ET, extraterminal domain; CTM, C-terminal motif b, Western blot of co-IP samples of IgG or anti-BRD2/3/4 antibodies from cell lysate of LNCaP cells treated with 20 µM MG132 for 8 hours. c, Western blot of whole cell lysate (WCL) of 293T cells transfected with indicated plasmids and treated with or without 20 µM MG132 for 8 hours. Actin was used as a loading control. d, Western blot of WCL of different cell lines transfected with indicated siRNAs. e, Western blot of the products of in vivo ubiquitination assay performed using cell lysate of 293T cells transfected with indicated plasmids and treated with 20 µM MG132 for 8 hours. f, Western blot of the products of in vitro ubiquitination assay performed by incubating the reconstituted SPOP-CUL3-RBX1 E3 ligase complex with E1, E2, Ub, and His-BRD4-N (amino acids 1-500) at 30° C. for 2 hours.

from three replicates. k and l, RT-qPCR (k) and western blot (l) analysis of RAC1 expression in C4-2 cells infected with lentivirus as indicated. The expression level of RAC1 mRNA was first normalized to the level of GAPDH mRNA (internal control) and then further normalized to the value in control (EV-shC) C4-2 cells. Data are shown as mean values±SD (n=3 technical replicates), and similar results were obtained from two independent experiments. Comparing to the data in control (EV-shC) C4-2 cells. m, RT-qPCR analysis of RAC1 mRNA expression in C4-2 infected with lentivirus and JQ1 as in (a). RAC1 mRNA level was first normalized to the level of GAPDH mRNA and then further normalized to the value in EV-expressed C4-2 cells treated with vehicle. Data are shown as means±SD (n=3 technical replicates), and similar results were obtained from two independent experiments. Two-tailed Student's t test was used. n, Western blot of WCL of C4-2 cells infected with lentivirus as indicated and treated with JQ1 (1 μM) for 24 hours before being harvested. Western blot signal intensity RAC1 was first normalized to β-tubulin level, and the value was further normalized to the one in control cells. o, Western blot of WCL of C4-2 cells infected with lentivirus expressing empty vector (EV) or SPOPF133V in combination with control shRNA (shC) or RAC1-specific shRNAs and treated with or without JQ1 (1 μM) for 24 hours before being harvested. p, C4-2 cells were infected with lentivirus as in (o) and treated with JQ1 (0.25 μM) every other day. Cell growth was measured by cell proliferation assay. Data are shown as means±SD (n=6 biological replicates).

FIG. 13. Cholesterol biosynthesis genes are BRD4-binding targets and contribute to JQ1 resistance in SPOP-mutated prostate cancer cells. a, A scheme shows the cholesterol biosynthesis pathway, which is modified from the website (https://en.wikipedia.org/wiki/Biosynthesis). The genes whose expression was affected by JQ1 and SPOP-F133V in C4-2 cells are highlighted by red boxes. b, BRD4 ChIP-seq signals in the cholesterol synthesis gene promoters in C4-2 cells infected with lentivirus expressing empty vector (EV) or SPOP-F133V mutant or transfected with HA-BRD4 expression vector and treated with or without JQ1 (1 μM) for 24 hours. H3K4me3 ChIP-seq signals in LNCaP cells are included. c, ChIP-qPCR analysis of BRD4 binding at the cholesterol synthesis gene promoters in C4-2 cells infected with lentivirus and treated with or without JQ1 as in (b). Data are shown as mean values±SD (n=3 technical replicates), and similar results were obtained in two independent experiments. d, ChIP-qPCR analysis of H3K27ac, H4K5ac, and H4K8ac binding at the MVD, FDFT1, DHCR7, and DHCR24 gene promoters in C4-2 cells transfected with empty vector (Control), SPOP F133V, or BRDs. All data shown are mean values±SD (error bar) from three replicates. e, RT-qPCR analysis of FDFT1, DHCR24, DHCR7, and MVD mRNA expression in RNA samples infected with indicated lentivirus. Target gene mRNA level was first normalized to GAPDH mRNA and then further normalized to the value in control cells. Data are shown as means±SD (n=3 technical replicates), and similar results were obtained from two independent experiments. f, RT-qPCR analysis of FDFT1, DHCR24, DHCR7, and MVD mRNA expression in C4-2 cells infected with lentivirus and treated with JQ1 as in (c). Data are shown as mean values±SD (n=3 technical replicates), and similar results were obtained from two independent experiments. Two tailed Student's t test was used. g, Western blot of WCL of C4-2 cells infected with lentivirus and treated with JQ1 as in (c) for 24 hours before being harvested. h, Western blot of WCL of C4-2 cells infected with lentivirus expressing empty vector (EV) or SPOP F133V in combination with control shRNA (shC) or gene-specific shRNAs for cholesterol synthesis genes including FDFT1, DHCR24, DHCR7, and MVD and treated with or without JQ1 (1 μM) for 24 hours before being harvested. Asterisk indicates the exogenous HA-SPOP-F133V. i, C4-2 cells were infected with lentivirus and treated with JQ1 as in (h). Cell growth was measured by cell proliferation assay. Data are shown as mean values±SD (n=6 biological replicates). j, Cholesterol level analysis in C4-2 cells transfected with empty vector (Control), SPOP F133V, or BRDs. The cholesterol/protein ratio was determined in the whole cell lysis. All data shown are mean values±SD (error bar) from three replicates. k, A schematic diagram depicts a model where both RAC1 and cholesterol synthesis pathways are needed for BET inhibitor resistance in SPOP-mutated prostate cancer cells. Elevation of BRD4 due to SPOP mutation in prostate cancer cells leads to increased expression of RAC1 and cholesterol synthesis genes, both of which are needed for hyperactivation of the AKT-mTORC1 pathway, given that RAC1 directly binds to mTOR and activates AKT and mTORC1 and that formation of cholesterol and glycosphingolipid-enriched lipid rafts/membrane microdomains is needed for AKT activation. l, UCSC genome browser screen shots showing signal profiles of FOS and JUN ChIP-seq in the gene region of the MVD, FDFT1, DHCR7, DHCR24, and RAC1 genes in HeLa (FOS) and K562 (JUN) cells. m, ChIP-qPCR analysis of FOS and JUN binding at the MVD, FDFT1, DHCR7, and DHCR24 promoters of the indicated genes in C4-2 cells. All data shown are mean values±SD (error bar) from three replicates. FOS/JUN ChIP vs IgG. n and o, RT-qPCR (n) and Western blot (o) analysis of indicated proteins in whole cell lysate of C4-2 cells infected with empty vector (EV) or SPOP F133V expressed vectors and with or without FOS or JUN knockdown for 48 hours before being harvested. p, Western blot analysis of indicated proteins in whole cell lysate of C4-2 cells infected with empty vector (EV) or SPOP F133V expressed vectors and with or without knockdown of BRD4, FOS/JUN, or SRC3 for 48 hours before being harvested.

FIG. 14. Assessment of the effect of the AKT pathway on SPOP F133V-mediated JQ1 resistance and a hypothetical model for the current study. a, Western blot analysis of expression of receptor tyrosine kinases (RTKs) including HER3, INSR, and IGF1R in C4-2 cells infected with lentivirus expressing empty vector (EV) or SPOP F133V mutant. Cells were treated with vehicle (DMSO) or 1 μM JQ1 for 24 hours before being harvested. β-tubulin was used as a loading control. b-g, C4-2 cells were infected with lentivirus expressing empty vector (EV) or SPOP F133V mutant in combination with control shRNA (shC) or shRNAs specific for HER3 (b), IGF1R (c), INSR (d), AKT (e), mTOR (f), or Raptor (g). Cells were treated with vehicle (DMSO) or JQ1 (1 μM) for 24 hours before being harvested for Western blot (all the left panels). β-tubulin was used as a loading control. For cell proliferation assay (the right panels), cells were treated with vehicle (DMSO) or JQ1 (0.25 μM) every other day, and cell growth was measured at indicated time points. Data are shown as means±SD (n=6). Statistical significance was determined by two-tailed Student's t-test for cells treated with JQ1 at day 4. h, C4-2 cells were infected with lentivirus expressing empty vector (EV) or SPOP F133V mutant and treated with vehicle (DMSO) or JQ1 (0.25 μM, 5 days for proliferation; or 1 μM, 24 hours for WB) and/or the AKT inhibitor MK2206 (1 μM, 5 days for proliferation; or 5 μM, 24 hours for WB). Western blot analysis of indicated proteins was performed (left panel), and cell growth was measured by cell proliferation assay at different time points (right panel). Data are shown as means±SD (n=6). Statistical significance was determined by two-tailed Student's t-test at day 5. i, C4-2 cells were infected with lentivirus expressing empty vector (EV) or SPOP F133V mutant and treated with vehicle (DMSO) or JQ1 (0.25 µM, 5 days for proliferation; or 1 µM, 24 hours for WB) and/or the AKT inhibitor GDC-0068 (0.2 µM, 5 days for proliferation; or 1 µM, 24 hours for WB). Western blot analysis of indicated proteins was performed (left panel), and cell growth was measured by cell proliferation assay at different time points (right panel). Data are shown as means±SD (n=6). Statistical significance was determined by two-tailed Student's t-test at day 5. j, A model proposed according to the results provided herein. Left, wild-type SPOP inhibits the activity of BET proteins BRD2, BRD3, and BRD4 by binding to and targeting these proteins for ubiquitination and proteasomal degradation, thereby sensitizing prostate cancer cells to JQ1 treatment (left panel). Middle, prostate cancer-associated SPOP mutations impair SPOP mediated degradation of BET proteins and other target proteins including AR, SRC-3, and ERG. The results provided herein demonstrate that activities of AR and ERG can be inhibited by JQ1 even in SPOP mutated cells which could be due to JQ1-sensitive, acetylation (red dot)-dependent interaction of AR and ERG with BET proteins. In contrast, the results provided herein also demonstrate that deregulation of BET proteins due to SPOP mutation leads to upregulation of RAC1 and cholesterol biosynthesis genes (Chol. Syn. Genes), both of which are needed for aberrant activation of the AKTm-TORC1 pathway and thereby contribute to JQ1-resistance in SPOP-mutated prostate cancer cells. Right, treatment of SPOP mutated cancer cells (e.g., SPOP mutated prostate cancer cells) and xenografts with AKT inhibitors completely overcomes SPOP mutation-conferred BET inhibitor resistance in cancer cells (e.g., SPOP mutated prostate cancer cells).

DETAILED DESCRIPTION

This document provides methods and materials for identifying and/or treating cancers having at least a partial resistance to treatment with a BET inhibitor. For example, this document provides methods and materials for identifying a mammal (e.g., a human) as having a cancer at least partially resistant to BET inhibitor treatment. Any appropriate mammal can be identified as having a cancer at least partially resistant to BET inhibitor treatment. For example, humans and other primates such as monkeys can be identified as having a cancer at least partially resistant to BET inhibitor treatment. In some cases, dogs, cats, horses, cows, pigs, sheep, mice, or rats can be identified as having a cancer at least partially resistant to BET inhibitor treatment as described herein.

Any appropriate cancer can be assessed as described herein to determine whether it is at least partially resistant to BET inhibitor treatment. For example, prostate cancer, lung adenocarcinoma cancer, small cell lung cancer, colorectal adenocarcinoma cancer, acral melanoma cancer, or oral squamous cell carcinoma cancer can be assessed as described herein to determine whether it is at least partially resistant to BET inhibitor treatment.

As described herein, a mammal (e.g., a human) can be identified as having a cancer at least partially resistant to BET inhibitor treatment by detecting cancer cells having a mutated SPOP polypeptide. Examples of mutated SPOP polypeptides that can be detected and used to classify a mammal (e.g., a human) as having cancer at least partially resistant to BET inhibitor treatment include, without limitation, SPOP polypeptides having one or more amino acid mutations present within the MATH domain of the SPOP polypeptide. A wild-type human SPOP polypeptide can have the amino acid sequence as set forth in GenBank Accession No. CAA04199 (see also, 2695708), and the MATH domain of a human SPOP polypeptide can extend from amino acid residue 28 to amino acid residue 166. Examples of human SPOP polypeptides having one or more amino acid mutations present within the MATH domain that can be used to identify a mammal (e.g., a human) as having cancer at least partially resistant to BET inhibitor treatment as described herein include, without limitation, F133V SPOP polypeptides, F133L SPOP polypeptides, F102C SPOP polypeptides, Y87C SPOP polypeptides, Y87N SPOP polypeptides, S119N SPOP polypeptides, F125V SPOP polypeptides, K129E SPOP polypeptides, W131C SPOP polypeptides, W131G SPOP polypeptides, K134N SPOP polypeptides, and Q165P SPOP polypeptides.

Any appropriate method can be used to determine if a mammal (e.g., a human) has cancer cells containing a mutated SPOP polypeptide. For example, a cancer cell biopsy sample obtained from a mammal (e.g., a human) having cancer can be assessed for the presence of nucleic acid encoding a mutant SPOP polypeptide using nucleic acid sequencing techniques, nucleic acid hybridization techniques, and/or mutation-specific polymerase chain reaction (PCR). In some cases, nucleic acid probes specific for particular nucleic acid mutations can be used to detect the presence of nucleic acid encoding a mutant SPOP polypeptide, thereby identifying the mammal as having cancer cells with a mutant SPOP polypeptide. In some cases, immunological techniques such as cell staining techniques, Western blot analyses, and/or ELIZAs can be used to detect the presence of cancer cells having a mutant SPOP polypeptide. For example, antibodies specific for a mutant version of an SPOP polypeptide with no binding to wild-type SPOP polypeptides can be used in an immunological assay to detect the presence of cancer cells having a mutant SPOP polypeptide.

Also as described herein, a mammal (e.g., a human) can be identified as having a cancer at least partially resistant to BET inhibitor treatment by detecting cancer cells having an elevated level of BET polypeptide expression. Examples of BET polypeptides that can be assessed for having an elevated level and used to classify a mammal (e.g., a human) as having cancer at least partially resistant to BET inhibitor treatment include, without limitation, BRD2, BRD3, BRD4, and BRDT (a testis-specific BET polypeptide that also contains the conserved SBC (amino acids ADTTT) motif). A human BRD2 polypeptide can have the amino acid sequence as set forth in GenBank Accession No. NP_001106653. A human BRD3 polypeptide can have the amino acid sequence as set forth in GenBank Accession No. NP_031397. A human BRD4 polypeptide can have the amino acid sequence as set forth in GenBank Accession No. NP_490597. A human BRDT polypeptide can have the amino acid sequence as set forth in GenBank Accession No. AAB87862. The term "elevated level" as used herein with respect to a BET polypeptide expression level refers to a level of polypeptide expression by cancer cells (e.g., prostate cancer cells) that is greater (e.g., at least 5, 10, 25, 35, 45, 50, 55, 65, 75, 80, 90, or 100 percent greater) than the median expression level of that polypeptide in adjacent non-malignant (e.g., "normal") tissue or cells of the same organ or type known not to have a mutant SPOP polypeptide from the same mammal.

Any appropriate method can be used to identify cancer cells as having an elevated level of one or more BET polypeptides. For example, polypeptide-based assays such as antibody staining techniques, ELISAs, or antibody array hybridization assays using antibodies can be performed to detect the presence of cancer cells expressing an elevated level of one or more BET polypeptides.

Once a mammal (e.g., a human) is identified as having cancer cells with a mutant SPOP polypeptide as described herein and/or an elevated level of one or more BET polypeptides as described herein, the mammal can be classified as having cancer that is at least partially resistant to BET inhibitor treatment. For example, a human identified as having cancer cells with a mutant SPOP polypeptide (e.g., a F133V SPOP polypeptide) can be classified as having cancer that is at least partially resistant to BET inhibitor treatment.

As described herein, this document also provides methods and materials for increasing the susceptibility of a cancer to treatment with a BET inhibitor. For example, a mammal (e.g., a human) identified as having cancer that is at least partially resistant to BET inhibitor treatment can be administered one or more AKT inhibitors to increase the susceptibility of that cancer to treatment with a BET inhibitor.

Any appropriate mammal identified as having a cancer at least partially resistant to BET inhibitor treatment can be administered one or more AKT inhibitors to increase the susceptibility of that cancer to treatment with a BET inhibitor. For example, humans and other primates such as monkeys identified as having a cancer at least partially resistant to BET inhibitor treatment can be administered one or more AKT inhibitors to increase the susceptibility of that cancer to treatment with a BET inhibitor. In some cases, dogs, cats, horses, cows, pigs, sheep, mice, or rats identified as having a cancer at least partially resistant to BET inhibitor treatment as described herein can be administered one or more AKT inhibitors to increase the susceptibility of that cancer to treatment with a BET inhibitor. In addition, any appropriate cancer identified as being at least partially resistant to BET inhibitor treatment as described herein can be exposed to one or more AKT inhibitors to increase the susceptibility of that cancer to treatment with a BET inhibitor. For example, prostate cancer, lung adenocarcinoma cancer, small cell lung cancer, colorectal adenocarcinoma cancer, acral melanoma cancer, or oral squamous cell carcinoma cancer identified as being at least partially resistant to BET inhibitor treatment can be exposed to one or more AKT inhibitors to increase the susceptibility of that cancer to treatment with a BET inhibitor.

Any appropriate AKT inhibitor or combination of AKT inhibitors can be administered to a mammal identified as having a cancer at least partially resistant to BET inhibitor treatment to increase the susceptibility of that cancer to treatment with a BET inhibitor. Examples of AKT inhibitors that can be used as described herein to increase the susceptibility of that cancer to treatment with a BET inhibitor include, without limitation, MK-2206 2HCl (available commercially from Selleck Chemicals, Houston, Tex.; Catalog #S1078), Perifosine (KRX-0401; available commercially from Selleck Chemicals, Houston, Tex.; Catalog #S1037), GSK690693 (available commercially from Selleck Chemicals, Houston, Tex.; Catalog #S1113), Ipatasertib (GDC-0068; available commercially from Selleck Chemicals, Houston, Tex.; Catalog #S2808), AZD5363 (available commercially from Selleck Chemicals, Houston, Tex.; Catalog #S8019), Miransertib HCl (ARQ 092 HCl; available commercially from Selleck Chemicals, Houston, Tex.; Catalog #S8339), Deguelin (available commercially from Selleck Chemicals, Houston, Tex.; Catalog #S8132), PF-04691502 (available commercially from Selleck Chemicals, Houston, Tex.; Catalog #S2743), AT7867 (available commercially from Selleck Chemicals, Houston, Tex.; Catalog #S1558), Triciribine (available commercially from Selleck Chemicals, Houston, Tex.; Catalog #S1117), CCT128930 (available commercially from Selleck Chemicals, Houston, Tex.; Catalog #S2635), A-674563 (available commercially from Selleck Chemicals, Houston, Tex.; Catalog #S2670), PHT-427 (available commercially from Selleck Chemicals, Houston, Tex.; Catalog #S1556), Miltefosine (available commercially from Selleck Chemicals, Houston, Tex.; Catalog #S3056), Honokiol (available commercially from Selleck Chemicals, Houston, Tex.; Catalog #S2310), TIC10 Analogue (available commercially from Selleck Chemicals, Houston, Tex.; Catalog #S7127), Uprosertib (GSK2141795; available commercially from Selleck Chemicals, Houston, Tex.; Catalog #S7492), TIC10 (available commercially from Selleck Chemicals, Houston, Tex.; Catalog #S7963), Akti-1/2 (available commercially from Selleck Chemicals, Houston, Tex.; Catalog #S7776), Afuresertib (GSK2110183; available commercially from Selleck Chemicals, Houston, Tex.; Catalog #S7521), AT13148 (available commercially from Selleck Chemicals, Houston, Tex.; Catalog #S7563), and SC79 (available commercially from Selleck Chemicals, Houston, Tex.; Catalog #S7863). In some cases, two or more (e.g., two, three, four, five, six, or more) AKT inhibitors can be administered to a mammal identified as having a cancer at least partially resistant to BET inhibitor treatment to increase the susceptibility of that cancer to treatment with a BET inhibitor. For example, two different AKT inhibitors can be administered to a human identified as having cancer (e.g., prostate cancer) at least partially resistant to BET inhibitor treatment to increase the susceptibility of that cancer to treatment with a BET inhibitor.

When using one or more AKT inhibitors to increase the susceptibility of cancer to treatment with a BET inhibitor as described herein, the AKT inhibitor(s) can increase that cancer's susceptibility to any appropriate BET inhibitor. Examples of such BET inhibitors include, without limitation, JQ1 (available commercially from Selleck Chemicals, Houston, Tex.; Catalog #S7110), I-BET 151 (GSK1210151A) (available commercially from Selleck Chemicals, Houston, Tex.; Catalog #S2780), I-BET 762 (GSK525762) (available commercially from Selleck Chemicals, Houston, Tex.; Catalog #S7189), OTX-015 (available commercially from Selleck Chemicals, Houston, Tex.; Catalog #S7360), TEN-010 (available commercially from APExBIO, Houston, Tex.; Catalog #A3692), CPI-203 (available commercially from Selleck Chemicals, Houston, Tex.; Catalog #S7304), CPI-0610 (available commercially from Selleck Chemicals, Houston, Tex.; Catalog #S7853), olinone, and RVX-208 (available commercially from Selleck Chemicals, Houston, Tex.; Catalog #S7295).

In some cases, one or more AKT inhibitors can be administered to a mammal once or multiple times over a period of time ranging from days to months. In some cases, one or more AKT inhibitors can be formulated into a pharmaceutically acceptable composition for administration to a mammal having cancer at least partially resistant to BET inhibitor treatment to increase the susceptibility of that cancer to treatment with a BET inhibitor. For example, a therapeutically effective amount of an AKT inhibitor (e.g., GDC-0068) can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules.

Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A pharmaceutical composition containing one or more AKT inhibitors can be designed for oral or parenteral (including subcutaneous, intramuscular, intravenous, and intradermal) administration. When being administered orally, a pharmaceutical composition can be in the form of a pill, tablet, or capsule. Compositions suitable for parenteral administration include aqueous and non-aqueous sterile injection solutions that can contain anti-oxidants, buffers, bacteriostats, and solutes that render the formulation isotonic with the blood of the intended recipient. The formulations can be presented in unit-dose or multi-dose containers, for example, sealed ampules and vials, and may be stored in a freeze dried (lyophilized) condition requiring only the addition of the sterile liquid carrier, for example, water for injections, immediately prior to use. Extemporaneous injection solutions and suspensions may be prepared from sterile powders, granules, and tablets.

In some cases, a pharmaceutically acceptable composition including one or more AKT inhibitors can be administered locally or systemically. For example, a composition provided herein can be administered locally by intravenous injection or blood infusion. In some cases, a composition provided herein can be administered systemically, orally, or by injection to a mammal (e.g., a human).

Effective doses can vary depending on the severity of the cancer, the route of administration, the age and general health condition of the subject, excipient usage, the possibility of co-usage with other therapeutic treatments, and the judgment of the treating physician.

An effective amount of a composition containing one or more AKT inhibitors can be any amount that increases a cancer's susceptibility to a BET inhibitor without producing significant toxicity to the mammal. For example, an effective amount of an AKT inhibitor such as GDC-0068 can be from about 0.25 mg/kg to about 100 mg/kg (e.g., from about 0.3 mg/kg to about 11 mg/kg, from about 1 mg/kg to about 10 mg/kg, from about 2 mg/kg to about 10 mg/kg, from about 5 mg/kg to about 10 mg/kg, from about 6 mg/kg to about 10 mg/kg, from about 6 mg/kg to about 8 mg/kg, or from about 7 mg/kg to about 9 mg/kg). In some cases, from about 100 mg to about 1000 mg (e.g., from about 250 mg to about 1000 mg, from about 300 mg to about 1000 mg, from about 400 mg to about 1000 mg, from about 100 mg to about 900 mg, from about 100 mg to about 800 mg, from about 400 mg to about 800 mg, or from about 500 mg to about 700 mg) of an AKT inhibitor can be administered to an average sized human (e.g., about 75-85 kg human) per administration (e.g., per daily or weekly administration) for about two to about twelve weeks. In some cases, an AKT inhibitor can be administered daily within one of these dose ranges for 21 days followed by a seven-day rest period.

If a particular mammal fails to respond to a particular amount, then the amount of an AKT inhibitor can be increased by, for example, two fold. After receiving this higher amount, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the condition (e.g., cancer) may require an increase or decrease in the actual effective amount administered.

The frequency of administration of an AKT inhibitor can be any amount that increases a cancer's susceptibility to a BET inhibitor without producing significant toxicity to the mammal. For example, the frequency of administration of an AKT inhibitor can be from about once a day to about once a month (e.g., from about once a week to about once every other week). The frequency of administration of an AKT inhibitor can remain constant or can be variable during the duration of treatment. A course of treatment with a composition containing an AKT inhibitor can include rest periods. For example, a composition containing one or more AKT inhibitors can be administered daily over a two-week period followed by a two-week rest period, and such a regimen can be repeated multiple times. As with the effective amount, various factors can influence the actual frequency of administration used for a particular application. For example, the effective amount, duration of treatment, use of multiple treatment agents, route of administration, and severity of the condition (e.g., cancer) may require an increase or decrease in administration frequency.

An effective duration for administering a composition containing one or more AKT inhibitors can be any duration that increases a cancer's susceptibility to a BET inhibitor without producing significant toxicity to the mammal. In some cases, the effective duration can vary from several days to several months. In general, the effective duration for increasing a cancer's susceptibility to a BET inhibitor can range in duration from about six weeks to about six months. Multiple factors can influence the actual effective duration used for a particular treatment. For example, an effective duration can vary with the frequency of administration, effective amount, use of multiple treatment agents, route of administration, and severity of the condition being treated.

In some cases, a course of treatment and/or the severity of one or more symptoms related to the condition being treated (e.g., cancer) can be monitored. Any appropriate method can be used to determine whether or not a cancer's susceptibility to a BET inhibitor is being increased. For example, cancer cell survival can be assessed following administration of a BET inhibitor to determine if the AKT inhibitor treatment increased the cancer's susceptibility to that BET inhibitor.

After administering one or more AKT inhibitors to a mammal to increase a cancer's susceptibility to a BET inhibitor, one or more BET inhibitors can be administered to the mammal to reduce the number of cancer cells within the mammal. For example, a human identified as having a cancer that is at least partially resistant to BET inhibitor treatment and administered one or more AKT inhibitors to increase that cancer's susceptibility to a BET inhibitor can be administered one or more BET inhibitors to reduce the number of cancer cells within the human.

In some cases, the one or more AKT inhibitors can be administered before, after, or together with the administration of one or more BET inhibitors. For example, one or more AKT inhibitors and one or more BET inhibitors can be administered daily for a period of time. In some cases, one or more AKT inhibitors and one or more BET inhibitors can be formulated into a single composition that can be administered to a mammal identified as having a cancer that is at least partially resistant to BET inhibitor treatment.

As described herein, this document also provides methods and materials for treating cancer that is at least partially resistant to BET inhibitor treatment. For example, a mammal (e.g., a human) identified as having cancer (e.g., a mammal identified as having a cancer that is at least partially resistant to BET inhibitor treatment) can be administered one or more AKT inhibitors to increase the susceptibility of that cancer to treatment with a BET inhibitor and can be administered one or more BET inhibitors to reduce the number of cancer cells within the mammal. Any appropriate mammal identified as having a cancer at least partially resistant to BET inhibitor treatment can be administered one or more AKT inhibitors to increase the susceptibility of that cancer to treatment with a BET inhibitor and one or more BET inhibitors to reduce the number of cancer cells within the mammal. For example, humans and other primates such as monkeys identified as having a cancer at least partially resistant to BET inhibitor treatment can be administered one or more AKT inhibitors to increase the susceptibility of that cancer to treatment with a BET inhibitor and one or more BET inhibitors to reduce the number of cancer cells within the mammal. In some cases, dogs, cats, horses, cows, pigs, sheep, mice, or rats identified as having a cancer at least partially resistant to BET inhibitor treatment as described herein can be administered one or more AKT inhibitors to increase the susceptibility of that cancer to treatment with a BET inhibitor and one or more BET inhibitors to reduce the number of cancer cells within the mammal. In addition, any appropriate cancer identified as being at least partially resistant to BET inhibitor treatment as described herein can be exposed to one or more AKT inhibitors to increase the susceptibility of that cancer to treatment with a BET inhibitor and one or more BET inhibitors to reduce the number of cancer cells within the mammal. For example, prostate cancer, lung adenocarcinoma cancer, small cell lung cancer, colorectal adenocarcinoma cancer, acral melanoma cancer, or oral squamous cell carcinoma cancer identified as being at least partially resistant to BET inhibitor treatment can be exposed to one or more AKT inhibitors to increase the susceptibility of that cancer to treatment with a BET inhibitor and one or more BET inhibitors to reduce the number of cancer cells within the mammal.

Any appropriate AKT inhibitor or combination of AKT inhibitors can be administered to a mammal identified as having a cancer at least partially resistant to BET inhibitor treatment to increase the susceptibility of that cancer to treatment with a BET inhibitor. Examples of AKT inhibitors that can be used as described herein to increase the susceptibility of that cancer to treatment with a BET inhibitor include, without limitation, VQD-002, MK-2206 2HCl, Perifosine (KRX-0401), GSK690693 Ipatasertib (GDC-0068), AZD5363, Miransertib HCl (ARQ 092 HCl), Deguelin, PF-04691502, AT7867, Triciribine, CCT128930, A-674563, PHT-427, Miltefosine, Honokiol, TIC10 Analogue, Uprosertib (GSK2141795), TIC10, Akti-1/2, Afuresertib (GSK2110183), AT13148, and SC79. In some cases, two or more (e.g., two, three, four, five, six, or more) AKT inhibitors can be administered to a mammal identified as having a cancer at least partially resistant to BET inhibitor treatment to increase the susceptibility of that cancer to treatment with a BET inhibitor. For example, two different AKT inhibitors can be administered to a human identified as having cancer (e.g., prostate cancer) at least partially resistant to BET inhibitor treatment to increase the susceptibility of that cancer to treatment with a BET inhibitor.

Any appropriate BET inhibitor or combination of BET inhibitors can be administered to a mammal identified as having a cancer at least partially resistant to BET inhibitor treatment to reduce the number of cancer cells within the mammal. Examples of such BET inhibitors include, without limitation, JQ1, I-BET 151 (GSK1210151A), I-BET 762 (GSK525762), OTX-015, TEN-010, CPI-203, CPI-0610, olinone, and RVX-208.

In some cases, one or more AKT inhibitors and one or more BET inhibitors can be administered to a mammal once or multiple times over a period of time ranging from days to months. In some cases, one or more AKT inhibitors and one or more BET inhibitors can be formulated into a pharmaceutically acceptable composition for administration to a mammal having cancer at least partially resistant to BET inhibitor treatment to increase the susceptibility of that cancer to treatment with a BET inhibitor and to reduce the number of cancer cells within the mammal. For example, a therapeutically effective amount of an AKT inhibitor (e.g., GDC-0068) in combination with a therapeutically effective amount of a BET inhibitor (e.g., JQ1) can be formulated together with one or more pharmaceutically acceptable carriers (additives) and/or diluents. A pharmaceutical composition can be formulated for administration in solid or liquid form including, without limitation, sterile solutions, suspensions, sustained-release formulations, tablets, capsules, pills, powders, and granules.

Pharmaceutically acceptable carriers, fillers, and vehicles that may be used in a pharmaceutical composition described herein include, without limitation, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

A pharmaceutical composition containing one or more BET inhibitors can be designed for oral or parenteral (including subcutaneous, intramuscular, intravenous, and intradermal) administration. When being administered orally, a pharmaceutical composition can be in the form of a pill, tablet, or capsule. Compositions suitable for parenteral administration include aqueous and non-aqueous sterile injection solutions that can contain anti-oxidants, buffers, bacteriostats, and solutes that render the formulation isotonic with the blood of the intended recipient. The formulations can be presented in unit-dose or multi-dose containers, for example, sealed ampules and vials, and may be stored in a freeze dried (lyophilized) condition requiring only the addition of the sterile liquid carrier, for example, water for injections, immediately prior to use. Extemporaneous injection solutions and suspensions may be prepared from sterile powders, granules, and tablets.

In some cases, a pharmaceutically acceptable composition including one or more BET inhibitors can be administered locally or systemically. For example, a composition provided herein can be administered locally by intravenous injection or blood infusion. In some cases, a composition provided herein can be administered systemically, orally, or by injection to a mammal (e.g., a human).

Effective doses can vary depending on the severity of the cancer, the route of administration, the age and general health condition of the subject, excipient usage, the possibility of co-usage with other therapeutic treatments, and the judgment of the treating physician.

An effective amount of a composition containing one or more BET inhibitors can be any amount that reduces the number of cancer cells within a mammal without producing significant toxicity to the mammal. For example, an effective amount of a BET inhibitor such as JQ1 can be from about 0.25 mg/kg to about 50 mg/kg (from about 0.25 mg/kg to about 40 mg/kg, from about 0.25 mg/kg to about 30 mg/kg, from about 0.25 mg/kg to about 25 mg/kg, from about 0.25 mg/kg to about 20 mg/kg, from about 0.25 mg/kg to about 15 mg/kg, from about 0.25 mg/kg to about 10 mg/kg, from about 0.25 mg/kg to about 5 mg/kg, from about 0.5 mg/kg to about 25 mg/kg, from about 1 mg/kg to about 25 mg/kg, from about 2 mg/kg to about 25 mg/kg, from about 5 mg/kg to about 25 mg/kg, from about 0.5 mg/kg to about 5 mg/kg, or from about 0.75 mg/kg to about 3 mg/kg). In some cases, from about 10 mg to about 100 mg (e.g., from about 15 mg to about 100 mg, from about 20 mg to about 100 mg, from about 25 mg to about 100 mg, from about 50 mg to about 100 mg, from about 10 mg to about 90 mg, from about 10 mg to about 80 mg, from about 50 mg to about 90 mg, or from about 60 mg to about 80 mg) of a BET inhibitor can be administered to an average sized human (e.g., about 75-85 kg human) per administration (e.g., per daily or weekly administration) for about two to about twelve weeks. If a particular mammal fails to respond to a particular amount, then the amount of a BET inhibitor can be increased by, for example, two fold. After receiving this higher amount, the mammal can be monitored for both responsiveness to the treatment and toxicity symptoms, and adjustments made accordingly. The effective amount can remain constant or can be adjusted as a sliding scale or variable dose depending on the mammal's response to treatment. Various factors can influence the actual effective amount used for a particular application. For example, the frequency of administration, duration of treatment, use of multiple treatment agents, route of administration, and severity of the condition (e.g., cancer) may require an increase or decrease in the actual effective amount administered.

The frequency of administration of a BET inhibitor can be any amount that reduces the number of cancer cells within a mammal without producing significant toxicity to the mammal. For example, the frequency of administration of a BET inhibitor can be from about once a day to about once a month. The frequency of administration of a BET inhibitor can remain constant or can be variable during the duration of treatment. A course of treatment with a composition containing a BET inhibitor can include rest periods. For example, a composition containing one or more BET inhibitors can be administered daily over a two-week period followed by a two-week rest period, and such a regimen can be repeated multiple times. As with the effective amount, various factors can influence the actual frequency of administration used for a particular application. For example, the effective amount, duration of treatment, use of multiple treatment agents, route of administration, and severity of the condition (e.g., cancer) may require an increase or decrease in administration frequency.

An effective duration for administering a composition containing one or more BET inhibitors can be any duration that reduces the number of cancer cells within a mammal without producing significant toxicity to the mammal. In some cases, the effective duration can vary from several days to several months. In general, the effective duration for reducing the number of cancer cells within a mammal can range in duration from about six weeks to about six months. Multiple factors can influence the actual effective duration used for a particular treatment. For example, an effective duration can vary with the frequency of administration, effective amount, use of multiple treatment agents, route of administration, and severity of the condition being treated.

In certain instances, a course of treatment and/or the severity of one or more symptoms related to the condition being treated (e.g., cancer) can be monitored. Any appropriate method can be used to determine whether or not the number of cancer cells within a mammal is being reduced. For example, cancer imaging techniques and/or patient symptom assessments can be performed to determine if the BET inhibitor is reducing the number of cancer cells within a mammal (e.g., a human).

In some cases, a phosphoinositide 3-kinase (PI3K) inhibitor can be used in addition to or in place of an AKT inhibitor for any of the methods or materials described herein. For example, a PI3K inhibitor can be used in place of an AKT inhibitor to increase the susceptibility of a cancer to BET inhibitor treatment as described herein. An example of a PI3K inhibitor that can be used as described herein includes, without limitation, LY294002 (available commercially from Selleck Chemicals, Houston, Tex.; Catalog #S1105).

The invention will be further described in the following examples, which do not limit the scope of the invention described in the claims.

EXAMPLES

Example 1—Intrinsic BET Inhibitor Resistance in SPOP-Mutated Prostate Cancer is Mediated by BET Protein Stabilization and AKT-mTORC1 Activation Antibodies and Chemicals The following antibodies were used: SPOP (ab137537; Abcam), SPOP (16750-1-AP; Proteintech), BRD2 (A302-583A; Bethyl), BRD2 (ab139690; Abcam), BRD3 (A302-368A; Bethyl), BRD4 (ab128874; Abcam), BRD4 (A301-985A; Bethyl), Myc (9E10; Sigma-Aldrich), Myc (SC-40; Santa Cruz Biotechnology), FLAG (M2; Sigma), HA (MM5-101R; Convance), Actin (AC-74; Sigma-Aldrich), DEK (13962S; Cell Signaling Technology), ERG (SC-352; Santa Cruz Biotechnology), AR (SC-816; Santa Cruz Biotechnology), SRC-3 (611104; BD), phospho-AKT-5473 (9471; Cell Signaling Technology), phospho-AKT-T308 (9275S; Cell Signaling Technology), AKT (9272; Cell Signaling Technology), phospho-S6K-T389 (9205; Cell Signaling Technology), S6K (9202; Cell Signaling Technology), (3-tubulin (T4026; Sigma-Aldrich), RAC1 (23A8; BD), FDFT1 (ab195046; Abcam), DHCR24 (ab137845; Abcam), DHCR7 (ab103296; Abcam), MVD (ab12906; Abcam), HER3 (12708S; Cell Signaling Technology), INSR (ab131238; Abcam), IGF1R (SC-9038; Santa Cruz Biotechnology), mTOR (2972, Cell Signaling Technology), and Raptor (24C12, Cell Signaling Technology). MG132 and cycloheximide were purchased from Sigma-Aldrich, while MLN4924, Bortezomib, and MK2206 were purchased from Selleckchem. JQ1 was obtained from Dr. James Bradner and purchased from Sigma-Aldrich. i-BET762 (i-BET) was obtained from MedchemExpress, and GDC-0068 was obtained from Calbiochem.

Plasmids and Mutagenesis

Expression vectors for SPOP-WT or mutants were described elsewhere (An et al., Cell Rep., 6:657-669 (2014)). FLAG-BRD2 and BRD3 constructs were obtained from Dr. S. J. Flint (Princeton University). FLAG-BRD4 constructs were obtained from Dr. Tasuku Honjo (Kyoto University). FLAG-BRD2/3/4 mutants were generated by KOD Plus Mutagenesis Kit (TOYOBO) following the manufacturer's instructions. LenticrisprV2 plasmid (#52961) was purchased from Addgene (USA).

Cell Culture, Transfection, and Lentivirus Infection

LNCaP, 22Rv1, and 293T cells were obtained from the American Type Culture Collection (ATCC). C4-2 cells were purchased from Uro Corporation (Oklahoma City, Okla.). BPH-1 cells were obtained from Dr. Simon Hayward (Hayward et al., In Vitro Cell Dev. Biol. Anim., 31:14-24 (1995)). 293T cells were maintained in DMEM medium with 10% FBS, while LNCaP, C4-2, 22Rv1, and BPH-1 cells were maintained in RPMI medium with 10% FBS. Cells were transiently transfected using Lipofectamine RNAi MAX (for siRNA transfection) or 3000 (for plasmids transfection) (Thermo Fisher Scientific) according to manufacturer's instructions. pTsin-HA-SPOP-F133V mutant expression or pLKO-based gene knocking down lentivirus vectors or lenticrisprV2-BRD4 and packing constructs were transfected into 293T cells. Virus supernatant was collected 48 hours after transfection. C4-2 and 22Rv1 cells were infected with viral supernatant in the presence of polybrene (8 μg/mL) and were then selected in growth media containing 1.5 μg/mL puromycin. Sequences of gene-specific shRNAs are listed in Table 1. All the cell lines used were tested and authenticated by karyotyping, and prostate cancer cell lines also were authenticated by examining AR expression and SPOP mutation status. Plasmocin (InvivoGen) was added to cell culture media to prevent *mycoplasma* contamination. *Mycoplasma* contamination was tested regularly using Lookout *Mycoplasma* PCR Detection Kit from Sigma-Aldrich.

TABLE 1

Primers used for RT-qPCR in cultured cell lines, FFPE prostate cancer tissues, ChIP and sequences of shRNAs Primers for RT-PCR with cell line samples

| Gene name | F: 5'-3' (SEQ ID NO:) | R: 5'-3' (SEQ ID NO:) |
|---|---|---|
| BRD2 | CTACGTAAGAA ACCCCGGAAG (10) | GCTTTTTCTCC AAAGCCAGTT (11) |
| BRD3 | CCTCAGGGAGA TGCTATCCA (12) | ATGTCGTGGTA GTCGTGCAG (13) |
| BRD4 | AGCAGCAACAG CAATGTGAG (14) | GCTTGCACTTG TCCTCTTCC (15) |
| FDFT1 | ACTATGTTGCT GGGCTGGTC (18) | ACCTGCTCCAA ACCTCTTGA (19) |
| DHCR24 | CAAAGGAAATG AGGCAGAGC (20) | TGTGGTACAAG GAGCCATCA (21) |
| DHCR7 | TGACATCTGCC ATGACCACT (22) | ACAGGTCCTTC TGGTGGTTG (23) |
| MVD | ACGACAGCAAC CAGTTCCAC (24) | CACACAGCAGC CAGAAACTC (25) |
| RAC1 | TCCCTAAGGAG ATTGGTGCT (16) | GCAAAGCGTAC AAAGGTTCC (17) |
| PSA | GGCAGCATTGA ACCAGAGGAG (26) | GCATGAACTTG GTCACCTTCTG (27) |
| TMPRSS2 | CCTGCAAGGAC ATGGGTAT (28) | CGGCACTTGTG TTCAGTTTC (29) |
| KLK2 | CTGCCCATTGC CTAAAGAAG (54) | TGGGAAGCTGT GGCTGAC (55) |
| MYC | GGATTCTCTGC TCTCCTC (30) | CTTGTTCCTCC TCAGAGTC (31) |
| AR | GCAGGAGCTAT TCAGGAAGC (52) | AGGTGGAGAGC AAATGCAAC (53) |
| GAPDH | TGCACCACCAA CTGCTTAGC (34) | GGCATGGACTG TGGTCATGAG (35) |

Primers for RT-PCR with FFPE patient tumor samples

| BRD2 | GACCTTCTGGA GCCAAGTGCC (56) | ATCGTAACTCA TGGGCCTGC (57) |
|---|---|---|
| BRD3 | TCAAATTGAAC CTGCGGGATT (58) | TGCATACATTC GCTTGCACTC (59) |
| BRD4 | ACCTCCAACCC TAACAAGCC (60) | TTTCCATAGTG TCTTGAGCACC (61) |
| 18s RNA | ACCCGTTGAAC CCCATTCGTGA (62) | GCCTCACTAAA CCATCCAATCG G (63) |

Primers for ChIP-qPCR

| RAC1 prompter | CCAAAGTGTTG GGATTACGG (36) | CGGAGTTTCTC TGGACTTCG (37) |
|---|---|---|
| FDFT1 prompter | ACATCACATGA AGGCCGTTT (38) | GACCTTCCACC AACCACCTA (39) |
| DHCR24 prompter | CCCTGAGTCAG TCACCCTTT (40) | ACAATGGAGCT CACCACTCC (41) |
| DHCR7 prompter | GCACATTGATG GAGCGTATG (42) | TAATAAGCAGG CCACCCAGA (43) |
| MVD prompter | CGCATTACCTC TCAGCCAAT (44) | AGACAGGTAGC CCCCAGAG (45) |
| AR prompter | GGTGAGTGCTG GCCTCCAGG (64) | GCGCTAAGCCC TGCCTAGTG (65) |
| PSA enhancer | CTCAGCCTTTG TCTCTGATGAA G (66) | TCAGATCCAGG CTTGCTTACTG (67) |
| TMPRSS2 enhancer | GTCTCCCTGCA CCACTAACTAG (68) | GCAAACATTGA AAAGAGCCT (69) |
| KLK2 enhancer | CAAAGGTGAGC AACCTAGGCTT A (79) | ATGTTCCTCCA GAGTAGGTCT (80) |

TABLE 1-continued

Primers used for RT-qPCR in cultured cell lines, FFPE prostate cancer tissues, ChIP and sequences of shRNAs

| | | |
|---|---|---|
| MYC enhancer | GGCTTACAGGA TACCCCAACT(81) | GGGCTATCACA CCTCGCCC(82) |

| Gene name | Sequence(SEQ ID NO:_) |
|---|---|
| shSPOP#2 | CCGGCAAGGTAGTGAAATTCTCCTACTCG AGTAGGAGAATTTCACTACCTTGTTTTTT(83) |
| shSPOP#4 | CCGGCACAAGGCTATCTTAGCAGCTCTCG AGAGCTGCTAAGATAGCCTTGTGTTTTTT(84) |
| shBRD4#1 | CCGGCAGTGACAGTTCGACTGATGACTCG AGTCATCAGTCGAACTGTCACTGTTTTT(85) |
| shBRD4#2 | CCGGCCTGGAGATGACATAGTCTTACTCG AGTAAGACTATGTCATCTCCAGGTTTTT(86) |
| shBRD3#1 | CCGGCCCAAGAGGAAGTTGAATTATCTCG AGATAATTCAACTTCCTCTTGGGTTTTT(87) |
| shBRD3#2 | CCGGGCTGATGTTCTCGAATTGCTACTCG AGTAGCAATTCGAGAACATCAGCTTTTT(88) |
| shBRD2#1 | CCGGCGGTTTGCTGTGACACTTCTTCTCG AGAAGAAGTGTCACAGCAAAGGGTTTTT(89) |
| shBRD2#2 | CCGGCCCTGCCTACAGGTTATGATTCTCG AGAATCATAACCTGTAGGCAGGGTTTTT(90) |
| shFOS#1 | CCGGGCGGAGACAGACCAACTAGAACTCG AGTTCTAGTTGGTCTGTCTCCGCTTTTT(91) |
| shFOS#2 | CCGGTCTGCTTTGCAGACCGAGATTCTCG AGAGTCTCGGTCTGCAAAGCAGATTTTT(92) |
| shJUN#1 | CCGGCGGACCTTATGGCTACAGTAACTCG AGTTACTGTAGCCATAAGGTCCGTTTTG(93) |
| shJUN#2 | CCGGCGCAAACCTCAGCAACTTCAACTCG AGTTGAAGTTGCTGAGGTTTGCGTTTTG(94) |
| shAR#1 | CCGGCCTGCTAATCAAGTCACACATCTCG AGATGTGTGACTTGATTAGCAGGTTTTT(95) |
| shAR#2 | CCGGCGCGACTACTACAACTTTCCACTCG AGTGGAAAGTTGTAGTAGTCGCGTTTTT(96) |
| shSRC-3#1 | CCGGCCATACATTTAATTGCCGTATCTCG AGATACGGCAATTAAATGTATGGTTTTT(97) |
| shSRC-3#2 | CCGGGCAGTCTATTCGTCCTCCATACTCG AGTATGGAGGACGAATAGACTGCTTTTT(98) |
| shDEK#1 | CCGGGCGAGTGCTAACTTGGAAGAACTCG AGTTCTTCCAAGTTAGCACTGGCTTTTT(99) |
| shDEK#2 | CCGGTGAAATTGAGAGGATACATTTCTCG AGAAATGTATCCTCTCAATTTCATTTTT(100) |
| shRAC1#1 | CCGGCCCTACTGTCTTTGACAATTACTCG AGTAATTGTCAAAGACAGTAGGGTTTTT(101) |
| shRAC1#2 | CCGGGCTAAGGAGATTGGTG€TGTACTCG AGTACAGCACCAATCTCCTTAGCTTTTT(102) |
| shMVD#1 | CCGGTATGCCCAGTTCTCTGAGAAACTCG AGTTTCTCAGAGAACTGGGCATATTTTG(103) |
| shMVD#2 | CCGGTCTGCACCAGGACCAGTTAAACTCG AGTTTAACTGGTCCTGGTGCAGATTTTG(104) |
| shFDFT1#1 | CCGGACTTGCTACAAGTATCTCAATCTCG AGATTGAGATACTTGTAGCAAGTTTTTG(105) |
| shFDFT1#2 | CCGGCAACGATCTCCCTTGAGTTTACTCG AGTAAACTCAAGGGAGATCGTTGTTTTG(106) |
| shDHCR7#1 | GTACCGGACTTCAAGCTGTTCTTCAATGC TCGAGCATTGAAGAACAGCTTGAAGTTTT TTTG(107) |
| shDHCR7#2 | CCGGGGGCCAAGACTCCACCTATAACTCG AGTTATAGGTGGAGTCTTGGCGCTTTTG(108) |
| shDHCR2#1 | CCGGCCAACACATCTGCACTGCTTACTCG AGTAAGCAGTGCAGATGTGTTGGTTTTG(109) |
| shDHCR2#2 | CCGGGCTCTCGCTTATCTTCGATATCTCG AGATATCGAAGATAAGCGAGAGCTTTTG(110) |

Organoid Cultures and Cell Viability Assay

Organoid cells were obtained from Dr. Yu Chen from MSKCC and cultured according to the methodology as described elsewhere (Drost et al., Nat. Protoc., 11:347-358 (2016)). In brief, organoid cells were imbedded in 40 μL Matrigel each drop and cultured in FBS free DMEM/F12 medium supplied with several growth factors. Cell viability assays were conducted by plating 2,000 organoid cells per well of a collagen coated 96-well cell culture plate in 100 mL media with vehicle (DMSO) control or JQ1 (0.05~1 μM). Viable cells were counted by using a CellTiter-Glo (Promega) Luminescent Cell Viability Assay Kit.

Prostate Cancer Patient Samples

Treatment-naive prostate cancer and matched benign tissues were collected from a radical prostatectomy series. Haematoxylin and eosin (H&E) slides of frozen and formalin-fixed paraffin-embedded (FFPE) human tumor tissues and matched benign tissues were examined by a general pathologists and a genitourinary pathologist to confirm histological diagnosis, Gleason score, and high-density cancer foci (>80%) of the selected tumor tissue. The frozen blocks for DNA/RNA extraction were examined by the pathologists, followed by consecutive ten 10-μm sections of each tumor. These qualified samples were then used for DNA/RNA isolation. FFPE tissues were used for immunohistochemistry (IHC).

Detection of SPOP Mutation Prostate Cancer Patient Specimens by Whole-Genome and Sanger Sequencing For whole genome sequencing, DNA was extracted by phenol-chloroform and purified by the ethanol precipitation method from 32 paired tumor and benign frozen patient samples. DNA samples were fragmented in fragmentation buffer using Covaris Ultrasonicator system. The fragmented DNA with average length of 500 bp was subjected to DNA library construction. Libraries were constructed according to Illumina's protocol with DNA samples. High-throughput short-gun sequencing was performed on the IlluminaHiSeq 2000 platform. For DNA sequencing, pair-end reads with length of 90 bp were generated. Raw reads of DNA sequencing were filtered using an in-house pipeline. Clean DNA reads were processed with SAMTools to remove the PCR duplicates and aligned to the human reference genome hg19 with Burrows-Wheeler Aligner (http://bio-bwa.sourceforge.net/). The whole genome sequencing data were deposited in The European Genome-phenome Archive with the accession #EGAS00001000888.

For Sanger sequencing, DNA was extracted from all 99 cases of FFPE prostate cancer tissues using a QIAamp DNA FFPE Tissue kit. PCR was performed, and PCR products were purified using a GeneJET Extraction kit according to manufacturer's instruction and used for Sanger sequencing. The primers used for DNA amplification were: Amp-Exon6-Forward 5'-ACCCATAGCTTTGGT-TTCTTCTCCC-3' (SEQ ID NO:1); Amp-Exon6-Reverse 5'-TATCTGTTT TGGACAGGTGTTTGCG-3' (SEQ ID NO:2); Amp-Exon7-Forward 5'-ACTCA-TCAGATCTGGGAACTGC-3' (SEQ ID NO:3); Amp-Exon7-Reverse 5'-AGTTG-TGGCTTTGATCTGGTT-3' (SEQ ID NO:4). Amp-Exon6-Reverse and Amp-Exon7-Forward were also used for Sanger sequencing.

Yeast Two-Hybrid Screen

Yeast two-hybrid screen was performed with the full-length SPOP cloned in-frame with the GAL4 DNA binding domain in vector PGBKT7 (Clontech). The yeast cells were transformed with PGBKT7-SPOP and the human fetal brain cDNA library. A total of $2 \times 10^7$ independent clones were screened by growth in deficient medium and X-gal staining. The positive clones were subsequently retested in fresh yeast cells, and the identities of prey were determined with interaction sequence tags (ISTs) obtained by DNA sequencing. The reading frame was verified.

RNA Interference

Non-specific control siRNA and gene-specific siRNAs for human SPOP and BRD4 were purchased from Thermo Fisher Scientific Dharmacon. siRNA transfection of cells was performed following the manufacturer's instructions. The sequences of siRNA oligos were: siSPOP #1 5'-GGAUGAUGUAAAUGAGCAA-3' (SEQ ID NO:5); siSPOP #2 5'-GGACAGCGACTCTGAATCT-3' (SEQ ID NO:6); siBRD4 #1 5'-GAACCUCCCUGAUUACUAU-3' (SEQ ID NO:7); siBRD4 #2 5'-AGCUGAACCUCC-CUGAUUA-3' (SEQ ID NO:8); and non-specific control siRNA (siC) 5'-ACAGACUUCGGAGUACCUG-3' (SEQ ID NO:9).

Co-Immunoprecipitation (Co-IP)

To immunoprecipitate the ectopically expressed FLAG-tagged proteins, transfected cells were lysed 24 hours post-transfection in BC100 buffer. The whole-cell lysates were immunoprecipitated with the monoclonal anti-FLAG antibody-conjugated M2 agarose beads (Sigma-Aldrich) at 4° C. overnight. After three washes with lysis buffer, followed by two washes with BC100 buffer, the bound proteins were eluted using FLAG-Peptide (Sigma-Aldrich) prepared in BC100 for 3 hours at 4° C. The eluted protein sample was resolved by SDS-PAGE. To immunoprecipitate the endogenous proteins, cells were lysed with 1× cell lysis buffer (Cell Signaling Technology), and the lysate was centrifuged. The supernatant was precleared with protein A/G beads (Sigma-Aldrich) and incubated with the indicated antibody and protein A/G beads at 4° C. overnight. Beads were washed five times with lysis buffer and resuspended in sample buffer and analyzed by SDS-PAGE.

Western Blot

Cell lysates or immunoprecipitates were subjected to SDS-PAGE, and proteins were transferred to nitrocellulose membranes (GE Healthcare Sciences). The membranes were blocked in Tris-buffered saline (TBS, pH 7.4) containing 5% non-fat milk and 0.1% Tween-20, washed twice in TBS containing 0.1% Tween-20, and incubated with primary antibody overnight at 4° C., followed by secondary antibody for 1 hour at room temperature. The proteins of interest were visualized using ECL chemiluminescence system (Santa Cruz Biotechnology). Densitometry analysis of protein bands was analyzed on the Gel-Pro Analyzer software.

In Vitro Ubiquitination Assay

An in vitro ubiquitination assay was carried out using a protocol as described elsewhere (An et al., *Molecular Cell*, 59:904-916 (2015)). Briefly, 2 μg APP-BP1/Uba3, 2 μg His-UBE2M enzymes, and 5 μg NEDD8 were incubated at 30° C. for 2 hours in the presence of ATP. The thioester loaded His-UBE2M-NEDD8 was further incubated with 3 μg His-DCNL2, 6 μg CUL3/RBX1 at 4° C. for 2 hours to obtain the NEDDylated CUL3/RBX1. The NEDDylated CUL3/RBX1, 5 μg GST-SPOP, 5 μg Ub, 500 ng E1, 750 ng E2 (UbcH5a and UbcH5b), and 5 μg His-BRD4-N (amino acids 1-500) were incubated with 0.6 μL 100 mM ATP, 1.5 μL 20 μM ubiquitin aldehyde, 3 μL 10× ubiquitin reaction buffer (500 mM Tris-HCl (pH7.5), 50 mM KCl, 50 mM NaF, 50 mM MgCl$_2$ and 5 mM DTT), 3 μL 10× energy regeneration mix (200 mM creatine phosphate and 2 μg/μL creatine phosphokinase), 3 μL 10× protease inhibitor cocktail at 30° C. for 2 hours, followed by western blot analysis. The Ub, E1, E2, and CUL3/RBX1 were purchased from UBIQUIGENT.

In Vivo Ubiquitination Assay

For the in vivo ubiquitination assay, C4-2 cells were transfected with plasmids for HA-Ub, FLAG-BRD4, and other indicated proteins. C ells were treated with 20 μM MG132 for 8 hours before being harvested and lysed with lysis buffer (50 mM Tris-HCl, pH 7.5, 150 mM NaCl, 1% NP40, 0.5% sodium deoxycholate, 1× protease inhibitor cocktail (PIC)). The lysate was subjected to co-immunoprecipitation using anti-FLAG-conjugated agarose beads as described in the Co-IP assay.

Quantitative RT-PCR

Total RNA was isolated from transiently transfected cells using the Trizol reagent (Thermo Fisher Scientific), and cDNA was reverse-transcribed using the Superscript RT kit (TOYOBO, Japan) according to the manufacturer's instructions. PCR amplification was performed using the SYBR Green PCR master mix Kit (TOYOBO, Japan). All quantization was normalized to the level of endogenous control GAPDH. The primer sequences for the SYBR green qPCR used were as follows: BRD2-F: 5'-CTACGTAAGAAACCCCGGAAG-3' (SEQ ID NO:10); BRD2-R: 5'-GCTTTTTCTCCAAAGCCAGTT-3' (SEQ ID NO:11); BRD3-F: 5'-CCTCAGGGAGATGCTATCCA-3' (SEQ ID NO:12); BRD3-R: 5'-ATGTCGTGG-TAGTCGTGCAG-3' (SEQ ID NO:13); BRD4-F: 5'-AGCAGCAACAGCAATGT-GAG-3' (SEQ ID NO:14); BRD4-F: 5'-GCTTGCACTTGTCCTCTTCC-3' (SEQ ID NO:15); RAC1-F: 5'-TGGCTAAGGAGATTGGTGCT-3' (SEQ ID NO:16); RAC1-R: 5'-GCAAAGCGTA-CAAAGGTTCC-3' (SEQ ID NO:17); FDFT1-F: 5'-ACTAT-GTTGCTGGGCTGGTC-3' (SEQ ID NO:18); FDFT1-R: 5'-ACCTGCTCCA-AACCTCTTGA-3' (SEQ ID NO:19); DHCR24-F: 5'-CAAAGGAAATGAGGCA-GAGC-3' (SEQ ID NO:20); DHCR24-R: 5'-TGTGGTACAAGGAGC-CATCA-3' (SEQ ID NO:21); DHCR7-F: 5'-TGA-CATCTGCCATGACCACT-3' (SEQ ID NO:22); DHCR7-R: 5'-ACAGGTCCTTCTGGTGGTTG-3' (SEQ ID NO:23); MVD-F: 5'-AGGACAGCAACCAGTTCCAC-3' (SEQ ID NO:24); MVD-R: 5'-CACAC-AGCAGCCACAAACTC-3' (SEQ ID NO:25); PSA-F: 5'-GGCAGCATTGAAC-CAGAGGAG-3' (SEQ ID NO:26); PSA-R: 5'-GCAT-GAACTTGGTCACCTTCTG-3' (SEQ ID NO:27); TMPRSS2-F: 5'-CCTGCAAGGACATG-GGTAT-3' (SEQ ID NO:28); TMPRSS2-R: 5'-CGGCACTTGTGTTCAGTTTC-3' (SEQ ID NO:29);

MYC-F: 5'-GGATTCTCTGCTCTCCTC-3' (SEQ ID NO:30); MYC-R: 5'-CTTGT-TCCTCCTCAGAGTC-3' (SEQ ID NO:31); AR-F: 5'-GACGCTTCTACCAGC-TCACC-3' (SEQ ID NO:32); AR-R: 5'-GCTT-CACTGGGTGTGGAAAT-3' (SEQ ID NO:33); GAPDH-F: 5'-TGCACCACCAACTGCTTAGC-3' (SEQ ID NO:34); and GAPDH-R: 5'-GGCATGGACTGTGGTCATGAG-3' (SEQ ID NO:35).

Cell Proliferation Assay

CellTiter 96® AQueous One Solution Cell Proliferation Assay (MTS) (Promega) was used to measure cell growth according to the manufacturer's instructions. Briefly, cells were plated in 96-well plates at a density of 2,000 cells per well. At the indicated times, 20 µL of Cell Titer 96R Aqueous One Solution Reagent was added to medium. After incubating for 1 hour at 37° C. in the cell incubator, cell growth was measured in a microplate reader at 490 nm.

Trypan Blue Assay

Trypan blue assay was performed to measure cell growth according to the manufacturer's instructions. Briefly, cells were plated in 6-well plates at a density of about $5 \times 10^4$ to about $1 \times 10^5$ cells per well. At the indicated time points, cells were trypsinized and suspended in 1 mL 1×PBS. 100 µL cells and 100 µL trypan blue solution (Sigma-Aldrich) were mixed, and the number of viable cells was measured using the Bio-Rad automated cell counter.

Immunohistochemistry (IHC)

FFPE tumor samples from patients or C4-2 xenograft tumors were deparaffinized, rehydrated, and subjected to heat-mediated antigen retrieval. UltraSensitive TM S-P (Rabbit) IHC Kit (KIT-9706, Fuzhou Maixin Biotech) was used by following the manufacturer's instructions with minor modification as described elsewhere (Patel et al., *Cell Rep.*, 6:81-92 (2014)). Briefly, the sections were incubated with 3% $H_2O_2$ for 15 minutes at room temperature to quench endogenous peroxidase activity. After antigen retrieval using unmasking solution (Vector Labs), slides were blocked with normal goat serum for 1 hour and then incubated with primary antibody at 4° C. overnight. IHC analysis of tumor samples was performed using primary antibodies against BRD2 (dilution 1:250; Abcam; catalog number: ab139690), BRD3 (dilution 1:200; Bethyl; catalog number: A302-368A), and BRD4 (dilution 1:500; Bethyl; catalog number: A301-985A100). The sections were then washed 3 times in 1×PBS and treated for 30 minutes with biotinylated goat-anti-rabbit IgG secondary antibodies (Fuzhou Maixin Biotech).

After washing three times in 1×PBS, sections were incubated with streptavidin-conjugated HRP (Fuzhou Maixin Biotech). After washing three times in 1×PBS for 5 minutes each, specific detection was developed with 3'3-diaminobenzidine (DAB-2031, Fuzhou Maixin Biotech). Images were taken by using an Olympus camera and matched software. The IHC staining was scored by two independent pathologists based on the 'most common' criteria.

RNA Extraction from FFPE Patient Tissues and RT-qPCR

These experiments were performed using a method described elsewhere (Renwick et al., *J. Clin. Invest.*, 123: 2694-2702 (2013); An et al., *Mol. Cell*, 59:904-916 (2015); and Zhao et al. *Cell Rep.*, 15:599-610 (2016)). Briefly, a 4-µm pre-cut H&E stained section was obtained and reviewed by a pathologist. Only blocks with >80% tumor cells were used. Total RNA was isolated from FFPE tissue sections from the same cohorts of patients using the RNeasy FFPE Kit (Qiagen, Catalog no. 73504) using the method as described elsewhere (Mittempergher et al., *PLoS One*, 6:e17163 (2011)). The NanoDrop 2000 spectrophotometer (Thermo Fisher Scientific) was used to assess the RNA yield and quality. The cDNA was synthesized using Prime-Script™ RT reagent Kit (Perfect Real Time) according to the manufacturer's instructions (TaKaRa, Catalog no. RR037A) with minor modifications. qPCR was performed using SYBR® Premix Ex Taq™ II (Tli RNaseH Plus) (TaKaRa, Catalog no. RR820A) on a StepOnePlus Real-Time PCR system (Thermo Fisher Scientific) according to TaKaRa's recommended cycling conditions (95° C. for 30 seconds, followed by 40 cycles of 95° C. for 5 seconds, 60° C. for 30 seconds and a melt curve analysis). 18S RNA served as internal reference as described elsewhere (Hagen et al., *Exp. Mol. Pathol.*, 95:98-104 (2013)). The primers used in RT-qPCR were listed in Table 1. All the samples were run in triplicate on the same plate, and the expression level of BRD2/3/4 mRNA was automatically calculated by the StepOnePlus Real-Time PCR system (Thermo Fisher Scientific). The comparison of the expression level of BRD2/3/4 mRNA was performed with Mann-Whitney test by the MedCalc statistical software Version 10.4.7.0 (MedCalc Software bvba, Mariakerke, Belgium). Two-sided P<0.05 was considered statistically significant.

RNA-Seq and Data Analysis

C4-2 cells infected with lentivirus expressing empty vector (EV), HA-SPOP-F133V, or BRD2/3/4 were treated with or without JQ1 (1 µM) for 24 hours. Total RNAs were isolated from cells using the methods as described elsewhere (Wang et al., *Embo J.*, 32:1584-1597 (2013)). Briefly, RNA was isolated using RNeasy Plus Mini Kit (Qiagen). High quality (Agilent Bioanalyzer RIN>7.0) total RNAs were employed for the preparation of sequencing libraries using Illumina TruSeq Stranded Total RNA/Ribo-Zero Sample Prep Kit. A total of 500-1,000 ng of riboRNA-depleted total RNA was fragmented by RNase III treatment at 37° C. for 10-18 minutes, and RNase III was inactivated at 65° C. for 10 minutes. Size selection (50 to 150 bp fragments) was performed using the FlashPAGE denaturing PAGE-fractionator (Thermo Fisher Scientific) prior to ethanol precipitation overnight. The resulting RNA was directionally ligated, reverse-transcribed, and RNase H treated.

Samples with biological triplicates were sequenced using the Illumina HiSeq2000 platform. Pre-analysis quality control was performed using FastQC (http://www.bioinformatics.babraham.ac.uk/projects/fastqc/) and RSeQC software (Wang et al., *Bioinformatics*, 28:2184-2185 (2012)) to ensure that raw data were in excellent condition and suitable for downstream analyses. Pair-end raw reads were aligned to the human reference genome (GRch37/hg19) using Tophat (Trapnell et al., *Bioinformatics*, 25:1105-1111 (2009)). Genome-wide coverage signals were represented in BigWig format to facilitate convenient visualization using the UCSC genome browser. Gene expression was measured using RPKM (Reads Per Kilo-base exon per Million mapped reads) as described elsewhere (Mortazavi et al., *Nature Methods*, 5:621-628 (2008)). EdgeR (Robinson et al., *Genome Biol.*, 11:R25 (2010)) was used to identify genes that were differentially expressed between EV-expressing and SPOP-F133V-expressing C4-2 cells treated with or without JQ1. Raw and processed data were deposited into NCBI Gene Expression Omnibus with accession number GSE88872.

Chromatin Immunoprecipitation (ChIP) Sequencing (ChIP-Seq) and Data Analysis, and ChIP-qPCR ChIP was performed as described elsewhere (Boyer et al., *Cell*, 122:947-956 (2005)). ChIP-seq libraries were prepared using the methods as described elsewhere (Boyer et al., *Cell*, 122:947-956 (2005)), and high throughput sequencing was performed using the Illumina HiSeq2000 platforms. The data were analyzed using the following pipeline: ChIP-seq raw reads were aligned to the human reference genome (GRCh37/hg19) using Bowtie2 (2.2.9), and reads mapped to one or two locations were kept for further analysis. Peak calling was performed by MACS2 (2.1.1) with p-value threshold of 1e-5. BigWig files were generated for visualization with the UCSC genome browser or IGV. GREAT (http://bejerano.stanford.edu/great/public/html/) was used to assign peaks to their potential target genes (a peak-gene association was determined if the peak fell into 2 kb region centering on the transcription start site of the gene). The common BRD4 target genes induced by SPOP F133V and HA-BRD4 expression were determined independently in each of two biological repeat experiments. Raw and processed data were deposited into NCBI Gene Expression Omnibus with accession number GSE88872.

For ChIP-qPCR experiments, DNAs pulled down by antibodies or non-specific IgG were amplified by real-time PCR. The ChIP primers used were: RAC1 ChIP-F: 5'-CCAAAGTGTTGGGATTACGG-3' (SEQ ID NO:36); RAC1 ChIP-R: 5'-CGGAGTTTCTCTGGACTTCG-3' (SEQ ID NO:37); FDFT1 ChIP-F: 5'-ACA-TCACAT-GAAGGCCGTTT-3' (SEQ ID NO:38); FDFT1 ChIP-R: 5'-GACCTTCC-ACCAACCACCTA-3' (SEQ ID NO:39); DHCR24 ChIP-F: 5'-CCCTGAGTCAGT-CACCCTTT-3' (SEQ ID NO:40); DHCR24 ChIP-R: 5'-ACAATGGAGCT-CACCA-CTCC-3' (SEQ ID NO:41); DHCR7 ChIP-F: 5'-GCACATTGATGGAGCGTATG-3' (SEQ ID NO:42); DHCR7 ChIP-R: 5'-TAATAAGCAGGCCACCCAGA-3' (SEQ ID NO:43); MVD ChIP-F: 5'-CGCAT-TACCTCTCAGCCAAT-3' (SEQ ID NO:44); MVD ChIP-R: 5'-AGACAGGTAGCCCCCACAG-3' (SEQ ID NO:45); PSA promoter ChIP-F: 5'-CCCTCCCCTTCCACAGC-3' (SEQ ID NO:46); PSA promoter ChIP-R: 5'-GCCC-TATAAAACCTTCATTCCCCAGG-3' (SEQ ID NO:47); TMPRSS2 ChIP-F: 5'-CGCCCCAGAGTCCCTTAT-3' (SEQ ID NO:48); TMPRSS2 ChIP-R: 5'-TAATCTCAG-GAGGCGGTGTC-3' (SEQ ID NO:49); MYC ChIP-F: 5'-AGGGATCGCGCTGAGTATAA-3' (SEQ ID NO:50); MYC ChIP-R: 5'-TGCCT-CTCGCTGGAATTACT-3' (SEQ ID NO:51); AR ChIP-F: 5'-GCAGGAGCTATTC-AG-GAAGC-3' (SEQ ID NO:52); and AR ChIP-R: 5'-AGGTG-GAGAGCAAATGC-AAC-3' (SEQ ID NO:53). Detailed information regarding PCR primers at the enhancer and promoters of all analyzed genes are also summarized in Table 1.

Meta-Analysis of BRD4 and Histone Mark ChIP-Seq Data

BRD4 ChIP-seq data in HEK293T and HeLa cells (accession number GSE51633; Liu et al., *Cell*, 155:1581-1595 (2013)), H2171 and U87 cells (accession number GSE44931; Loven et al., *Cell*, 153:320-334 (2013)), and mouse acute myeloid leukemia (AML) cells (accession number GSE66122; Roe et al., *Mol. Cell.*, 58:1028-1039 (2015)) as well as H3K4me1 and H3K4me3 ChIP-seq data in LNCaP cells (Wang et al., *Nature*, 474:390-394 (2011)) were downloaded from NCBI Gene Expression Omnibus. If the original alignments were based on hg18/GRCh36, they were converted into hg19/GRCh37 based-alignments using CrossMap (Zhao et al., *Bioinformatics*, 30:1006-1007 (2014)). Peak calling was performed using MACS2 (v2.0.10; Zhang et al., *Genome Biol.*, 9:R137 (2008)).

Analysis of JQ1-Resistant Gene Expression in the TCGA Dataset and Pathway Analysis Primary tumor samples from the prostate cancer cohort in TCGA were classified into SPOP-MUT (with mutation, N=48) and SPOP-WT (without mutation, N=449) groups according to the mutation status of SPOP. Differential expression between the above two groups for the JQ1-resistant genes (n=1,017) were investigated by Mann-Whitney test with the significance threshold of P-value<0.001. A total of 129 genes were identified as up-regulated in SPOP-MUT samples. A heat-map was generated using the z-score transformed expression of each gene across all samples. Pathway analyses were performed using Ingenuity IPA.

Cholesterol Analysis

The cells were washed with PBS with twice and lysed in the buffer (10 mM Tris-HCl (pH7.6), 500 mM NaCl, 1% Triton X-100, 10 mM β-methylphenethylamine, 2 mM $Na_3VO_4$, and 1 mM PMSF) for 30 minutes on ice. The lysates were extracted in the chloroform/methanol/HCl as described elsewhere (Zhuang et al., *J. Clin. Invest.*, 115: 959-968 (2005)). The cholesterol concentration was measured using the Infinity reagent (Thermo Fisher Scientific).

Generation and Treatment of Prostate Cancer Xenografts in Mice 6-week-old NOD-SCID IL-2-receptor gamma null (NSG) mice were generated and randomly divided into different experimental groups as indicated. All mice were housed in standard conditions with a 12-hour light/dark cycle and access to food and water ad libitum. For BRD2/3/4 knock-down studies, C4-2 cells ($5\times10^6$), infected with lentivirus expressing empty vector (EV) or HA-SPOP-F133V mutant in combination with control shRNA or BRD2/3/4-specific shRNA, were mixed with Matrigel (in 100 µL 1×PBS plus 100 µL Matrigel (BD Biosciences)) and injected s.c. into the right flank of mice. After xenografts reached the size of about 100 $mm^3$, vehicle (10% beta cyclodextrin) or JQ1 (Sigma-Aldrich) at 50 mg/kg body weight was administered by i.p. injection 5 days a week. For studies with tumors treated with JQ1 and AKT inhibitor GDC-0068, C4-2 cells ($5\times10^6$) infected with lentivirus expressing empty vector (EV) or HA-SPOP-F133V mutant were mixed with Matrigel (in 100 µL 1×PBS plus 100 µL Matrigel (BD Biosciences)) and injected s.c. into the right flank of mice. After xenografts reached the size of about 100 $mm^3$, vehicle (10% beta cyclodextrin), JQ1 (50 mg/kg), or GDC-0068 (100 mg/kg) were administrated individually or in combination 5 days a week. Growth in tumor volume was measured in a blinded fashion using digital caliper, and tumor volumes were estimated using the formula $(L\times W2)/2$, where L is length of tumor and W is width. The volumes of tumors were compared, and P values were determined by a two-tailed Student's t test. Upon the completion of treatment, tumor grafts were harvested. Tumor tissues were divided, and a portion was subjected to FFPE. the rest was frozen for protein and RNA extraction.

Statistical Analysis

All data were shown as mean values±SD for experiments performed with at least three replicates. The difference between two groups was analyzed using paired Student's t-test unless otherwise specified. A P value less than 0.05 was considered statistically significant.

Results

Ubiquitously-expressed BET proteins including BRD2, BRD3 and BRD4 function as factors for transcriptional activation of distinct sets of cancer-related genes through context-specific interaction with acetylated histones and/or transcription factors (Filippakopoulos et al., *Nature*, 468: 1067-1073 (2010); and Nicodeme et al., *Nature*, 468:1119-1123 (2010)). Several small molecule inhibitors specifically targeting the bromodomains of BET proteins have been developed and display promising anti-cancer activity via selective blockage of expression of cancer promoters such as MYC in multiple myeloma and androgen receptor (AR) in prostate cancer (Filippakopoulos et al., *Nature*, 468:1067-1073 (2010); Nicodeme et al., *Nature*, 468:1119-1123 (2010); Delmore et al., *Cell*, 146:904-917 (2011); Dawson et al., *Nature*, 478:529-533 (2011); Zuber et al., *Nature*, 478: 524-528 (2011); and Asangani et al., *Nature*, 510:278-282 (2014)). While BET inhibitors are undergoing clinical trials for treatment of various cancer types, several mechanisms of drug resistance have been documented (Fong et al., *Nature*, 525:538-542 (2015); Rathert et al., *Nature*, 525:543-547 (2015); and Shu et al., *Nature*, 529:413-417 (2016)). At present, there are no genetic alterations that can be exploited as a biomarker to guide targeted use of these drugs.

SPOP is the substrate recognition subunit of the CUL-LIN3-RBX1 E3 ubiquitin ligase (CRL) complex. SPOP binding triggers the ubiquitination and proteasomal degradation of target proteins mediated by RBX1-dependent recruitment of E2 ubiquitin-conjugating enzyme into the CRL complex. Cancer whole genome- and exome-sequencing studies revealed that SPOP is the most frequently mutated gene in primary prostate cancer (Barbieri et al., *Nat. Genet.*, 44:685-689 (2012); and The Molecular Taxonomy of Primary Prostate Cancer, *Cell*, 163:1011-1025 (2015)). Notably, SPOP mutations detected in prostate cancer occur in the structurally defined substrate-binding motif termed MATH domain (meprin and TRAF homology domain; Barbieri et al., *Nat. Genet.*, 44:685-689 (2012); Theurillat et al., *Science*, 346:85-89 (2014); Geng et al., *Proc. Natl. Acad. Sci. USA*, 110:6997-7002 (2013); and An et al., *Mol. Cell*, 59:904-916 (2015)), possibly suggesting that the pathophysiology of SPOP mutations is likely mediated by impaired ubiquitination of substrates.

Figure 1B:
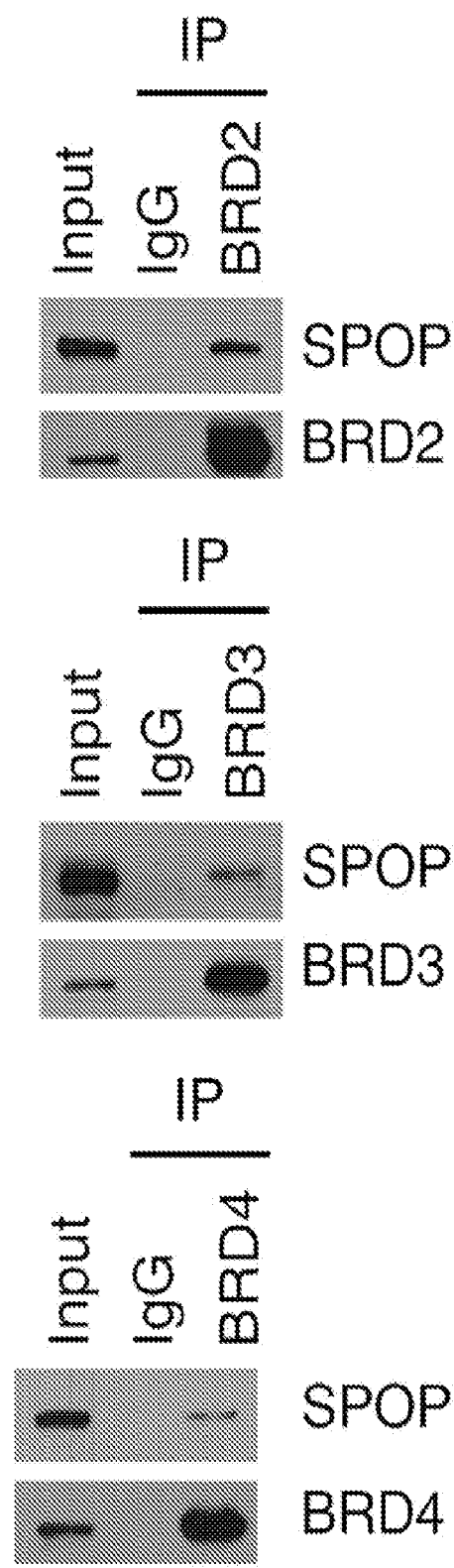
Figure 2A:
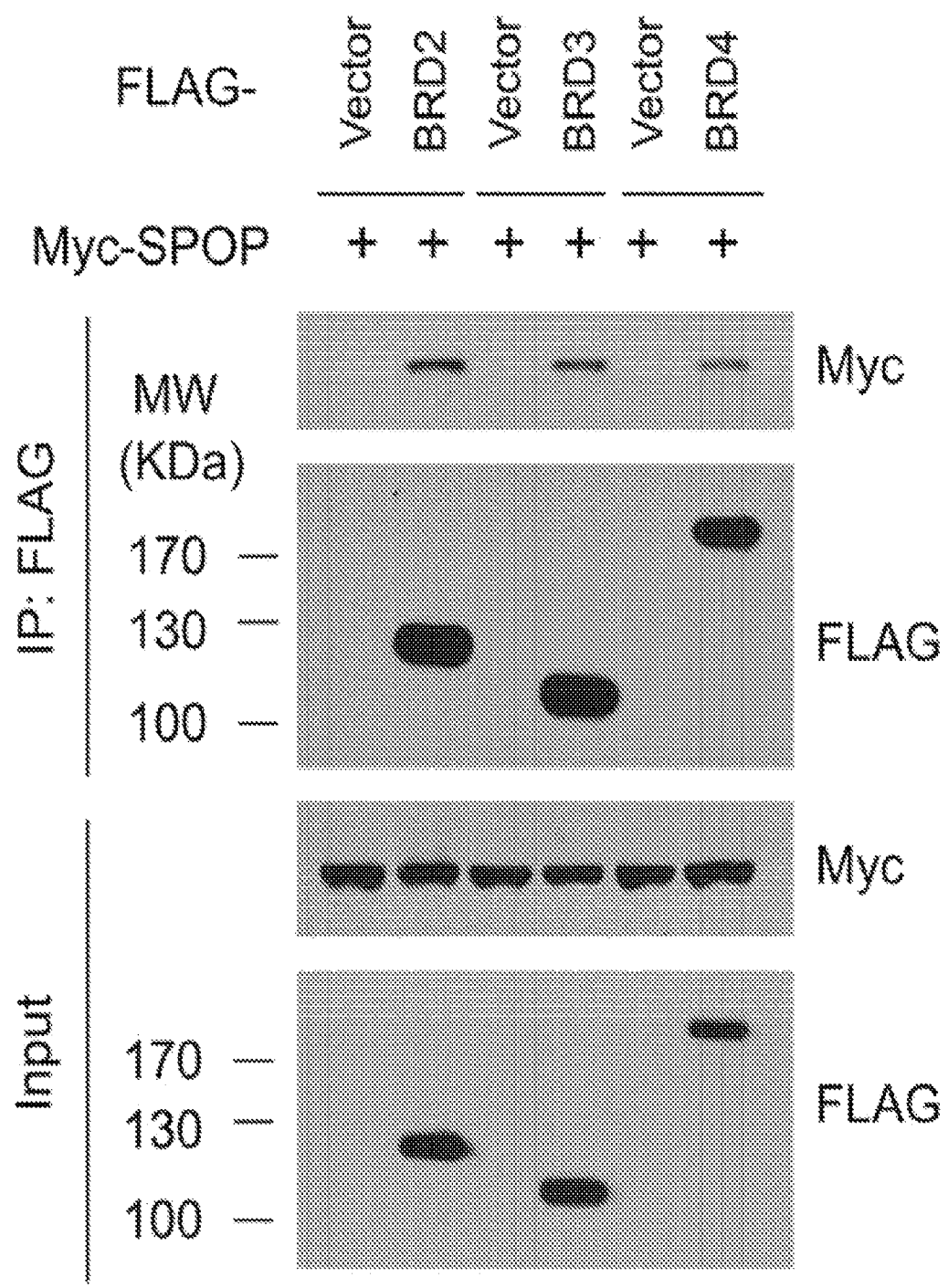
FIG. 2. SPOP promotes BRD2/3/4 protein degradation and ubiquitination. a, Western blot of whole cell lysate (WCL) and co-IP samples of anti-FLAG antibody from 293T cells transfected with indicated plasmids and treated with 20 µM MG132 for 8 hours. b, Western blot of WCL of LNCaP cells treated with DMSO, MLN4924 (200 nM), Bortezmib (200 nM) or MG132 (20 µM) for 8 hours. Actin was used as a loading control. c, RT-qPCR assessment of BRD2/3/4 mRNA expression in LNCaP cells treated as in (b). The level of GAPDH mRNA was used for normalization. Data are shown as means±SD (n=3 technical replicates), and similar results were obtained from two independent experiments. d and e, Western blot of WCL of LNCaP cells transfected with control siRNA (siC) or a pool of SPOP specific siRNAs for 48 hours and then treated with 50 µg/mL cycloheximide (CHX) and harvested at different time points (d). At each time point, the intensity of each BET protein was normalized to the intensity of actin and then to the value at 0 hours (e). Similar results were obtained from two independent experiments. f, RT-qPCR measurement of SPOP and BRD2/3/4 mRNA expression in LNCaP cells at 48 hours after being transfected with control and SPOP-specific siRNAs. Data are shown as means±SD (n=3 technical replicates), and similar results were obtained from two independent experiments. g, Western blot of WCL of 293T cells transfected with indicated plasmids. h, Western blot of the products of in vivo ubiquitination assay performed by using cell lysate from 293T cells transfected with indicated plasmids and treated with 20 µM of MG132 for 8 hours. K48O, K48-only ub, K63O, K63-only ub. i, Western blot of the products of in vivo ubiquitination assay performed by using anti-Ub or Ub-linkage specific (K48, K63) antibodies.

To identify new degradation substrates of SPOP, yeast two-hybrid screens using the full-length SPOP as bait were performed. A total of 246 positive clones were obtained, including known SPOP substrates DEK and SRC-3 (Table 2). Gene Ontology analysis showed that SPOP bound to a number of proteins involved in regulation of various signaling pathways, but the top hit was BET proteins (FIG. 1a and Table 3). Co-immunoprecipitation (co-IP) assays confirmed that ectopically expressed and endogenous SPOP and BRD2/3/4 proteins interacted with each other in 293T and LNCaP prostate cancer cells (FIGS. 1b and 2a). Thus, SPOP interacts with BET proteins in physiological conditions.

TABLE 2

Table 2. SPOP interacted proteins identified by yeast two hybrid screen

| No. | Positive clone name * | Full name |
|---|---|---|
| 2 | BRD2 | bromodomain containing 2 |
| 1 | CHD3 | chromodomain helicase DNA binding protein 3 |
| 3 | CAPRIN1 | cell cycle associated protein 1 |
| 4 | ZMYND8 | zinc finger MYND-type containing 8 |
| 5 | SETD2 | SET domain containing 2 |
| 6 | BRD4 | bromodomain containing 4 |
| 7 | GLI3 | GLI family zinc finger 3 |
| 8 | DAXX | death domain associated protein |
| 9 | H2AFY (MacroH2A) | H2A histone family member Y |
| 10 | SRRM1 | serine and arginine repetitive matrix 1 |
| 11 | INF2 | inverted formin, FH2 and WH2 domain containing |
| 12 | UBE2I | ubiquitin conjugating enzyme E2 I |
| 13 | RANBP9 | RAN binding protein 9 |
| 14 | ZCCHC12 | zinc finger CCHC-type containing 12 |
| 15 | SPOP | speckle type BTB/POZ protein |
| 16 | NUDCD3 | NudC domain containing 3 |
| 17 | GCC2 | GRIP and coiled-coil domain containing 2 |
| 18 | PIAS3 | protein inhibitor of activated STAT 3 |
| 19 | RBFOX2 | RNA binding protein, fox-1 homolog 2 |
| 20 | CBX4 | chromobox 4 |
| 21 | AMOTL2 | angiomotin like 2 |
| 22 | FAF1 | Fas associated factor 1 |
| 23 | BRD3 | bromodomain containing 3 |
| 24 | GLI2 | GLI family zinc finger 2 |
| 25 | RBPJ | recombination signal binding protein for immunoglobulin kappa J region |
| 26 | GCC2 | TOP1 binding arginine/serine rich protein |
| 27 | CHAF1A | chromatin assembly factor 1 subunit A |
| 28 | DEK | DEK proto-oncogene |
| 29 | PIAS1 | protein inhibitor of activated STAT 1 |
| 30 | TCOF1 | treacle ribosome biogenesis factor 1 |
| 31 | SUMO1 | small ubiquitin-like modifier 1 |
| 32 | RPRD2 | regulation of nuclear pre-mRNA domain containing 2 |
| 33 | MRE11A | MRE11 homolog A, double strand break repair nuclease |
| 34 | LRCH4 | leucine rich repeats and calponin homology domain containing 4 |
| 35 | KPNA5 | karyopherin subunit alpha 5 |
| 36 | NCOA3(SRC-3) | nuclear receptor coactivator 3 |
| 37 | HMGCS1 | 3-hydroxy-3-methylglutaryl-CoA synthase 1 |
| 38 | GMEB1 | glucocorticoid modulatory element binding protein 1 |
| 39 | DHX15 | DEAH-box helicase 15 |
| 40 | CTDSPL2 | CTD small phosphatase-like protein 2 |
| 41 | CACUL1 | CDK2 associated cullin domain 1 |

* Highlighted in red are the known substrates of SPOP

TABLE 3

Table 3. Gene Ontology (GO) analysis of SPOP binding partners indetified via yeast-two-hybrid screen

| p-value | q-value | pathway | source |
|---|---|---|---|
| 4.87E−07 | 3.21E−05 | Chemical Compounds to monitor Proteins | Wikipathways |
| 1.66E−06 | 5.30E−05 | regulation of transcriptional activity by pml | BioCarta |
| 2.41E−06 | 5.30E−05 | Androgen receptor signaling pathway | Wikipathways |
| 4.35E−06 | 6.87E−05 | TGF-Ncore | Signalink |
| 5.65E−06 | 6.87E−05 | Hedgehog signaling events mediated by Gli proteins | PID |
| 6.25E−06 | 6.87E−05 | Sumoylation by RanBP2 regulates transcriptional repression | PID |
| 1.48E−05 | 0.000139607 | Coregulation or Androgen receptor activity | PID |
| 3.19E−05 | 0.000234127 | SUMOylation of DNA damage response and repair proteins | Reactome |
| 3.19E−05 | 0.000234127 | SUMO E3 ligases SUMOylate target proteins | Reactome |
| 4.13E−05 | 0.000272801 | SUMOylation | Reactome |
| 8.99E−05 | 0.000458494 | GLI proteins bind promoters of Hh responsive genes to promote transcription | Reactome |
| 8.99E−05 | 0.000458494 | SUMO is transferred from E1 to E2 (UBE2I, UBC9) | Reactome |
| 8.99E−05 | 0.000458494 | basic mechanisms of sumoylation | BioCarta |
| 0.000111453 | 0.000525423 | Hedgehog on state | Reactome |
| 0.000214797 | 0.000945107 | Processing and activation of SUMO | Reactome |
| 0.000355359 | 0.001465857 | Signaling events mediated by HDAC Class I | PID |
| 0.000411644 | 0.001598146 | AndrogenReceptor | NetPath |
| 0.000538773 | 0.001871527 | Regulation of IFNG signaling | Reactome |
| 0.000538773 | 0.001871527 | sumoylation by ranbp2 regulates transcriptional repression | BioCarta |
| 0.000708275 | 0.002337307 | Hedgehog Signaling Pathway | Wikipathways |
| 0.000900261 | 0.002829392 | JAK-STAT-Ncore | Signalink |
| 0.001004619 | 0.003010155 | Interferon gamma signaling | Reactome |
| 0.001048993 | 0.003010155 | Signaling by Hedgehog | Reactome |
| 0.001114519 | 0.003064327 | fas signaling pathway (cd95) | BioCarta |
| 0.00120627 | 0.003184553 | C-MYB transcription factor network | PID |
| 0.001477203 | 0.003749824 | IL11 | NetPath |
| 0.001746219 | 0.004268536 | Hedgehog | NetPath |
| 0.003795858 | 0.005947379 | mRNA Processing | Wikipathways |
| 0.004010665 | 0.00912772 | Signaling events mediated by HDAC Class II | PID |
| 0.004230525 | 0.009307155 | TGF beta Signaling Pathway | Wikipathways |
| 0.004694393 | 0.009994524 | Ubiquitin mediated proteolysis - *Homo sapiens* (human) | KEGG |
| 0.004881859 | 0.010068834 | Hedgehog off state | Reactome |
| 0.005112111 | 0.010224223 | FAS pathway and Stress induction at HSP regulation | Wikipathways |
| 0.005347296 | 0.010380046 | Interleukin-11 Signaling Pathway | Wikipathways |
| 0.006082205 | 0.0114693 | IL6-mediated signaling events | PID |
| 0.007129675 | 0.01387107 | Hedgehog signaling pathway - *Homo sapiens* (human) | KEGG |
| 0.007965137 | 0.014288082 | Interferon type I signaling pathways | Wikipathways |
| 0.008664299 | 0.01466266 | RNA transport - *Homo sapiens* (human) | KEGG |
| 0.008943913 | 0.014757456 | TGF_beta_Receptor | NetPath |

Figure 1C:
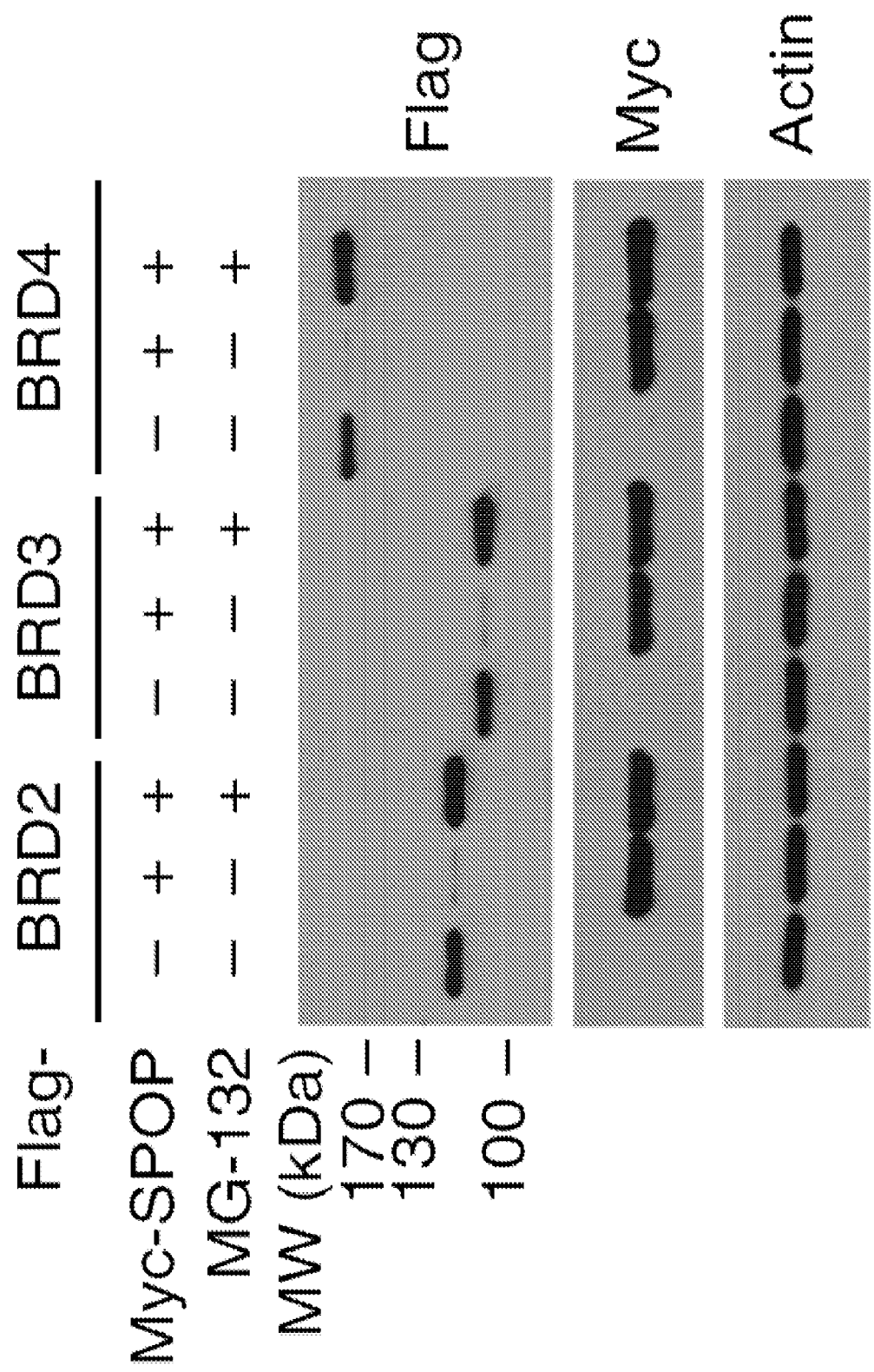
Figure 1D:
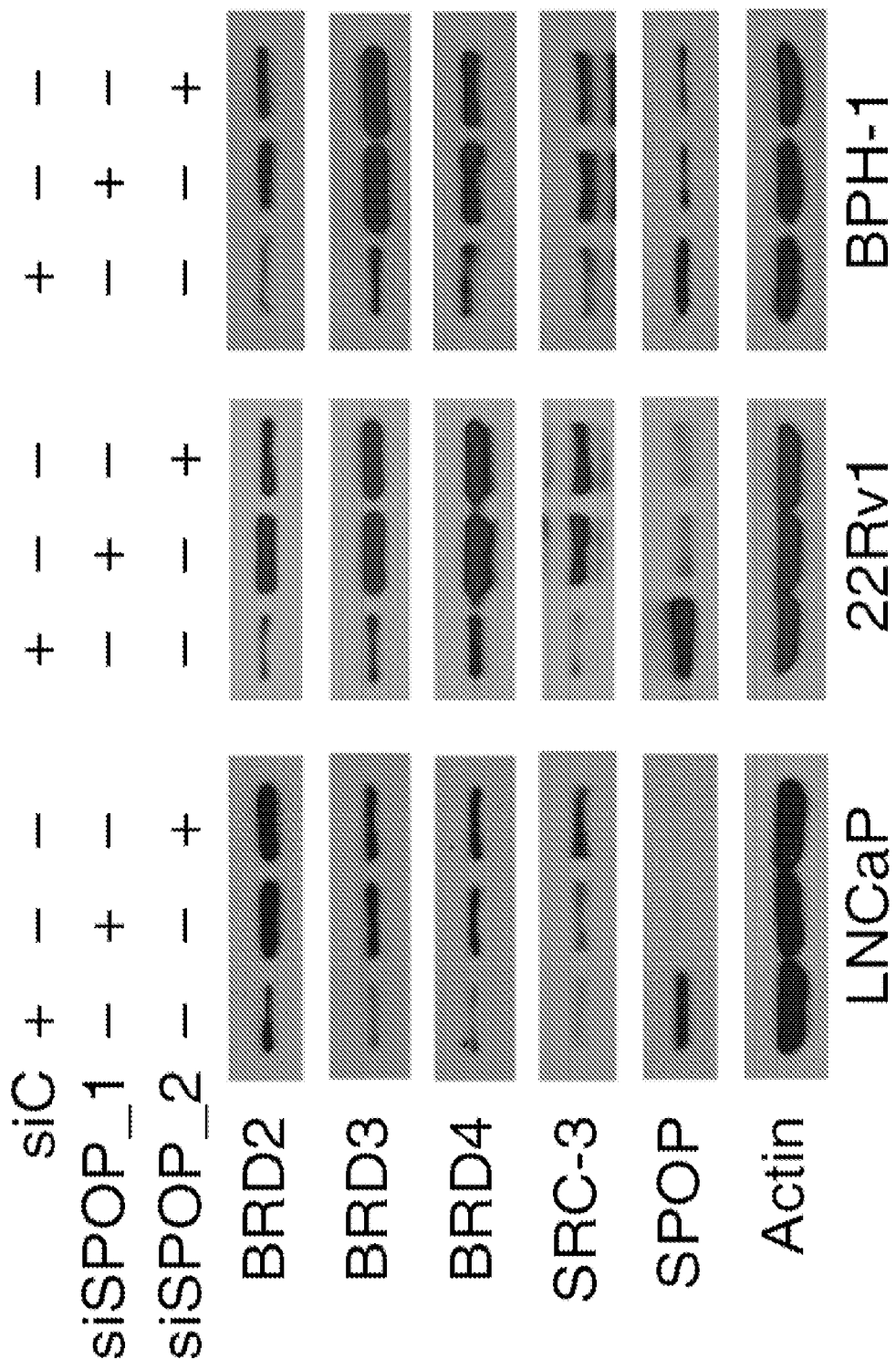
Figure 1E:
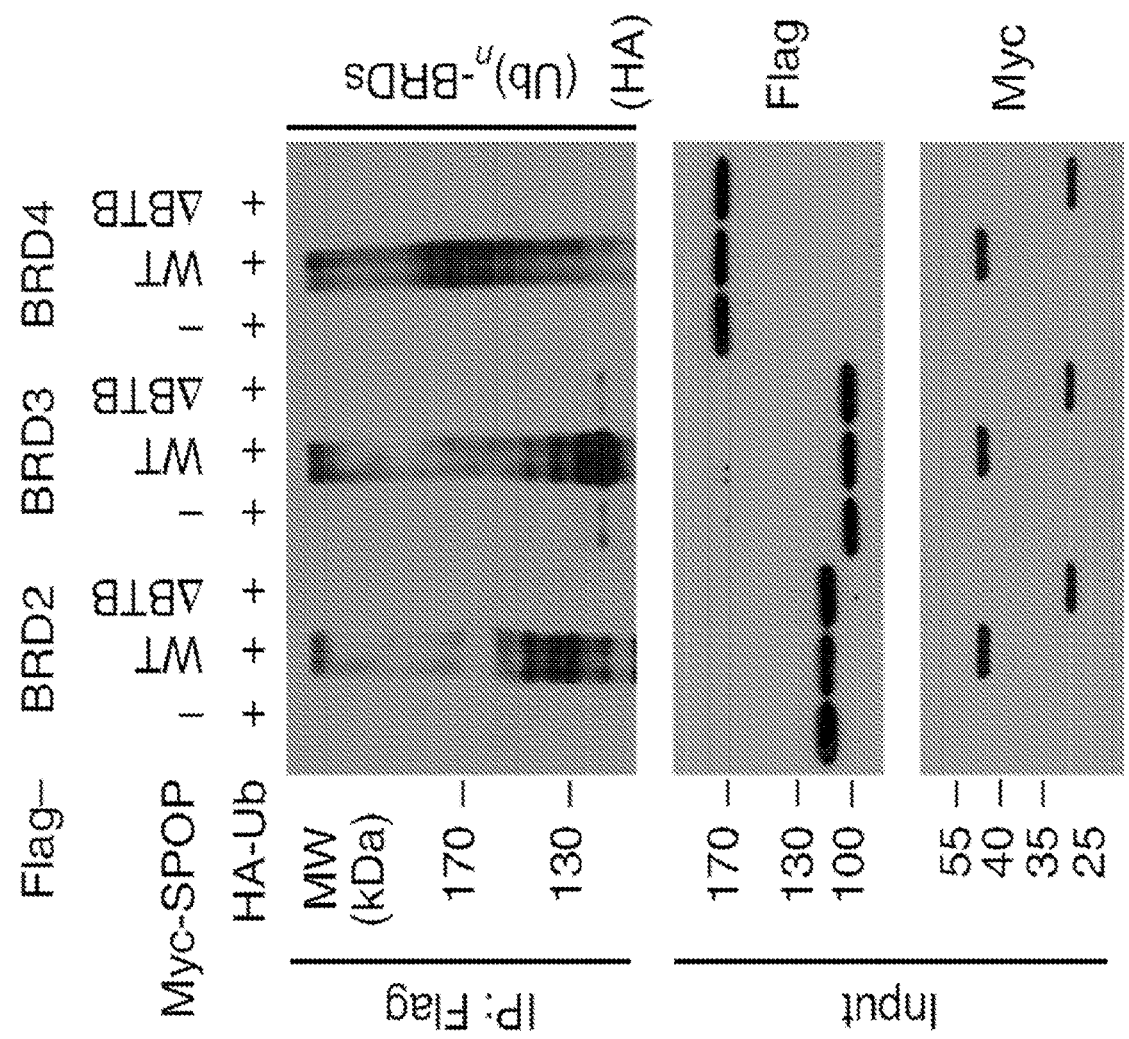
Figure 1F:
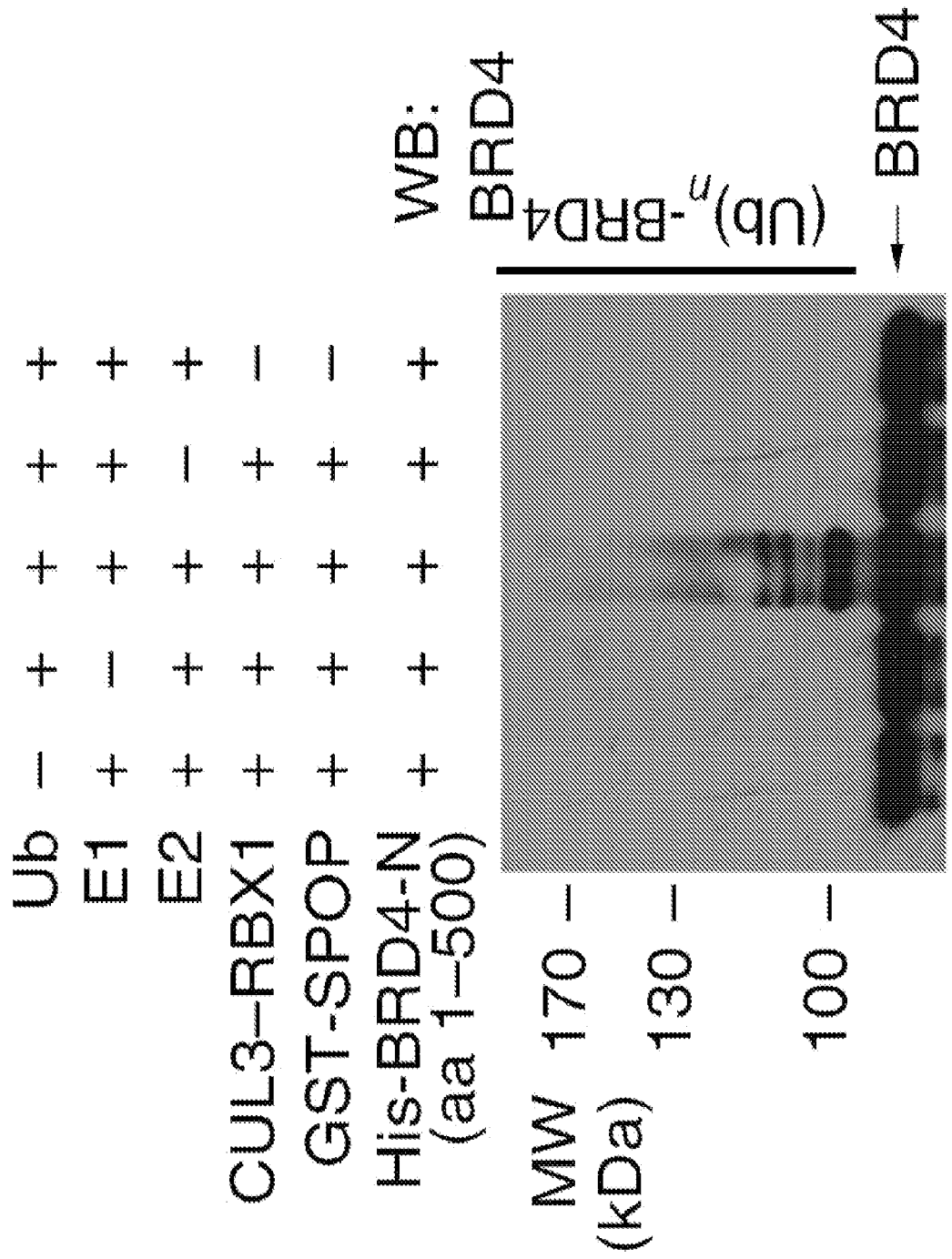
Figure 2B:
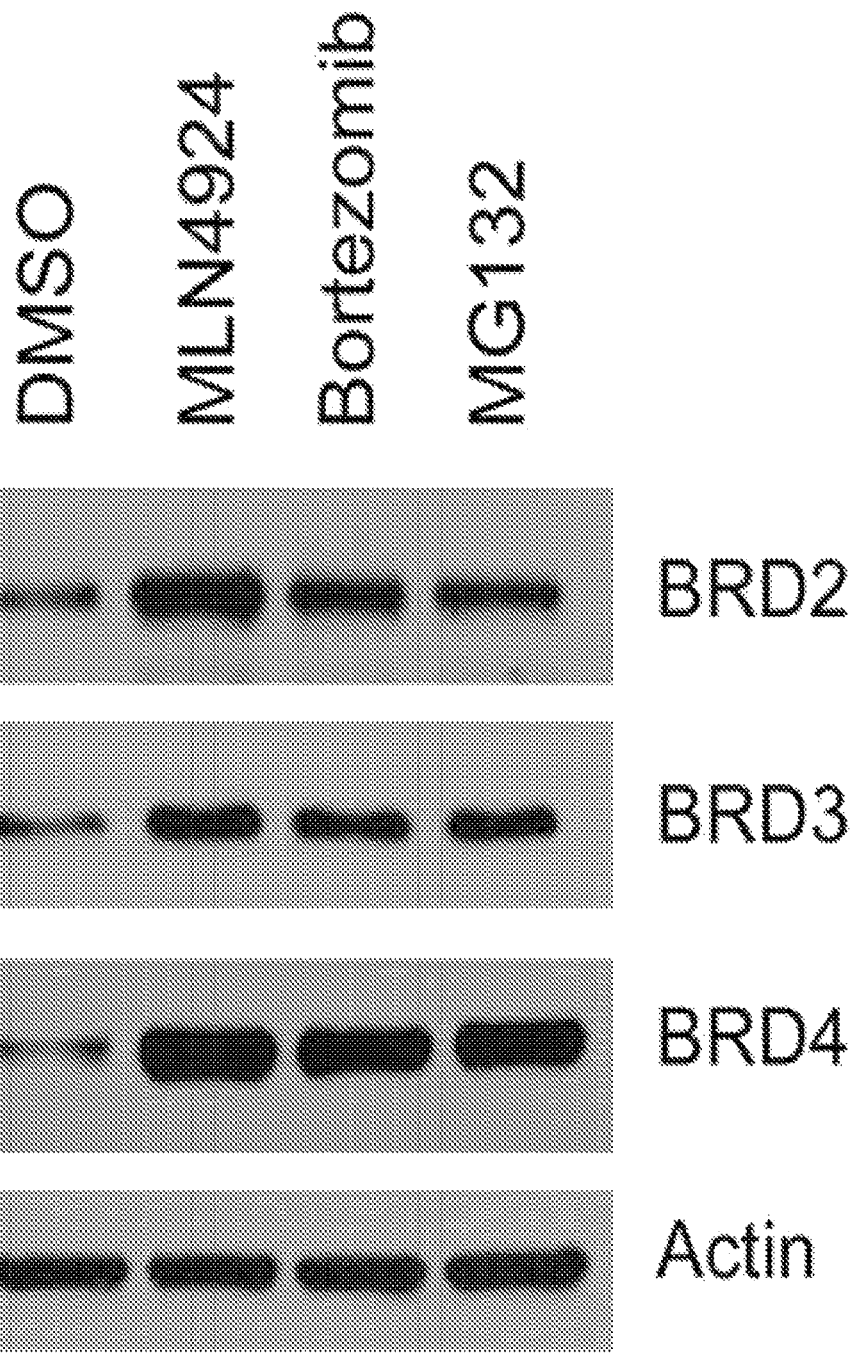
Figure 2C:
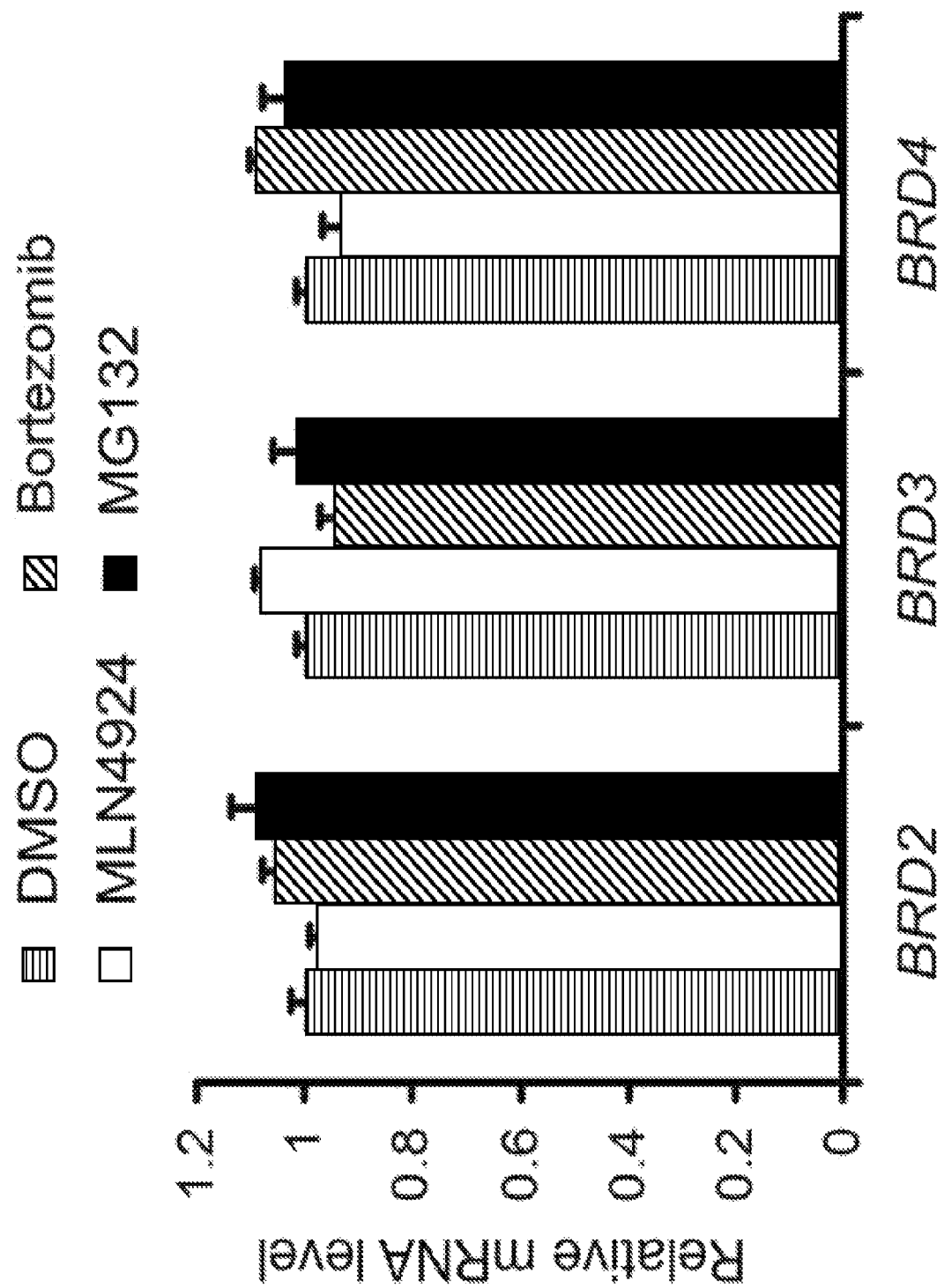
Figure 2D:
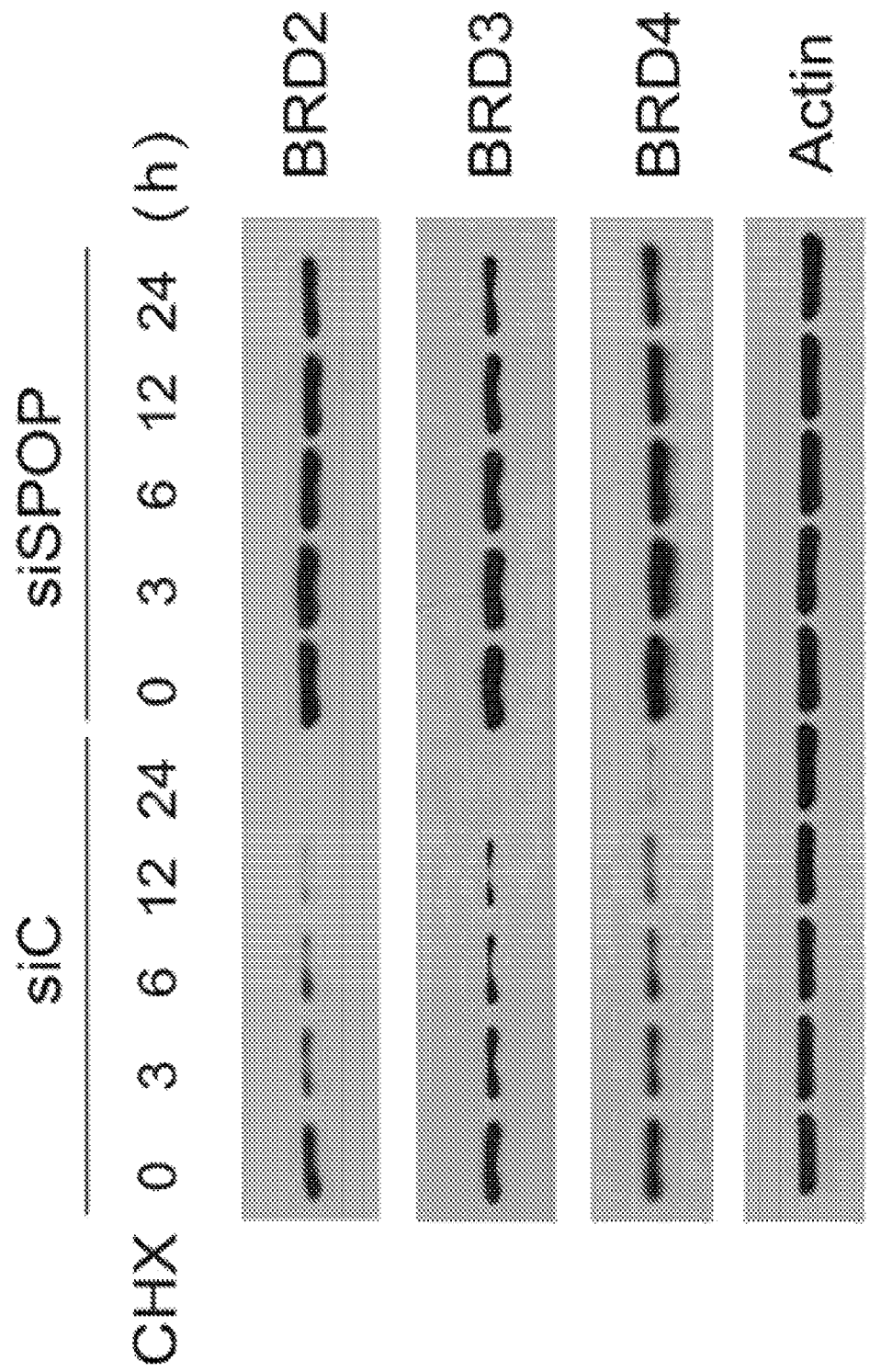
Figure 2E:
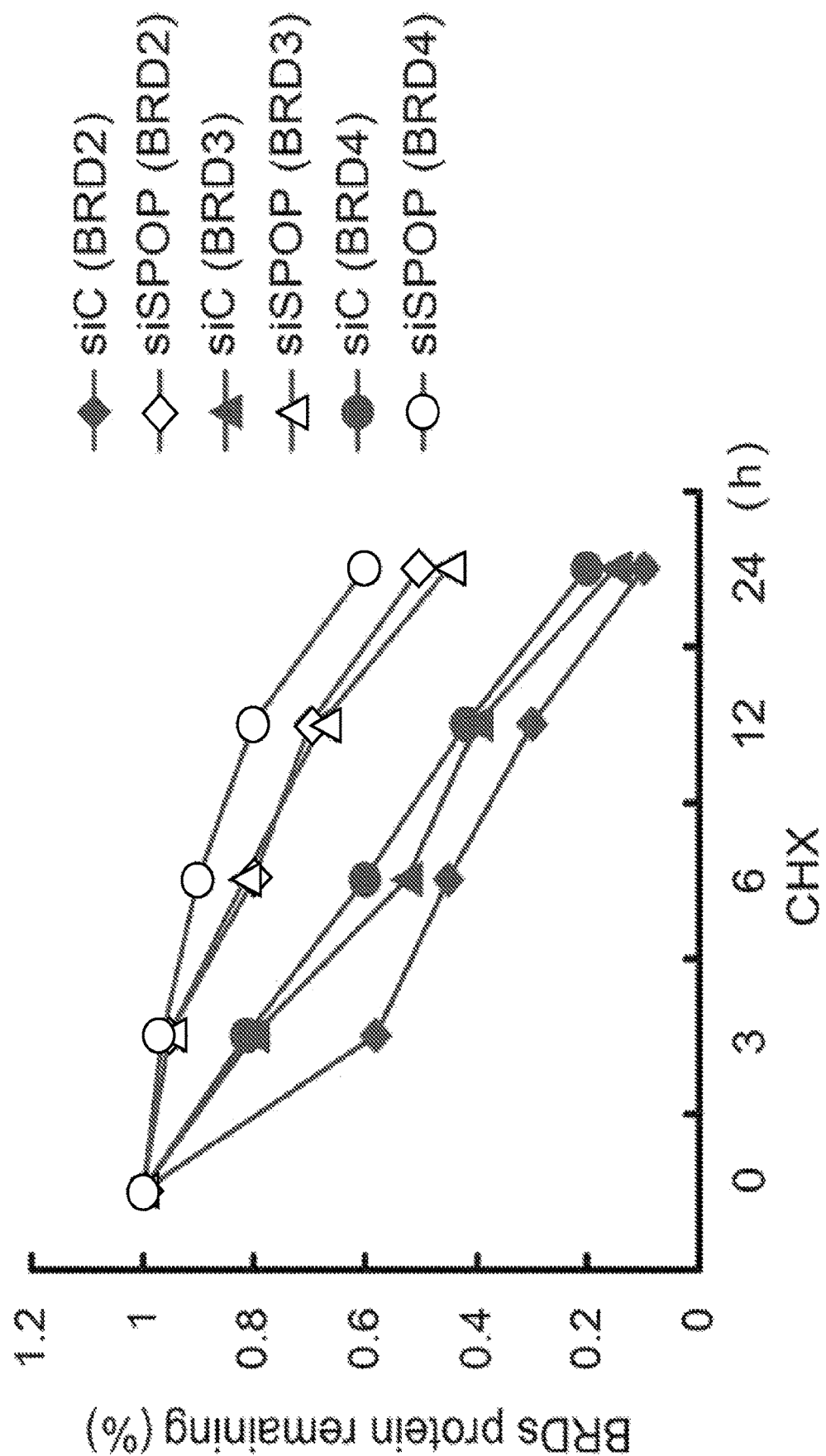
Figure 2F:
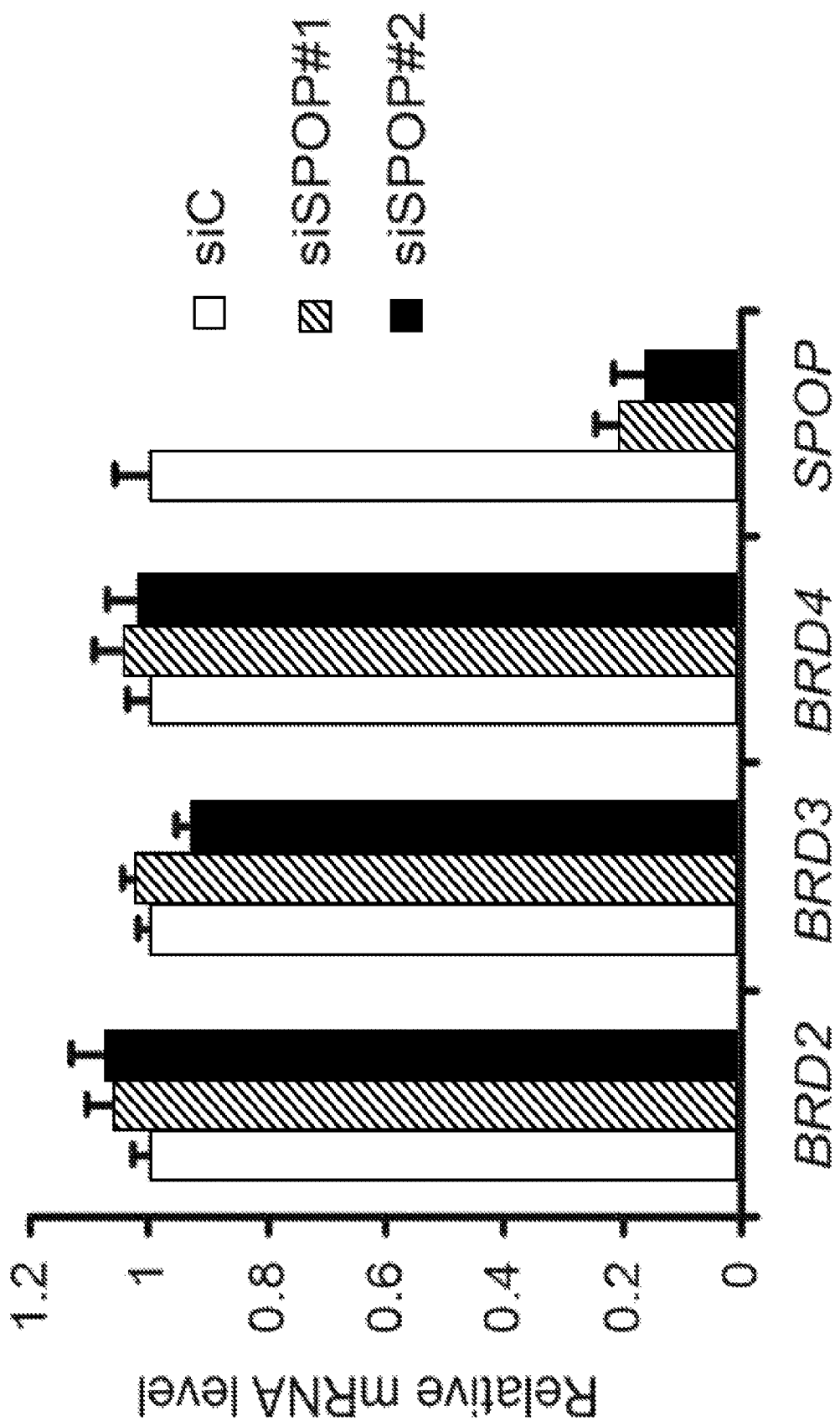
Figure 2G:
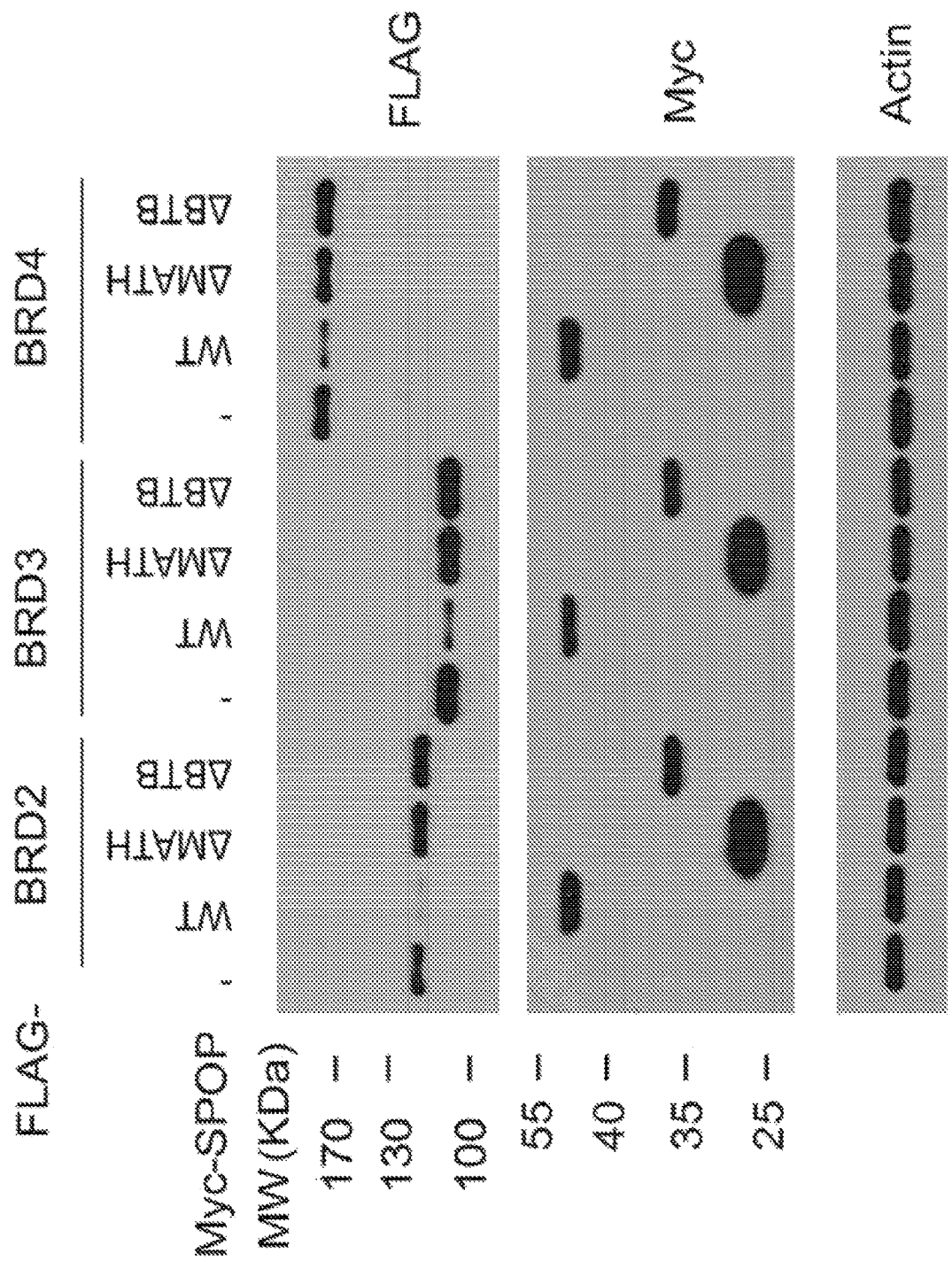
Figure 2H:
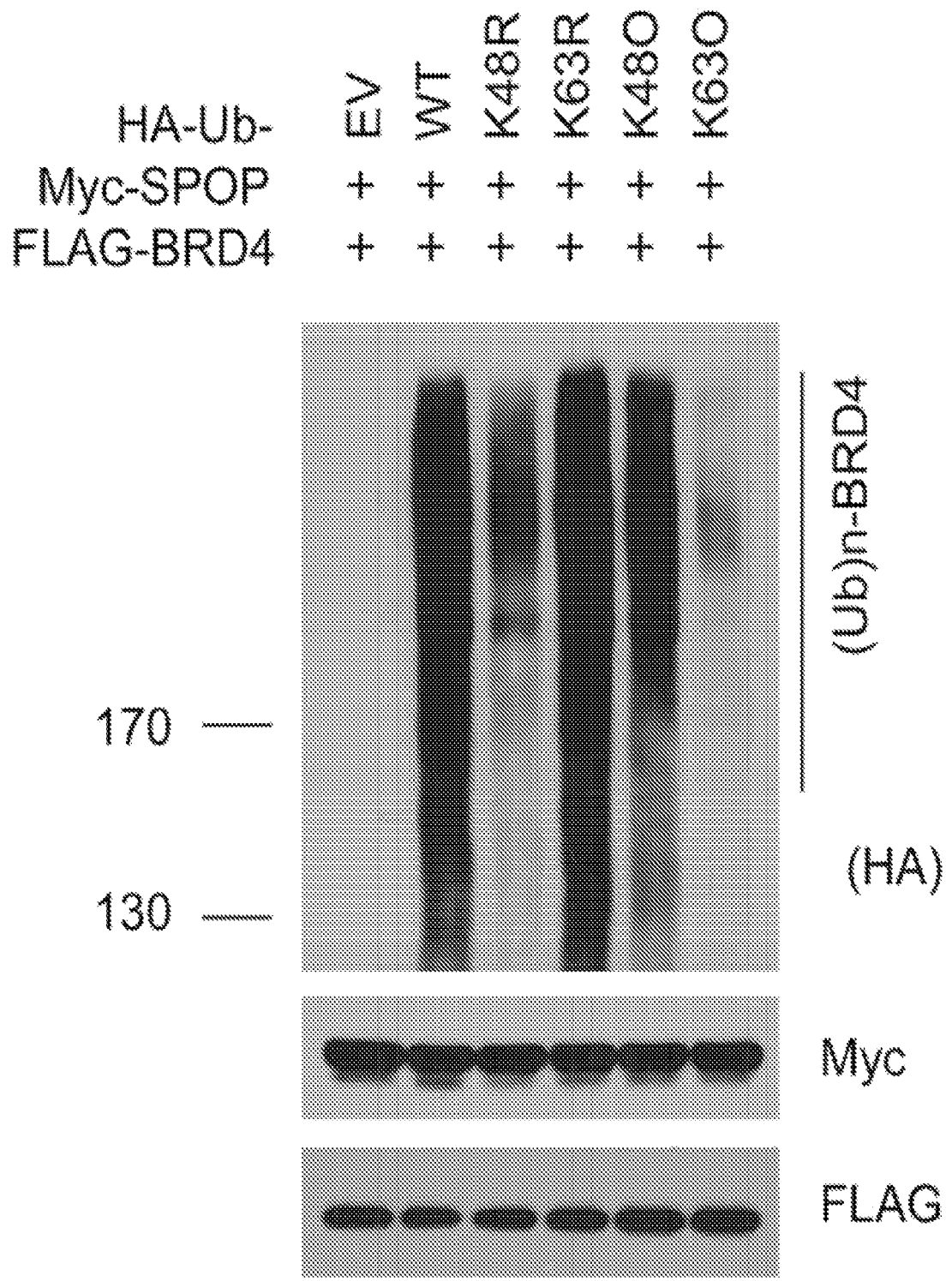
Figure 2I:
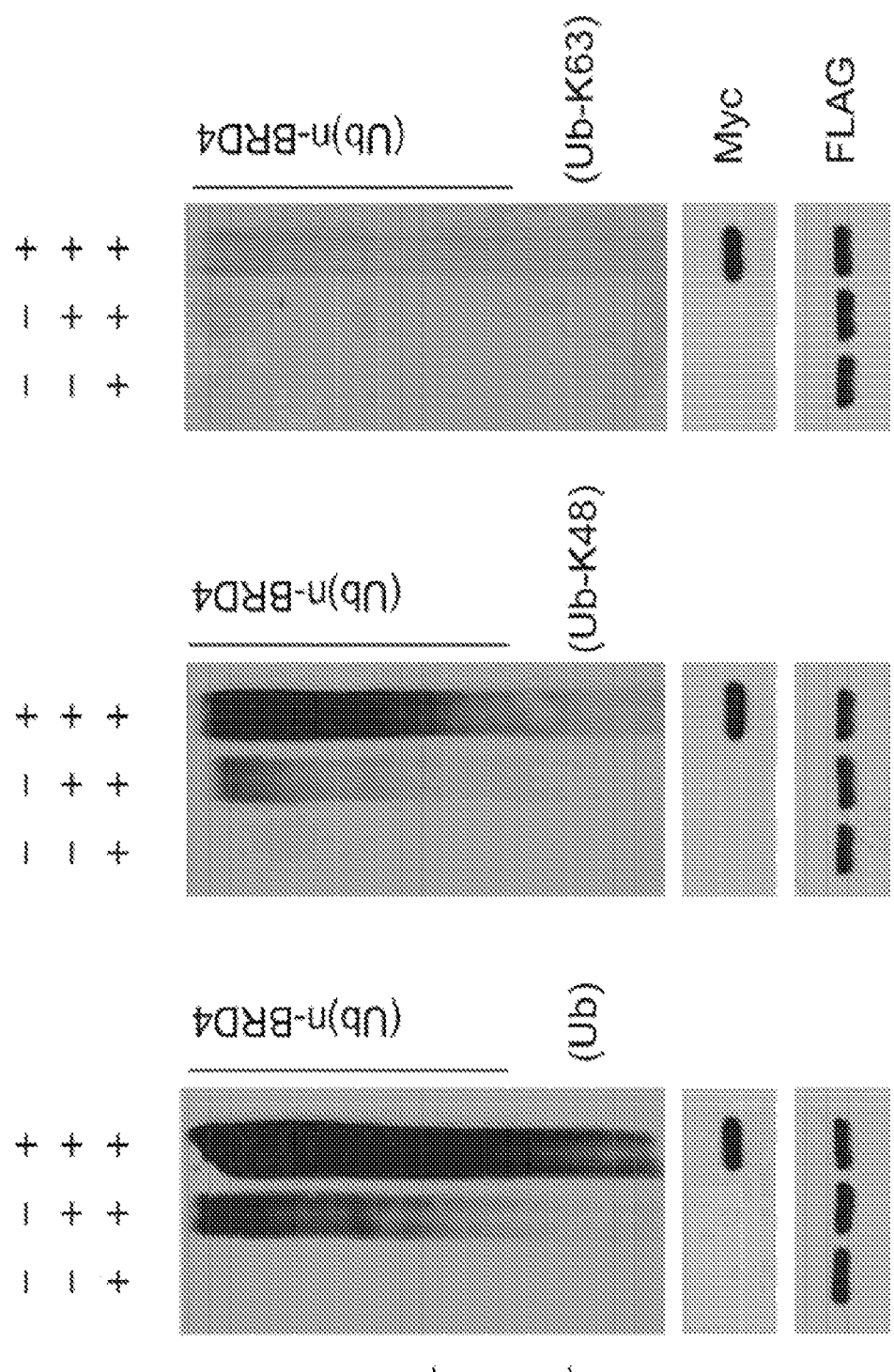
Figure 3B:
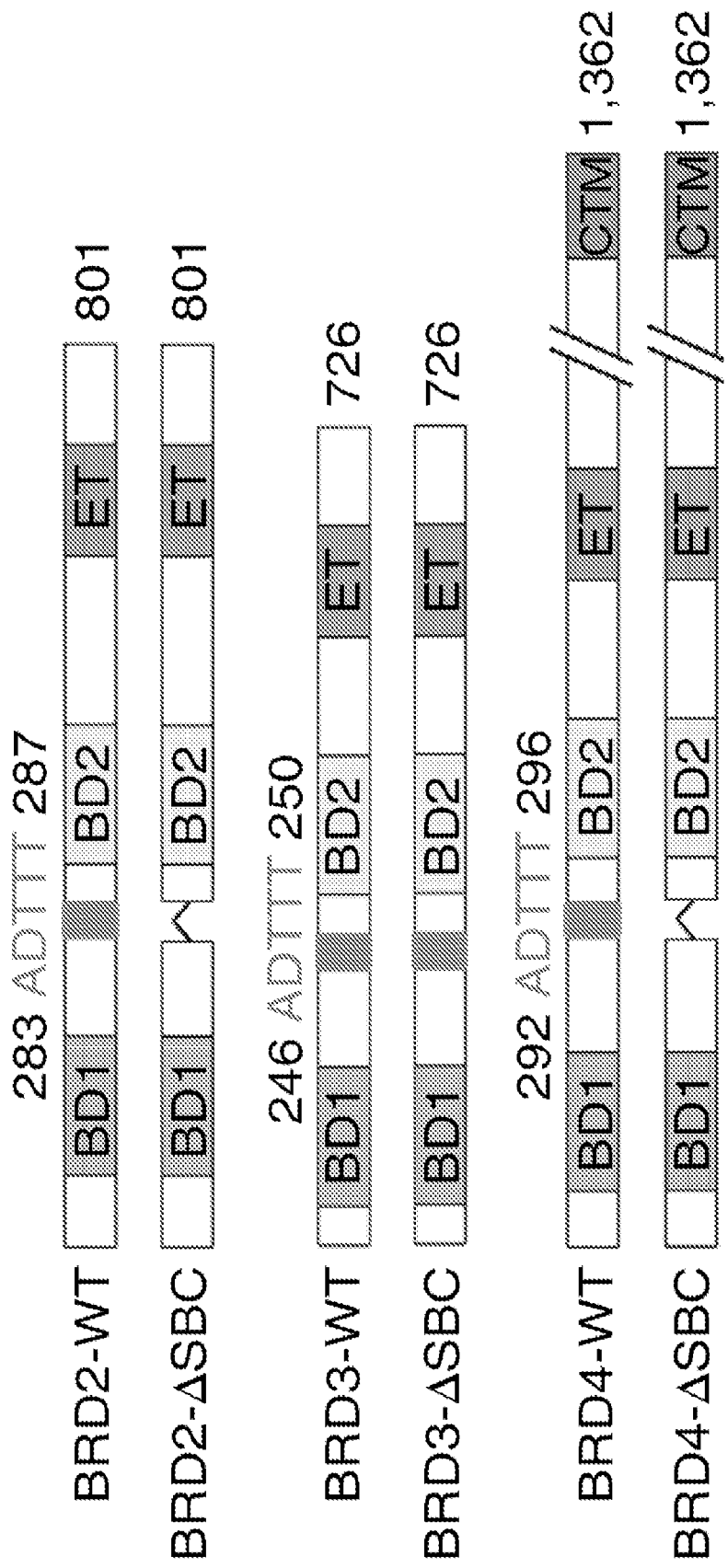
FIG. 3. The SBC motif in BRD2/3/4 is a SPOP-recognized degron. a, Amino acid (aa) sequencing alignment of a putative SBC motif in BRD2/3/4 (SEQ ID NOS:70-72, respectively). MacroH2A and DEK, positive controls (SEQ ID NOS:73 and 74, respectively). Φ represents a nonpolar residue, and 7E represents a polar residue. S, serine; T, threonine. b, Diagram showing the wild-type BRD2/3/4 and SBC motif-deleted mutants (ADTTT, SEQ ID NO:78). c, Western blot of WCL and co-IP samples of anti-FLAG antibody from 293T cells transfected with indicated plasmids and treated with 20 µM MG132 for 8 hours. d, Western blot of WCL of 293T cells transfected with indicated plasmids. e and f, Western blot of WCL of 293T cells transfected with indicated plasmids and treated with 50 µg/mL cycloheximide (CHX) and harvested at different time points (e). At each time point, the intensity of BET protein was normalized to the intensity of actin and then to the value at 0 hours (f). g, Western blot of the products of in vivo ubiquitination assay from 293T cells transfected with indicated plasmids and treated with 20 µM MG132 for 8 hours.
Figure 3C:
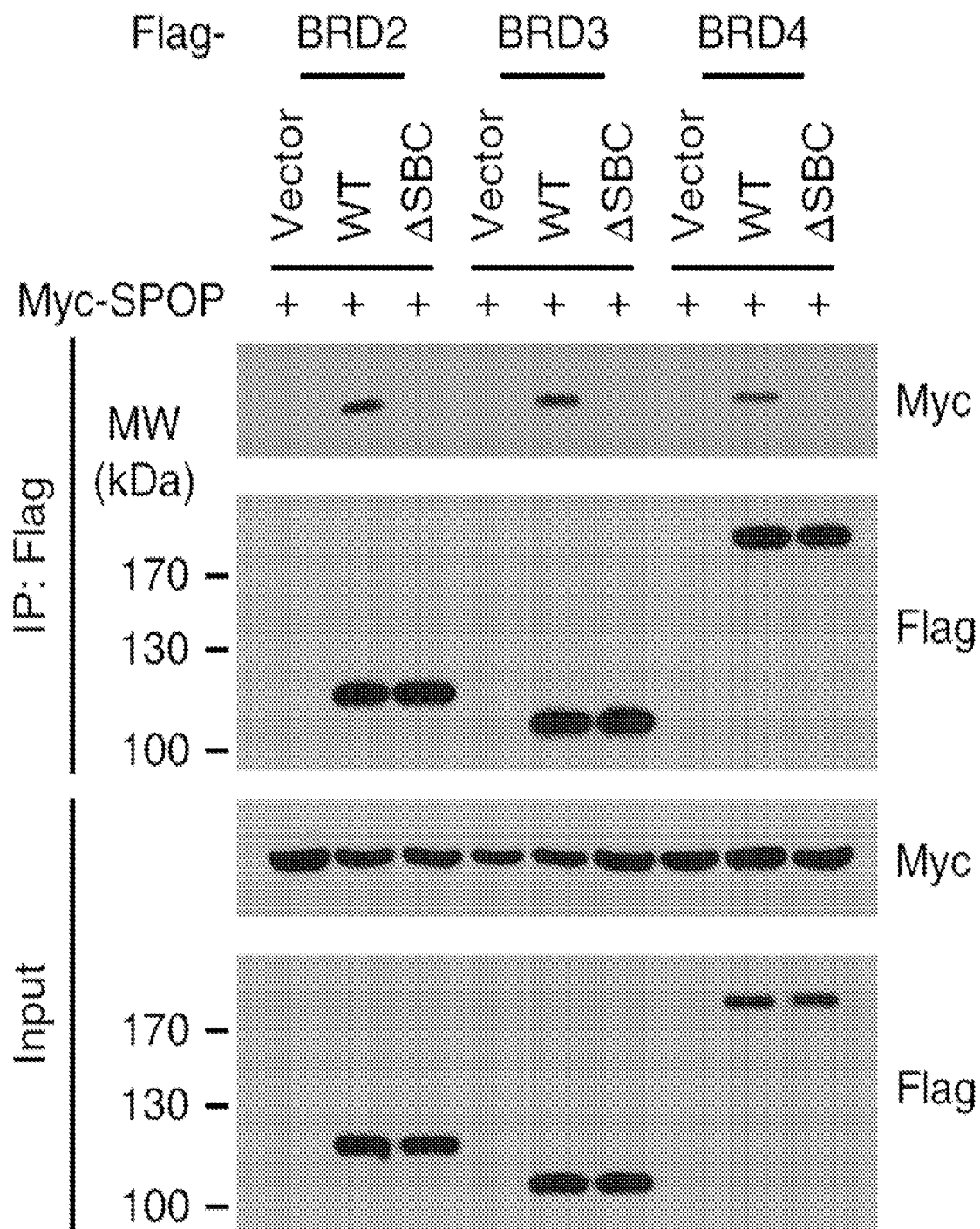
Figure 3D:
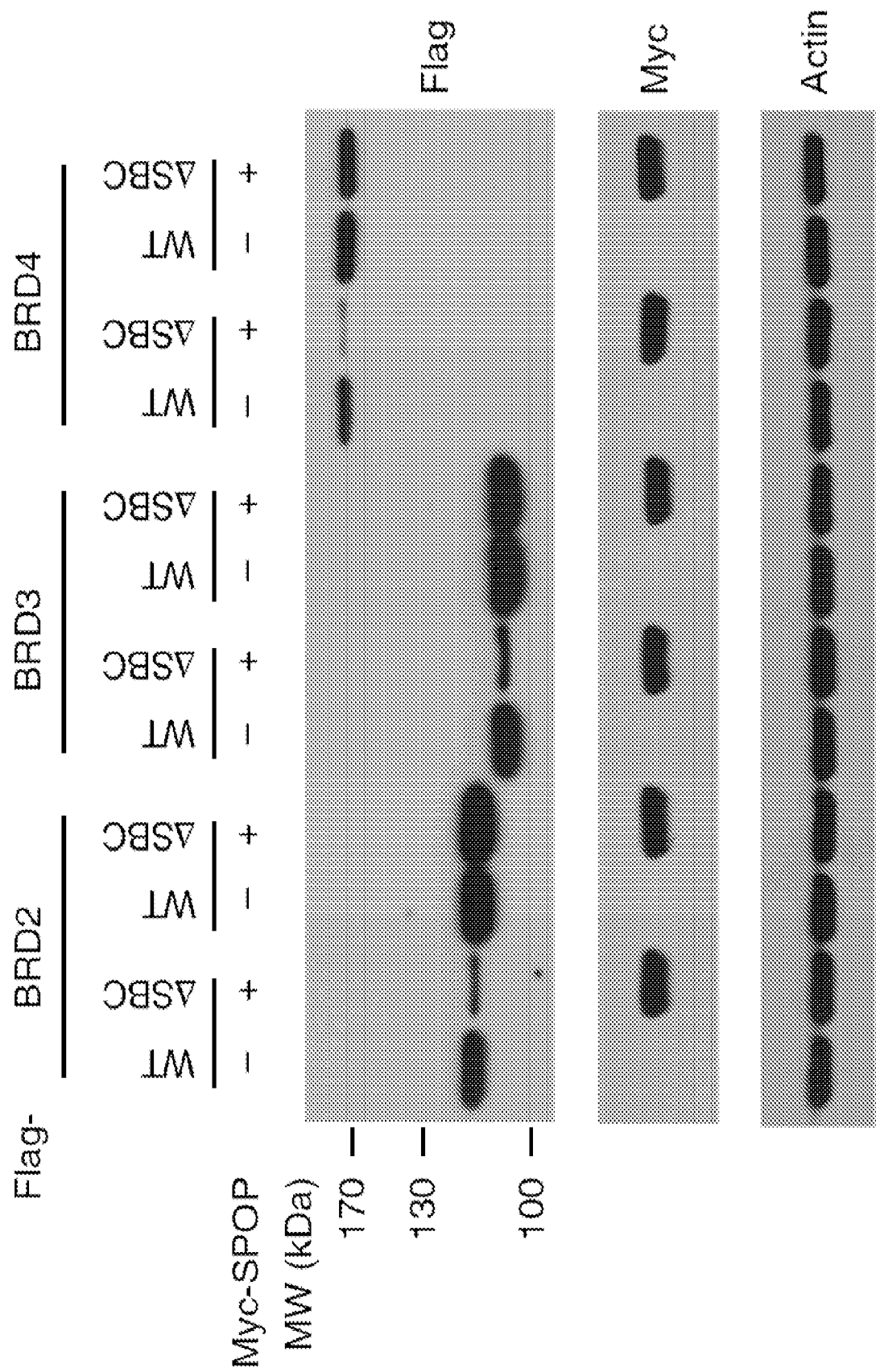
Figure 3E:
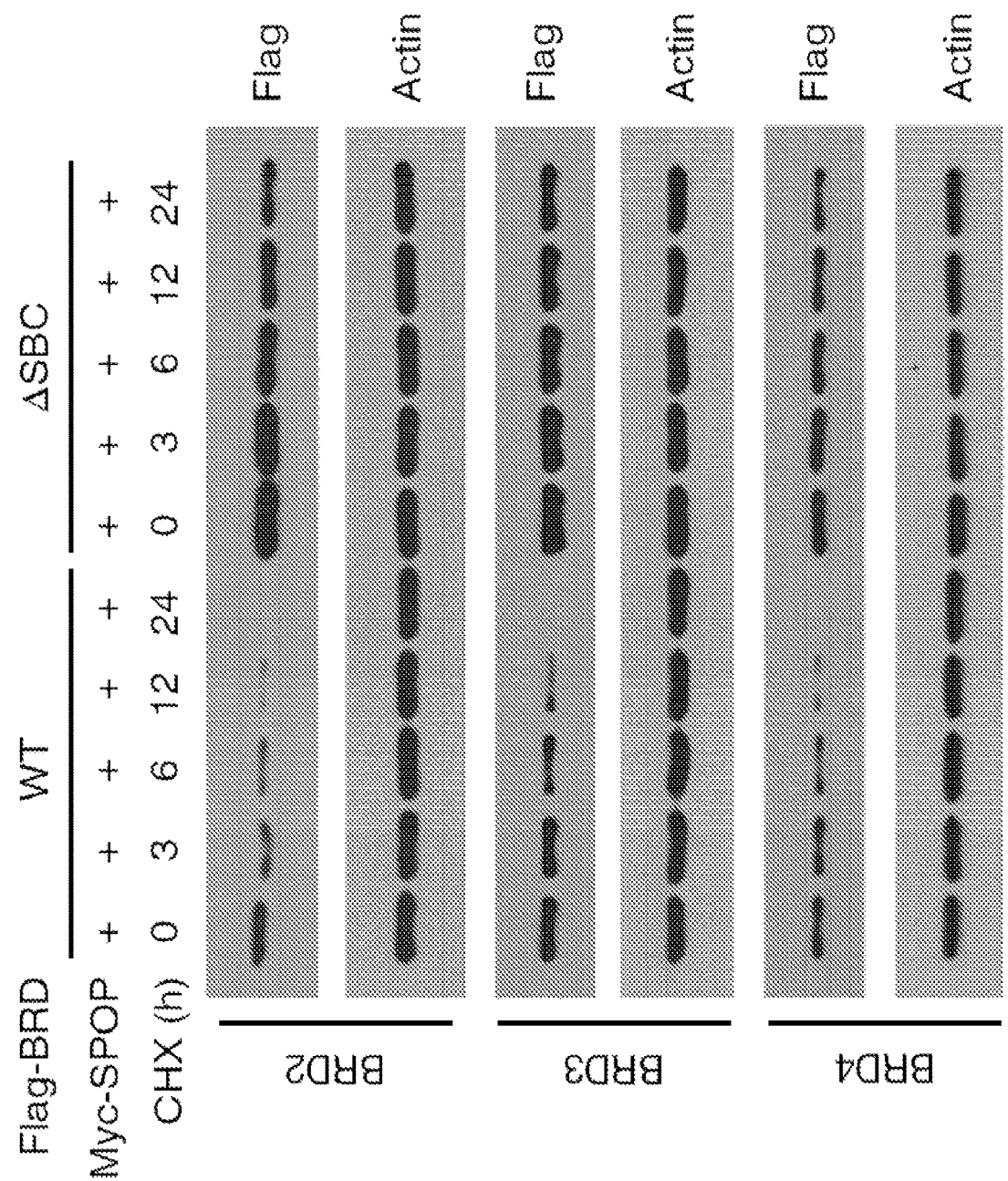
Figure 3F:
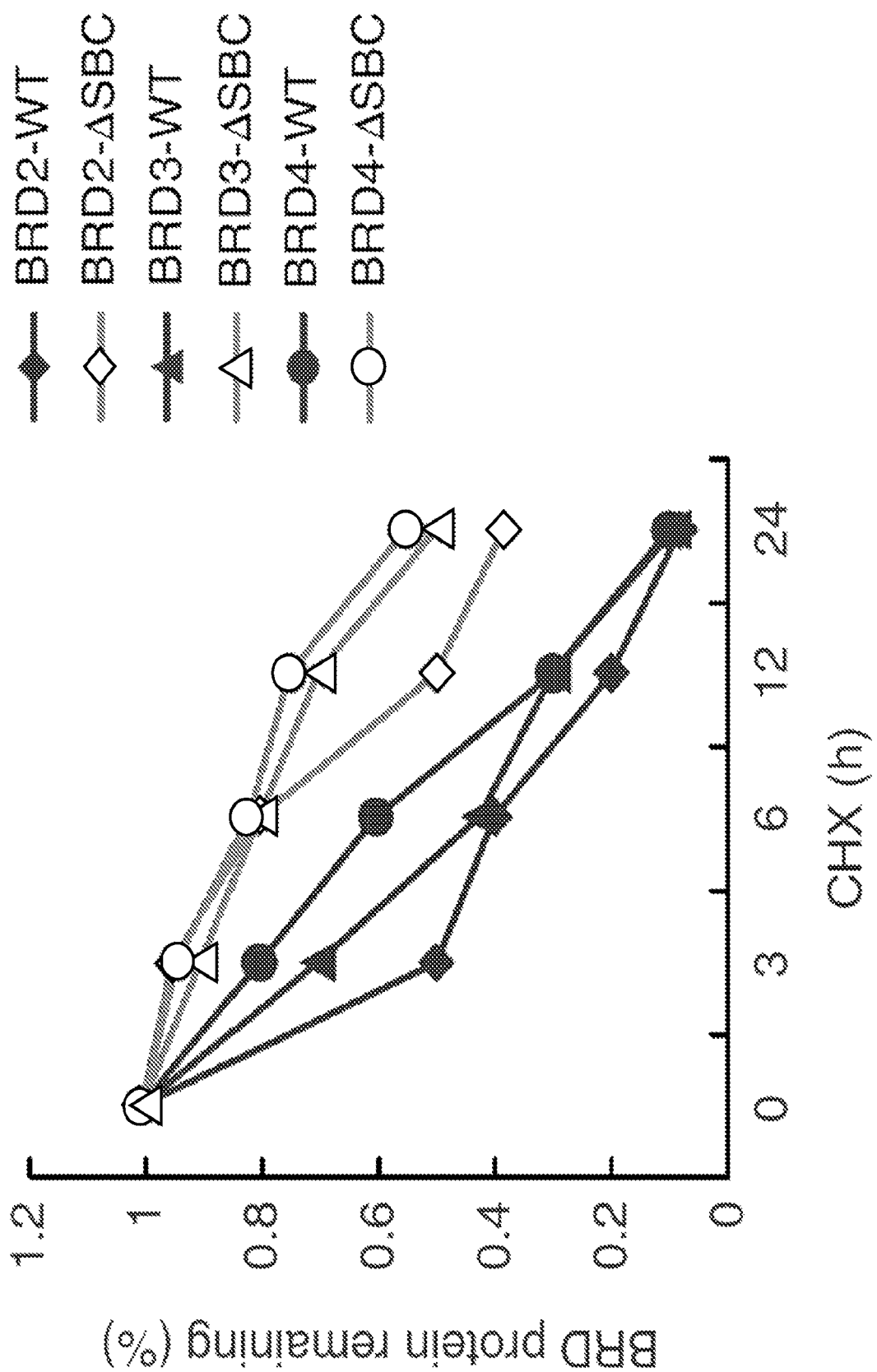
Figure 3G:
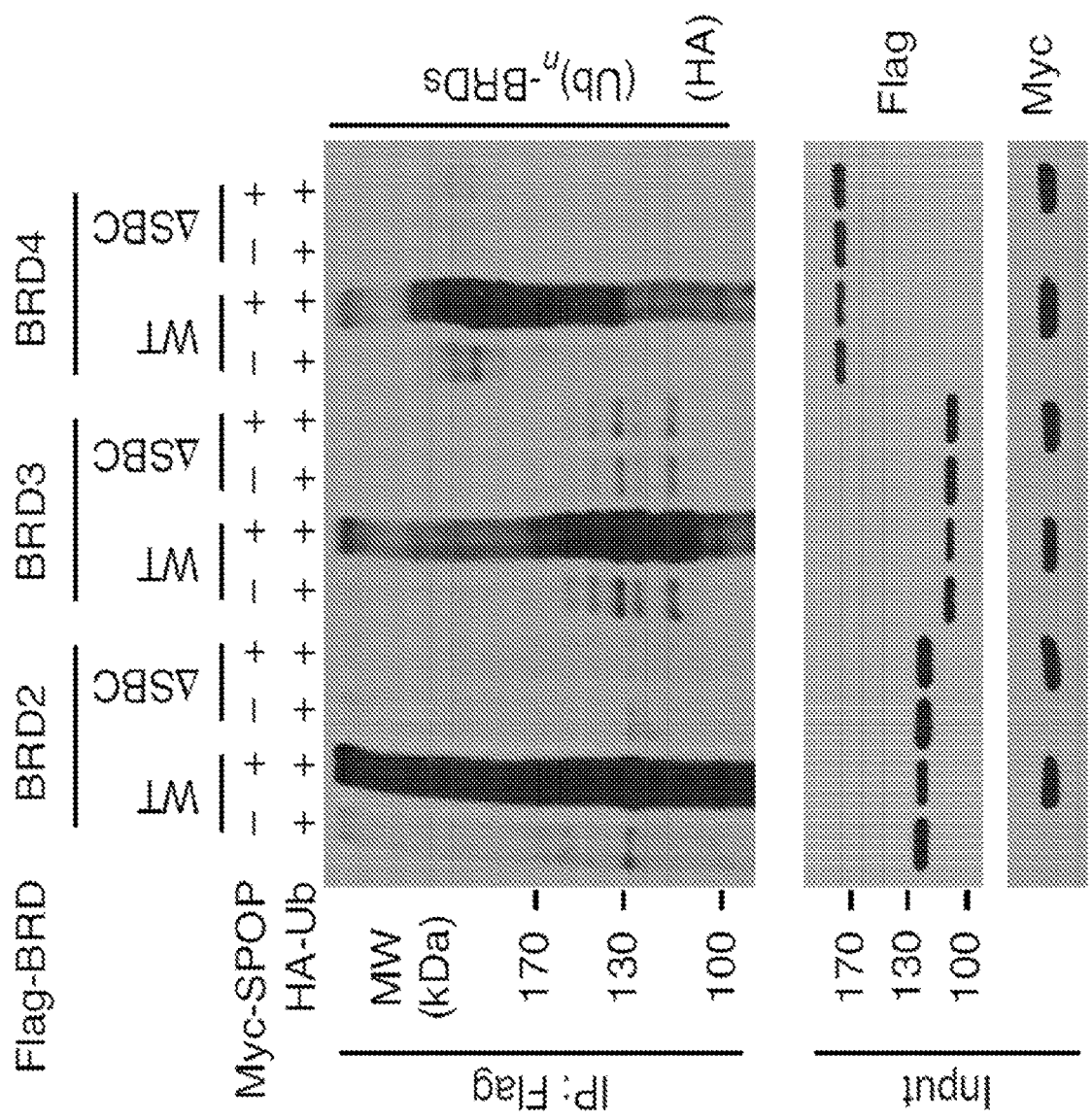

BET proteins play roles in epigenetic regulation and cancer, but little is known about their post-translational modifications and downstream functions. Treatment of LNCaP cells with proteasome inhibitors, Bortezomib and MG132, increased BRD2/3/4 protein, but not mRNA expression (FIGS. 2b and 2c). MLN4924, a small molecule inhibitor of NEDD8-activating enzyme that is required for activation of CRLs, also caused accumulation of BRD2/3/4 at protein level (FIGS. 2b and 2c). Expression of wild-type SPOP markedly decreased BRD2/3/4 proteins, and this effect was completely reversed by MG132 treatment (FIG. 1c). Knockdown of SPOP increased the steady-state level of endogenous BRD2/3/4 protein and prolonged the protein half-life, while having no overt effect on mRNA expression in LNCaP cells (FIGS. 1d and 2d-f). Similar results were obtained in 22Rv1 and BPH-1 prostatic cell lines (FIG. 1d). Moreover, only wild-type SPOP, but not substrate binding- and CUL3 binding-deficient mutants (ΔMATH and ΔBTB, respectively) degraded BRD2/3/4 proteins (FIG. 2g). Wild-type SPOP induced K48-dependent polyubiquitination of these proteins in cells, and this effect relied on its enzymatic activity (FIGS. 1e and 2h-i). The SPOP-CULLIN3-RBX1 complex was shown to catalyzed BRD4 ubiquitination in vitro (FIG. 10. Thus, functioning as a CRL substrate-binding adaptor, SPOP promoted ubiquitination and proteasomal degradation of BRD2/3/4 proteins in prostate cancer cells.

Substrate-binding consensus (SBC) motifs (Φ-π-S/T-S/T-S/T, where Φ is a nonpolar residue, and π is a polar residue (Zhuang et al., *Mol. Cell*, 36:39-50 (2009)) have been well characterized in known SPOP substrates such as MacroH2A and DEK12. The existence of a perfectly matched SBC motif in the region between bromodomain-1 (BD1) and BD2 in BRD2/3/4 proteins was found (FIGS. 3a and 3b), which also localized within the minimal SPOP-interaction region defined by yeast two-hybrid clones of BRD2/3/4 (FIG. 1a). Co-IP assays revealed that deletion of the putative SBC motif in BRD2/3/4 not only abolished SPOP binding and SPOP-mediated ubiquitination and degradation of BRD2/3/4, but also significantly prolonged the half-life of these proteins (FIGS. 3b-g). Thus, a common, functionally conserved SBC motif was identified in BRD2/3/4 proteins that was required for SPOP-dependent ubiquitination and degradation.

Figure 4A:
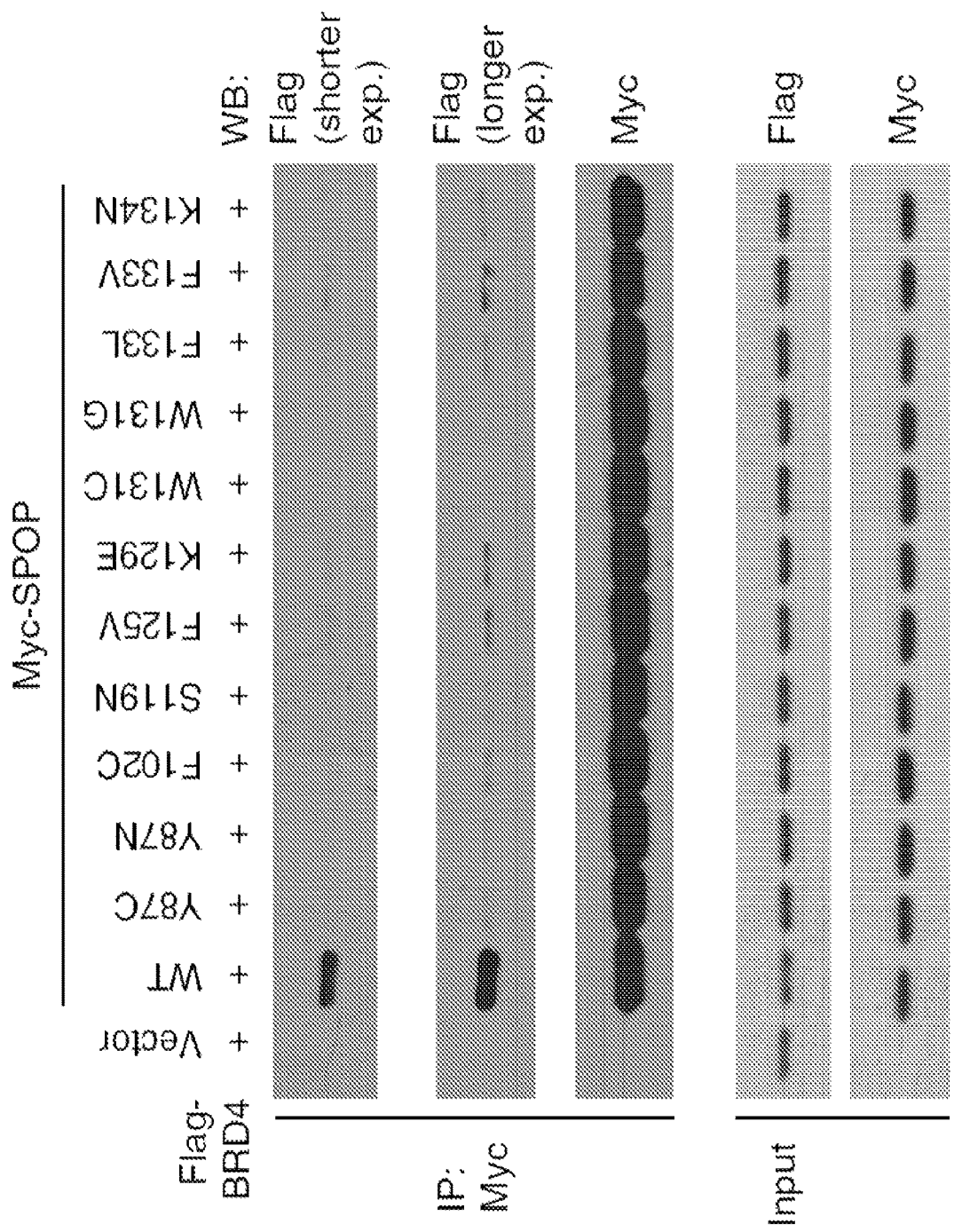
FIG. 4. Expression of BET proteins is elevated in SPOP mutant-expressing prostate cancer cells and patient specimens. a, Western blot of WCL and co-IP samples of anti-FLAG antibody from 293T cells transfected with indicated Myc- or FLAG-tagged plasmids and treated with 20 µM MG132 for 8 hours. b, Western blot of the products of in vivo ubiquitination assay from 293T cells transfected with indicated Myc- or FLAG-tagged plasmids and treated with 20 µM MG132 for 8 hours. c, Western blot of indicated proteins in WCL of C4-2 cells infected with lentivirus expressing empty vector (EV), wild-type (WT) or mutated SPOP. d and e, Representative images of BRD2/3/4 IHC in SPOP-WT and -mutated (MUT) prostate cancer tissues (d). The quantitative data of BRD2/3/4 staining are shown in (e). Statistical significance was determined by Wilcoxon rank sum test.
Figure 4B:
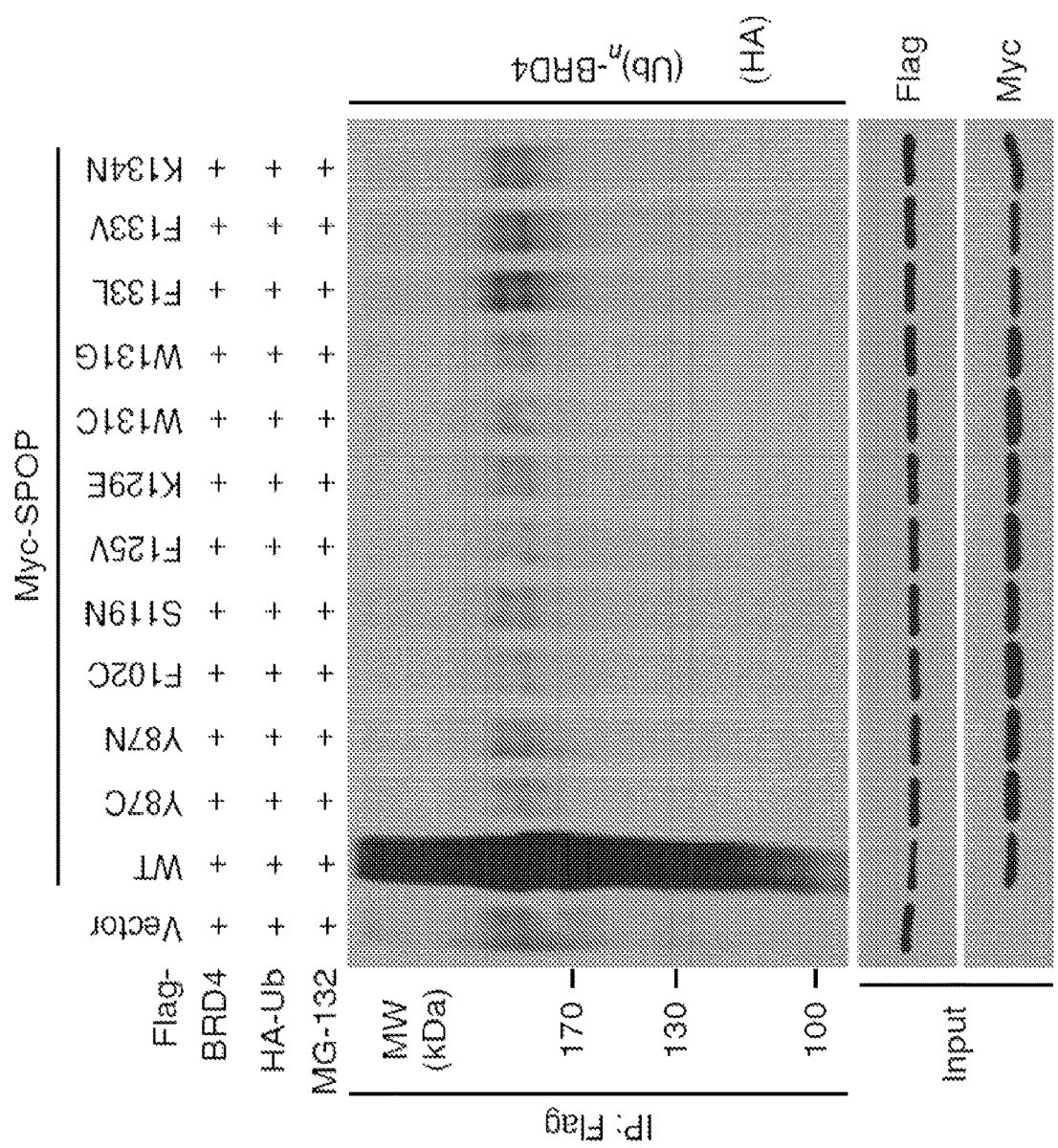
Figure 4C:
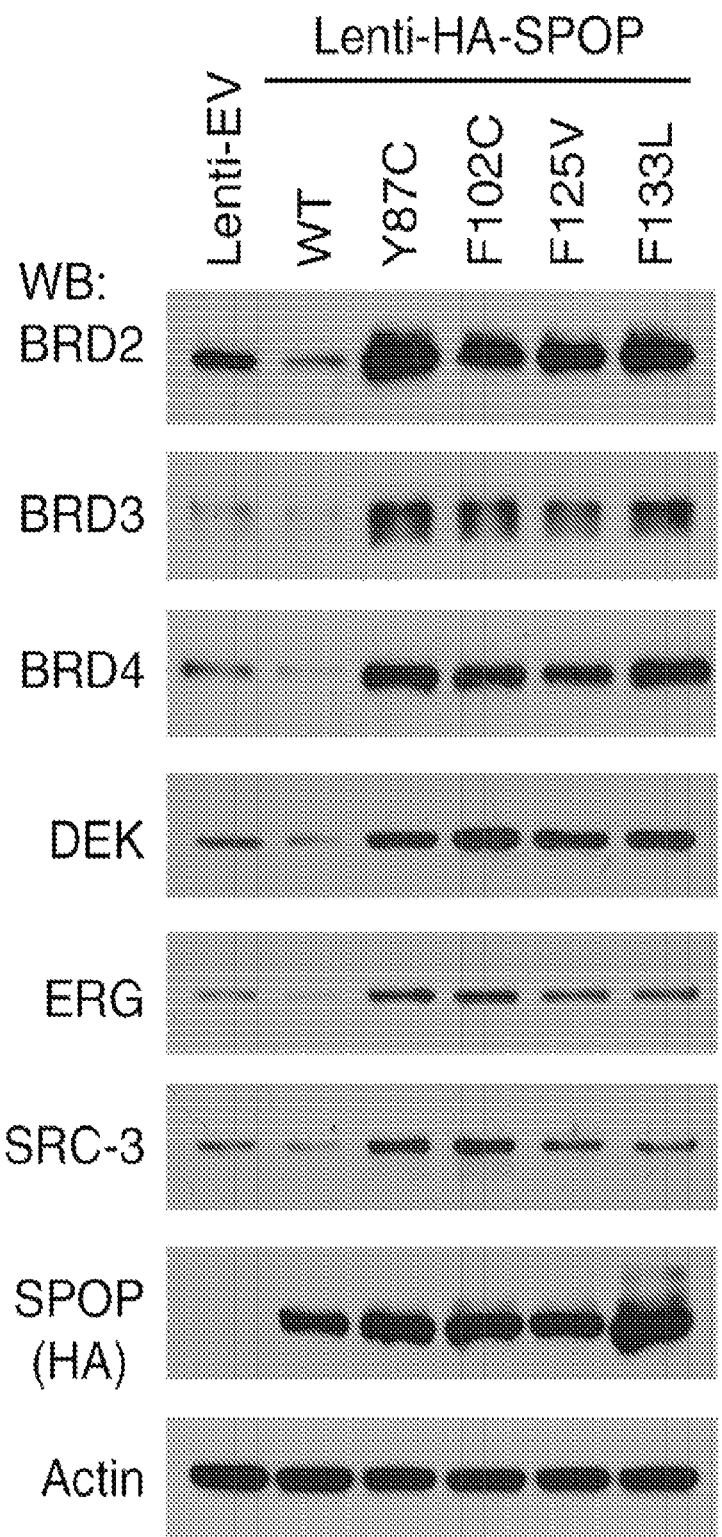
Figure 5A:
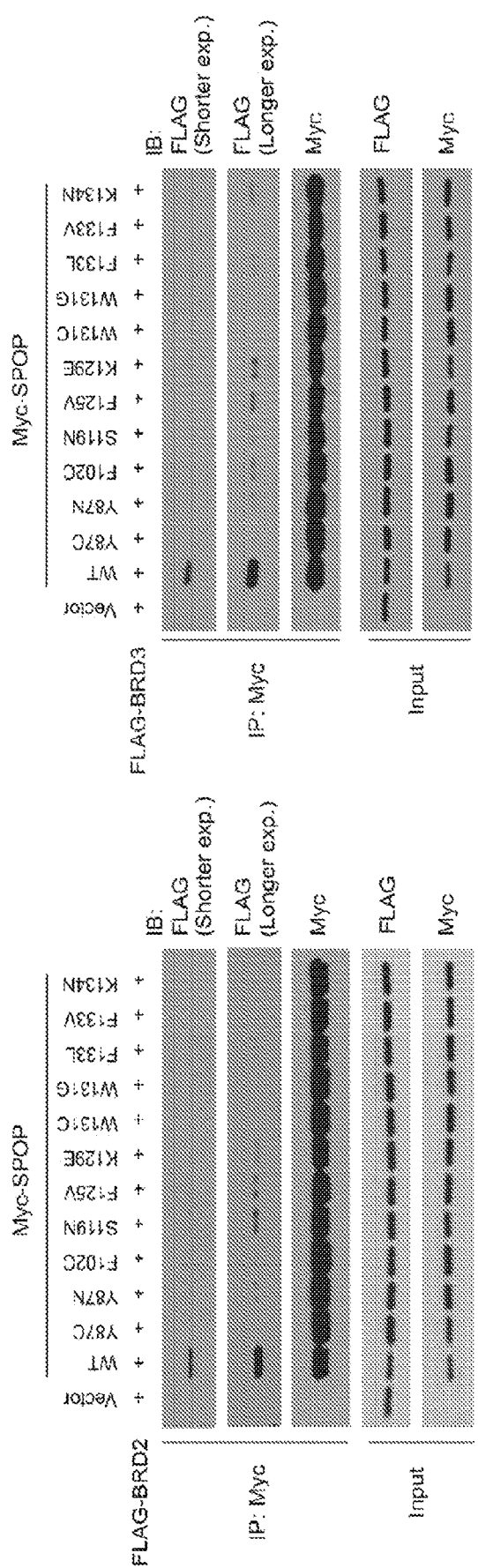
FIG. 5. The ability of prostate cancer-associated SPOP mutants to promote BRD2/3 protein degradation and ubiquitination, and expression of BRD2/3/4 mRNA in prostate cancer patient specimens. a, Western blot of WCL and co-IP samples of anti-FLAG antibody from 293T cells transfected with indicated plasmids and treated with 20 µM MG132 for 8 hours. exp., exposure. b, Western blot of the products of in vivo ubiquitination assay of 293T cells transfected with indicated plasmids and treated with 20 µM MG132 for 8 hours. c, RT-qPCR assessment of BRD2/3/4 mRNA expression in SPOP-WT and SPOP-MUT prostate tumors from 99 patients of Shanghai Changhai Hospital (Shanghai, China). BRD2/3/4 mRNA expression level in each tumor specimen was normalized by the expression level of 18S rRNA (internal control) and exhibited as a value of log 10. P values were determined by Mann-Whitney test (two-sided). d, Comparing BRD2/3/4 mRNA expression between SPOP-WT and SPOP-MUT patient tumors using The Cancer Genome Atlas (TCGA) RNA-seq data. Y-axis indicates the mean-centered gene expression level precalculated from pan-cancer analysis (downloaded from UCSC Cancer browser: https://genomecancer.ucsc.edu/). P values were determined by non-parametric Wilcoxon rank sum test (two sided).
Figure 5B:
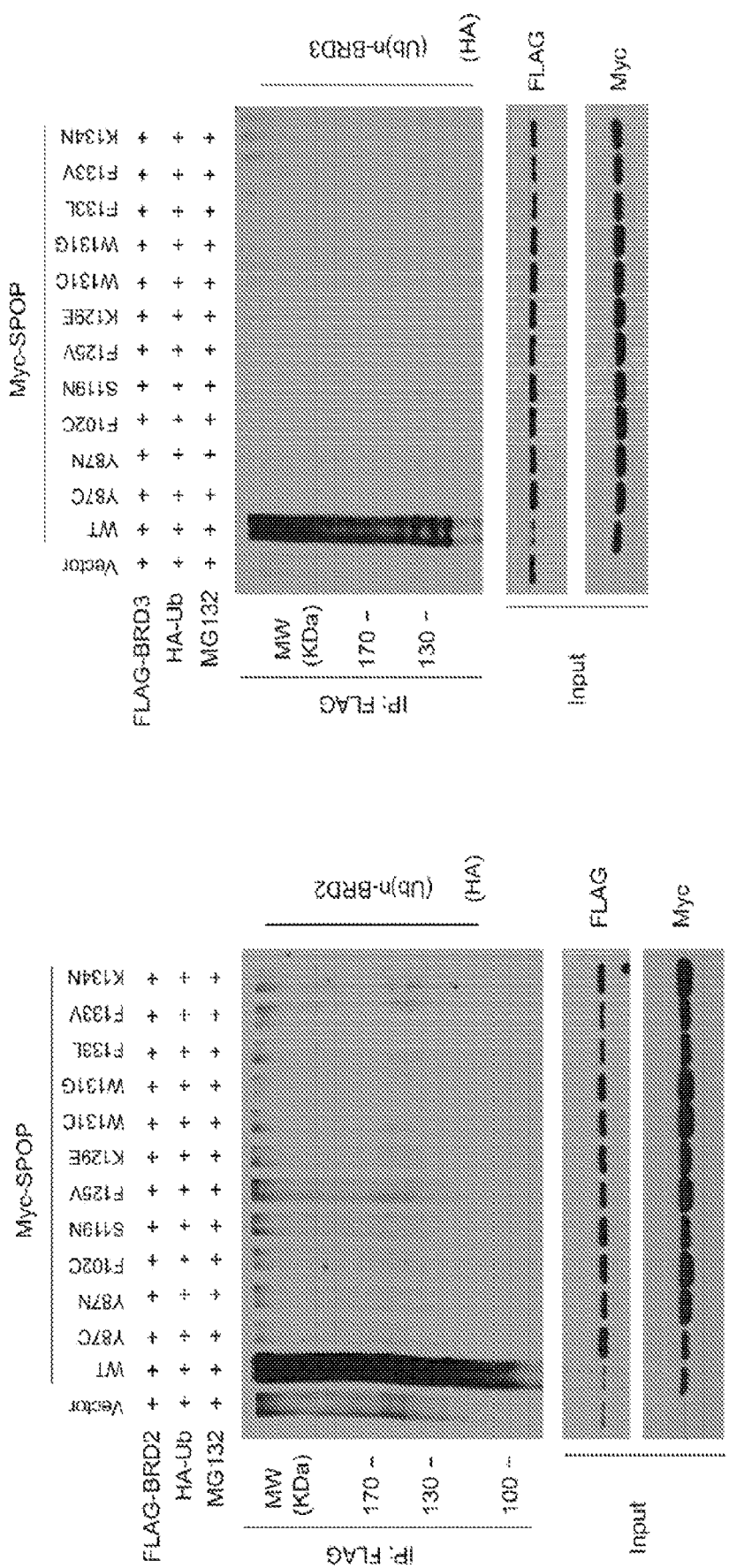

Because SPOP mutations in prostate cancers occur in the MATH domain that is responsible for substrate binding (Blattner et al., *Neoplasia*, 16:14-20 (2014)), it was hypothesized that prostate cancer-associated mutations impair the ability of SPOP to degrade BRD2/3/4. 11 prostate cancer-associated SPOP mutants were generated. Co-IP assays demonstrated that the BRD2/3/4-binding ability of all 11 SPOP mutants was largely impaired compared with wild-type SPOP (FIGS. 4a and 5a). SPOP-mediated ubiquitination of these proteins also was markedly attenuated by these mutations (FIGS. 4b and 5b). SPOP mutants failed to degrade, but rather elevated endogenous BRD2/3/4 protein levels, a dominant-negative effect similarly occurred to known SPOP substrates such as DEK, ERG and SRC-3 (FIG. 4c; Theurillat et al., Science, 346:85-89 (2014); Geng et al., Proc. Natl. Acad. Sci. USA, 110:6997-7002 (2013); and An et al., Mol. Cell, 59:904-916 (2015)). Thus, prostate cancer-associated SPOP mutants resulted in the stabilization of BRD2/3/4 proteins in prostate cancer cells.

Figure 4D:
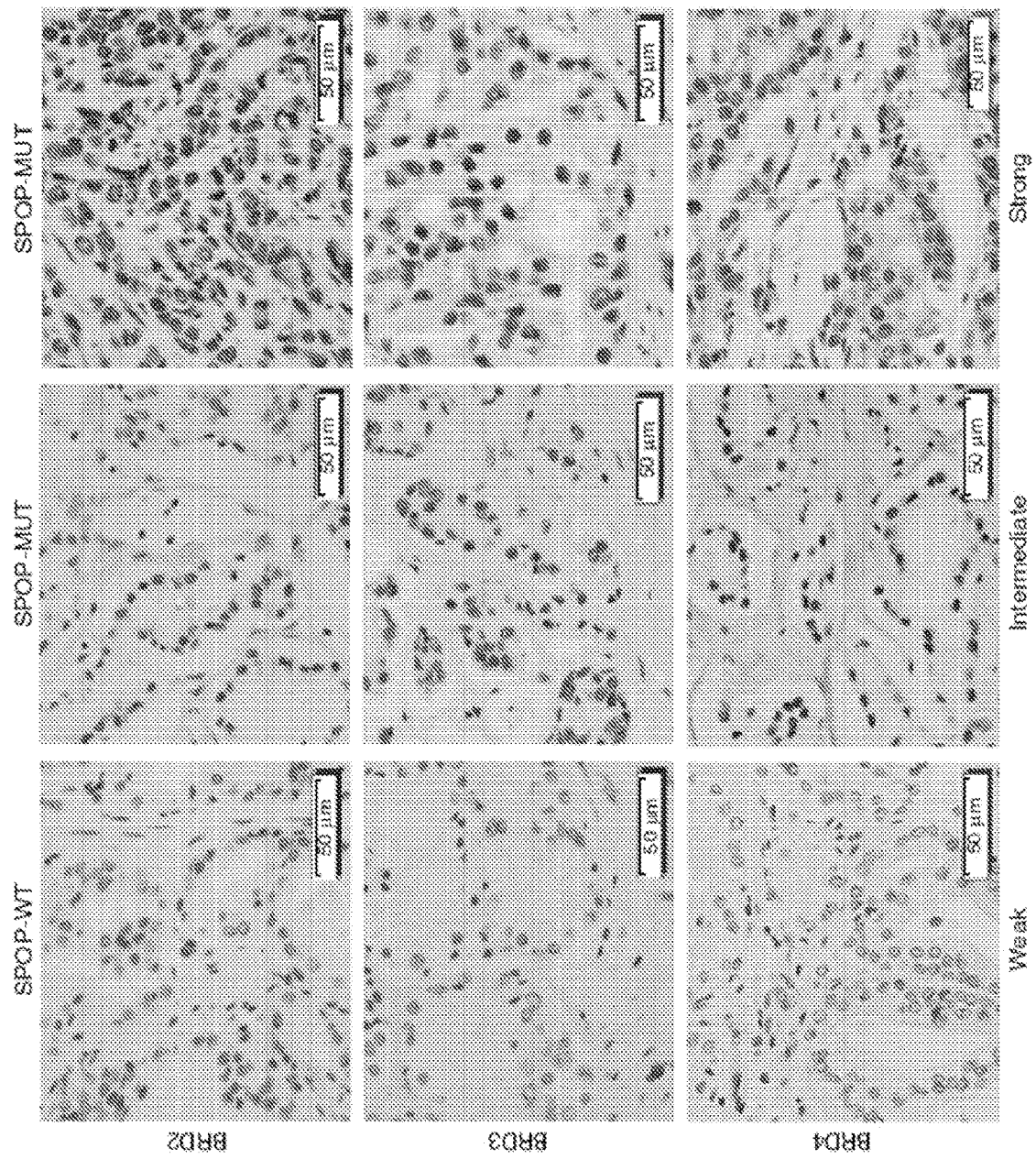
Figure 4E:
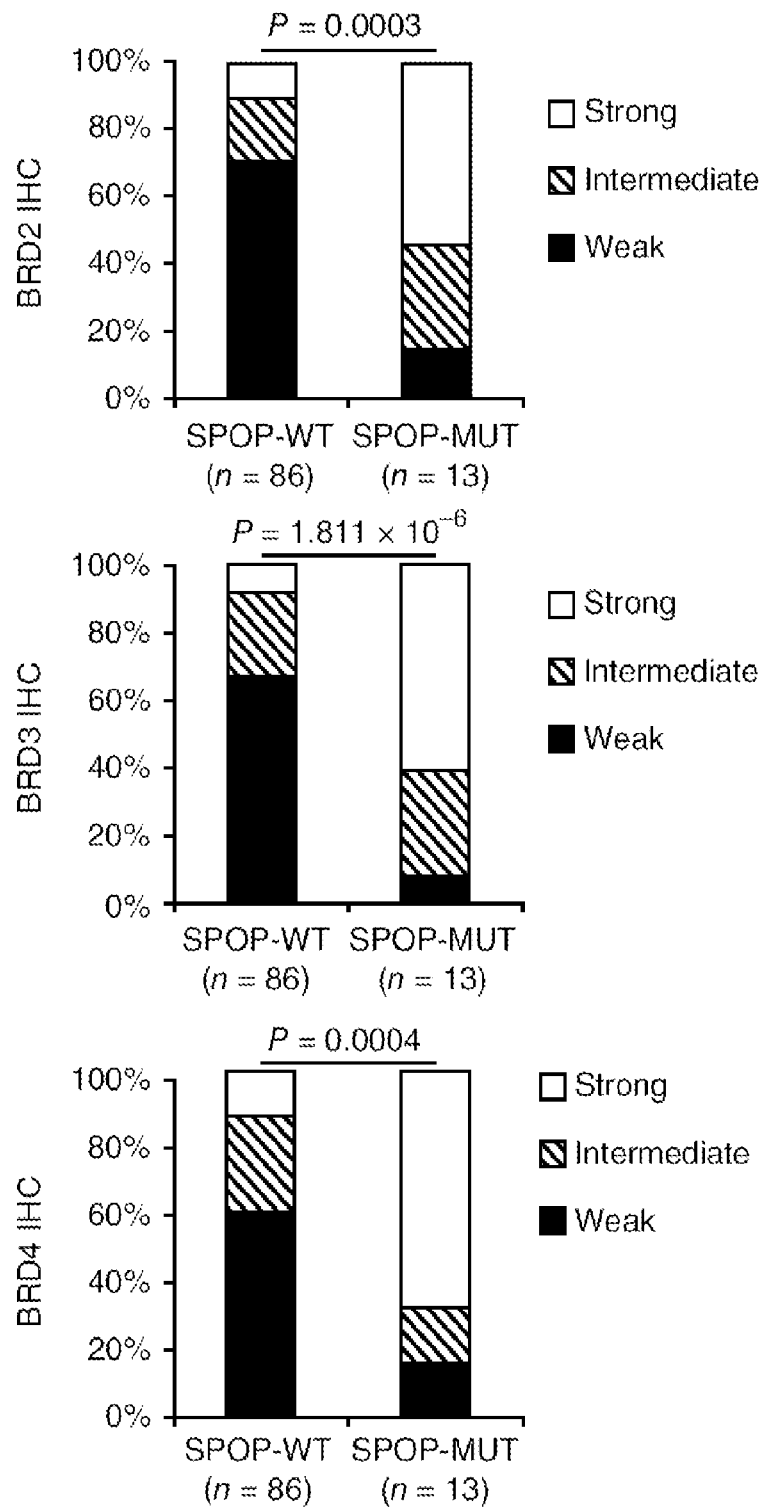
Figure 5C:
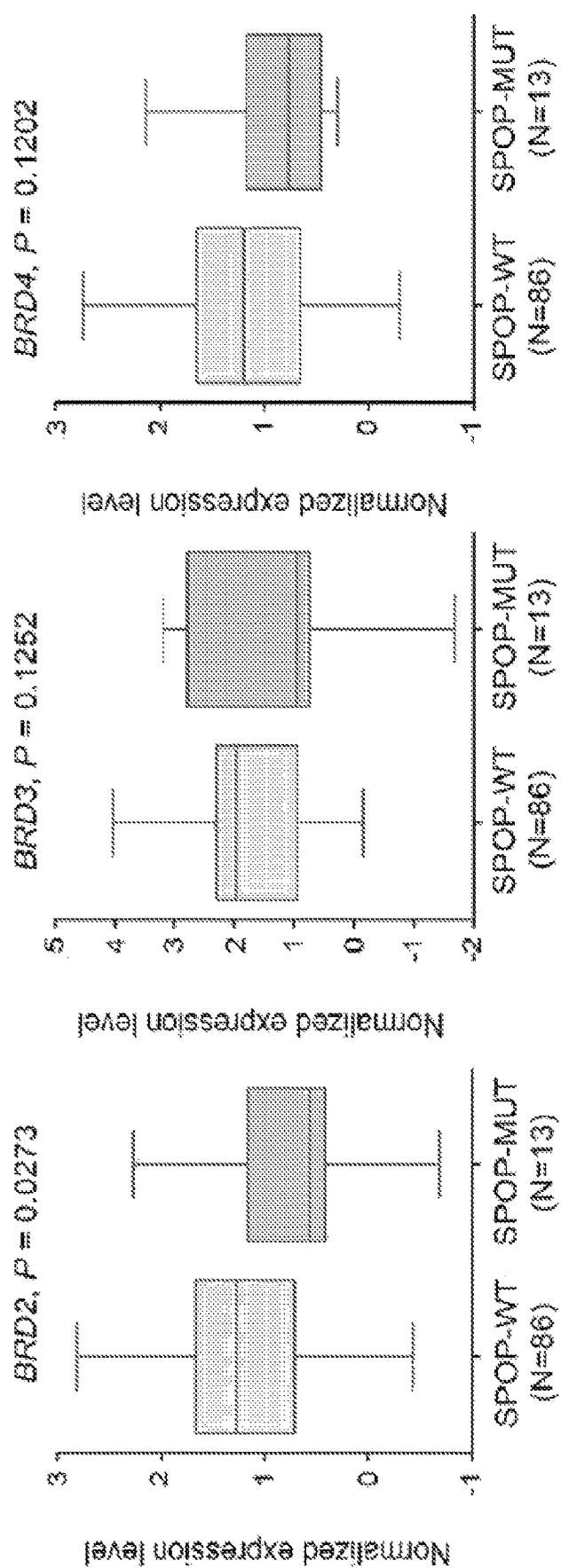
Figure 5D:
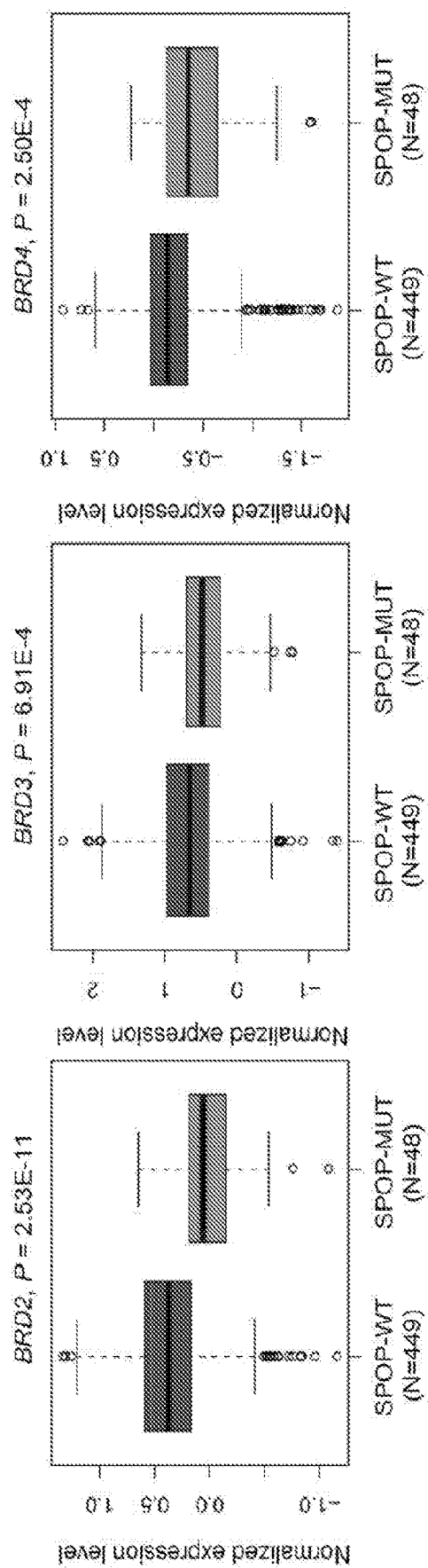

To examine the effect of SPOP mutations on BET protein levels in patient specimens, BRD2/3/4 protein levels were analyzed in two cohorts constituting 99 primary prostate tumors (Table 4). 13 SPOP-mutated tumors were identified through whole-genome sequencing and/or Sanger sequencing. The SPOP mutation frequency in these samples was consistent with the previous findings in different cohorts of prostate cancer (Barbieri et al., Nat. Genet., 44:685-689 (2012); and The Molecular Taxonomy of Primary Prostate Cancer, Cell, 163:1011-1025 (2015)). IHC revealed that approximately 85%, 92%, and 85% of SPOP-mutated tumors exhibited strong or intermediate straining of BRD2, BRD3 and BRD4 proteins, respectively (FIGS. 4d and 4e). In contrast, only 40% or less of SPOP-WT tumors exhibited strong or intermediate straining, whereas majority of them (approximately 71%, 66%, and 59% for BRD2, BRD3 and BRD4, respectively) exhibited weak staining (FIGS. 4d and 4e). BRD2/3/4 mRNA expression was relative lower in SPOP-mutated tumors than that in SPOP-WT specimens in these cohorts, although the difference did not reach statistical significance (except BRD2) (FIG. 5c). A similar trend was observed in The Cancer Genome Atlas (TCGA) dataset (FIG. 5d). These findings indicate that BRD2/3/4 protein levels were elevated in SPOP-mutated prostate cancer specimens and that this was unlikely caused by increases in mRNA levels.

TABLE 4

Table 4 SPOP mutation status, BRD2/3/4 IHC scores in 99 cases of prostate cancer specimens and the associated clinical i

| patient ID | SPOP Status(Two alies) | BRD2 IHC intensity | BRD3 IHC intensity | BRD4 IHC intensity | Age | Preoperative BMI (kg/m2) | Preoperative PSA level (ng/ml) | Clinical stage |
|---|---|---|---|---|---|---|---|---|
| CHH1 | WT/WT | 1 | 3 | 1 | 65 | 26.85 | 6.37 | T1 |
| CHH2 | WT/WT | 1 | 2 | 2 | 65 | 23.88 | 69.89 | T1 |
| CHH3 | WT/WT | 1 | 2 | 1 | 67 | 24.71 | 10.23 | T1 |
| CHH4 | WT/WT | 1 | 1 | 2 | 66 | 25.16 | 11.10 | T2 |
| CHH5 | F102C/WT | 2 | 2 | 2 | 78 | 26.81 | 22.75 | T2 |
| CHH6 | WT/WT | 1 | 2 | 2 | 65 | 23.20 | 14.14 | T2 |
| CHH7 | WT/WT | 1 | 1 | 1 | 64 | 25.39 | 52.23 | T2 |
| CHH8 | WT/WT | 1 | 1 | 2 | 78 | 25.59 | 8.01 | T1 |
| CHH9 | F102V/WT | 1 | 1 | 1 | 68 | 24.38 | 9.85 | T2 |
| CHH10 | WT/WT | 1 | 2 | 3 | 77 | 21.08 | 41.78 | T1 |
| CHH11 | WT/WT | 1 | 1 | 1 | 69 | 23.26 | 12.80 | T1 |
| CHH12 | WT/WT | 1 | 1 | 2 | 75 | 22.04 | 10.71 | T2 |
| CHH13 | F125C/WT | 3 | 3 | 3 | 68 | 26.50 | 9.68 | T2 |
| CHH14 | WT/WT | 1 | 2 | 1 | 74 | 24.53 | 8.96 | T2 |
| CHH15 | WT/WT | 1 | 1 | 2 | 67 | 25.15 | 21.12 | T1 |
| CHH16 | WT/WT | 1 | 3 | 1 | 73 | 23.23 | 23.62 | T2 |
| CHH17 | WT/WT | 1 | 2 | 1 | 75 | 26.33 | 18.47 | T2 |
| CHH18 | WT/WT | 1 | 1 | 2 | 70 | 28.37 | 8.68 | T2 |
| CHH19 | WT/WT | 1 | 2 | 2 | 74 | 25.26 | 63.83 | T2 |
| CHH20 | WT/WT | 2 | 2 | 1 | 76 | 23.44 | 11.56 | T1 |
| CHH21 | WT/WT | 3 | 3 | 3 | 55 | 20.76 | 87.11 | T2 |
| CHH22 | WT/WT | 1 | 1 | 2 | 70 | 20.95 | 10.07 | T2 |
| CHH23 | F133L/WT | 1 | 2 | 3 | 61 | 25.10 | 7.90 | T2 |
| CHH24 | WT/WT | 1 | 3 | 2 | 65 | 24.91 | 9.03 | T1 |
| CHH25 | WT/WT | 1 | 1 | 1 | 79 | 26.03 | 20.21 | T1 |
| CHH26 | WT/WT | 1 | 3 | 3 | 67 | 25.80 | 39.60 | T1 |
| CHH27 | WT/WT | 1 | 1 | 1 | 62 | 20.07 | 7.96 | T1 |
| CHH28 | WT/WT | 1 | 2 | 2 | 78 | 27.68 | 35.43 | T1 |
| CHH29 | WT/WT | 1 | 1 | 1 | 56 | 25.31 | 5.96 | T2 |
| CHH30 | WT/WT | 1 | 1 | 1 | 68 | 22.58 | 7.49 | T2 |
| CHH31 | WT/WT | 1 | 1 | 1 | 71 | 24.91 | 8.76 | T2 |
| CHH32 | W131G/WT | 2 | 2 | 3 | 70 | 23.44 | 31.19 | T2 |
| CHH33 | F102C/WT | 3 | 3 | 2 | 60 | 22.86 | 9.94 | T1 |
| CHH34 | WT/WT | 1 | 2 | 2 | 54 | 20.62 | 13.00 | T1 |
| CHH35 | F133V/WT | 2 | 2 | 1 | 73 | 23.15 | 21.79 | T1 |
| CHH36 | F133L/WT | 3 | 3 | 3 | 66 | 25.82 | 70.97 | T2 |
| CHH37 | WT/WT | 1 | 1 | 1 | 77 | 20.52 | 13.50 | T2 |
| CHH38 | T133L/WT | 3 | 3 | 3 | 76 | 27.18 | 9.87 | T1 |
| CHH39 | WT/WT | 1 | 1 | 1 | 61 | 23.88 | 14.87 | T2 |
| CHH40 | WT/WT | 2 | 1 | 1 | 60 | 25.61 | 10.67 | T1 |
| CHH41 | W131G/WT | 2 | 3 | 3 | 51 | 22.95 | 27.04 | T2 |
| CHH42 | WT/WT | 1 | 1 | 1 | 71 | 22.32 | 21.37 | T2 |
| CHH43 | WT/WT | 1 | 1 | 2 | 77 | 25.39 | 47.43 | T2 |
| CHH44 | WT/WT | 2 | 1 | 2 | 74 | 24.49 | 26.90 | T2 |
| CHH45 | WT/WT | 1 | 1 | 1 | 75 | 23.88 | 12.57 | T2 |
| CHH46 | WT/WT | 1 | 1 | 1 | 69 | 24.61 | 89.63 | T2 |
| CHH47 | WT/WT | 1 | 1 | 2 | 62 | 29.41 | 7.95 | T2 |
| CHH48 | WT/WT | 1 | 1 | 1 | 50 | 25.39 | 8.01 | T2 |
| CHH49 | WT/WT | 1 | 1 | 1 | 66 | 25.51 | 6.78 | T2 |
| CHH50 | WT/WT | 2 | 1 | 2 | 60 | 28.34 | 10.09 | T1 |

TABLE 4-continued

Table 4 SPOP mutation status, BRD2/3/4 IHC scores in 99 cases
of prostate cancer specimens and the associated clinical i

| patient ID | SPOP Status(Two alies) | BRD2 IHC intensity | BRD3 IHC intensity | BRD4 IHC intensity | Age | Preoperative BMI (kg/m2) | Preoperative PSA level (ng/ml) | Clinical stage |
|---|---|---|---|---|---|---|---|---|
| CHH51 | WT/WT | 1 | 1 | 3 | 71 | 21.77 | 51.65 | T1 |
| CHH52 | WT/WT | 1 | 2 | 2 | 62 | 21.11 | 5.80 | T2 |
| CHH53 | WT/WT | 1 | 1 | 1 | 72 | 21.11 | 7.40 | T2 |
| CHH54 | WT/WT | 3 | 2 | 3 | 74 | 22.84 | 18.74 | T2 |
| CHH55 | WT/WT | 1 | 1 | 1 | 55 | 26.30 | 7.44 | T1 |
| CHH56 | WT/WT | 1 | 1 | 1 | 65 | 26.22 | 7.60 | T2 |
| CHH57 | WT/WT | 1 | 1 | 1 | 80 | 21.34 | 16.54 | T2 |
| CHH58 | WT/WT | 1 | 1 | 1 | 61 | 25.35 | 14.58 | T2 |
| CHH59 | WT/WT | 2 | 2 | 1 | 50 | 27.10 | 14.87 | T1 |
| CHH60 | WT/WT | 1 | 1 | 2 | 55 | 25.76 | 30.82 | T1 |
| CHH61 | WT/WT | 1 | 1 | 1 | 73 | 19.61 | 13.11 | T1 |
| CHH62 | WT/WT | 2 | 2 | 1 | 68 | 24.69 | 14.00 | T2 |
| CHH63 | F133V/WT | 3 | 3 | 3 | 67 | 26.30 | 13.95 | T1 |
| CHH64 | WT/WT | 1 | 1 | 1 | 69 | 23.88 | 2.52 | T2 |
| CHH65 | WT/WT | 1 | 1 | 2 | 72 | 24.22 | 29.96 | T1 |
| CHH66 | WT/WT | 1 | 1 | 1 | 69 | 22.23 | 4.50 | T2 |
| CHH67 | WT/WT | 1 | 1 | 1 | 72 | 25.47 | 21.91 | T2 |
| CHH68 | WT/WT | 1 | 2 | 1 | 56 | 22.86 | 4.00 | T1 |
| CHH69 | F102S/WT | 3 | 3 | 3 | 72 | 23.44 | 48.13 | T1 |
| CHH70 | F102S/WT | 3 | 3 | 3 | 79 | 23.44 | 21.20 | T2 |
| CHH71 | WT/WT | 2 | 1 | 1 | 64 | 24.80 | 10.30 | T2 |
| CHH72 | WT/WT | 3 | 1 | 3 | 74 | 25.86 | 39.50 | T2 |
| CHH73 | WT/WT | 1 | 1 | 1 | 67 | 23.03 | 46.20 | T1 |
| CHH74 | WT/WT | 3 | 1 | 1 | 72 | 27.47 | 19.76 | T1 |
| CHH75 | WT/WT | 2 | 1 | 1 | 68 | 31.25 | 47.28 | T2 |
| CHH76 | WT/WT | 2 | 1 | 3 | 63 | 23.53 | 16.84 | T1 |
| CHH77 | WT/WT | 3 | 2 | 3 | 67 | 27.78 | 7.66 | T1 |
| CHH78 | WT/WT | 1 | 1 | 1 | 77 | 29.27 | 17.58 | T1 |
| CHH79 | WT/WT | 3 | 3 | 2 | 58 | 24.22 | 24.08 | T2 |
| CHH80 | WT/WT | 1 | 2 | 1 | 77 | 21.48 | 4.62 | T2 |
| CHH81 | WT/WT | 2 | 2 | 3 | 70 | 24.69 | 9.55 | T2 |
| CHH82 | WT/WT | 2 | 2 | 1 | 76 | 20.08 | 9.98 | T2 |
| CHH83 | WT/WT | 1 | 1 | 2 | 70 | 31.77 | 11.56 | T2 |
| CHH84 | WT/WT | 1 | 1 | 1 | 70 | 31.89 | 5.68 | T2 |
| CHH85 | WT/WT | 2 | 1 | 1 | 69 | 24.21 | 6.96 | T2 |
| CHH86 | WT/WT | 2 | 1 | 1 | 70 | 23.14 | 14.20 | T3 |
| CHH87 | WT/WT | 1 | 1 | 1 | 69 | 25.71 | 19.70 | T2 |
| CHH88 | WT/WT | 1 | 1 | 1 | 59 | 23.59 | 5.26 | T2 |
| CHH89 | WT/WT | 1 | 1 | 3 | 60 | 25.39 | 20.45 | T2 |
| CHH90 | WT/WT | 2 | 1 | 1 | 68 | 21.48 | 14.76 | T2 |
| CHH91 | WT/WT | 1 | 1 | 1 | 63 | 26.99 | 17.93 | T2 |
| CHH92 | WT/WT | 2 | 2 | 1 | 75 | 23.66 | 1.29 | T4 |
| CHH93 | WT/WT | 1 | 1 | 2 | 68 | 23.44 | 18.72 | T2 |
| CHH94 | WT/WT | 3 | 1 | 3 | 63 | 23.44 | 8.61 | T2 |
| CHH95 | WT/WT | 1 | 1 | 2 | 69 | 21.71 | 25.72 | T2 |
| CHH96 | WT/WT | 2 | 2 | 2 | 46 | 24.16 | 5.96 | T2 |
| CHH97 | WT/WT | 3 | 1 | 1 | 60 | 24.91 | 164.90 | T4 |
| CHH98 | WT/WT | 1 | 1 | 1 | 64 | 25.40 | 17.94 | T2 |
| CHH99 | WT/WT | 3 | 3 | 1 | 74 | 20.94 | 8.38 | T1 |

Figure 6A:
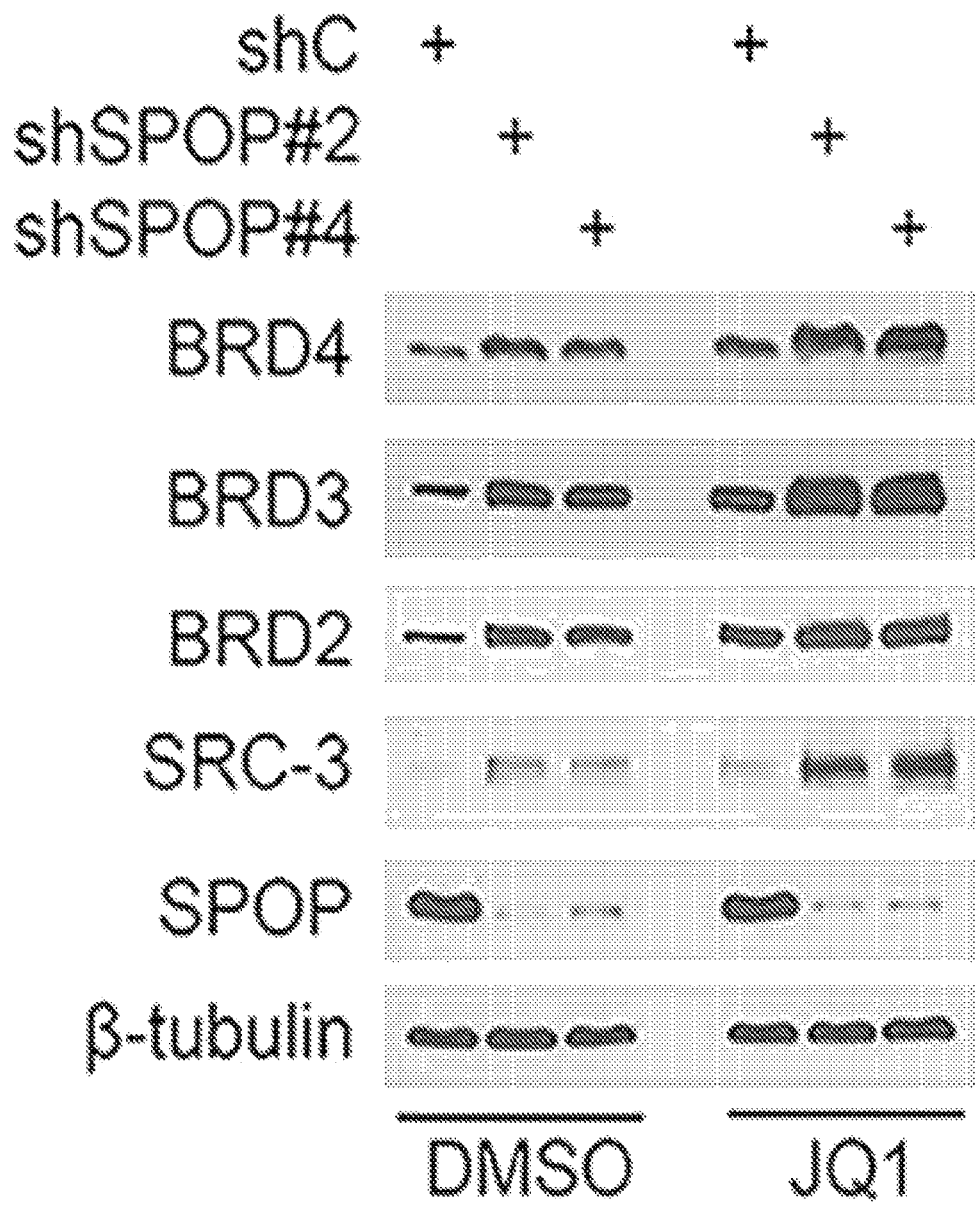
FIG. 6. SPOP knockdown and expression prostate cancer-associated mutant promote JQ1-resistant growth of prostate cancer cells. a, Western blot of WCL from C4-2 cells infected with lentivirus expressing control shRNA (shC) or SPOP-specific shRNA #2 or #4 and treated with or without JQ1 (1 µM) for 24 hours. β-tubulin was used as a loading control. b and c, C4-2 cells were infected with lentivirus as in (a) and then treated with or without JQ1 (0.25 µM) every other day. Cell growth was measured at indicated time points by cell proliferation assay (b) and trypan blue assay (c). Data are shown as means±SD (n=6 biological replicates). d and e, C4-2 cells infected with lentivirus expressing empty vector (EV) or SPOP F133V mutant in combination with control shRNA (shC), or BRD2/3/4 specific shRNAs. Cells were used for western blot analysis of indicated proteins in whole-cell lysate (d) or for analysis of cell growth measured by cell proliferation assay (left panel) and trypan blue assay (right panel) at indicated time points (e). β-tubulin was used as a loading control. Data are shown as means±SD (n=6). Statistical significance was determined by two-tailed Student's t-test for cells treated with JQ1 at day 4. f and g, 22Rv1 cells infected with lentivirus expressing empty vector (EV) or SPOP F133V mutant in combination with control shRNA (shC), or BRD2/3/4 specific shRNAs. Cells were used for western blot analysis of indicated proteins in whole-cell lysate (f) or for analysis of cell growth measured by cell proliferation assay (left panel) and trypan blue assay (right panel) at indicated time points (g). β-tubulin was used as a loading control. Data are shown as means±SD (n=6). Statistical significance was determined by two-tailed Student's t-test for cells treated with JQ1 at day 4. h-j, C4-2 cells were transfected with control siRNA (siC), a pool of BRD4- and/or SPOP specific siRNAs (siBRD4 or siSPOP) as indicated. At 48 hours after transfection, the first set of cells were harvested for measurement of BRD4 and SPOP mRNA expression by RT-qPCR (h); the second set of cells were harvested for measurement of BRD4 and SPOP protein expression by western blots (i); the third set of cells were treated with different doses of JQ1 for 24 hours, and cell viability were measured by MTS assay (j). Data are shown in (h) as means±SD (n=3 technical replicates), and similar results were obtained from two independent experiments. Data are shown in (j) as means±SD (n=6 replicates). Comparison of the data in cells treated with the highest concentration (500 nM) of JQ1. k and l, BRD4 KO C4-2 cells were transfected with control siRNA (siC), pool of SPOP-specific siRNAs, and/or BRD2/3 shRNAs (shBRD2/3 or siSPOP) as indicated. At 48 hours after transfection, the first set of cells were harvested for measurement of BRD2/3/4 and SPOP protein expression by western blots; the second set of cells were treated with different doses of JQ1 for 24 hours, and cell growth were measured by cell proliferation assay. Data are shown as means±SD (n=6 replicates). Statistical significance was determined by two-tailed Student's t-test for cells treated with the highest concentration (500 nM) of JQ1. m, Western blot of indicated proteins including AKT (Ser473) and S6K (Thr389) phosphorylation in WCL of C4-2 (left) and 22Rv1 (right) cells infected with lentivirus expressing empty vector (EV) or SPOP F133V mutant and treated with vehicle (DMSO) or 1 µM JQ1 for 24 hours. Western blot signal intensity of p-AKT and p-S6K was first normalized to pan AKT and S6K level, respectively, and the value was further normalized to the one in cells infected with EV without JQ1 treatment. Asterisk indicates the exogenous HA-SPOPF133V. n, C4-2 (top panels) and 22Rv1 (bottom panels) cells were infected with lentivirus as in (m) and then treated with or without JQ1 (0.25 µM) every other day. Cell growth was measured by cell proliferation assay (left panels) and trypan blue assay (right panels). Data are shown as means±SD (n=6 biological replicates). o, Western blot of indicated proteins in WCL of C4-2 cells infected with indicated lentivirus for 48 hours. p, C4-2 cell infected with lentivirus as in (o) were treated with vehicle (DMSO) or i-BET762 (i-BET, 0.5 µM) every other day, and cell growth were measured by trypan blue assay at indicated time points. Data are shown as means±SD (n=6 biological replicates). q, 22Rv1 cells was infected with lentivirus as in (m) and then treated with or without i-BET (0.5 µM) every other day. Cell growth was measured by trypan blue assay at indicated time points. Data are shown as means±SD (n=6 biological replicates).
Figure 6B:
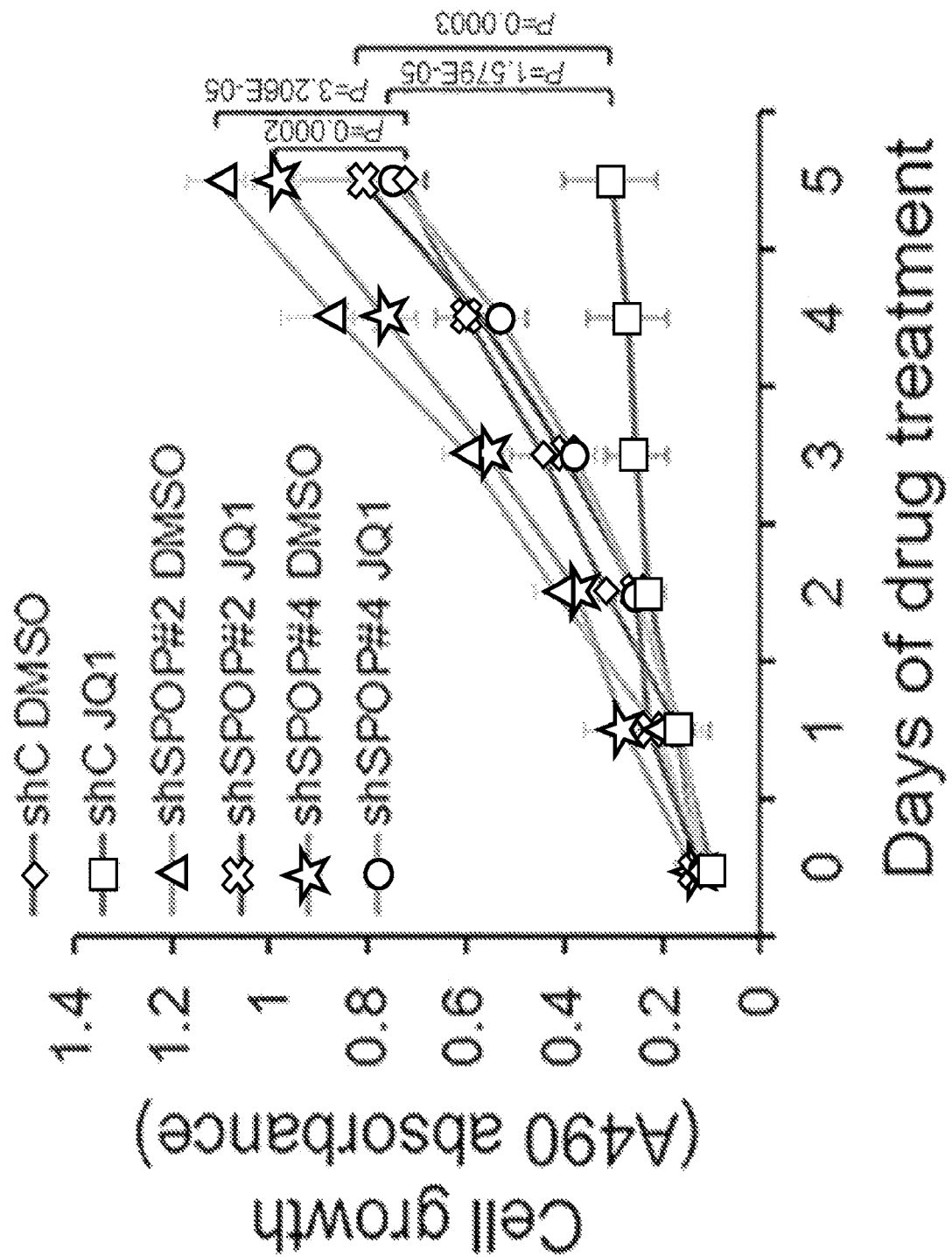
Figure 6C:
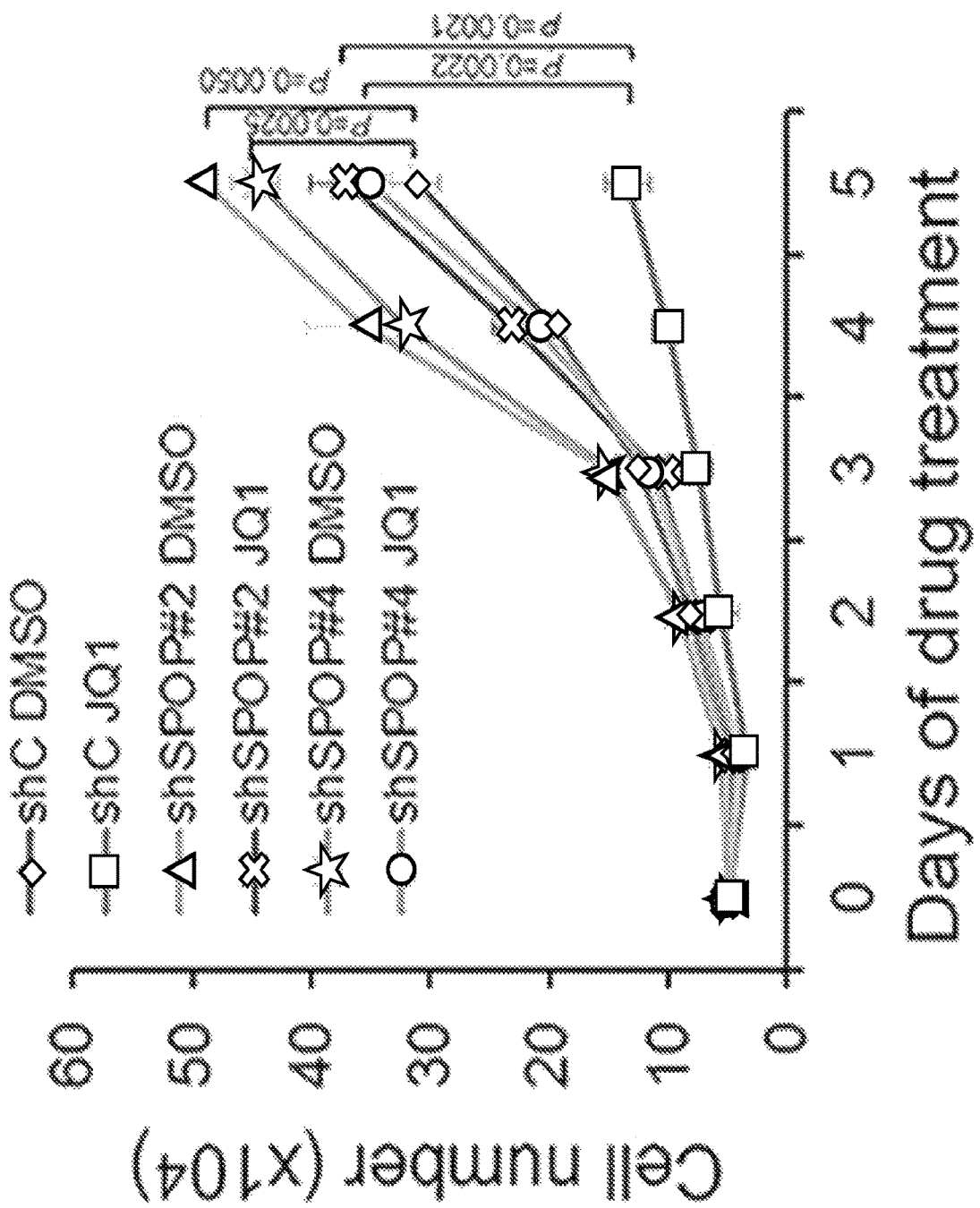
Figure 6D:
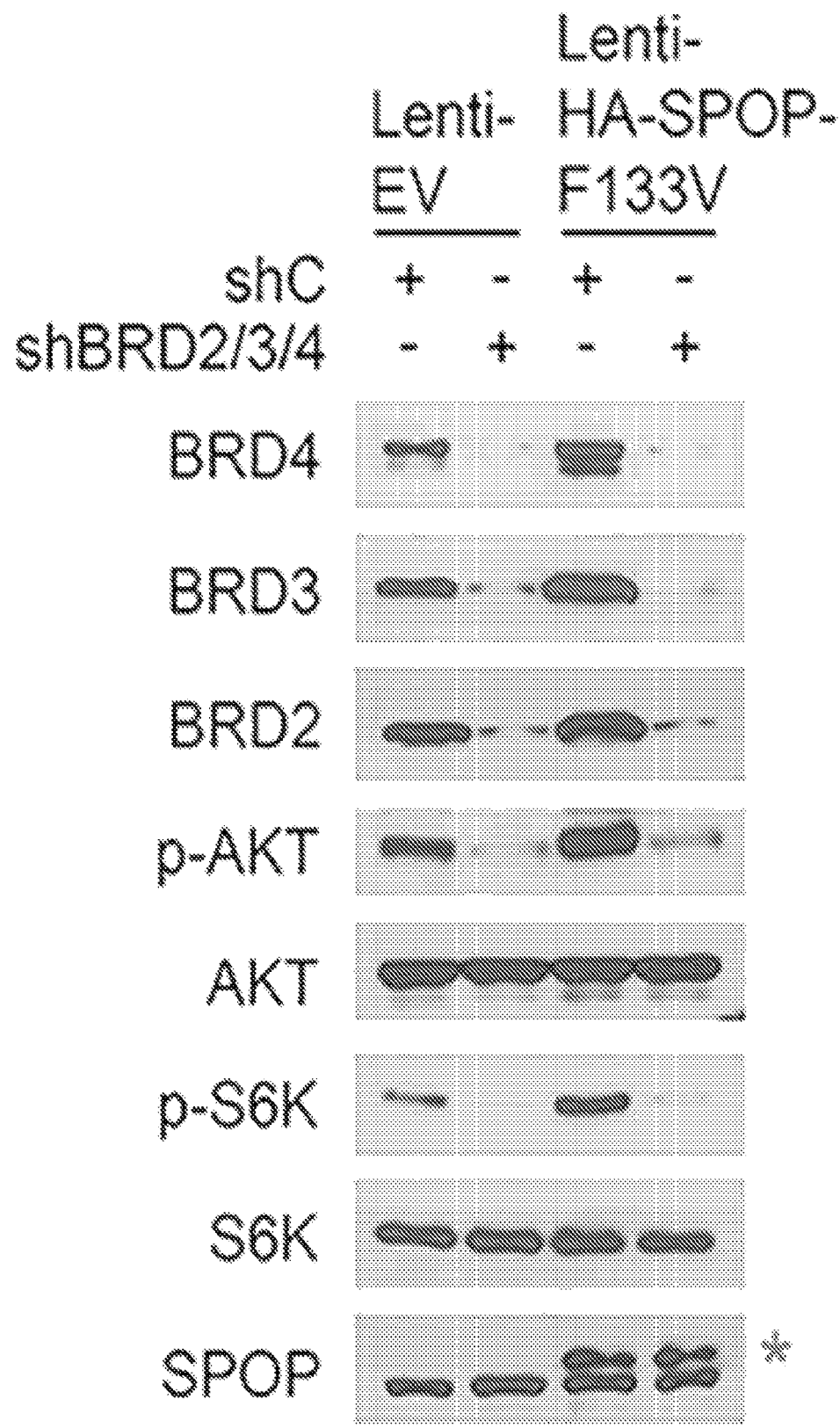
Figure 6E:
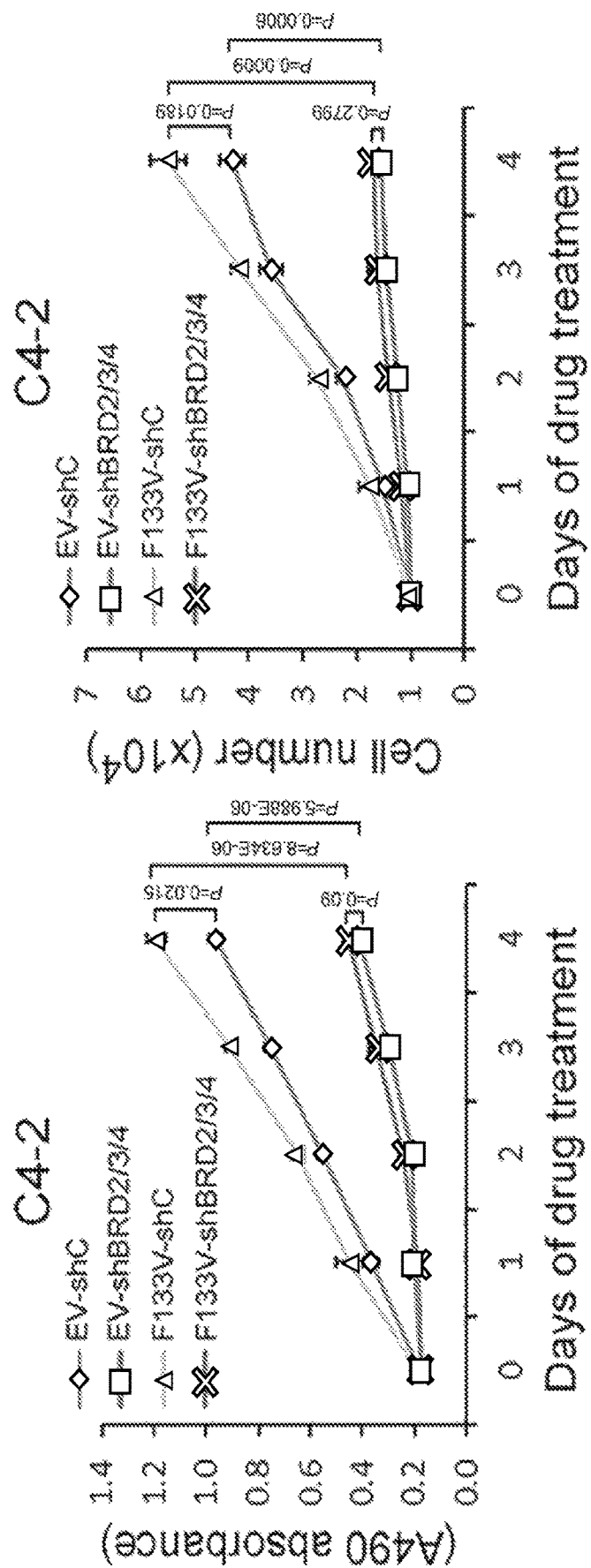
Figure 6F:
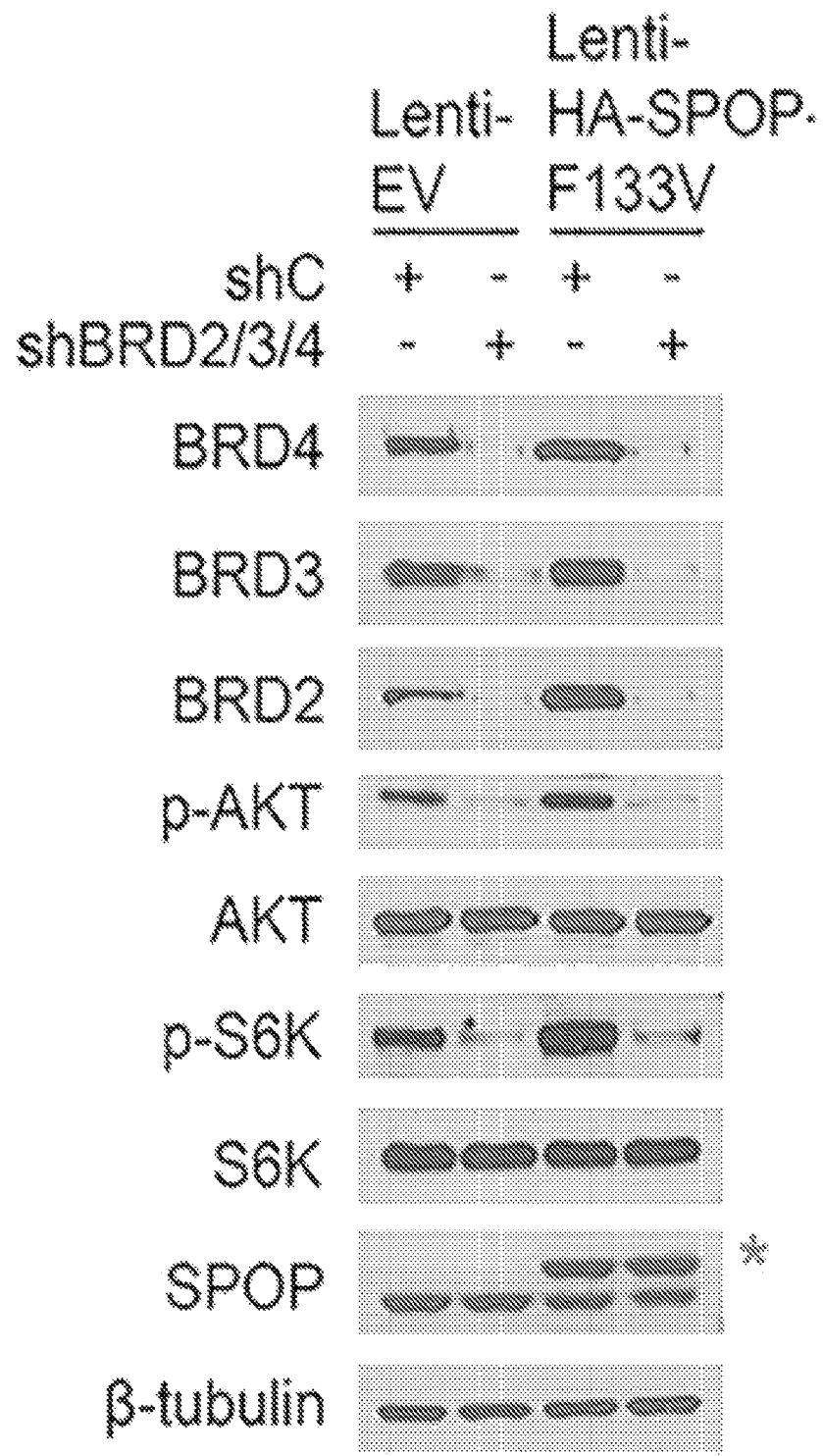
Figure 6G:
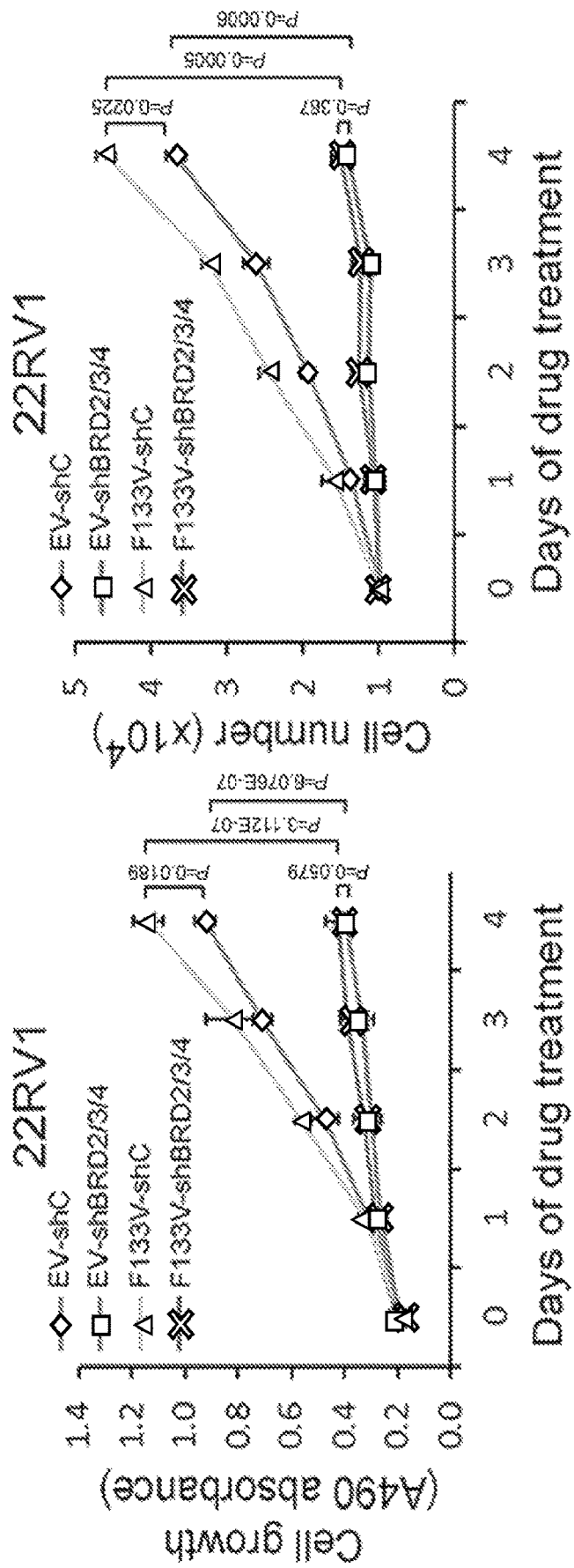
Figure 6H:
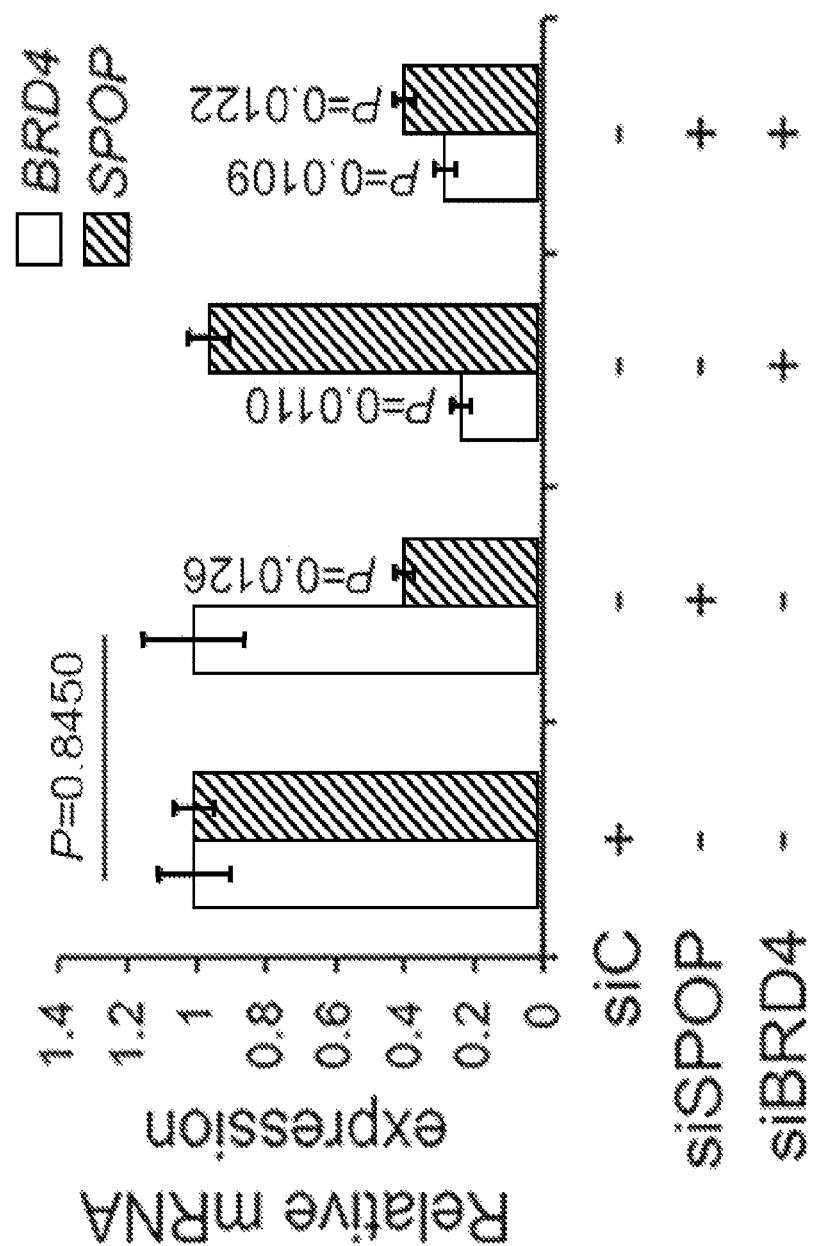
Figure 6I:
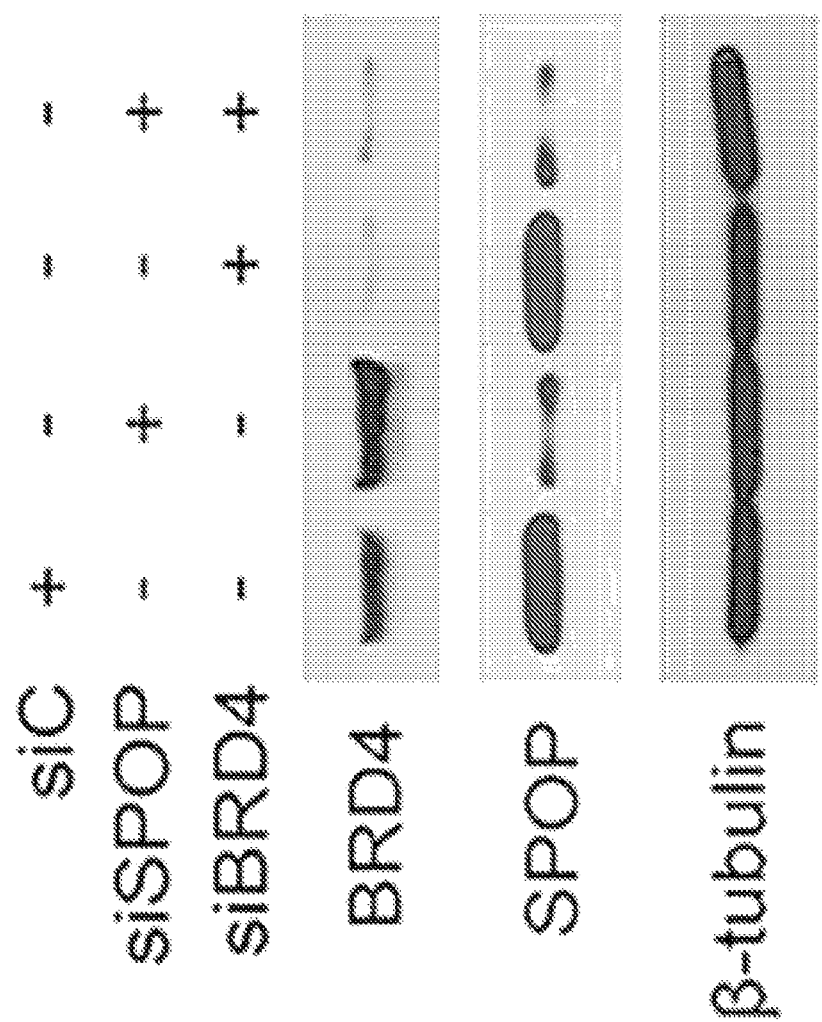
Figure 6J:
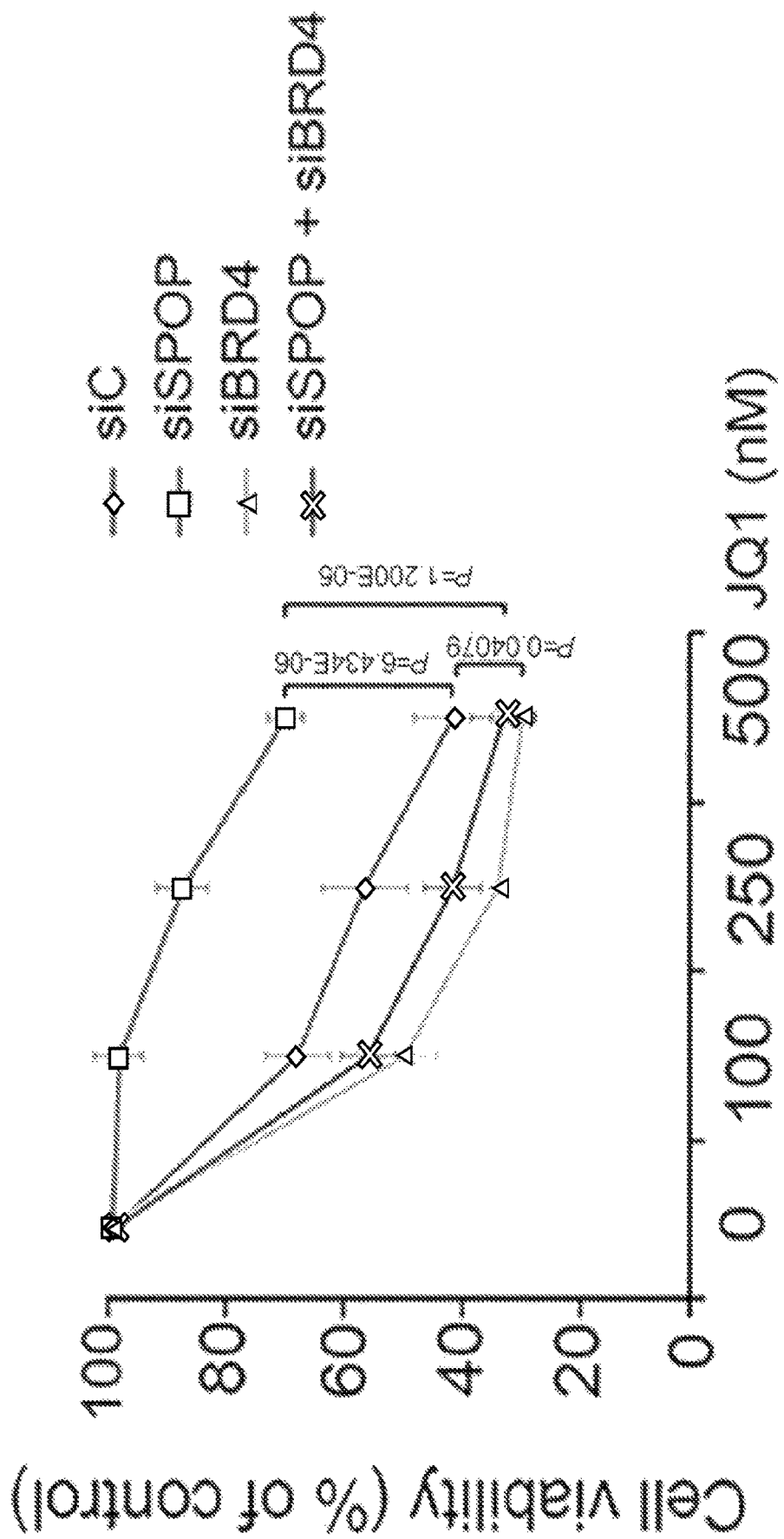
Figure 6K:
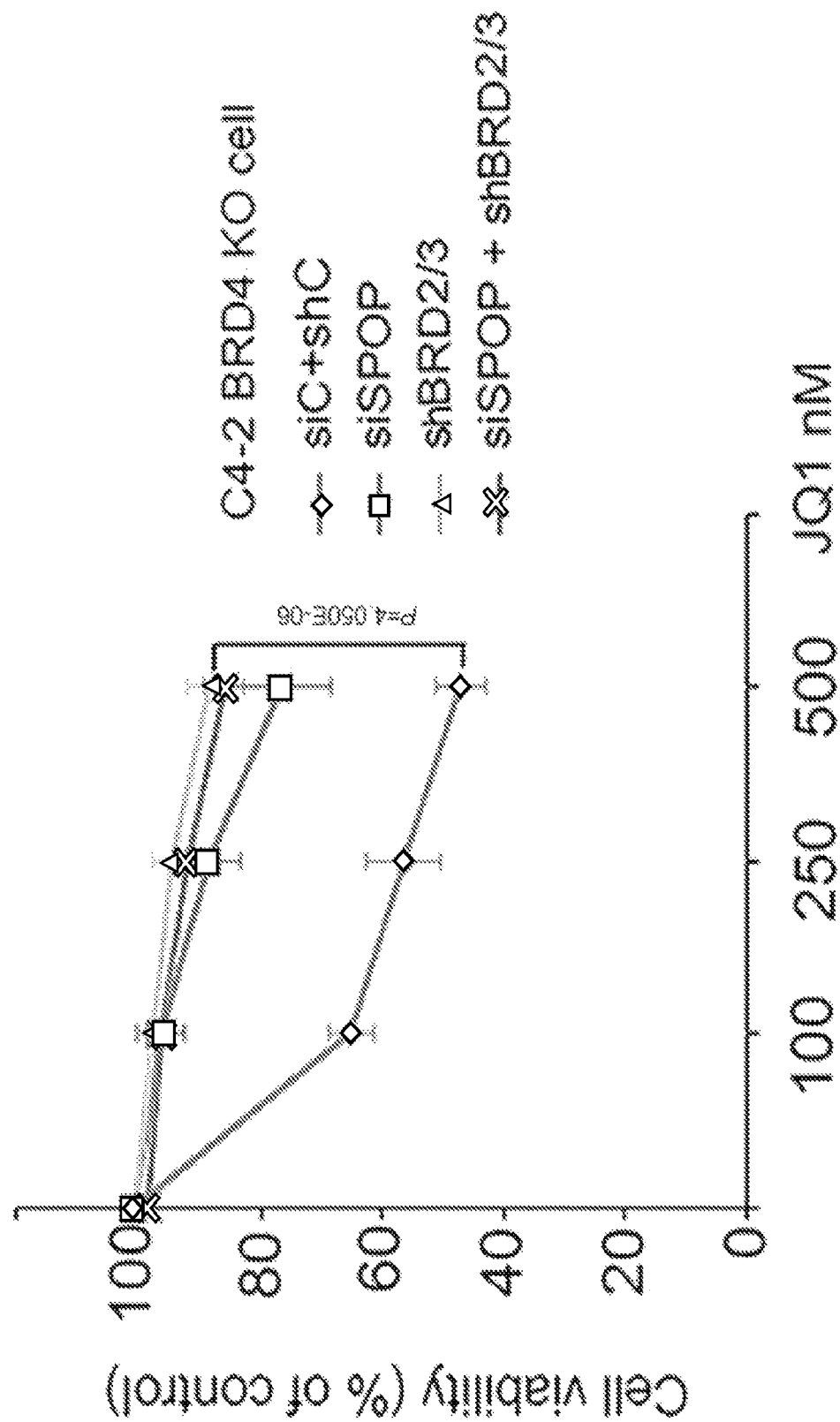
Figure 6L:
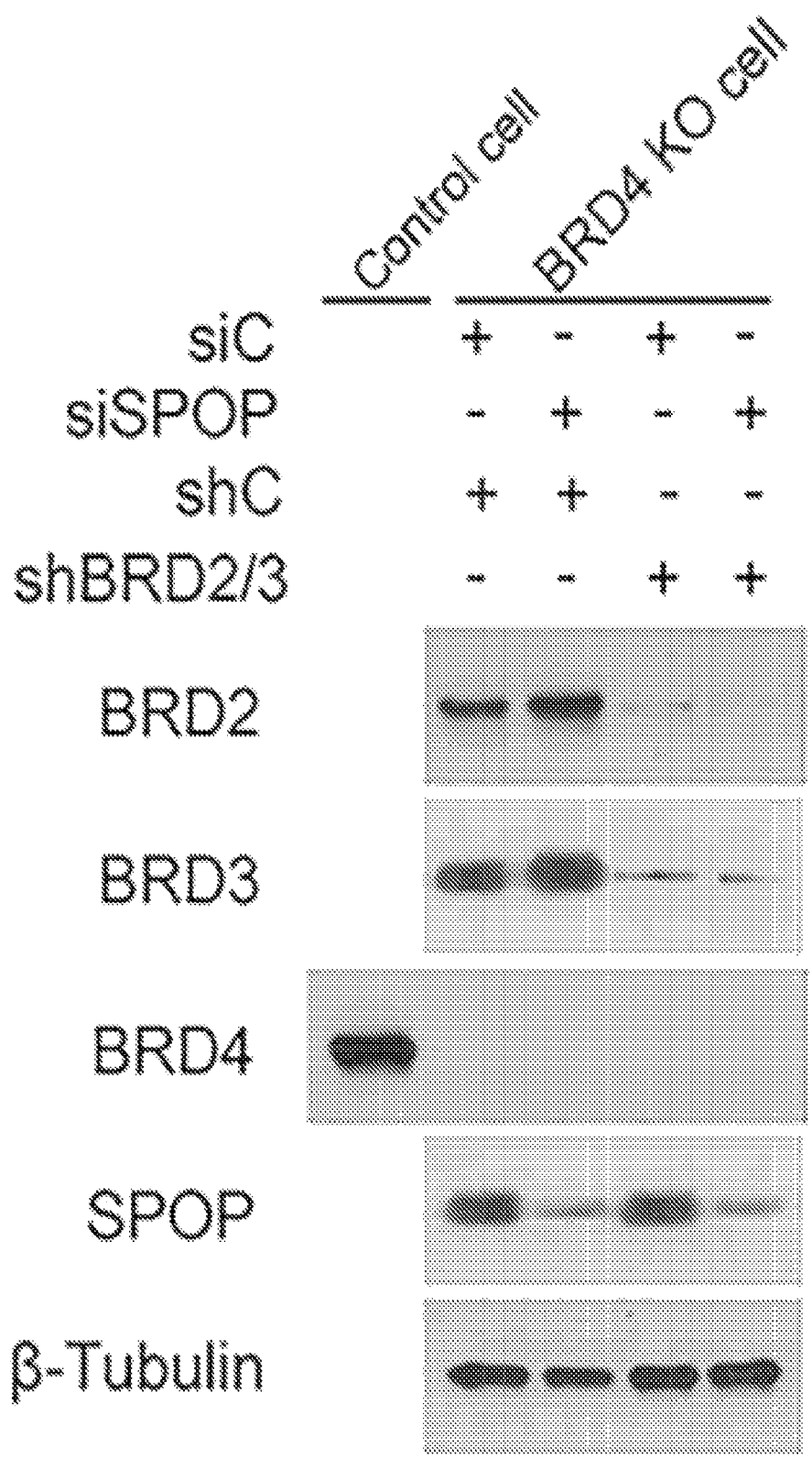

Small molecule inhibitors of BET proteins are being actively tested as promising epigenetic-targeted therapeutics of cancer (Mertz et al., Proc. Natl. Acad. Sci. USA, 108: 16669-16674 (2011); and Loven et al., Cell, 153:320-334 (2013)). The following was performed to examine if SPOP-mediated degradation of BET proteins influences the anti-cancer efficacy of BET inhibitors in prostate cancer cells. Knockdown of endogenous SPOP by small hairpin RNAs (shRNAs) not only increased BRD2/3/4 protein expression, but also enhanced proliferation in C4-2 cells, and this effect was abolished by co-knockdown of BRD2/3/4 proteins (FIGS. 6a-g). Consistent with a previous report (Asangani et al., Nature, 510:278-282 (2014)), the BET inhibitor JQ1 robustly inhibited prostate cancer cell growth, but this effect was largely attenuated in SPOP-knockdown cells (FIGS. 6a-c). SPOP depletion-mediated JQ1 resistance was reversed by knockdown of BRD4 alone (FIGS. 6h-j). However, BRD4 knockout cells became highly resistant to JQ1 when BRD2/3 were largely depleted (FIGS. 6k and 6l). These results are not surprising since little or no druggable targets (BRD2/3/4 proteins) were present in these cells. These data suggest that protein levels of BRD2/3/4 may represent a molecular determinant for JQ1 sensitivity in SPOP-deficient prostate cancer cells.

Figure 6M:
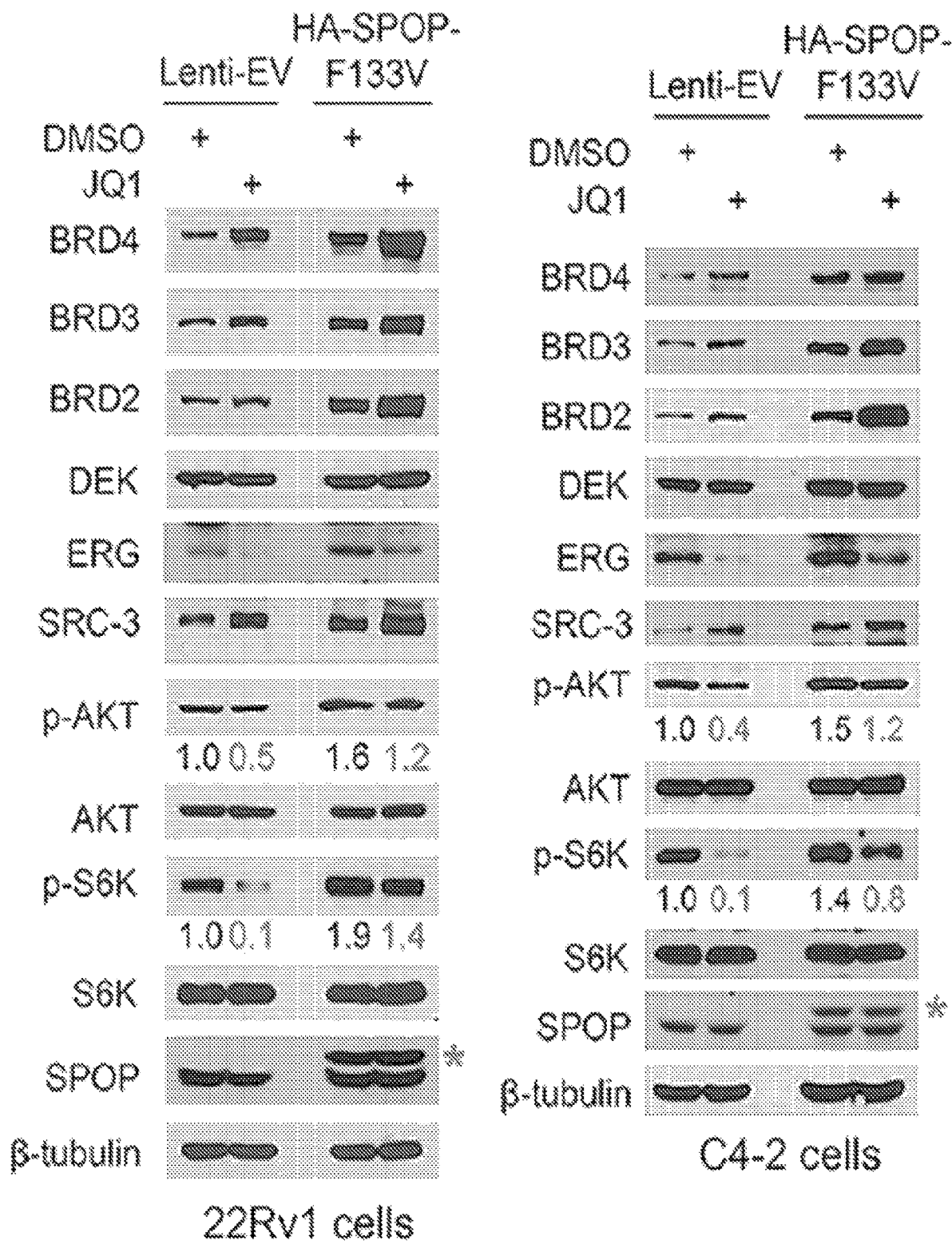
Figure 6N:
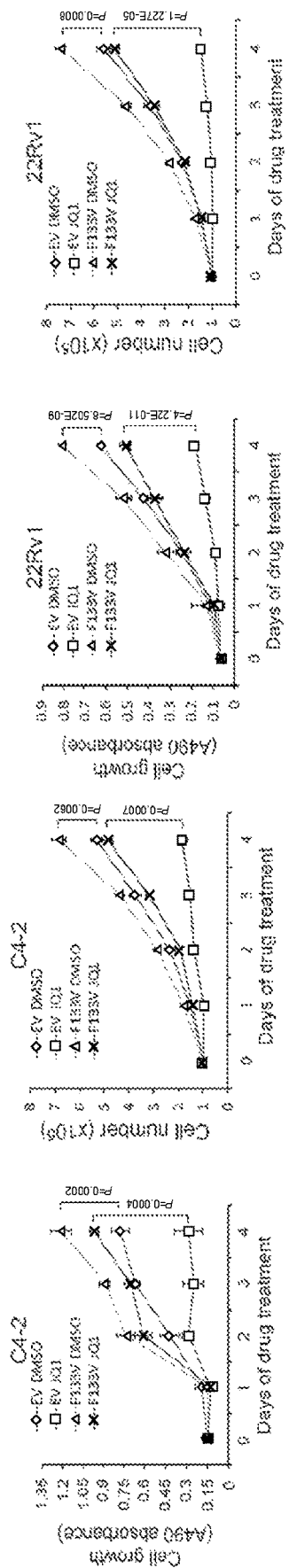
Figure 6O:
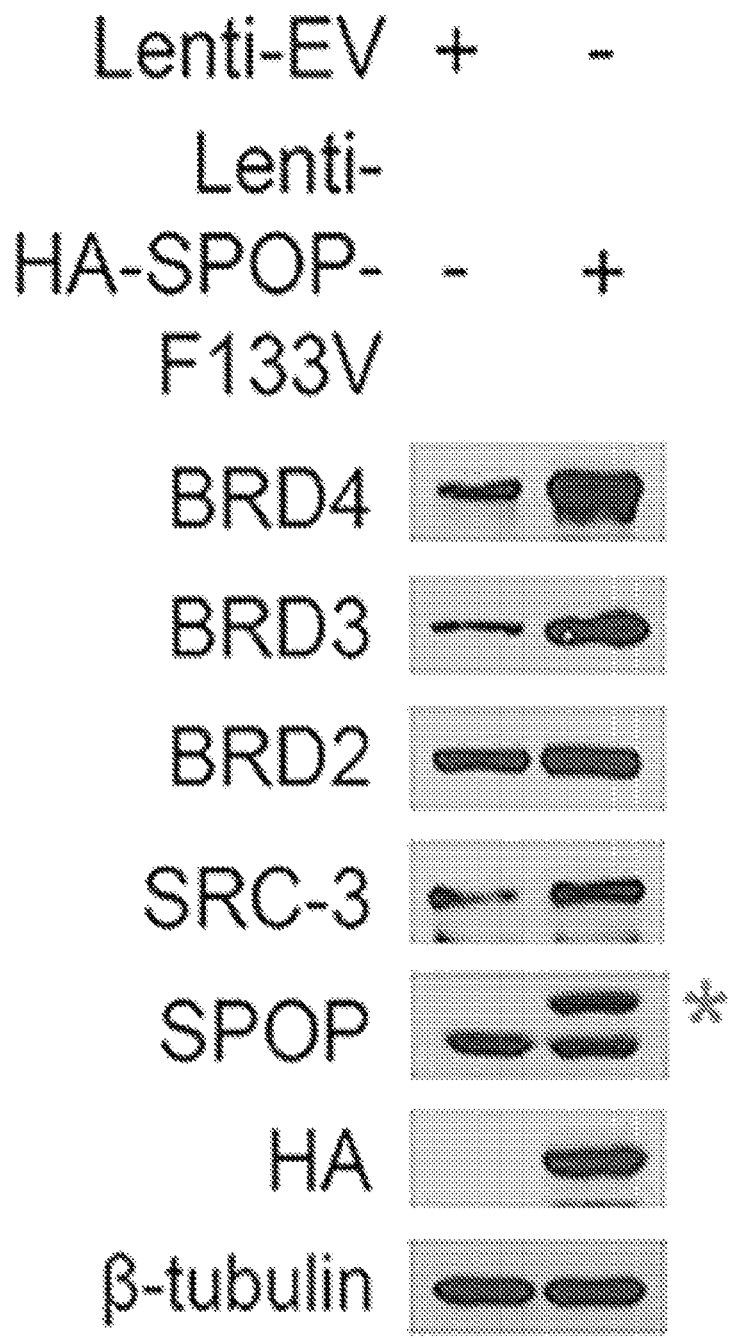
Figure 6P:
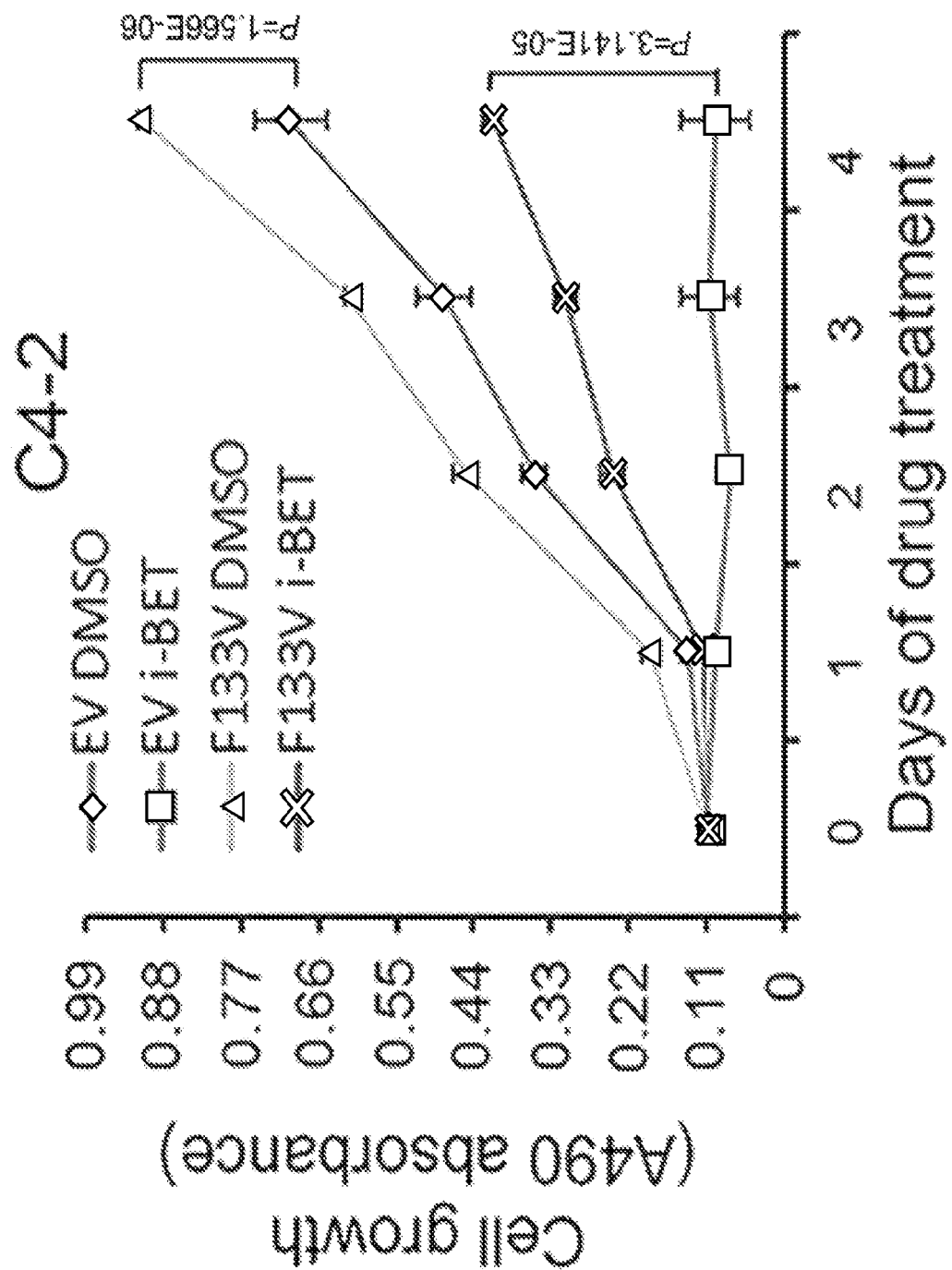
Figure 6Q:
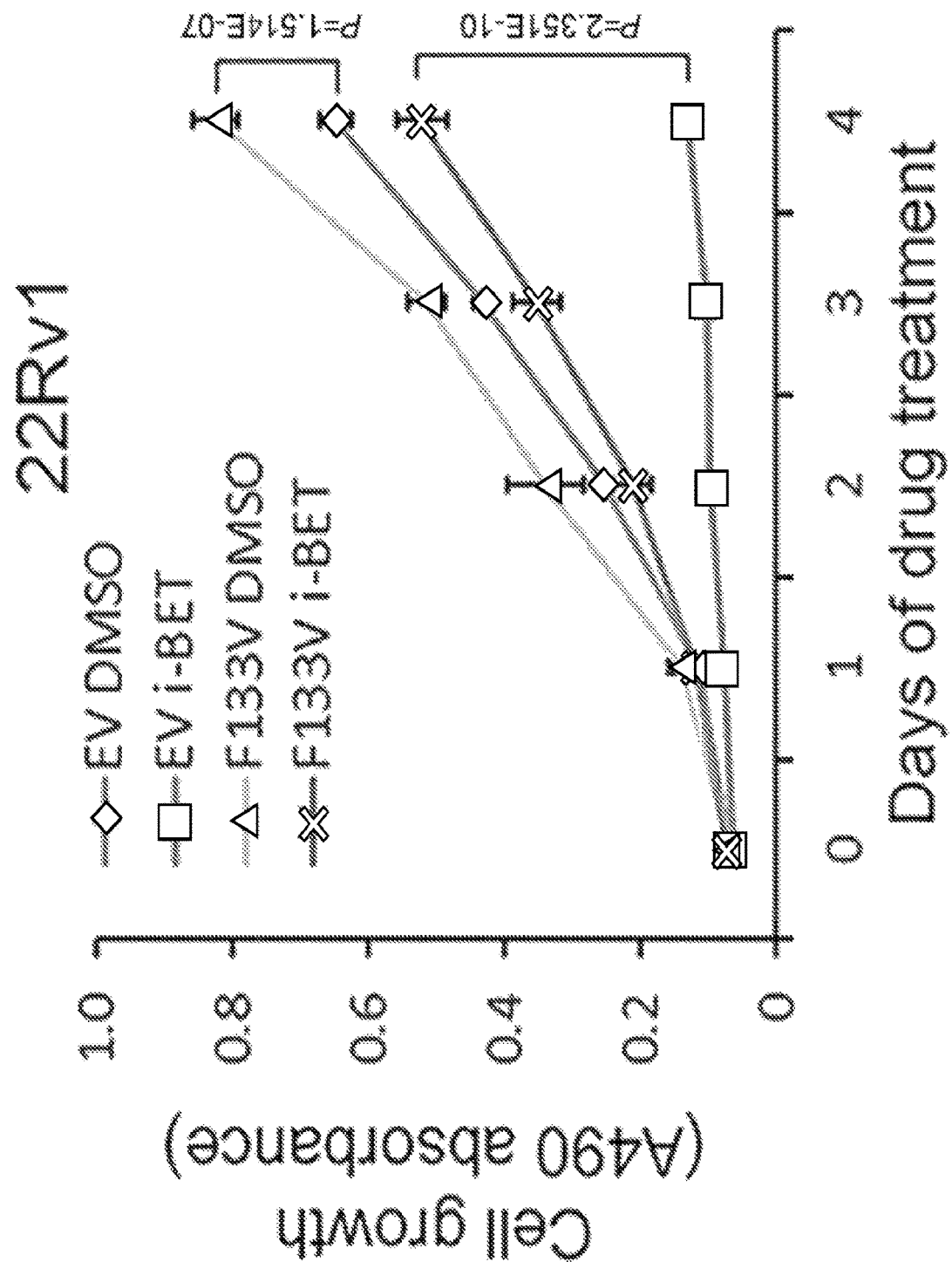
Figure 7A:
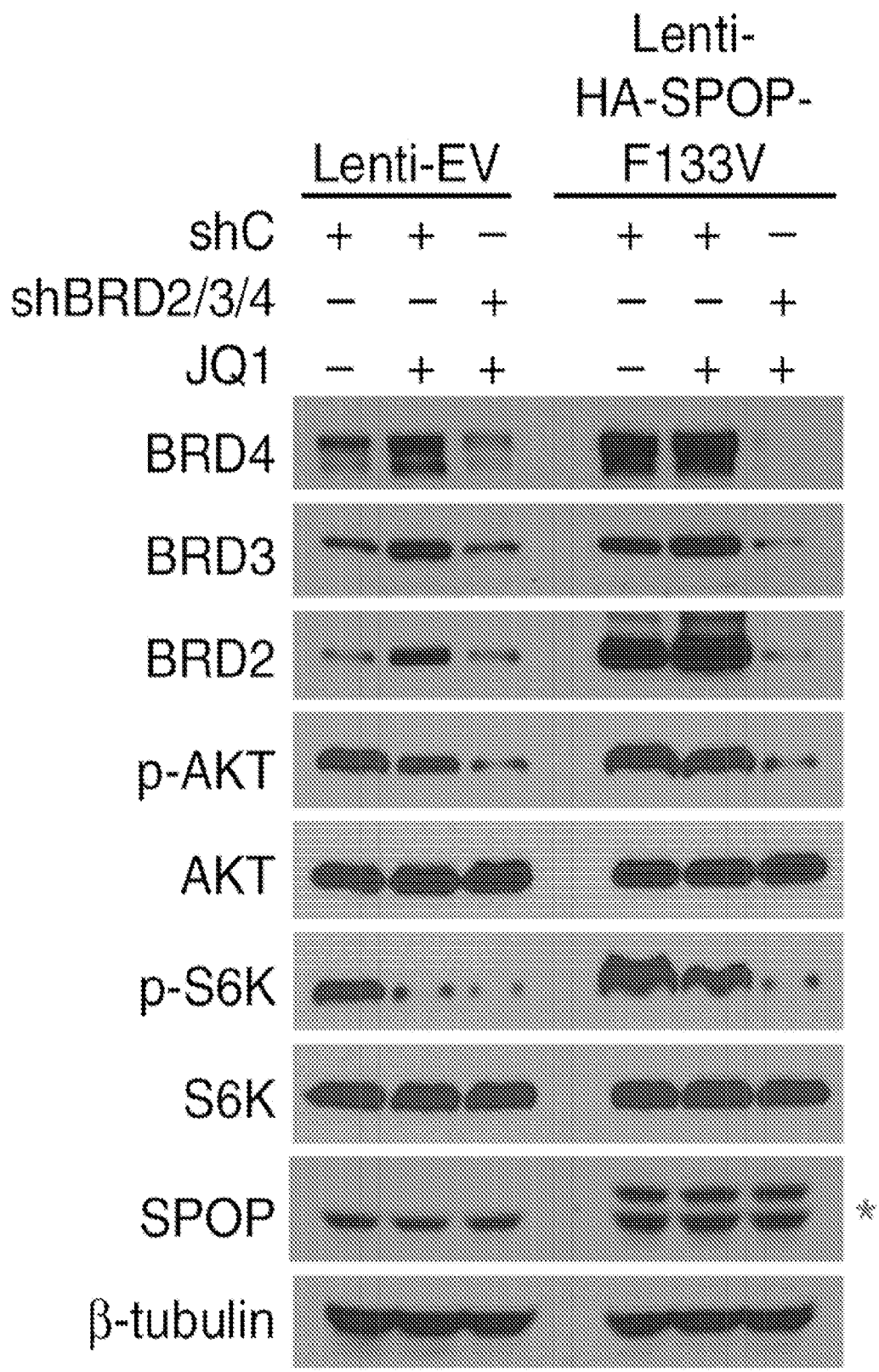
FIG. 7. Mechanism of BET inhibitor resistance in SPOP-mutated prostate cancer cells. a, Western blot of indicated proteins including p-AKT (Ser473) and p-S6K (Thr389) in C4-2 cells infected with lentivirus expressing empty vector (EV) or SPOP-F133V mutant in combination with control shRNA (shC) or BRD2/3/4-specific shRNAs. Cells were treated with or without JQ1 (1 µM) for 24 hours before being harvested. Asterisk indicates exogenous SPOP-F133V mutant. b, C4-2 cells infected with lentivirus as in (a) were implanted subcutaneously in mice (n=6/group). When tumors reached a size of approximately 100 mm$^3$, xenografted mice were treated with vehicle or JQ1 (50 mg/kg) 5 days a week. Tumors were measured by caliper twice a week. Data are shown as means±SD. Statistical significance was determined by two-tailed Student's t-test for tumors at day 21 of drug treatment. c, Image of tumors isolated from each group of mice at day 21 of drug treatment as shown in (b). d, Heat map of RNA-seq data shows expression of a cluster of genes (n=1,017) in C4-2 cells infected with lentivirus expressing EV or F133V and treated with or without JQ1 (1 µM) for 24 hours. e, Heat map showing expression of 129 genes associated with JQ1 resistance was upregulated in SPOP-mutated (MUT) prostate tumors compared to SPOP-WT tumors in the TCGA cohort. f, Venn diagram shows that JQ1-resistant genes upregulated in SPOP-mutated prostate tumors significantly overlapped with the common BRD4 target genes of SPOP F133V and HA-BRD4 overexpressed (OE) in C4-2 cells (P=9.407e-12, Permutation test). g, UCSC genome browser screen shots showing BRD4 ChIP-seq signal profiles in the RAC1 gene locus in C4-2 cells expressing EV, F133V, or HA-BRD4 treated with DMSO or JQ1 (1 µM) for 24 hours. H3K4me3 ChIP-seq was acquired from LNCaP cells as reported elsewhere (Wang et al., Nature, 474:390-394 (2011)). h, C4-2 cells infected with lentivirus as in (a) were implanted subcutaneously in mice (n=6/group). When tumors reached a size of approximately 100 mm$^3$, xenografted mice were treated with vehicle, JQ1 (50 mg/kg) or GDC-0068 (100 mg/kg) individually or in combination 5 days a week. Tumors were measured by caliper twice a week. Data are shown as means±SD. Statistical significance was determined by two-tailed Student's t-test for tumors at day 21 of drug treatment. i, Image of tumors isolated from each group of mice at day 21 of drug treatment as shown in (h).
Figure 7B:
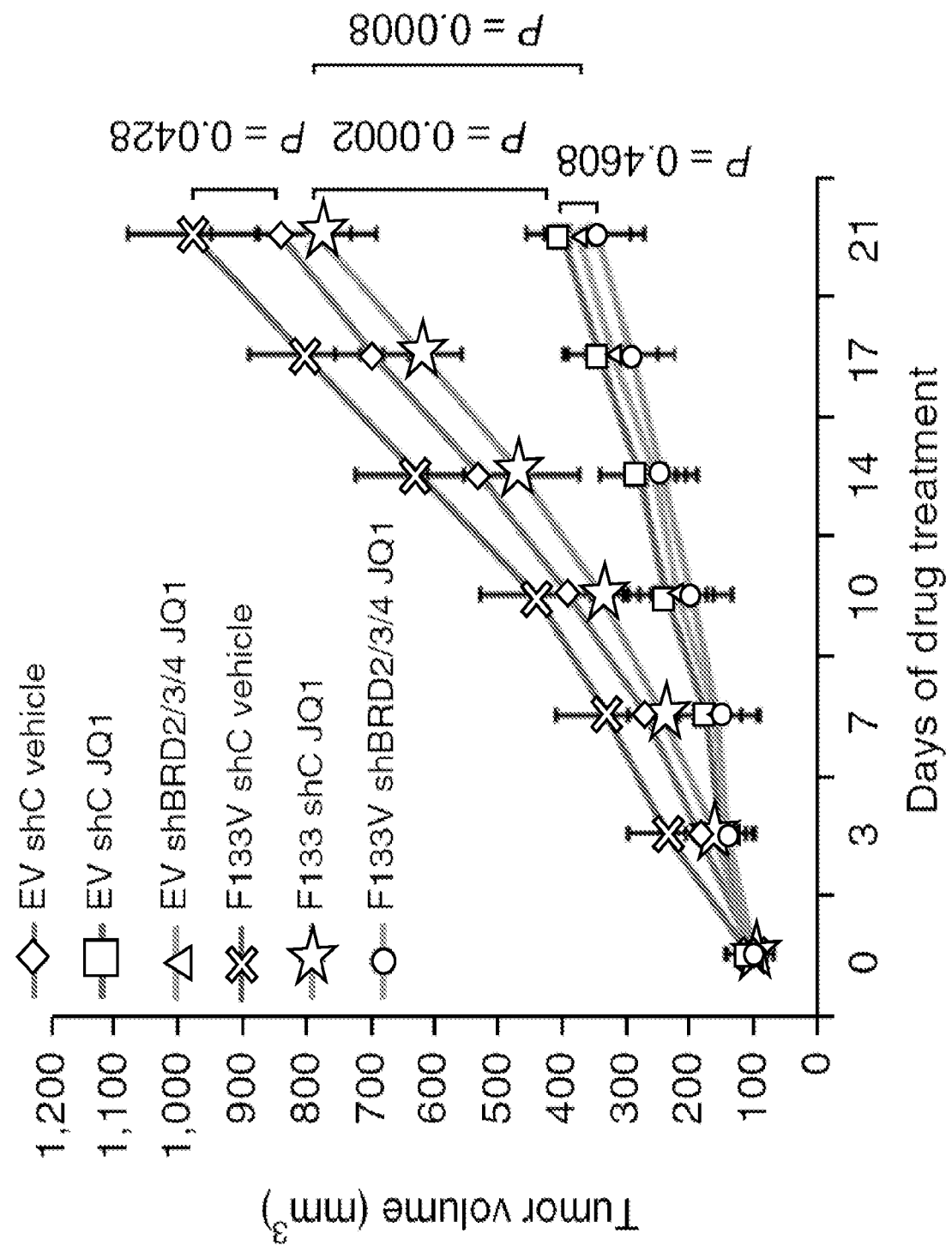
Figure 7C:
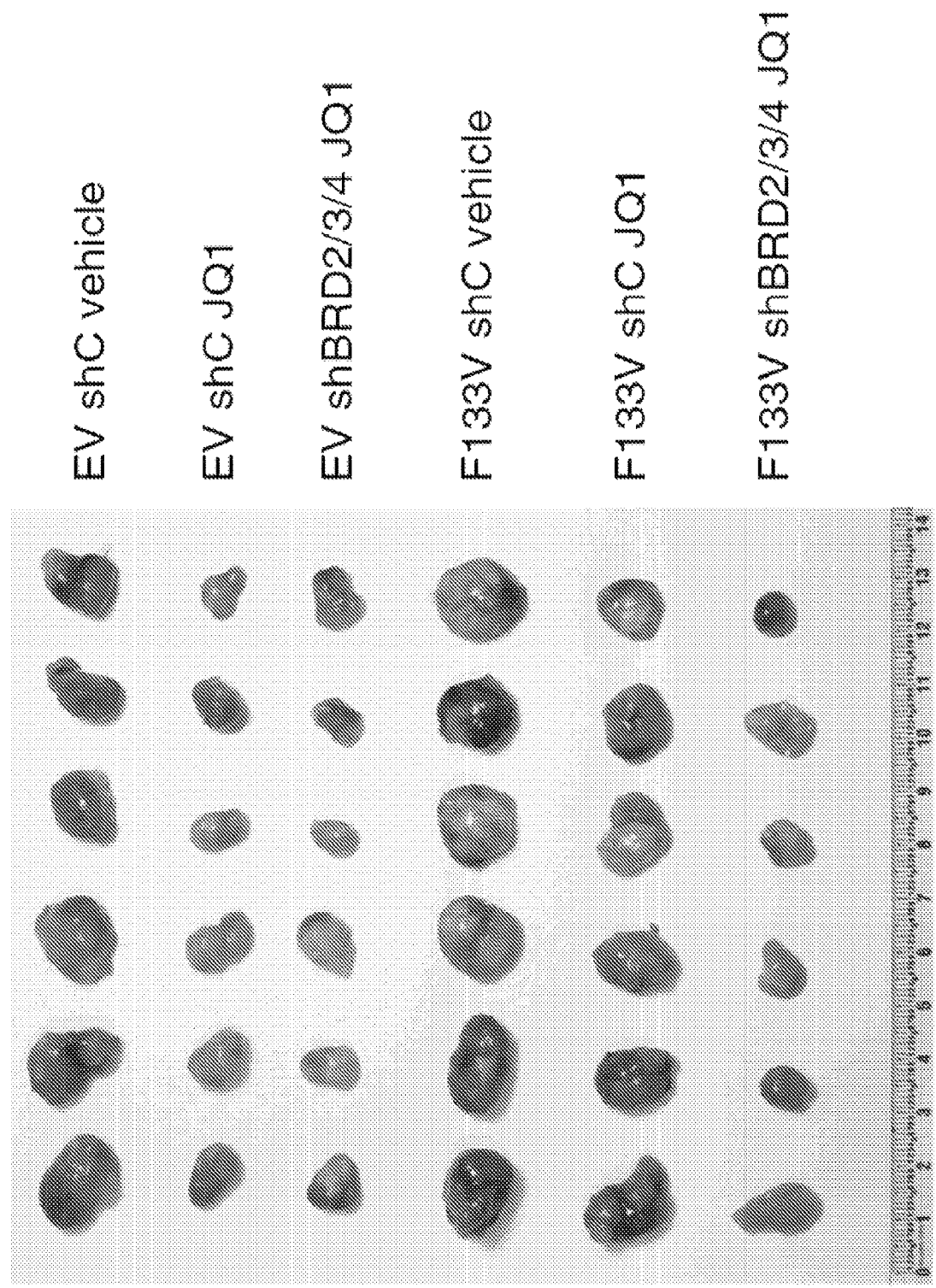
Figure 8A:
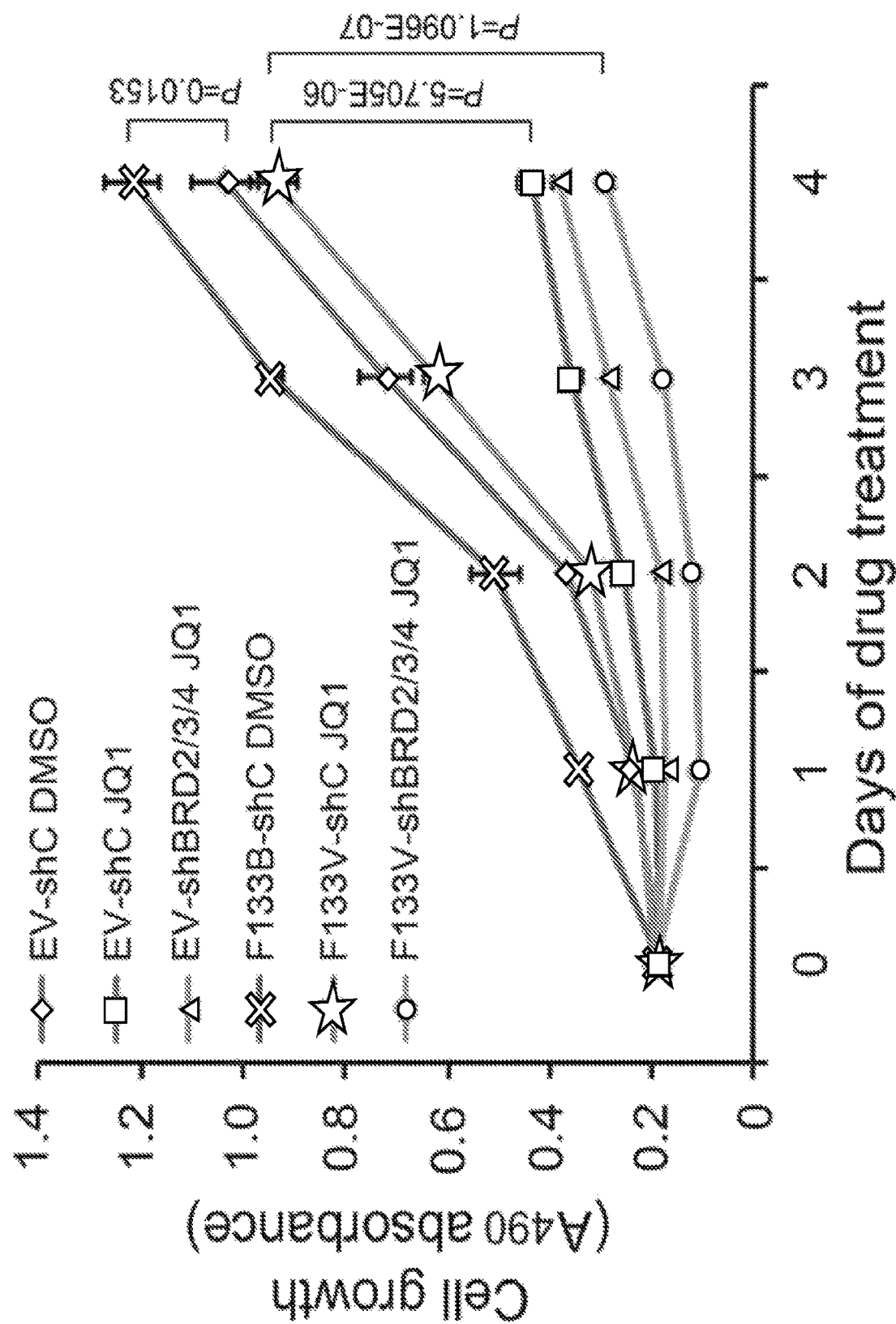
FIG. 8. SPOP mutated prostate cancer cells in culture and xenograft tumors in mice and their role in JQ1 resistance in SPOP-mutated cells. a, C4-2 cells were infected with lentivirus expressing empty vector (EV) or SPOP-F133V mutant in combination with control shRNA (shC) or BRD2/3/4-specific shRNAs as in FIG. 7a and treated with vehicle (DMSO) or JQ1 (0.25 µM) every other day. Cell growth was measured by cell proliferation assay at indicated time points. Data are shown as means±SD (n=6 biological replicates). b, Left, representative IHC images of BRD2/3/4 in xenograft tumors isolated from each groups of mice at day 21 of drug treatment as shown in FIG. 7c. The inset in each panel shows a high magnification image of the representative (framed) area. Scale bar, 50 µm. Scale bar in inset, 20 µm. Right, the quantitative data of BRD2/3/4 IHC staining indicate the percentage of the cells with different intensity of staining (weak, intermediate and strong) in each high-power field image. Similar results were obtained from three independent xenograft tumors in each group (n=3 xenograft tissues/group). Dash lines in green indicate the base-line level of strong staining of BRD2/3/4 proteins in control (EV-shC) C4-2 cells without JQ1 treatment. c, Left, representative IHC images of Ki-67 in xenograft tumors isolated from each groups of mice at day 21 of drug treatment as shown in FIG. 7c. The inset in each panel shows a high magnification image of the representative (framed) area. Scale bar, 50 µm. Scale bar in inset, 20 µm. Right, the quantitative data of Ki-67 IHC staining indicate the percentage of Ki-67-positive cells among population in each high-power field image. Data are shown as means±SD (n=3 xenograft tissues/group). d, Western blot of WCL from xenograft tumors in four groups as shown in FIG. 7c. Equal amount of tissues from 3 tumors per group were combined and lysed together prior to analysis. Asterisk indicates the exogenous HA-SPOP-F133V. e, Western blot of WCL of C4-2 cells infected with lentivirus expressing empty vector (EV) or SPOPF133V mutant in combination with control shRNA (shC), ERG-, DEK-, or SRC-3-specific shRNAs and treated with vehicle (DMSO) or JQ1 (1 µM) for 24 hours before being harvested. f, C4-2 cells were infected with lentivirus as in (e) and treated with vehicle (DMSO) or JQ1 (0.25 µM) every other day, and cell growth was measured by cell proliferation assay at indicated time points. Data are shown as means±SD (n=6 biological replicates).
Figure 8B:
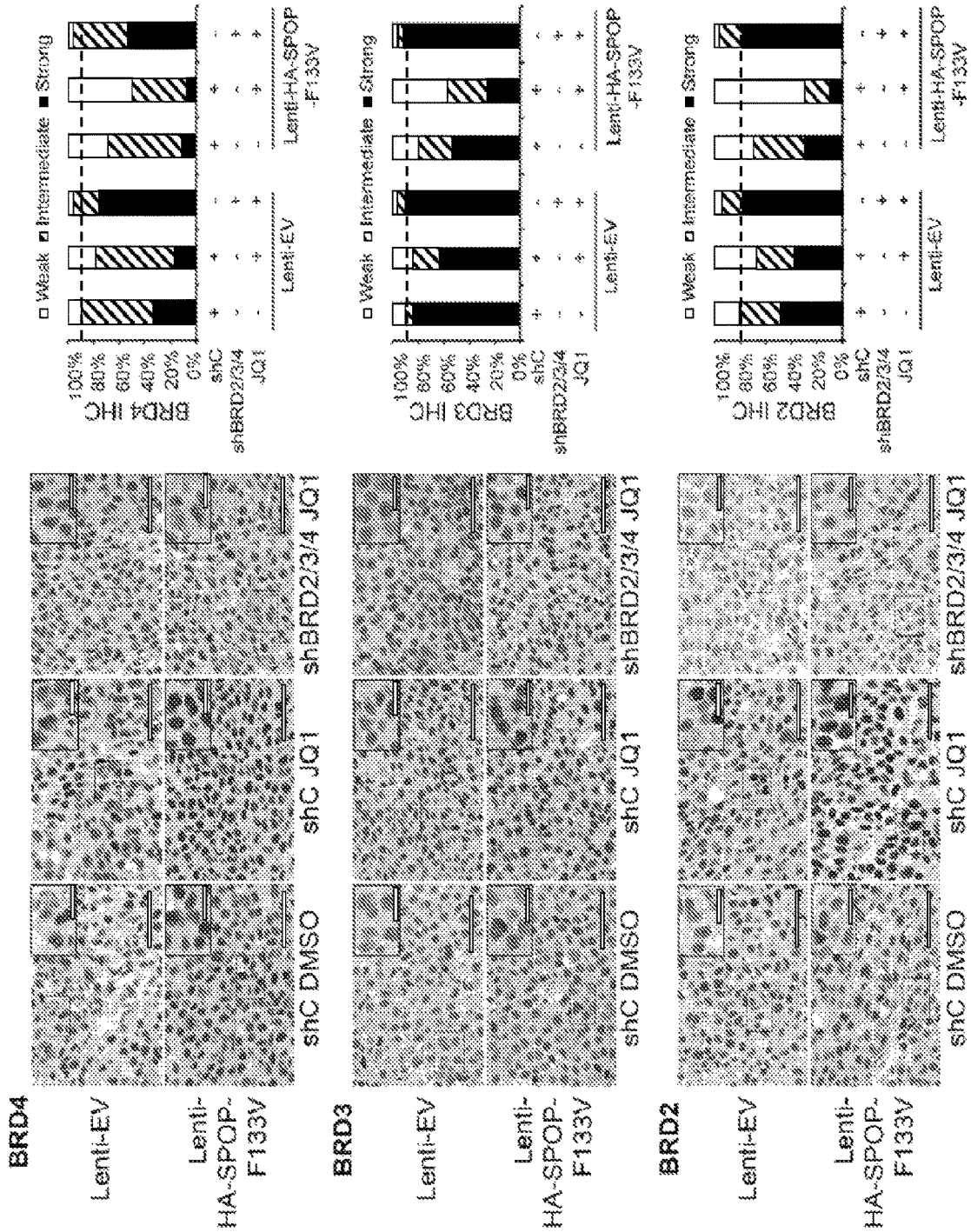
Figure 8C:
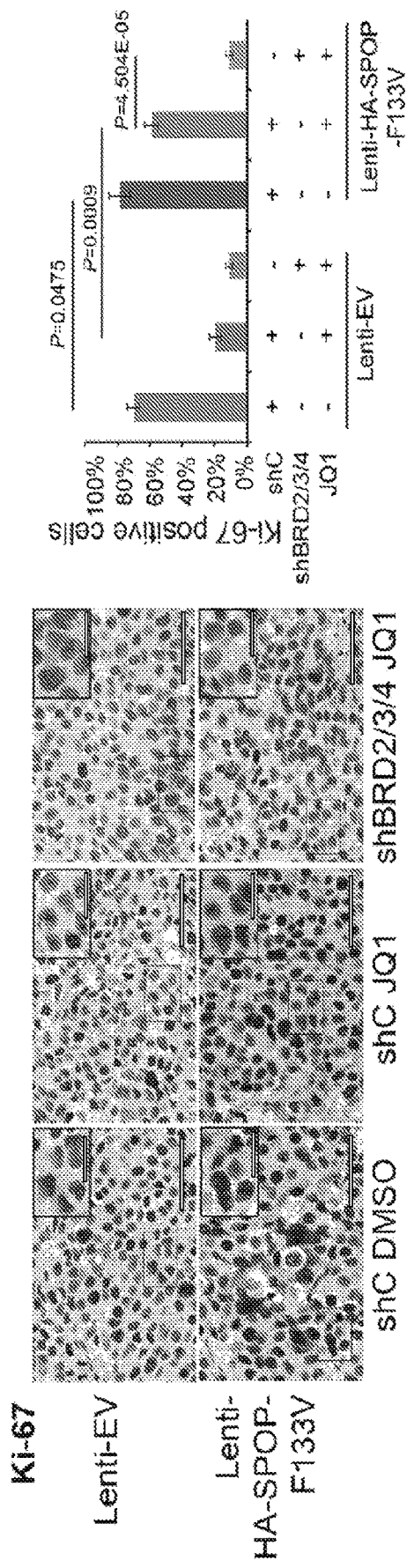
Figure 8D:
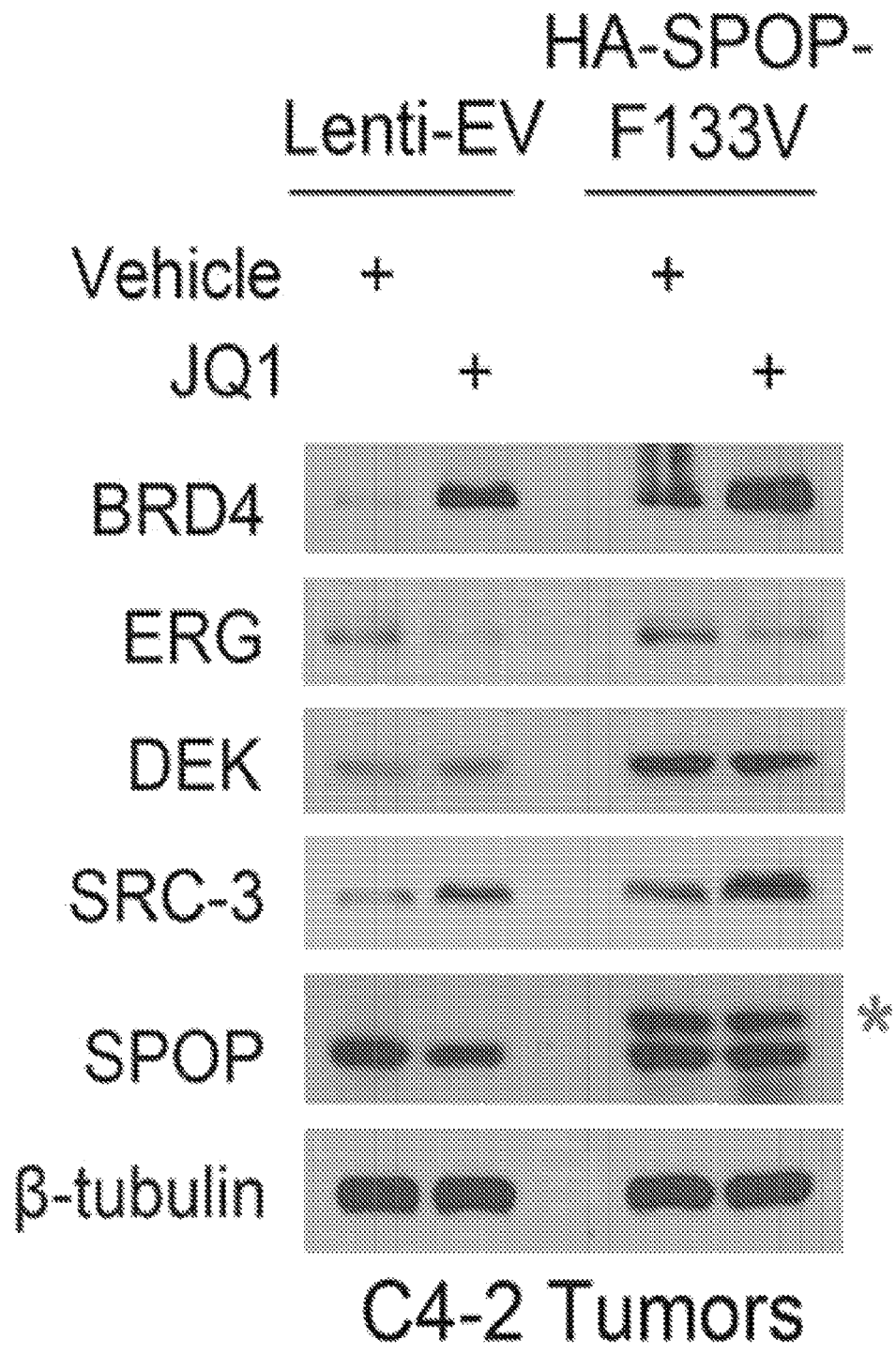
Figure 8E:
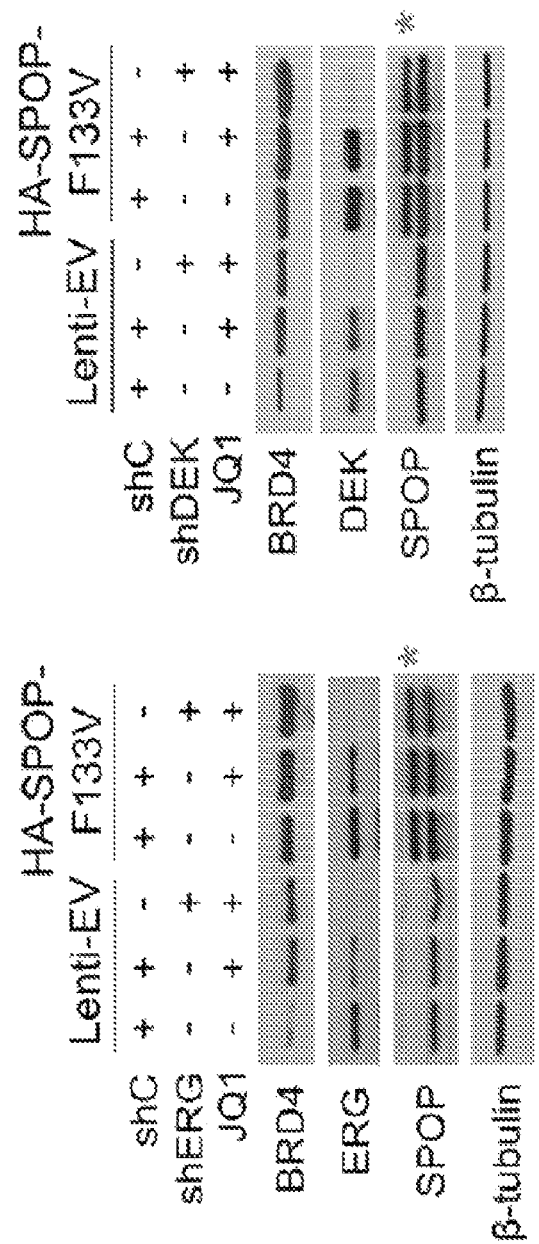
Figure 8E:
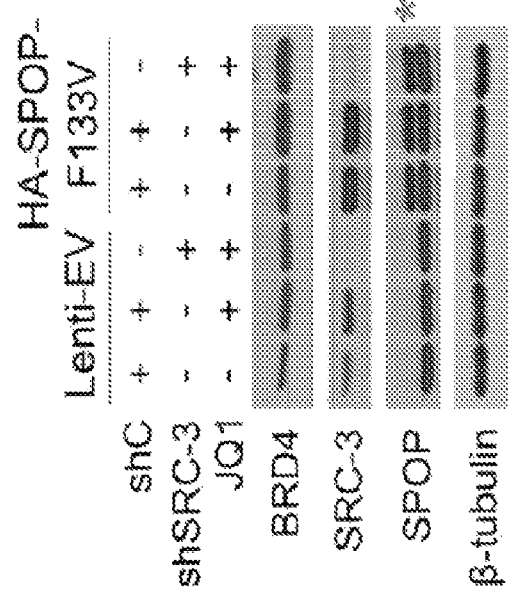
Figure 8F:
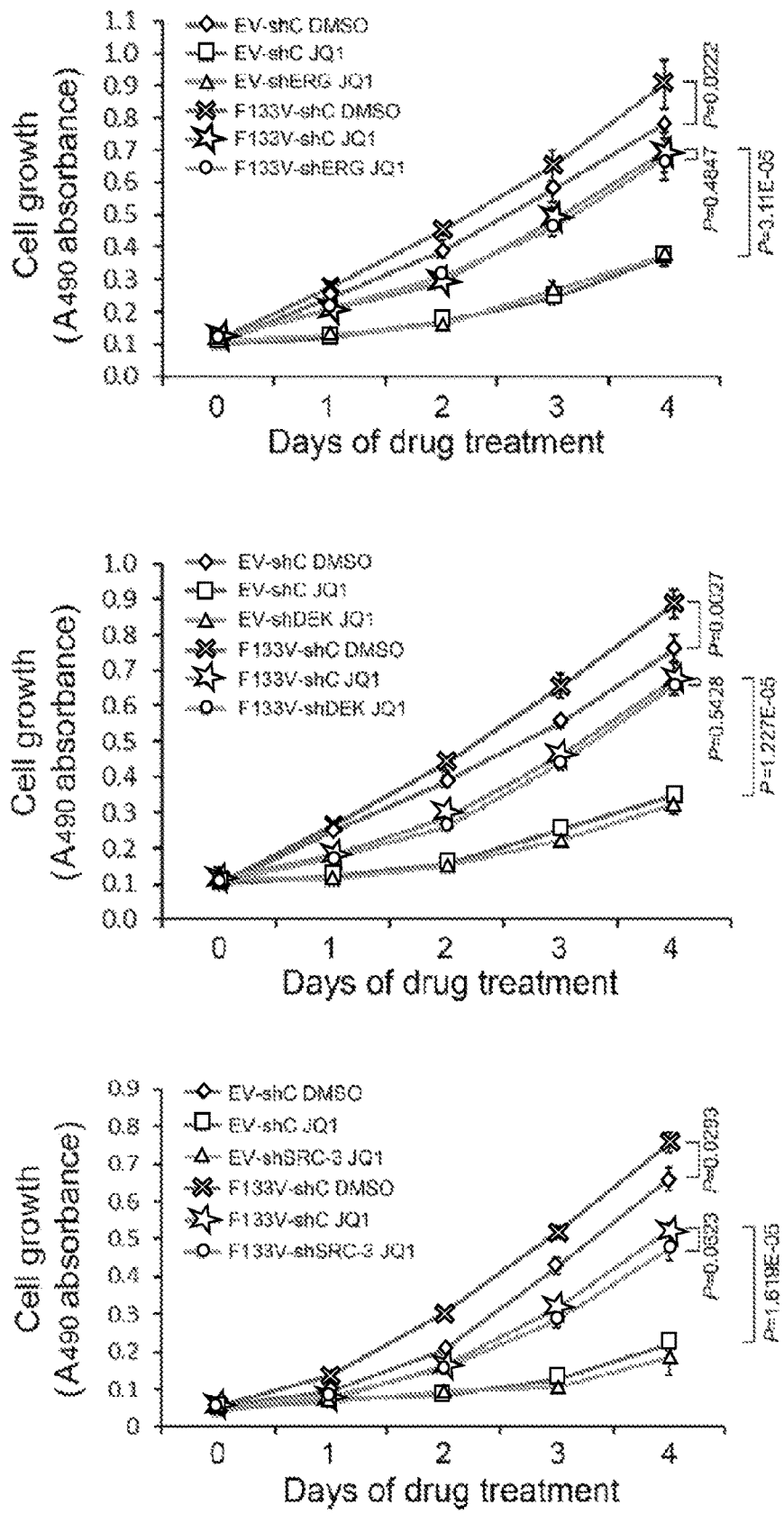

Phenylalanine 133 (F133) is the most frequently mutated residue in SPOP (Barbieri et al., Nat. Genet., 44:685-689 (2012)). To recapitulate the situation in patients, SPOP-F133V mutant was introduced into SPOP-WT-expressing C4-2 and 22Rv1 cells. Expression of SPOP-F133V not only induced accumulation of BRD2/3/4 proteins, but also caused a significant increase in proliferation in both cell lines (FIGS. 6m and 6n). While JQ1 treatment inhibited growth of empty vector (EV)-expressing C4-2 and 22Rv1 cells, the effect of JQ1 was largely impeded in SPOP-F133V-expressing cells (FIG. 6n). SPOP-F133V expression also caused similar resistance to another BET inhibitor (i-BET) in C4-2 and 22Rv1 cells (FIGS. 6o-q). The SPOP-F133V mutant also was shown to confer JQ1-resistance in C4-2 xenograft tumors in mice (FIGS. 7a-c). SPOP-F133V-mediated JQ1-resistance was completely reversed by co-depletion of BRD2/3/4 proteins in C4-2 cells in vitro and in C4-2 xenografts in mice (FIGS. 7a-c and 8a-c). SPOP-F133V expression also induced accumulation of known SPOP substrates ERG, DEK and SRC-3 in C4-2 and 22Rv1 cells and C4-2 tumors in mice (FIGS. 6m and 8d). However, JQ1 treatment largely decreased ERG expression (FIGS. 6m, 8d, and 8e), which was consistent with similar findings in acute myeloid leukemia cells (Roe et al., Mol. Cell, 58:1028-1039 (2015)). Knockdown of ERG by shRNAs had no overt effect on SPOP-F133V-mediated JQ1 resistance in C4-2 cells, and similar results were obtained in DEK-knockdown cells (FIGS. 8e and 8f). SRC-3 knockdown slightly sensitized SPOP-F133V cells to JQ1, but the effect was not statistically significant (FIGS. 8e and 8f). Thus, these results demonstrate that SPOP mutation-conferred BET inhibitor resistance is largely mediated by elevation of BRD2/3/4 proteins in prostate cancer cells.

Figure 9A:
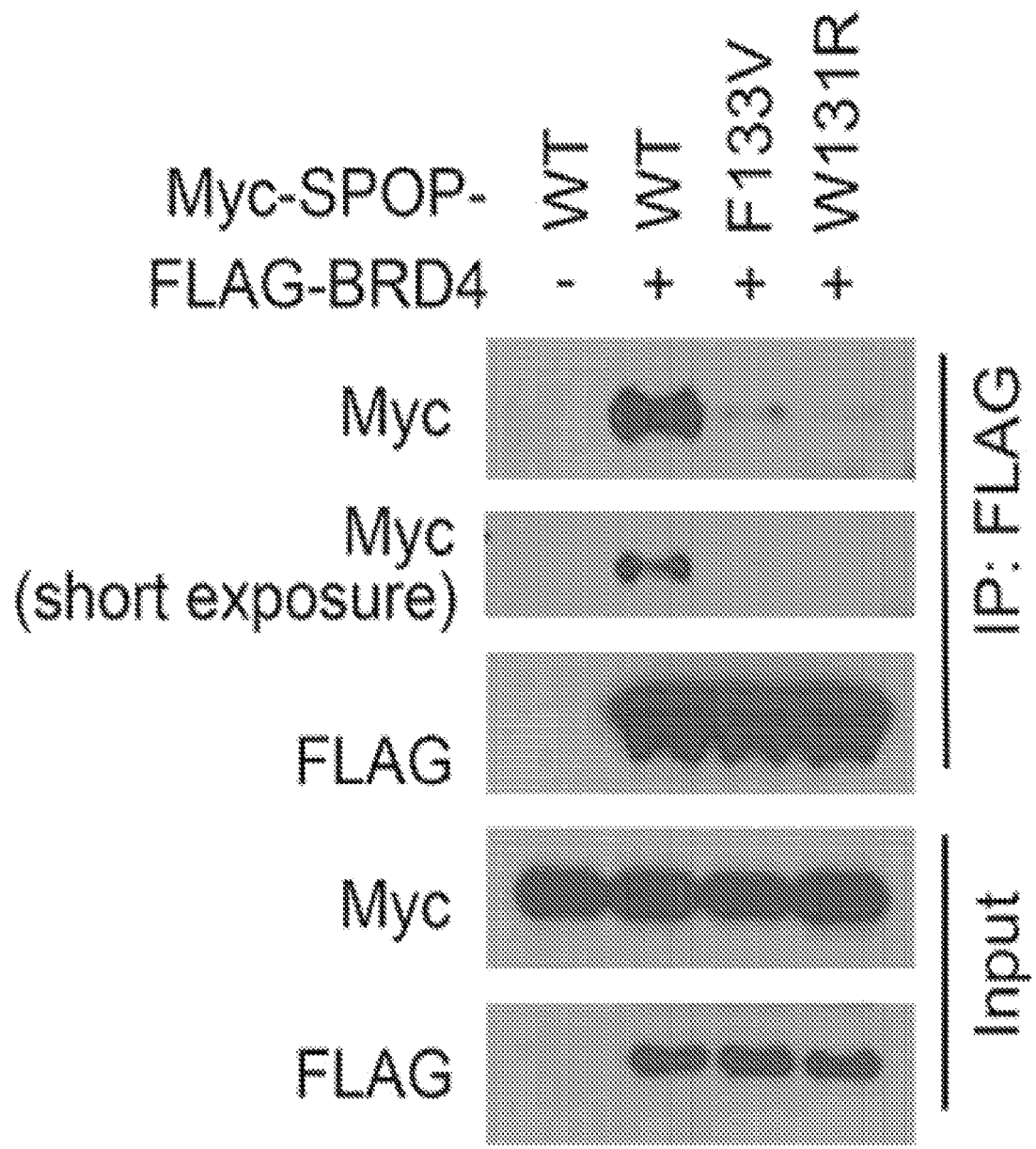
FIG. 9. SPOP mutated organoids are resistant to JQ1. a, Western blot of WCL and co-IP samples of anti-FLAG antibody from 293T cells transfected with indicated plasmids and treated with 20 µM MG132 for 8 hours. b, Western blot of indicated proteins in WCL of 293T cells transfected with indicated plasmids. c, Western blot of the products of in vivo ubiquitination assay from 293T cells transfected with indicated plasmids and treated with 20 µM MG132 for 8 hours. d, Western blot of the expression of BRD2, BRD3, BRD4, and SPOP in three patient-derived organoid cell lines. β-tubulin was used as a loading control. ASC1, SPOP-W131R mutation cells; BM1 and BMS, SPOP wild-type cells. e, Cell viability of organoids were measured by cell proliferation assay by treating with different concentration of JQ1 for 24 hours. f, Representative pictures of 3D cultured organoids treated with 0.2 µM JQ1 at day 7. Scale bars, 100 µm. g, The quantitative data of the size of organoids shown in (f). n=50.
Figure 9B:
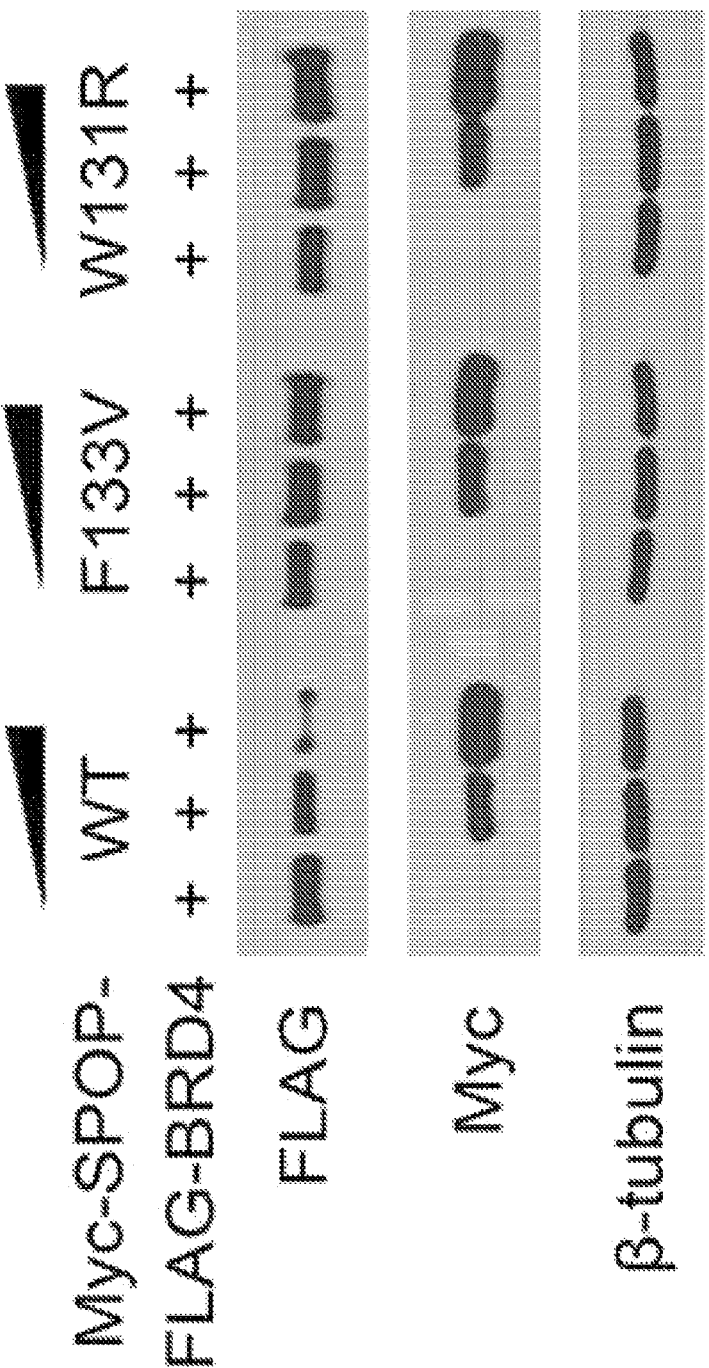
Figure 9C:
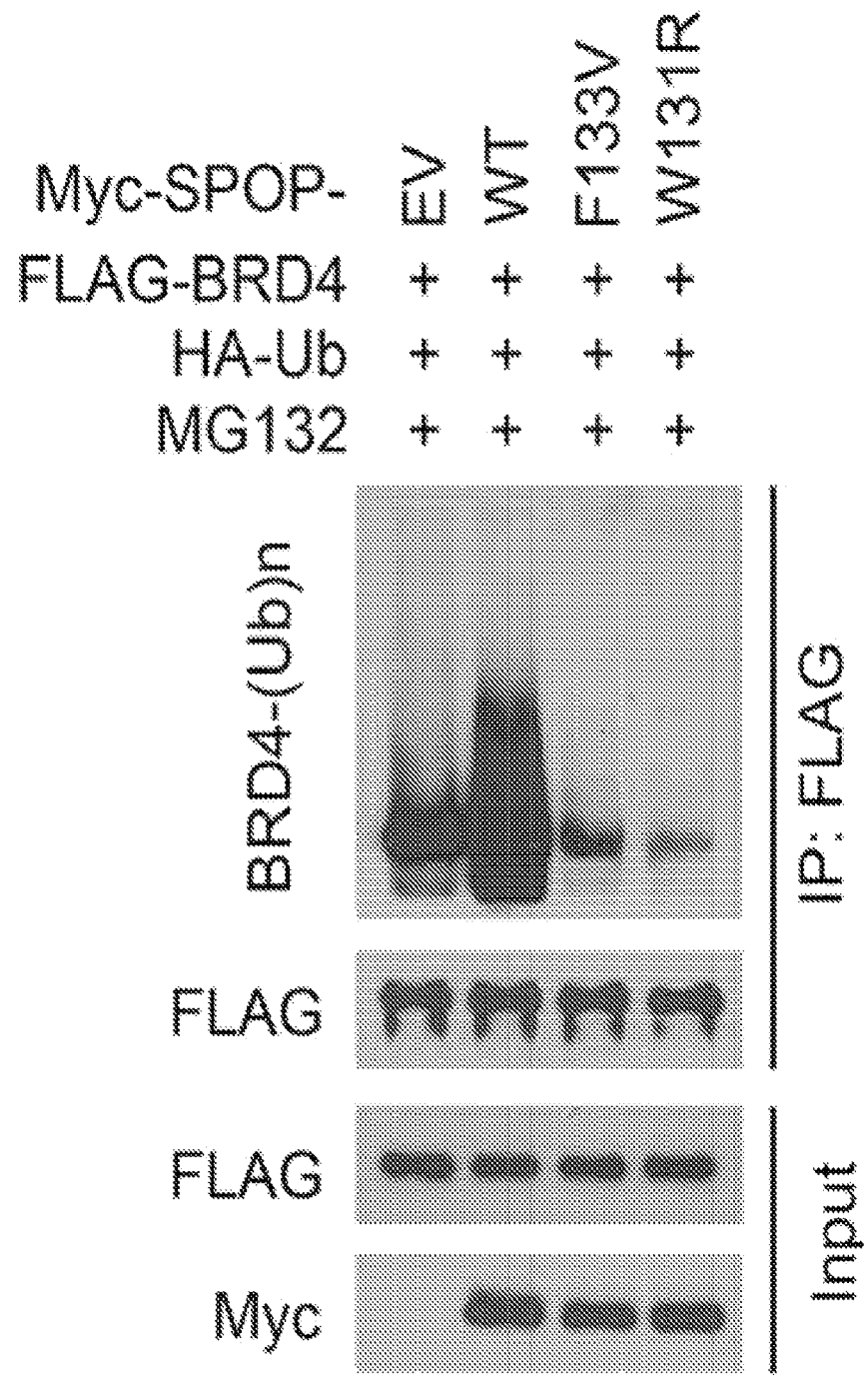
Figure 9D:
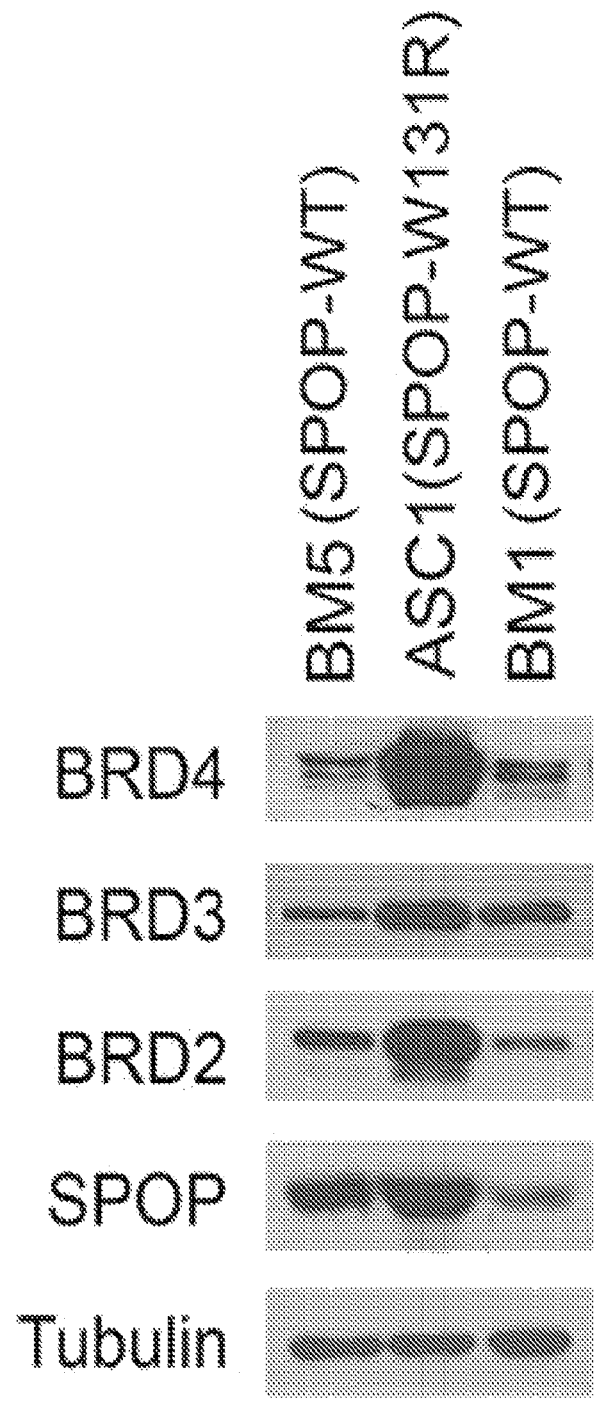
Figure 9E:
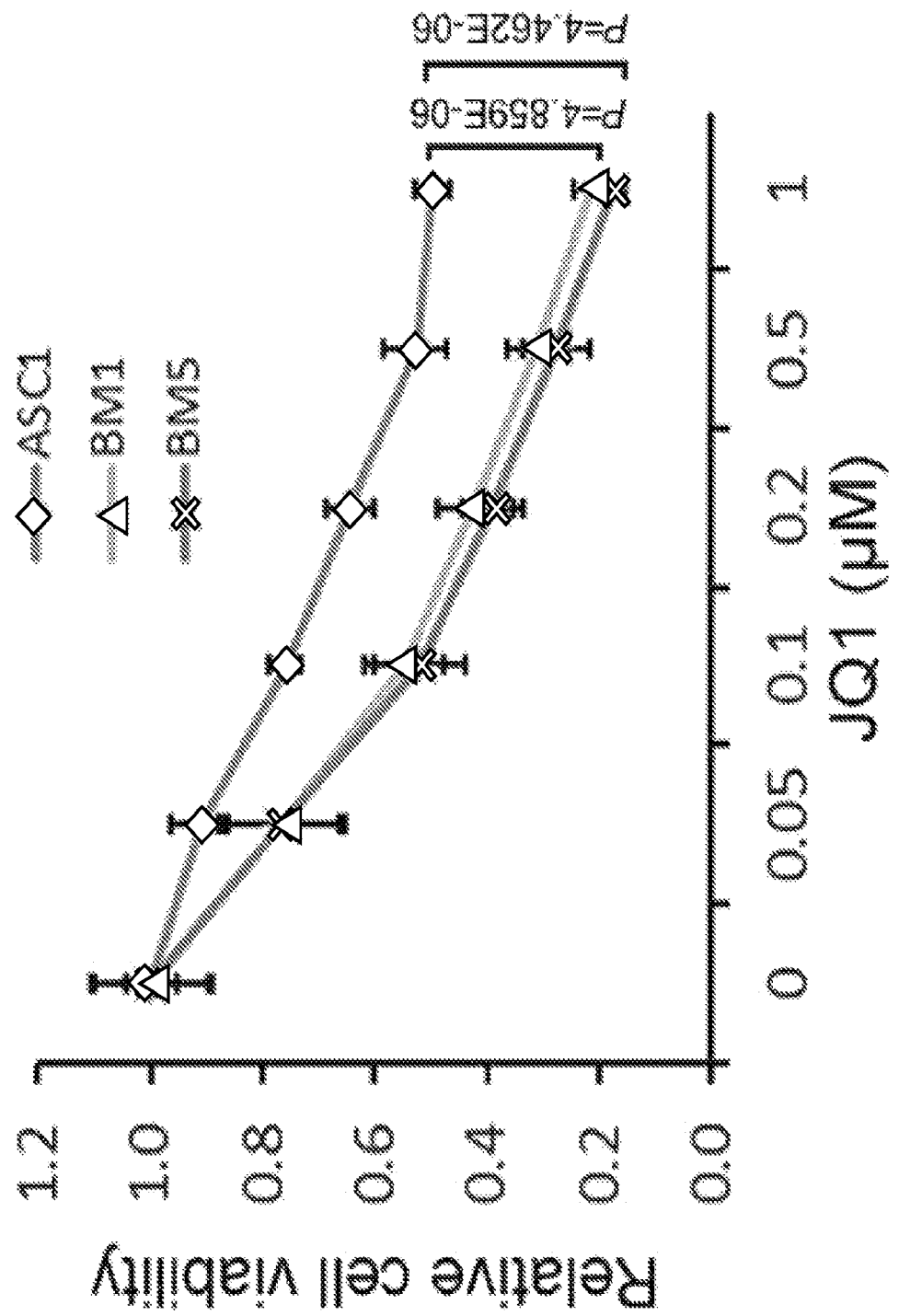
Figure 9F:
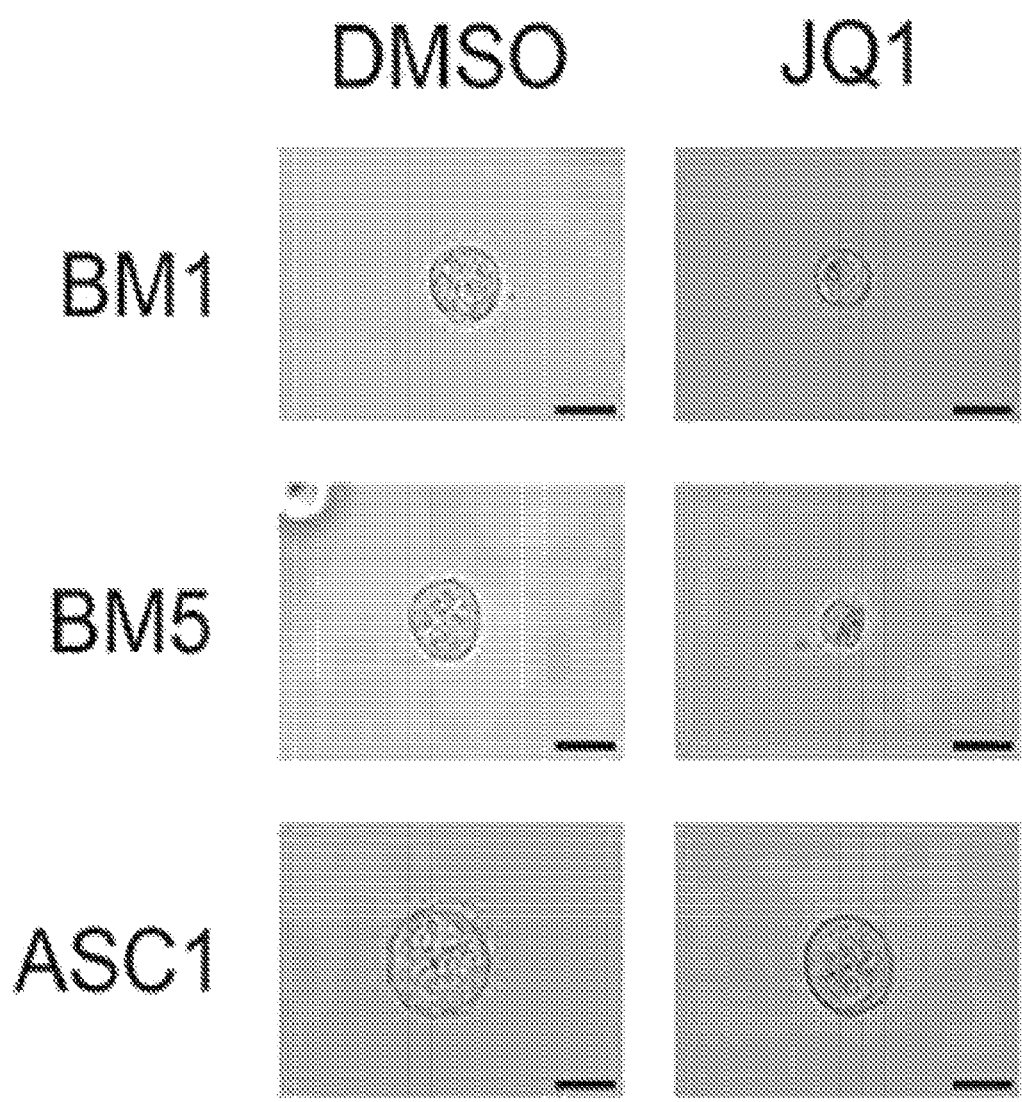
Figure 9G:
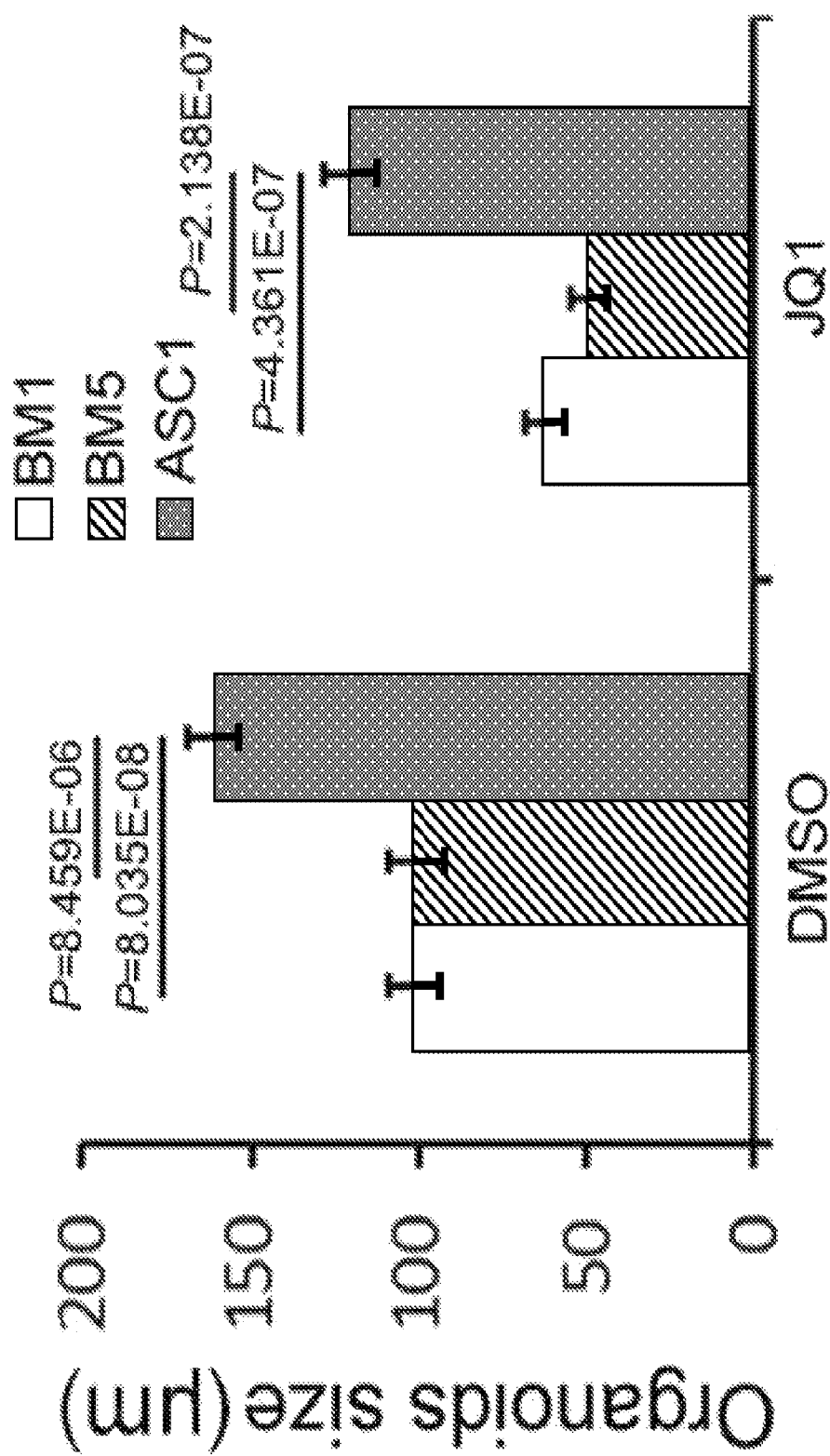
Figure 10A:
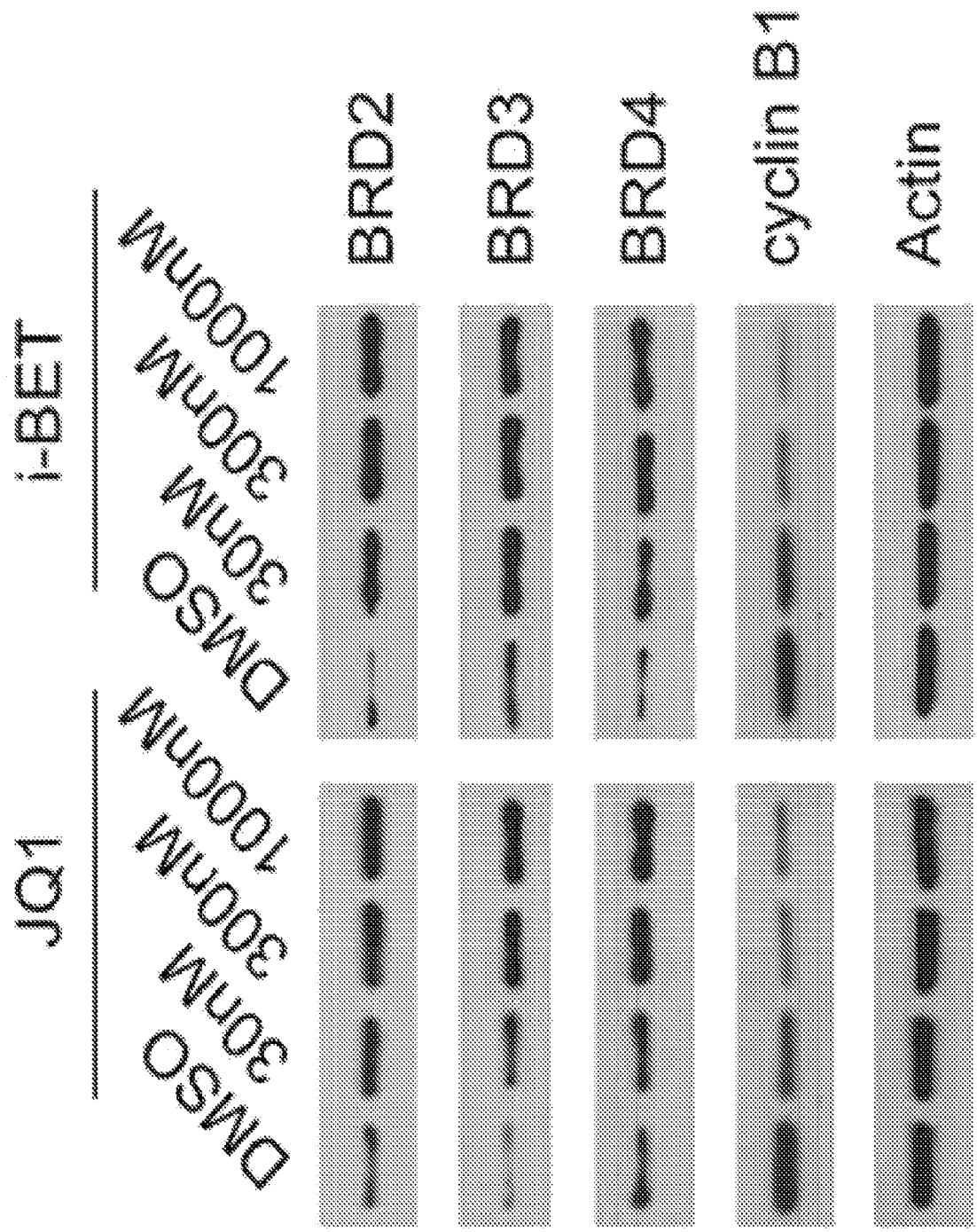
FIG. 10. Effects of JQ1 on BRD2/3/4 protein stability, the interaction between SPOP and BRD2/3/4, SPOP mediated ubiquitination and degradation of BRD2/3/4, and the half-life of BRD2/3/4 proteins. a, Western blot of WCL of C4-2 cells treated with vehicle (DMSO) or different doses of JQ1 or i-BET for 24 hours. Actin was used as a loading control. b, RT-qPCR assessment of BRD2/3/4 mRNA expression in C4-2 cells treated as in (a). The expression level of BRD2/3/4 mRNA was first normalized to the level of GAPDH mRNA (internal control) and then further normalized to the value in cells treated with vehicle. Data are shown as means±SD (n=3 technical replicates), and similar results were obtained from two independent experiments. c, Western blot of WCL of 293T cells transfected with indicated plasmids and treated with or without JQ1 (1 µM) or i-BET (1 µM) for 24 hours. Western blot signal intensity of FLAG-tagged BET proteins was first normalized to actin level (loading control), and the value was further normalized to the one in cells transfected with wild-type BRD2/3/4 without JQ1 treatment. d, Western blot of WCL of 293T cells co-transfected with SPOP and BRD4 and treated with or without JQ1 (1 µM) or i-BET (1 µM) for 24 hours. Western blot signal intensity of FLAG-tagged BET proteins was first normalized to actin level (loading control), and the value was further normalized to the one in cells transfected with empty vector without JQ1 treatment. e, Western blot of WCL and co-IP samples of anti-FLAG antibody from 293T cells transfected with indicated plasmids and treated with or without JQ1 (1 µM) for 24 hours. Western blot signal intensity of immunoprecipitated Myc-tagged SPOP proteins was first normalized to Myc-SPOP input level, and the value was further normalized to the one in cells without JQ1 treatment. f, Western blot of the products of in vivo ubiquitination assay in 293T cells transfected with indicated plasmids and treated with or without JQ1 (1 µM) for 24 hours. Cells were treated with MG132 (20 µM) 8 hours before being harvested. g and h, C4-2 cells infected with lentivirus expressing empty vector (EV) and SPOP F133V were treated with or without JQ1 (1 µM) for 24 hours. Cells were then treated with 50 µg/mL cycloheximide (CHX) and harvested at different time points for western blot (g). At each time point, the intensity of BET protein was normalized to the intensity of actin (loading control) and further normalized to the value at 0 hours (h). Similar results were obtained from two independent experiments.
Figure 10B:
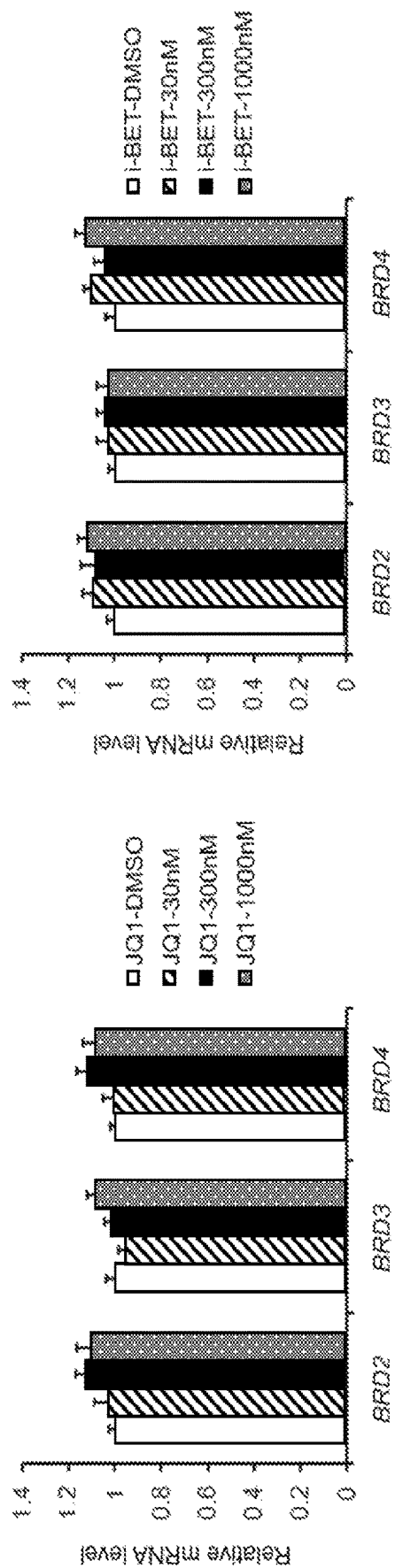
Figure 10C:
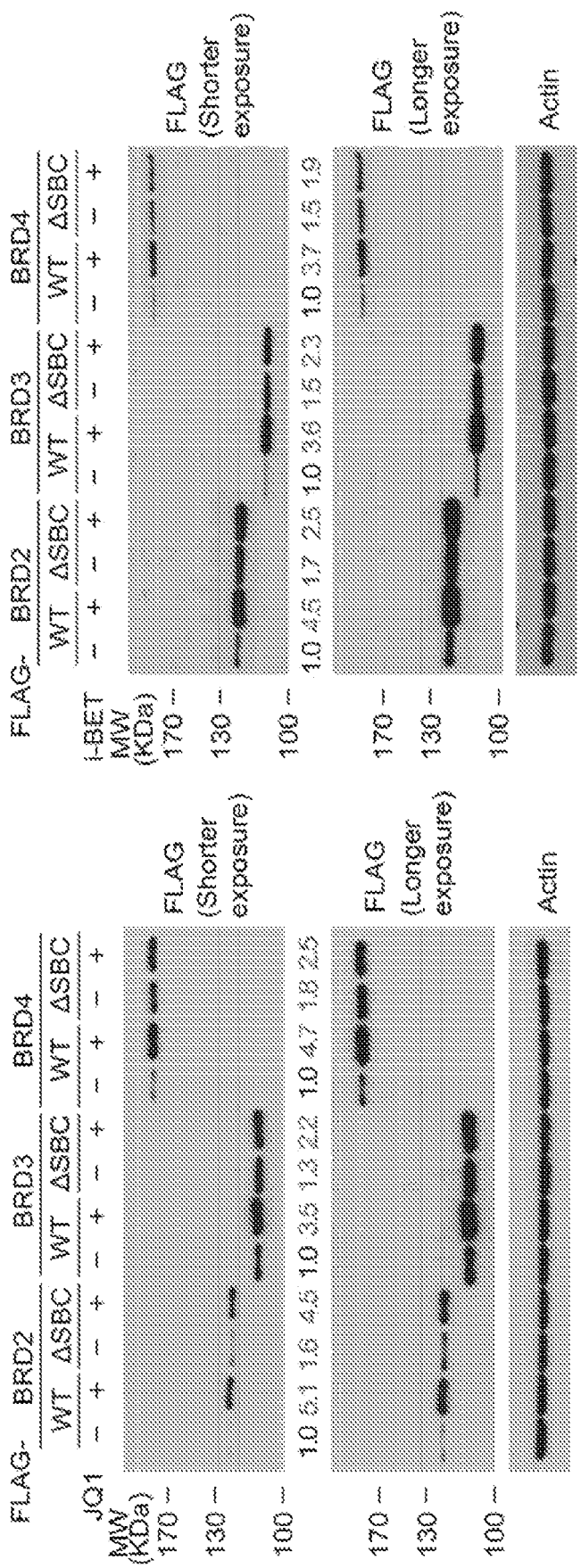
Figure 10D:
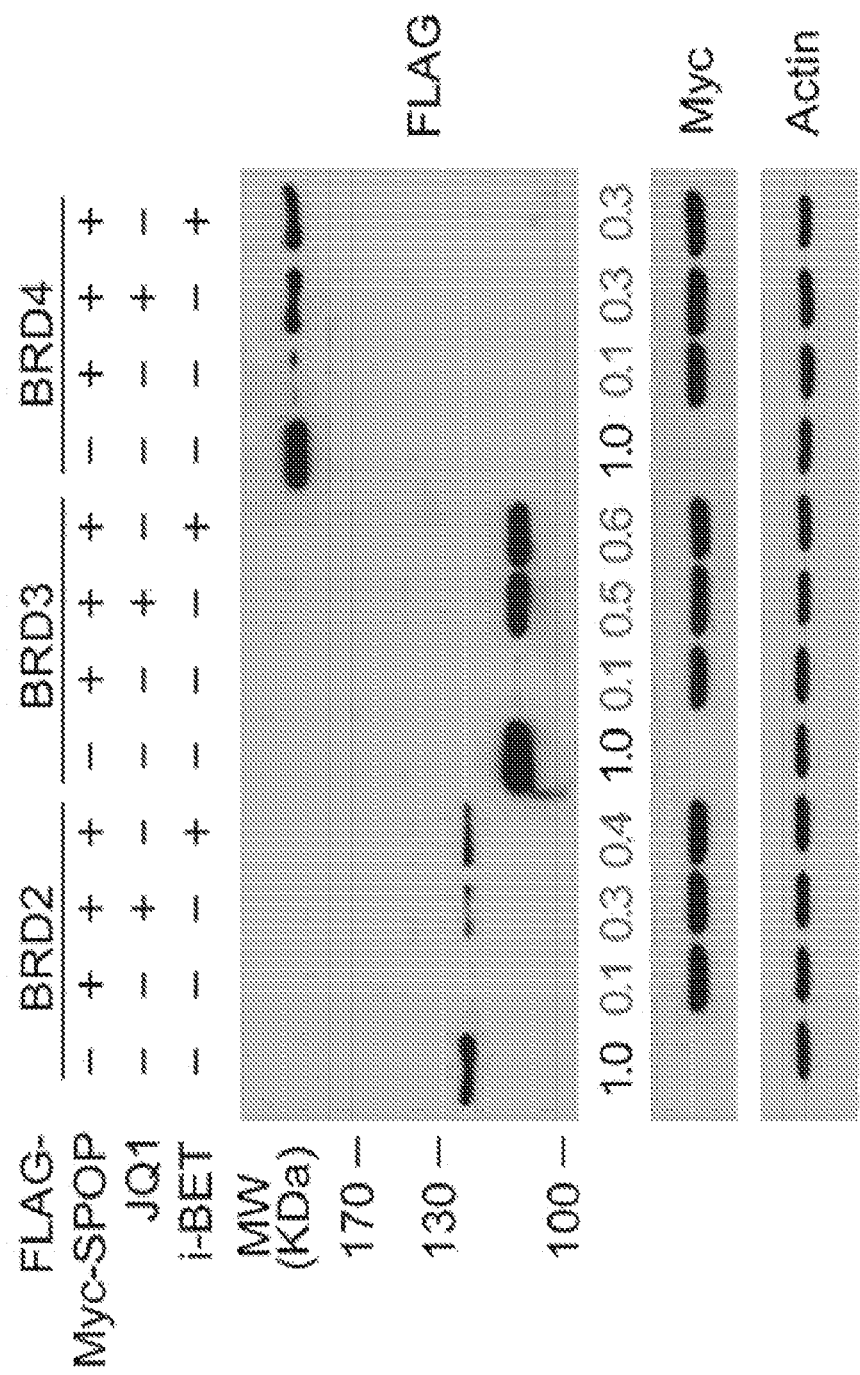
Figure 10E:
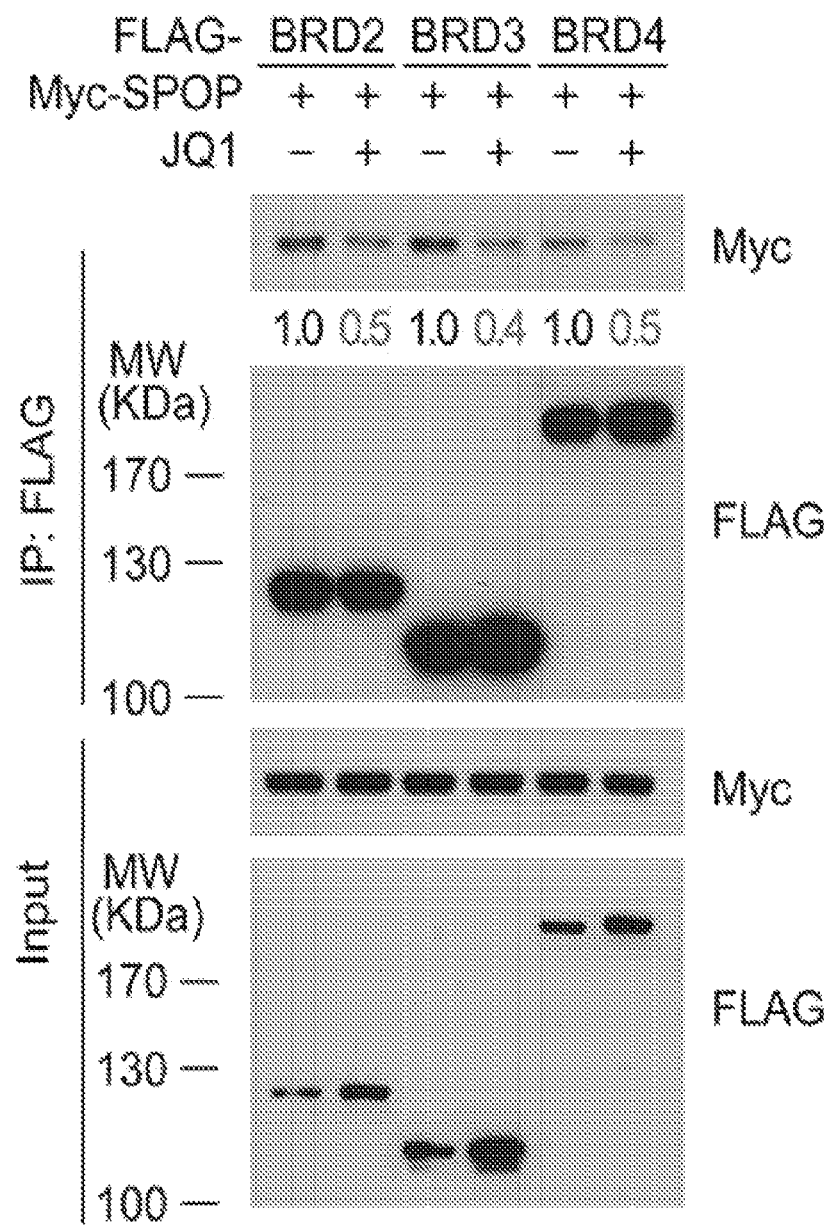
Figure 10F:
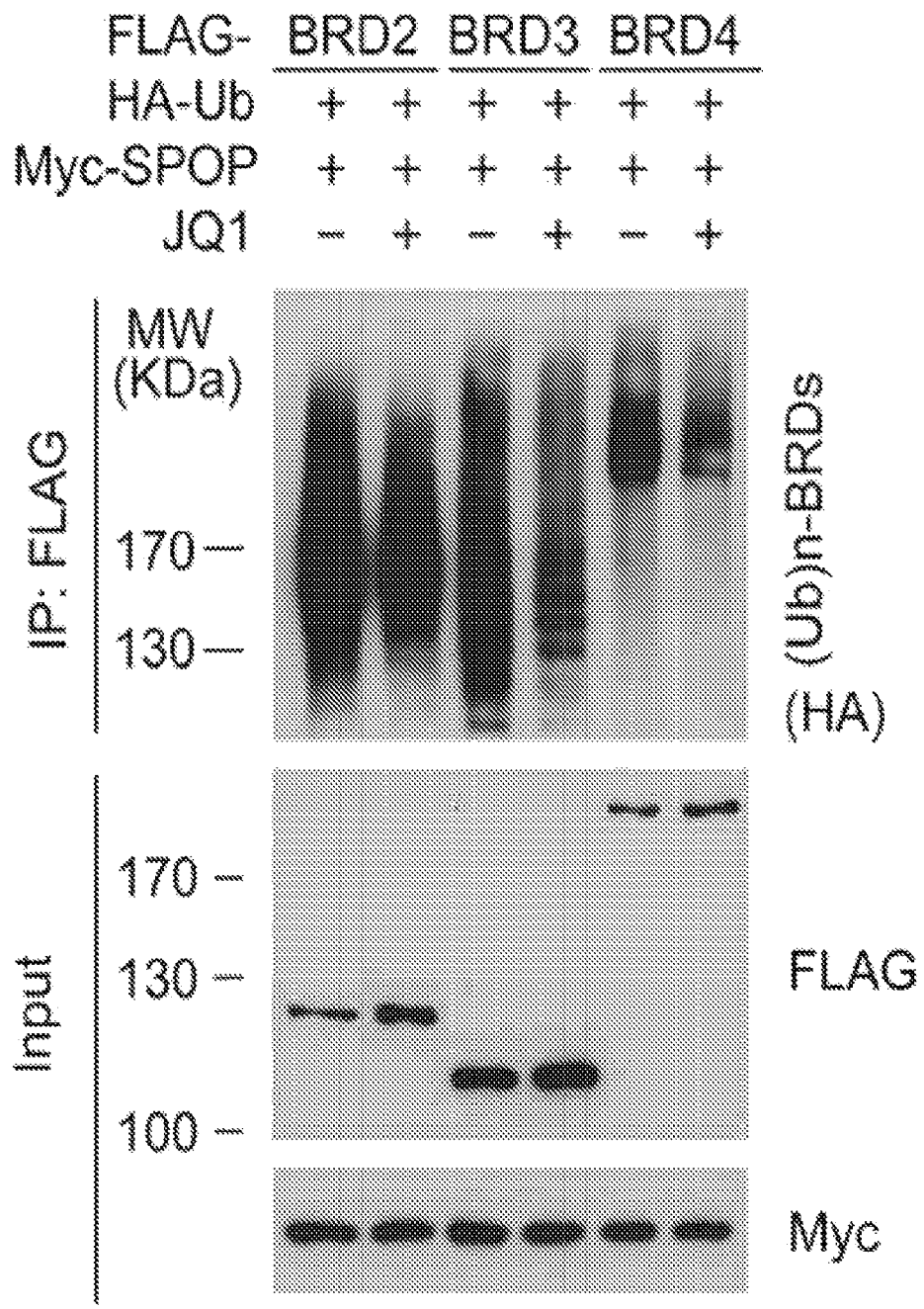
Figure 10G:
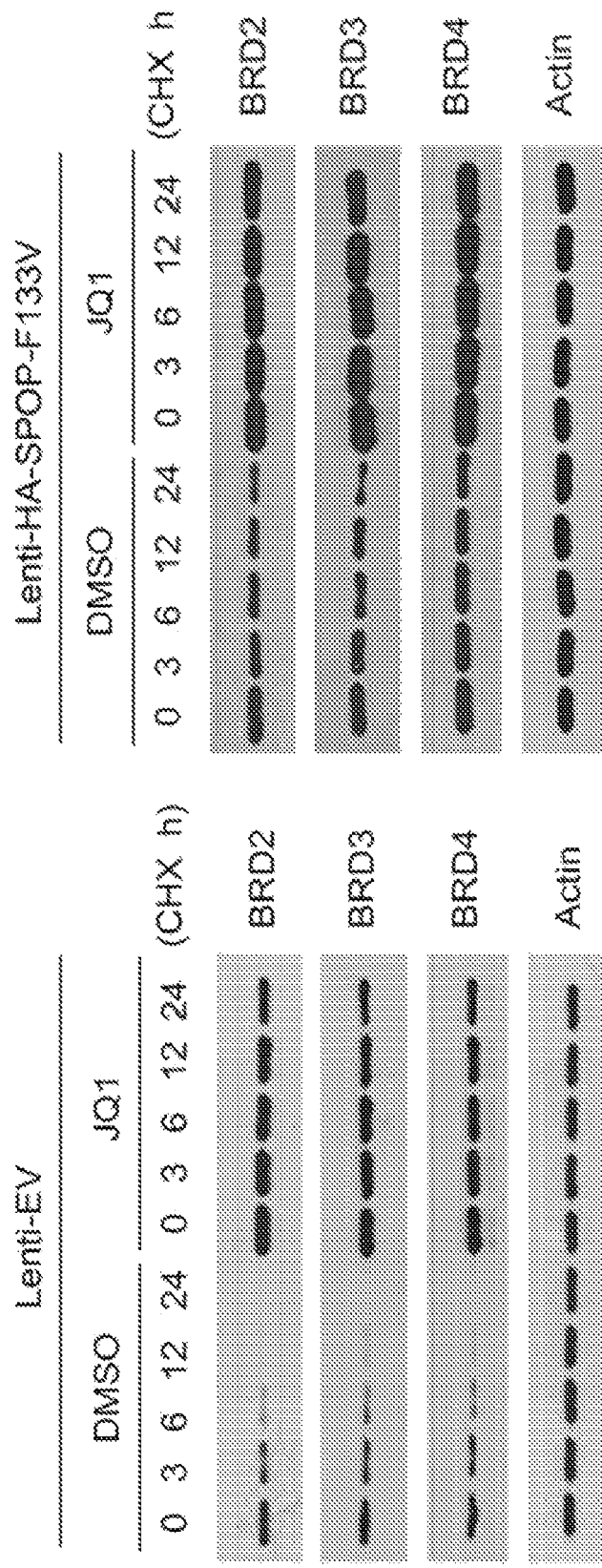
Figure 10H:
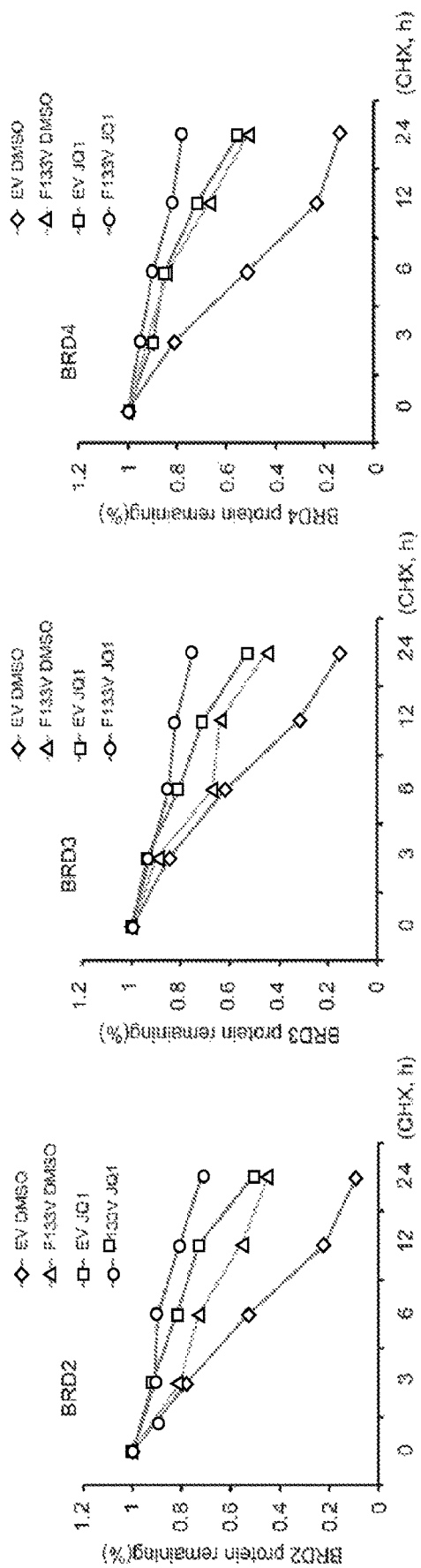

The following was performed to investigate the role of SPOP mutation-induced accumulation of BRD proteins in BET inhibitor resistance in clinically-oriented models. Among three prostate cancer patient-derived organoid lines examined, one harbors a W131R mutation in SPOP. W131 belongs to a conserved residue in the substrate-binding cleft (Barbieri et al., Nat. Genet., 44:685-689 (2012)). W131R mutation was deficient in binding to and mediating ubiquitination and degradation of BRD4 (FIGS. 9a-c). Most importantly, the W131R-expressing organoid expressed more BRD2/3/4 proteins and was resistant to JQ1 compared to two SPOP WT counterparts under both 2D and 3D growth conditions (FIGS. 9d-g). These results indicate that SPOP mutation confers BET inhibitor resistance in patient-derived primary cultures.

It is worth noting that BET inhibitors have been shown to induce BRD4 accumulation in different cell types, but the underlying mechanism was unclear (Asangani et al., Nature, 510:278-282 (2014); and Lu et al., Chem. Biol., 22:755-763 (2015)). The effect was shown to occur at post-transcriptional level (FIGS. 6m, 7a, 10a, and 10b). In addition, JQ1 diminished SPOP-BRD2/3/4 protein interaction, partially blocked SPOP-induced BRD2/3/4 ubiquitination and degradation, and prolonged protein half-life even in SPOP-F133V-expressing cells (FIGS. 10c-h). Thus, while inhibiting their activities, BET inhibitors undesirably disturb BET protein proteolysis, and this effect appears to be mediated by SPOP-dependent and -independent mechanisms.

Figure 11A:
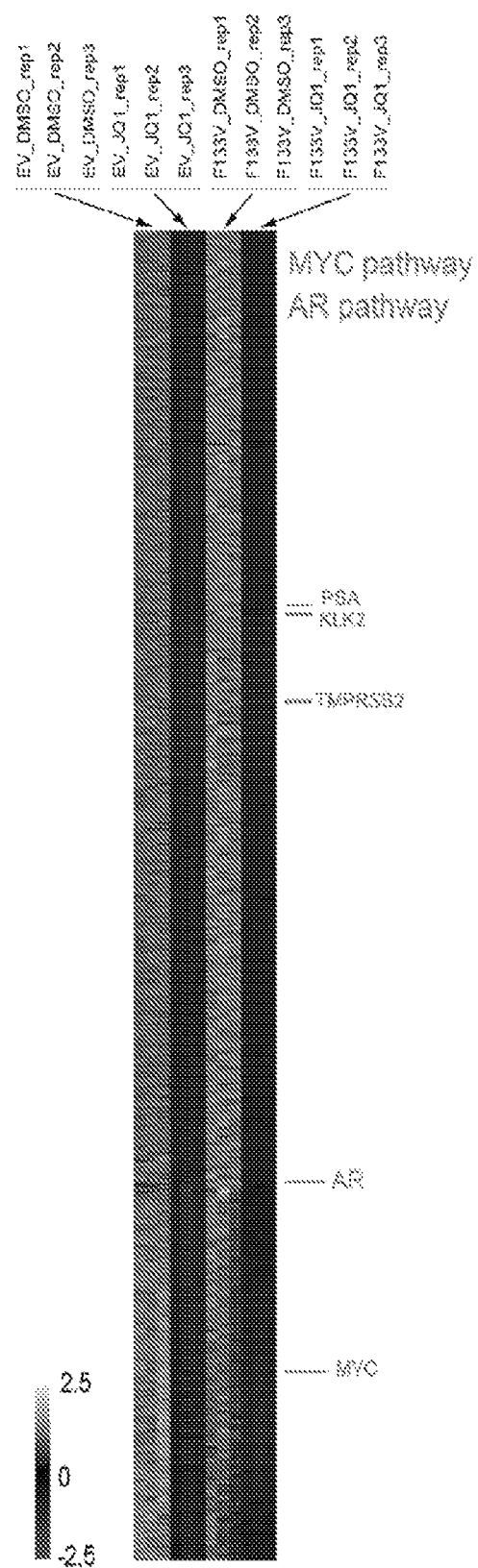
FIG. 11. Effect of JQ1 on the MYC and AR signaling pathways in both SPOP wildtype and mutant-expressing prostate cancer cells. a, Heat map of RNA-seq data showing a group of genes (n=5,079) whose expression was inhibited by JQ1 (1 µM, 24-hour treatment) in C4-2 cells infected with lentivirus expressing empty vector (EV) or SPOPF133V mutant. Representative genes in the MYC (purple) and AR (red) signaling pathways are highlighted. Rep, replicates. b, Western blot of WCL of C4-2 cells infected with lentivirus as in (a) and treated with or without JQ1 (1 µM) for 24 hours before being harvested. β-tubulin was used as a loading control. Asterisk indicates the exogenous HA-SPOP-F133V. c, UCSC genome browser screen shots showing signal profiles of BRD4 ChIP-seq in C4-2 cells infected with lentivirus expressing empty vector (EV) or SPOP-F133V or transfected with HA tagged BRD4 and ChIP-seq signaling profiles of H3K4me1 and H3K4me3 (histone markER for enhancer and promoter, respectively) in LNCaP cells (Wang et al., Nature, 474:390-394 (2011)). The promoter and enhancer regions are highlighted in yellow. d, ChIP-qPCR analysis of BRD4 binding at the MYC enhancer and the AR promoter in C4-2 cells infected with indicated lentivirus and treated with JQ1 as in (b). All data are shown as mean values±SD (n=3 technical replicates), and similar results were obtained from two independent experiments. e, RT-qPCR analysis of mRNA expression of the AR target genes PSA, TMPRSS2, and KLK2 in C4-2 cells infected with indicated lentivirus and treated with or without JQ1 as in (b). Data are shown as mean values±SD (n=3 technical replicates), and similar results were obtained from two independent experiments. f, ChIP-qPCR analysis of AR binding at the promoter of PSA, TMPRSS2, and KLK2 genes in C4-2 infected with indicated lentivirus and treated with or without JQ1 as in (b). Data are shown as mean values±SD (n=3 technical replicates), and similar results were obtained in two independent experiments. g, Western blot of WCL of C4-2 infected with lentivirus expressing empty vector (EV) or SPOPF133V in combination with control shRNA (shC) or AR-specific shRNAs and treated with or without JQ1 (1 µM) for 24 hours before being harvested. h, C4-2 cells were infected with lentivirus as in (g) and treated with vehicle (DMSO) or JQ1 (0.25 µM) every other day. Cell growth was measured by cell proliferation assay at different time points. Data are shown as mean values±SD (n=6 biological replicates).
Figure 11B:
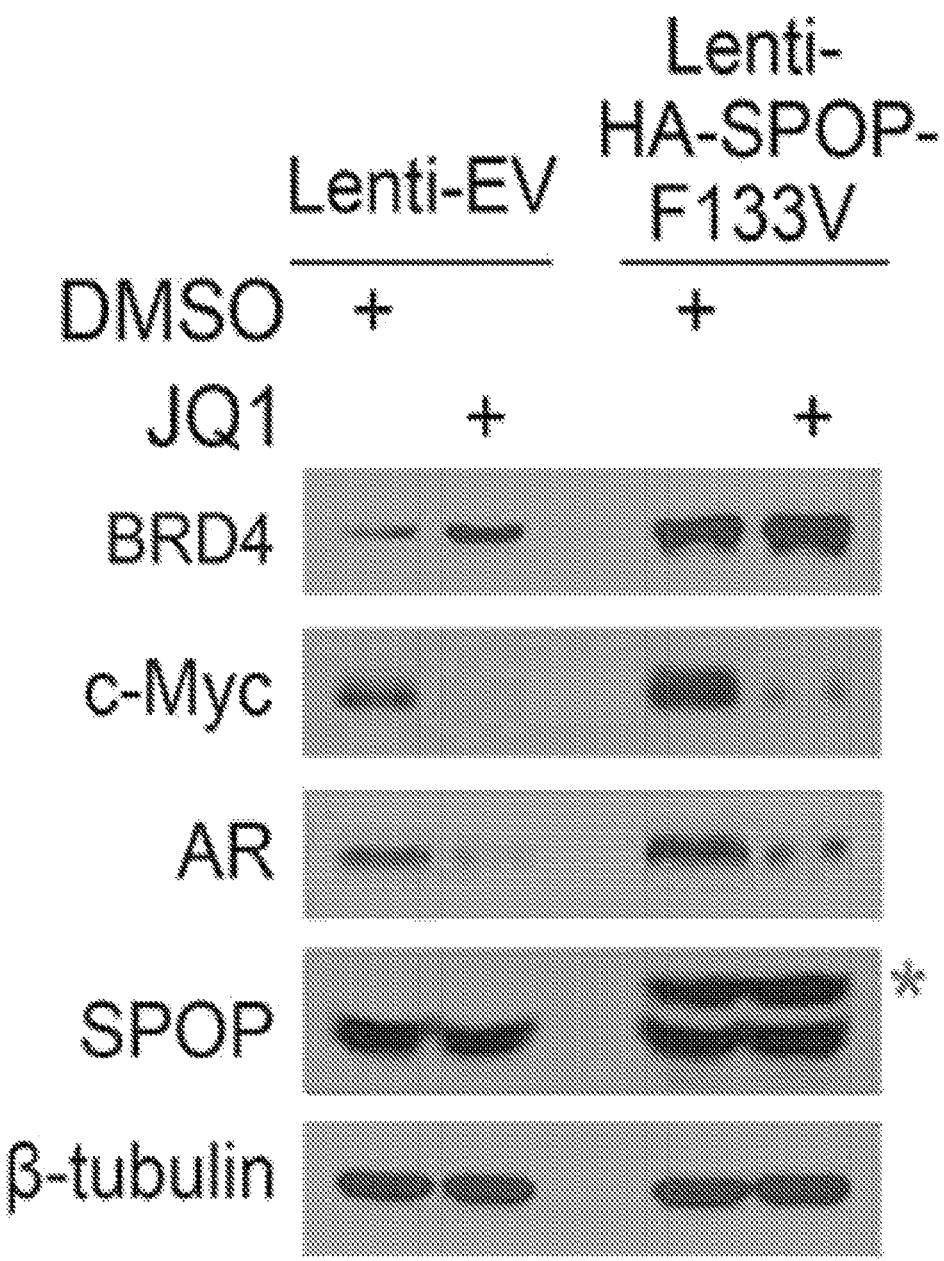
Figure 11C:
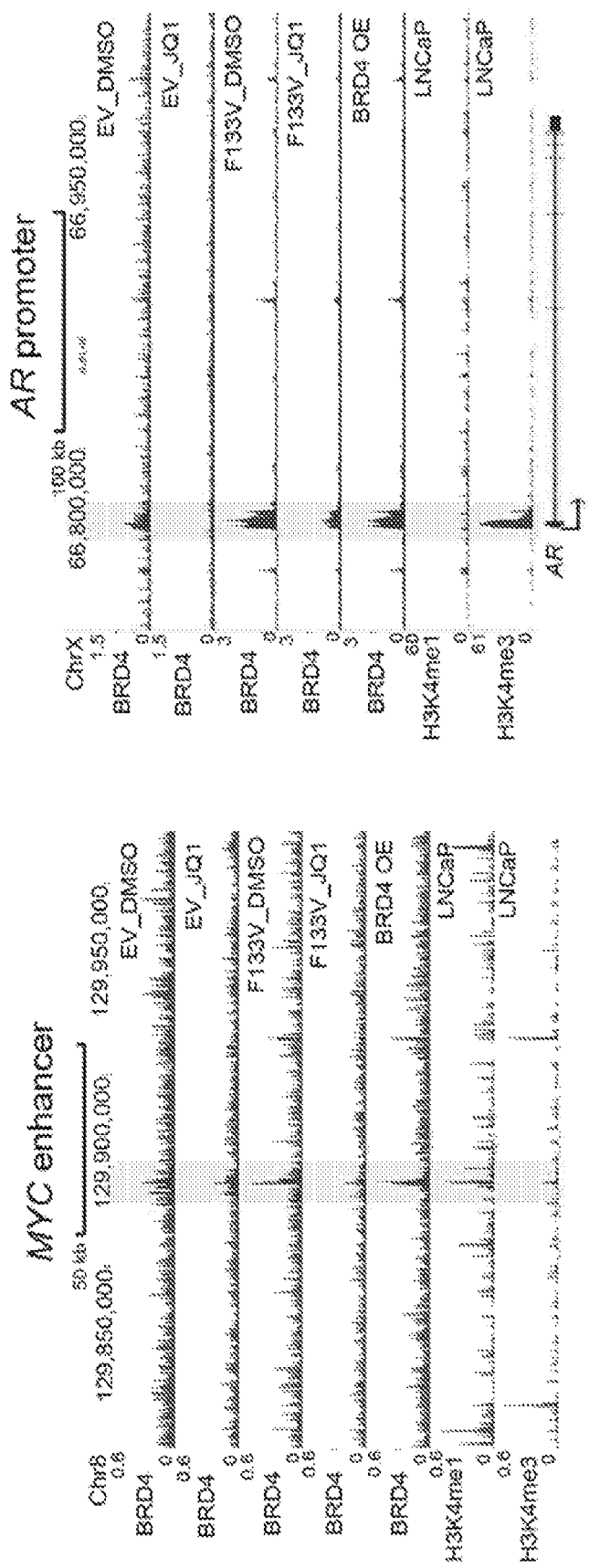
Figure 11D:
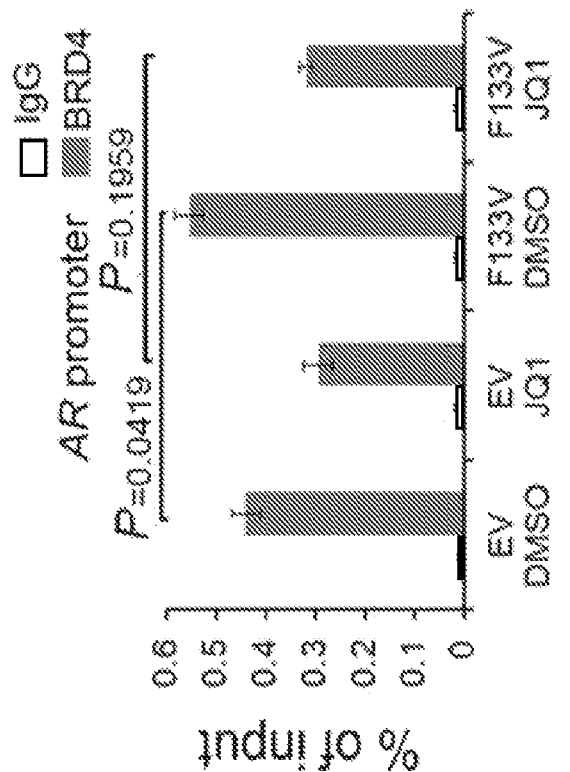
Figure 11D:
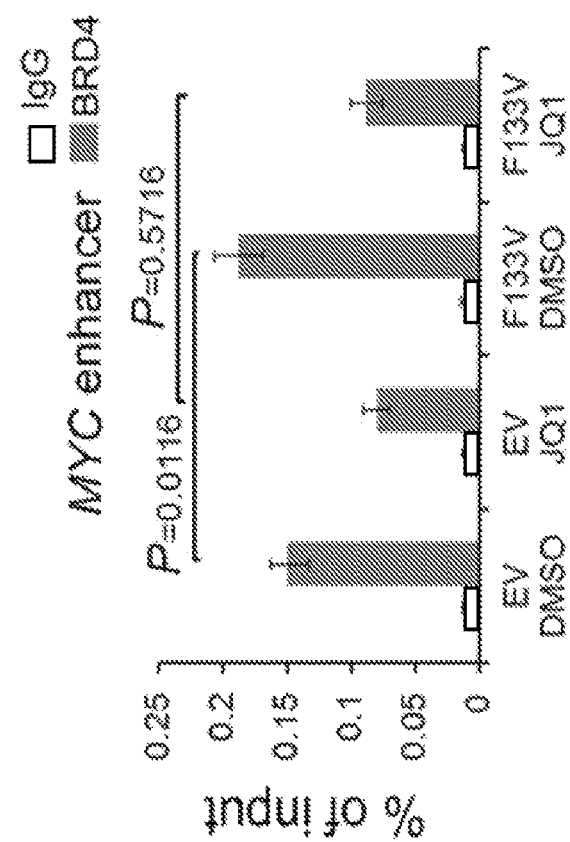
Figure 11E:
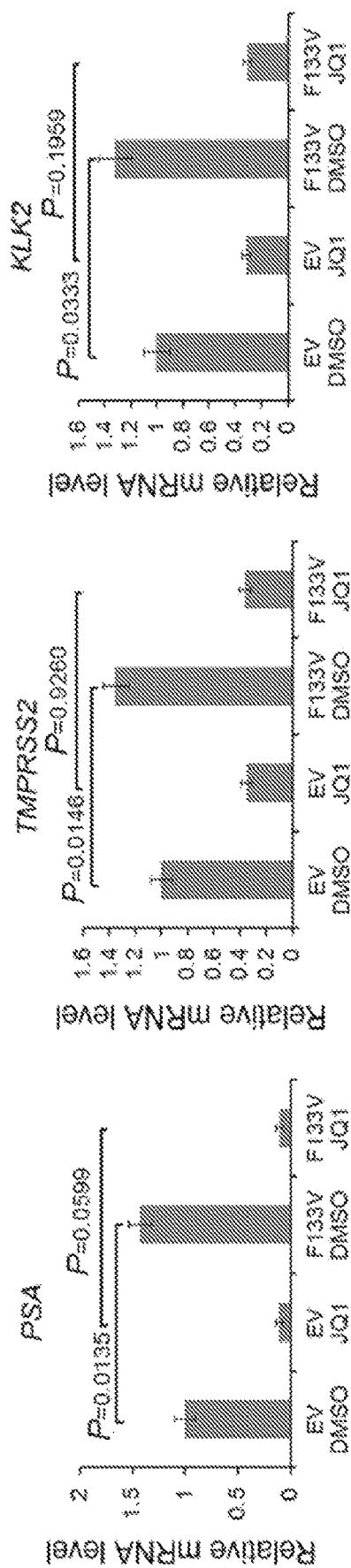
Figure 11F:
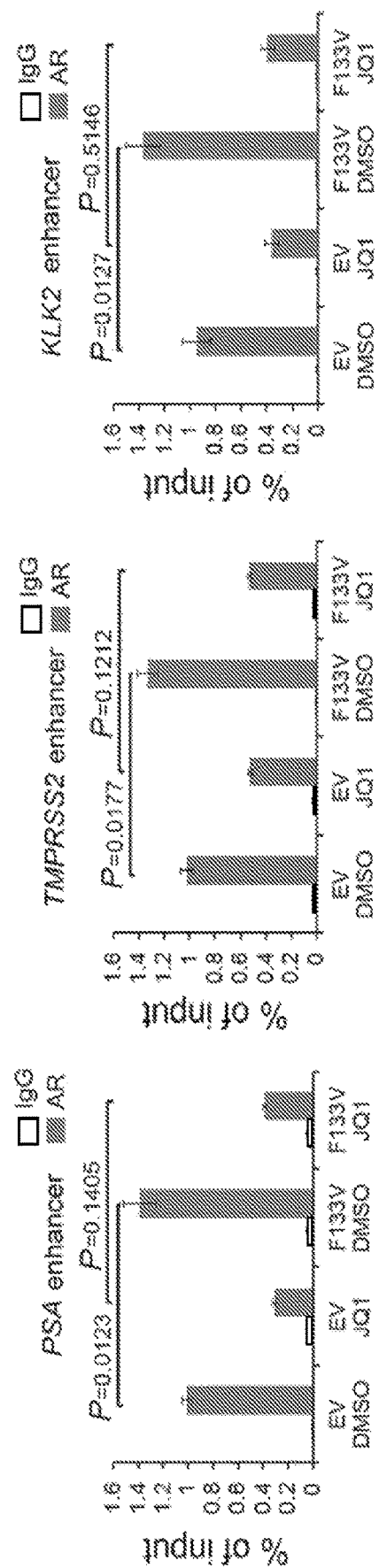
Figure 11G:
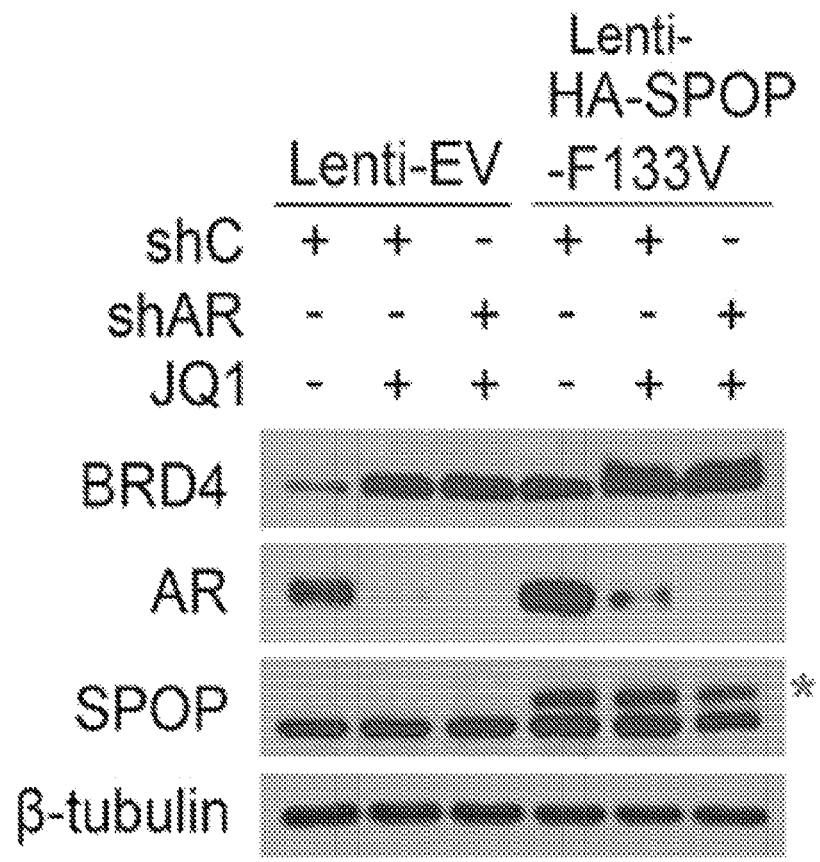
Figure 11H:
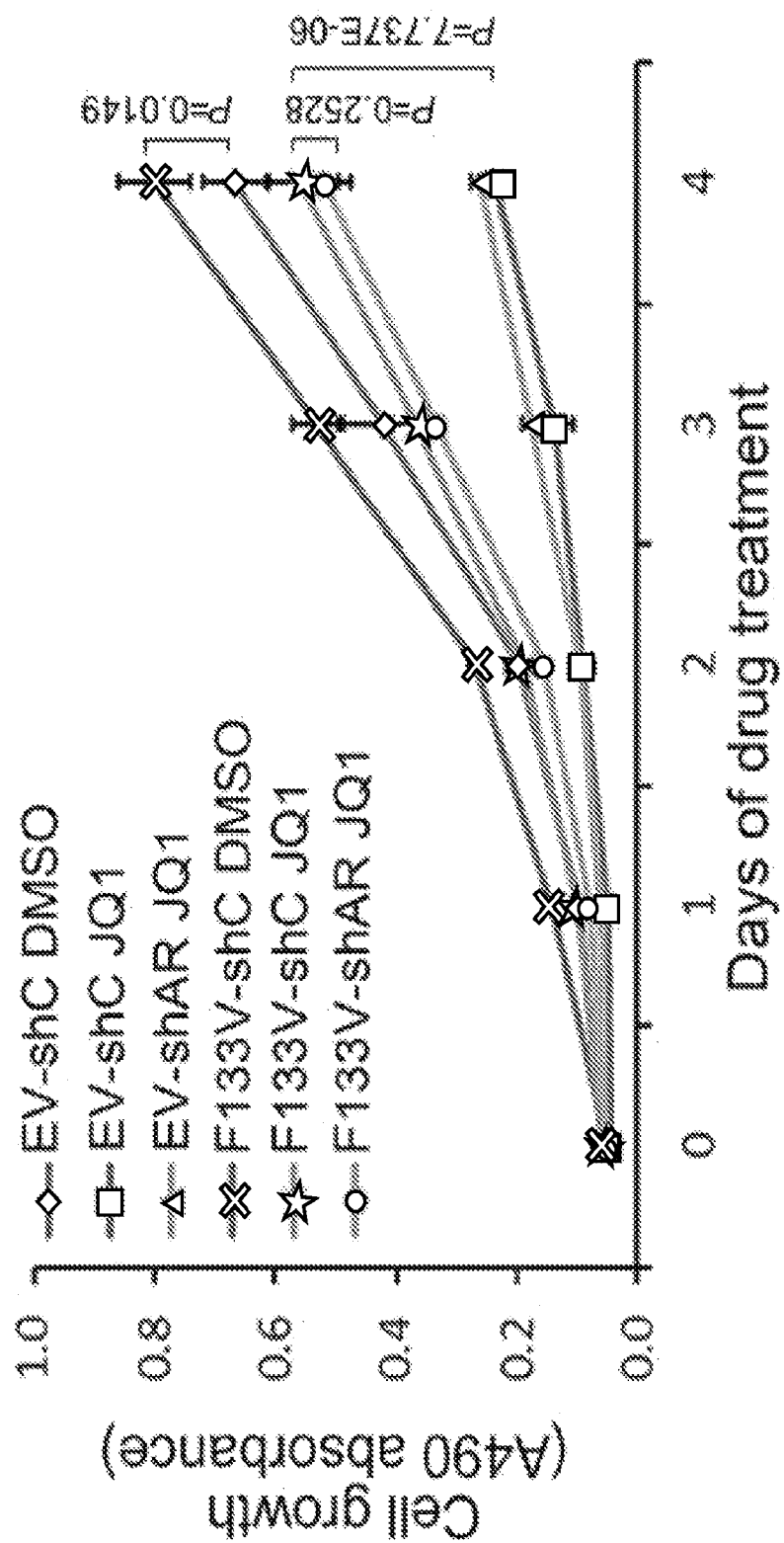

To define the signaling pathways that mediate BET inhibitor resistance in SPOP-mutated cells, transcriptome analysis was performed in control (EV) and SPOP-F133V-expressing C4-2 cells treated with or without JQ1. Through unsupervised cluster analysis, 5,079 JQ1-downregulated genes were identified in both control and SPOP-F133V cells, including MYC and AR, two known targets of BET inhibitors (Delmore et al., Cell, 146:904-917 (2011); Zuber et al., Nature, 478:524-528 (2011); and Asangani et al., Nature, 510:278-282 (2014)) (FIG. 11a). Previous studies suggest that MYC may not be the major anti-cancer target of JQ1 in prostate cancer cells (Asangani et al., Nature, 510:278-282 (2014)). In agreement with this report, JQ1 treatment markedly decreased MYC protein expression, which is consistent with substantial reduction of BRD4 binding in the MYC gene enhancer in both JQ1-sensitive (control) and -resistant (SPOP-F133V) C4-2 cells (FIGS. 11b-d). JQ1 also largely decreased AR protein level, BRD4 binding in the AR gene promoter, and AR transcriptional activity in both control and SPOP-F133V cells (FIGS. 11b-f), and further knockdown of AR by shRNAs did not affect JQ1 sensitivity in these cells (FIGS. 11g and 11h). Collectively, these results demonstrate that BET inhibitor resistance in SPOP-mutated prostate cancer cells is likely mediated by MYC- and AR-independent pathways.

Figure 7D:
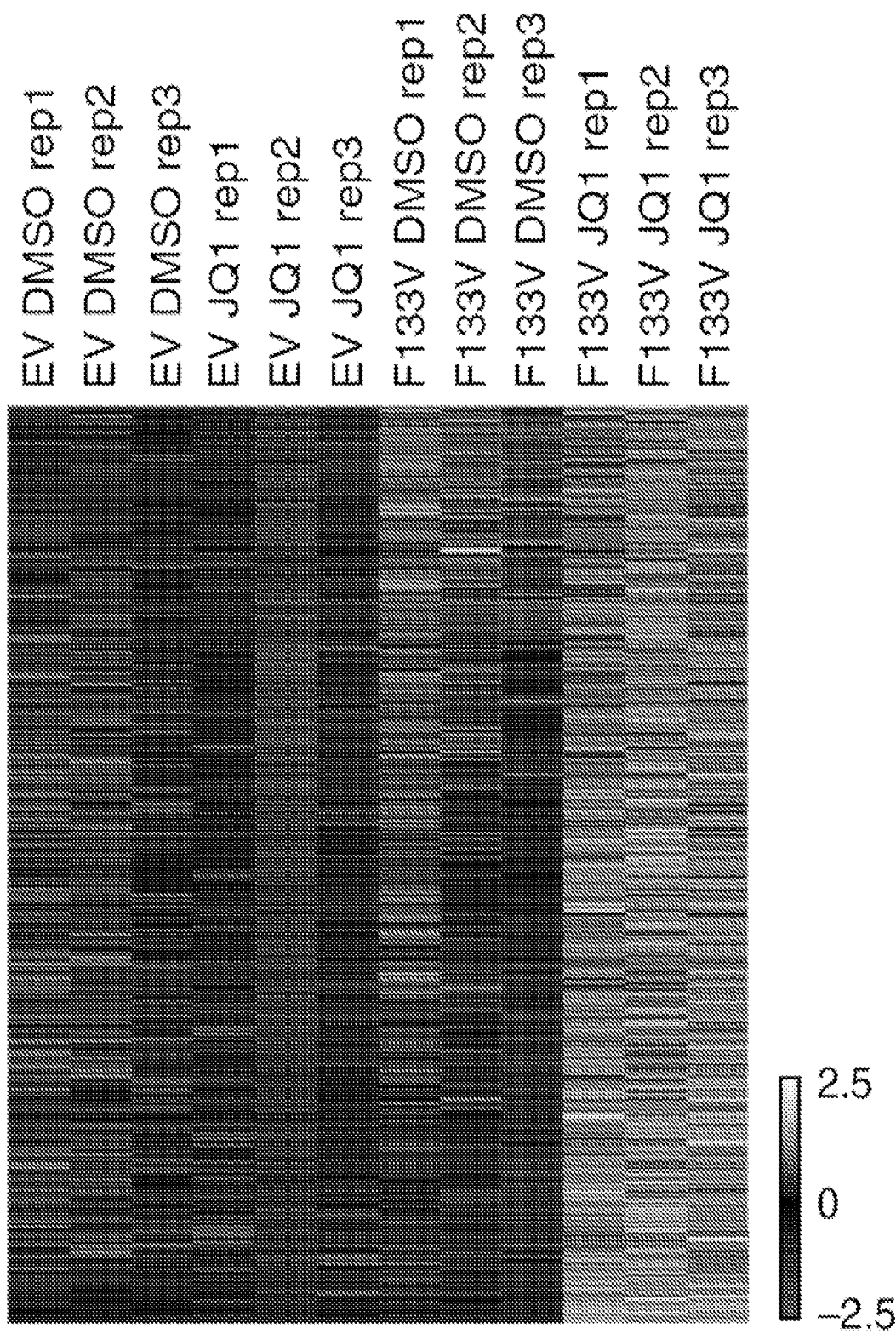
Figure 7E:
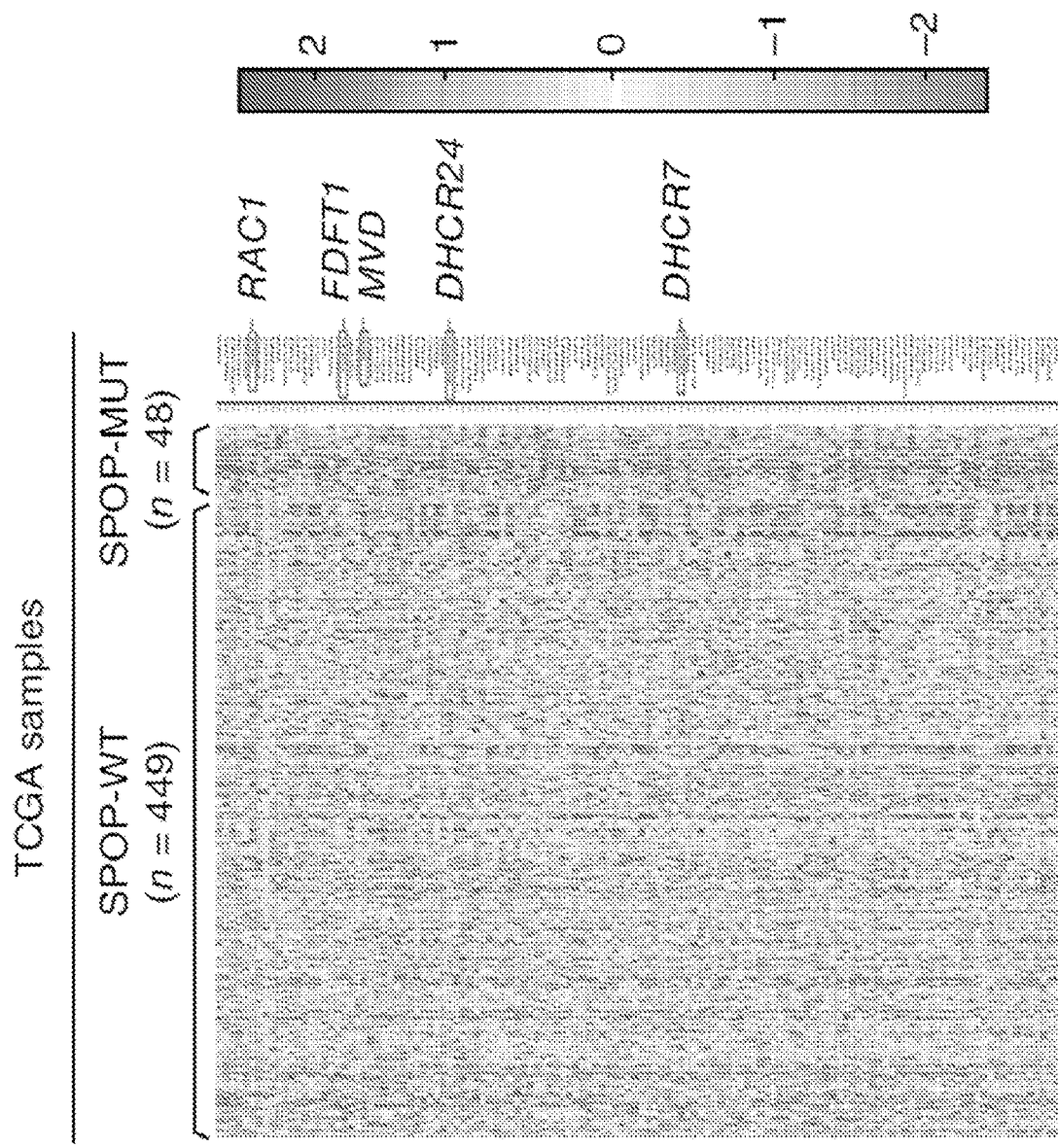
Figure 7F:
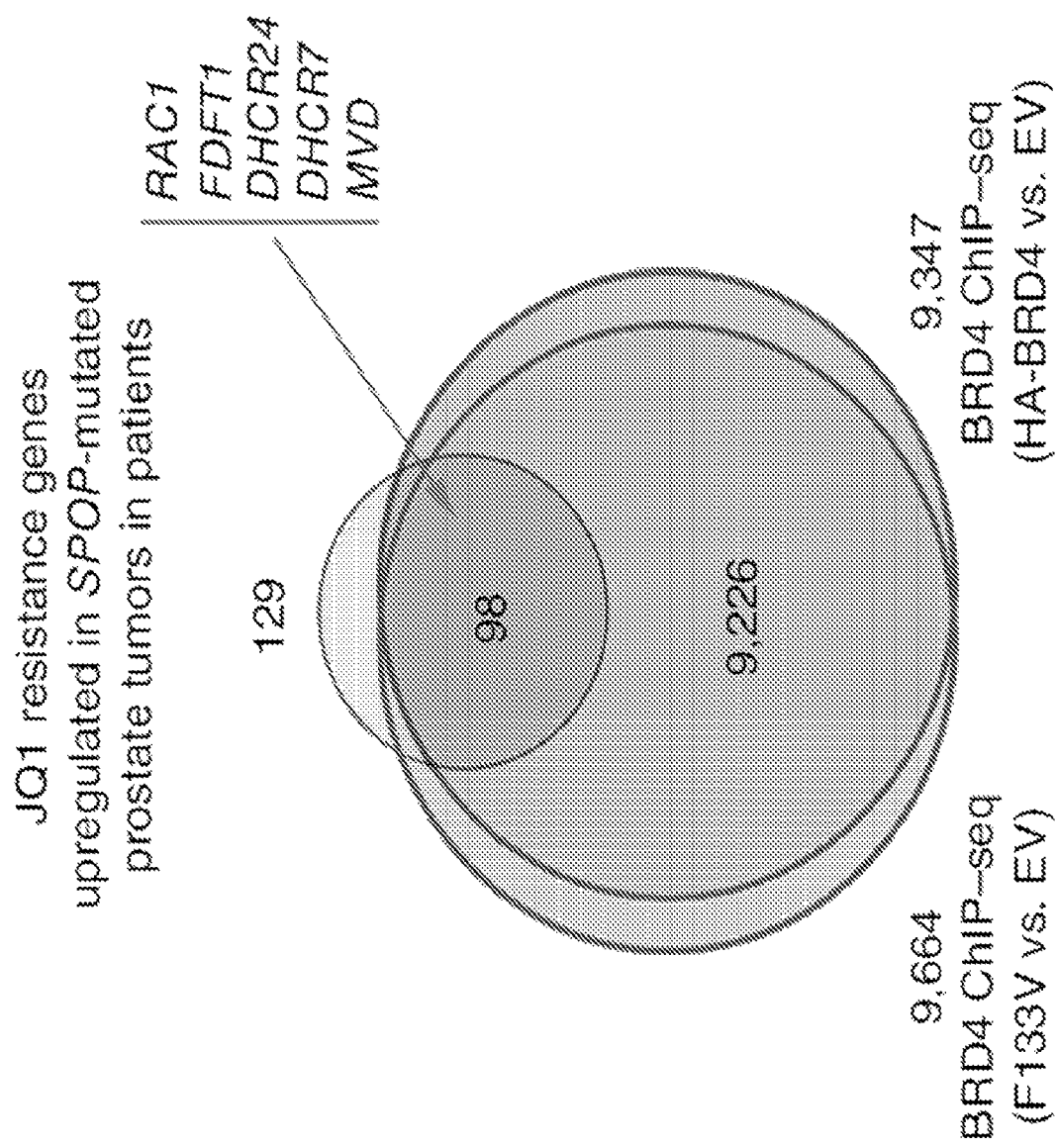
Figure 7G:
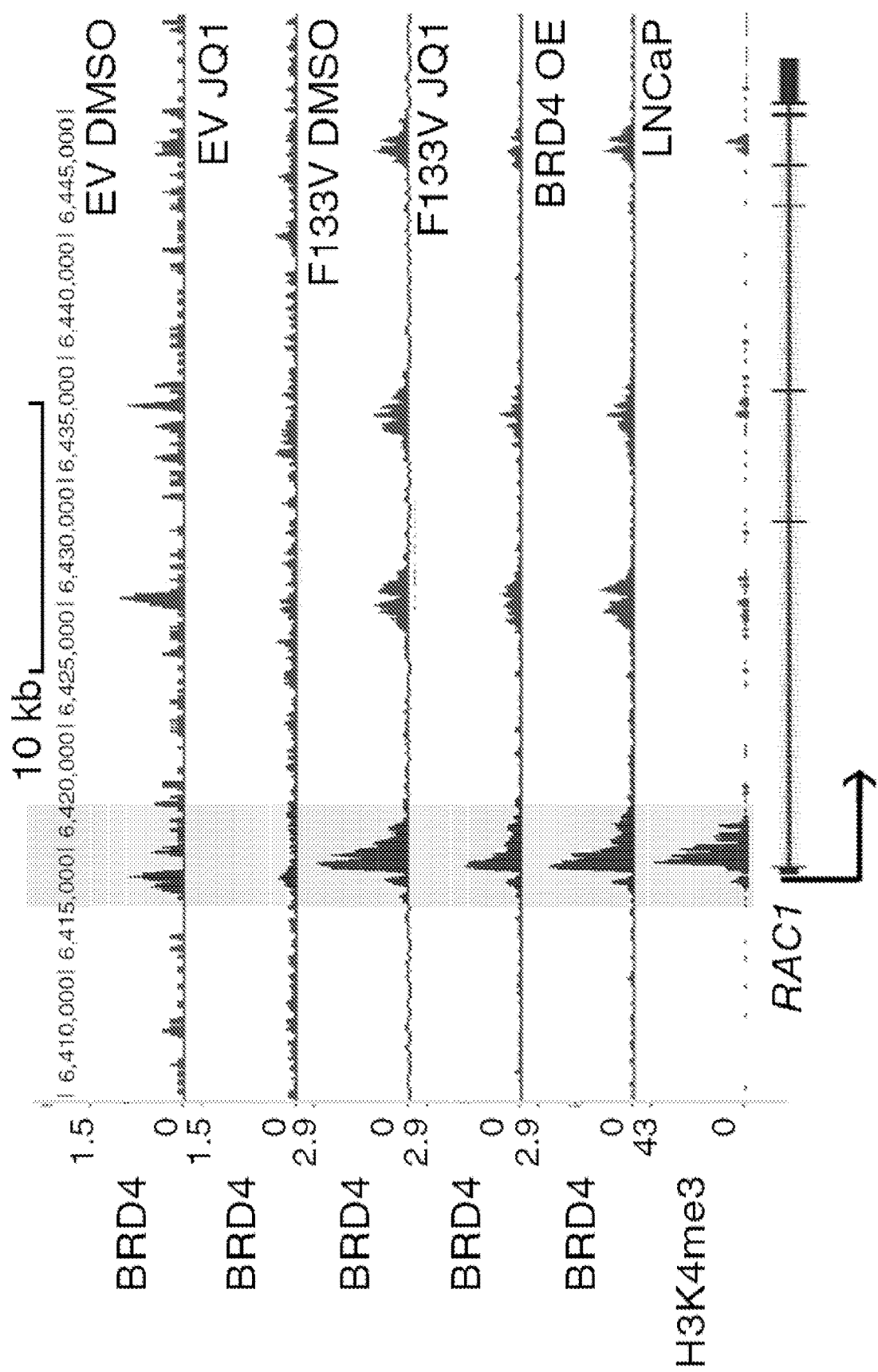

Further analysis of RNA-seq data revealed 1,017 genes whose expression was suppressed by JQ1 in control cells but remained either unchanged or upregulated in F133V-mutant cells (FIG. 7d). 129 of them were highly upregulated in SPOP-mutated prostate tumors compared to SPOP-WT tumors in the TCGA cohort (FIG. 7e and Table 5). Notably, these aberrantly upregulated genes significantly overlapped with the BRD4 target genes commonly identified in C4-2 cells transfected with SPOP-F133V or HA-BRD4 (FIGS. 7f and 12a-c). Ingenuity pathway analysis of the overlapped genes indicated that the top hit was the cholesterol biosynthesis pathway, and four members of this pathway including FDFT1, DHCR24, DHCR7 and MVD were upregulated in SPOP-mutated tumors (FIGS. 7e and 7f).

TABLE 5

Table 5. 129 genes highly expressed in SPOP mutated prostate cancers compared to SPOP wild-type counterparts in the TCGA dataset Gene symbol PREB
PHLDA2
ATPGV0E2
HMG20B
CYP2R1
RAC1
ZNF582
MAGEC2
EIF2AK1
PIGX
SEC61A1
ETHE1
BCAT2
CYP4F11
ENDOG
AF2S1
VGF
PRKRIR
ZDHHC12
FDFT1
ZNF695
GAS2L1
MVD
MEMO1
PCDHA2
PCDHA7
PCDHA4
PCDHA5
PCDHA8
MOSPD3
NRD1
PUSL1
GABRD
MBD3
RTN2
DHCR24
TCTEX1D2
PCDHA12
SLC25A39
TMEM52
FAM84A
PQLC1
FKBP2
ALCAM
NDOR1
CBLN2
DOLK
PCDHA9

TABLE 5-continued

Table 5. 129 genes highly expressed in SPOP mutated prostate cancers compared to SPOP wild-type counterparts in the TCGA dataset Gene symbol ABHD2
GNMT
CKMT1A
CKMT1B
ABHD11
HCN2
E4F1
SCYL1
NANS
TXNL4A
BPGM
PAFAH1B3
SLC25A33
DDAH1
CROT
PCK2
SEC61G
SEPW1
LIN7B
GMPR
TRPM4
FANK1
DHCR7
POLD4
FAM117A
PTS
SIAH2
MERTK
PQLC2
LMO7
NRIP1
NUDT8
ANXA4
FDXR
STK32C
SLC41A3
TMEM134
CTU2
CHMP1A
SNAPC2
HYAL3
TMEFF2
TBC1D4
CNTNAP2
SNHG6
GGH
PPFIA3
TBX10
MFSD5
BCL2L1
TMED1
TCIRG1
SESN2
ATP59L
SERINC2
POLR3H
TMEM120A
THAP10
SLC25A1
PRRG2
PCYT2
ECHS1
TUSC2
POLE4
CD9
GET4
BCL7B
DGKA
BTBD11
CLCF1
GNB2
GLRX2
FKBPL
IL17RC
NPDC1
GRTP1

TABLE 5-continued

Table 5. 129 genes highly expressed in SPOP mutated prostate cancers compared to SPOP wild-type counterparts in the TCGA dataset Gene symbol

SCAND1
SND1
MRPL41
PHF1
TTLL12

Figure 12A:
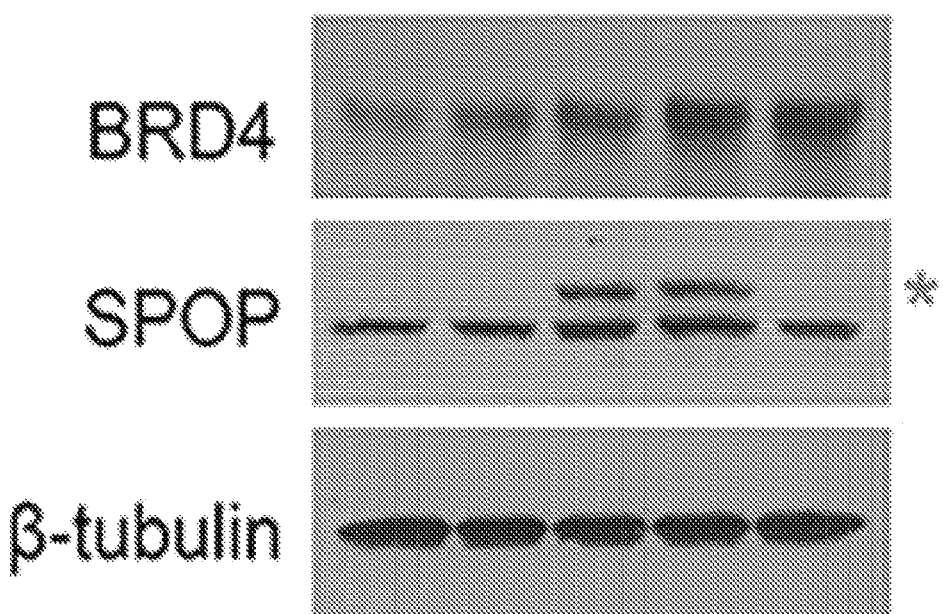
FIG. 12. RAC1 is a BRD4 binding target and upregulation of RAC1 contributes to JQ1-resistance in SPOP-mutated prostate cancer cells. a, Western blot of WCL of C4-2 cells infected with lentivirus expressing empty vector (EV) or SPOPF133V mutant or transfected with HA-BRD4 and treated with vehicle (DMSO) or 1 µM JQ1 for 24 hours before being harvested. Asterisk indicates the exogenous HA-SPOP-F133V. b, BRD4 binding corrects with 129 JQ1-resistant genes whose expression was upregulated in SPOP-mutated tumors. The red bar represents the percentage of 129 genes having BRD4 binding sites within 1 kb of the transcription start sites (TSS). The blue bell shape curve represents the background distribution as control, where 10,000 permutation tests were performed by randomly choosing 129 genes from refGenes and calculating the percentage of random genes with BRD4 binding in TSS. The enrichment of BRD4 binding at 129 upregulated genes over whole genome background is statistically significant. EV, empty vector. OE, overexpression. c, Data from a replicate of the experiment shown in FIGS. 7f and 7g. Top, Venn diagram showing the overlap of JQ1-resistant genes upregulated in SPOP-mutated prostate tumors with the common BRD4 target genes induced by SPOP F133V and HA-BRD4 expression in C4-2 cells. The overlap is statistically significant with P=6.591e-13 (Permutation test). Bottom, BRD4 ChIPseq signals in EV- and F133V-expressing C4-2 cells treated with or without JQ1 (1 µM) and H3K4me3 ChIP-seq signals in LNCaP cells (Wang et al., Nature, 474:390-394 (2011)). d, BRD4 ChIP-seq signals in the RAC1 promoter in several human cell lines including HEK293T, HeLa, H2171, and U87 and mouse acute myeloid leukemia (AML) cells (Roe et al., Mol. Cell., 58:1028-1039 (2015)). H3K4me3 ChIP-seq signals in LNCaP cells are included. e, Western blot analysis of indicated proteins in whole-cell lysate of C4-2 cells infected with empty vector (EV) or SPOP F133V or BRD2/3/4 expressed vectors for 48 hours before being harvested. f, Venn diagram shows that JQ1-resistant genes upregulated in SPOP-mutated prostate tumors significantly overlapped with the genes upregulated by BRD2/3/4 overexpression (OE) in C4-2 cells (P<0.001, Permutation test). g, UCSC genome browser screen shots showing signal profiles of RNA-seq in the gene region of the RAC1 gene in C4-2 cells transfected with empty vector (control) and BRD2/3/4 overexpressed (OE). h, ChIP-qPCR analysis of BRD4 binding at the RAC1 promoter in C4-2 cells infected and treated as in (a). All data are shown as mean values±SD (n=3 technical replicates), and similar results were obtained from two independent experiments. i, Western blot analysis of indicated proteins in whole cell lysate of C4-2 cells infected with empty vector (EV) or SPOP F133V or BRD2/3/4 expressed vectors for 48 hours before being harvested. j, ChIP-qPCR analysis of H3K27ac, H4K5ac, and H4K8ac binding at the RAC1 promoter of the indicated genes in C4-2 cells transfected with empty vector (Control), SPOP F133V or BRDs. All data shown are mean values±SD (error bar)
Figure 12B:
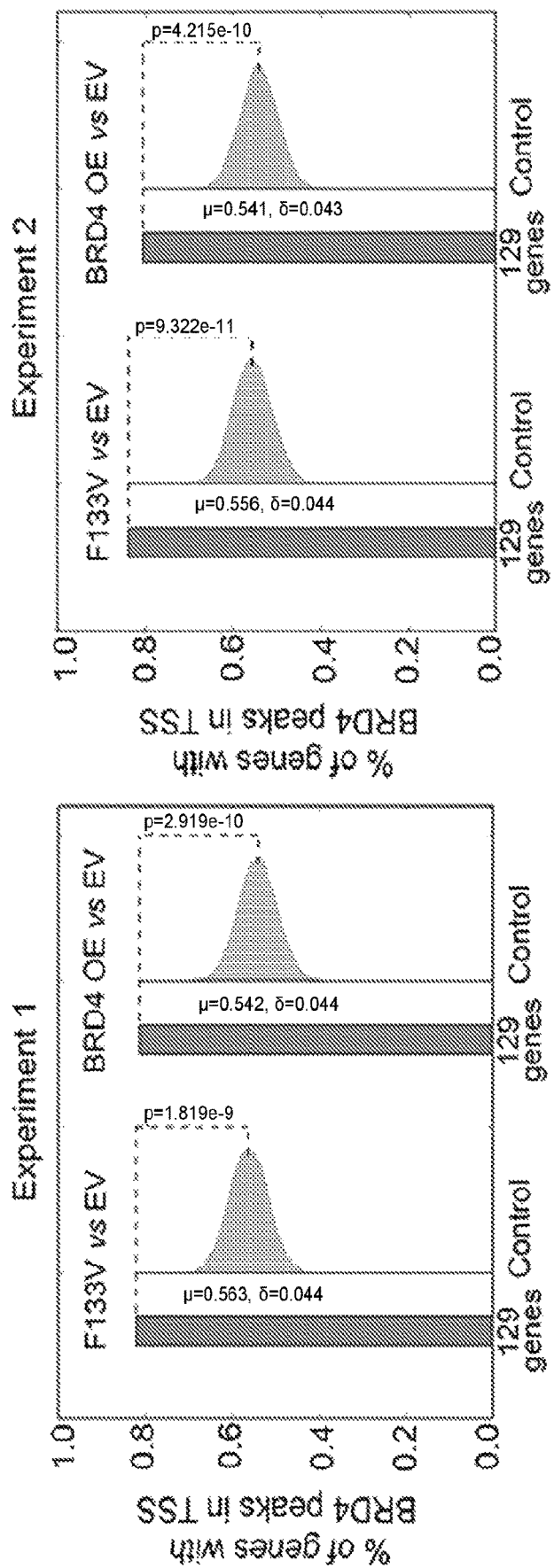
Figure 12C:
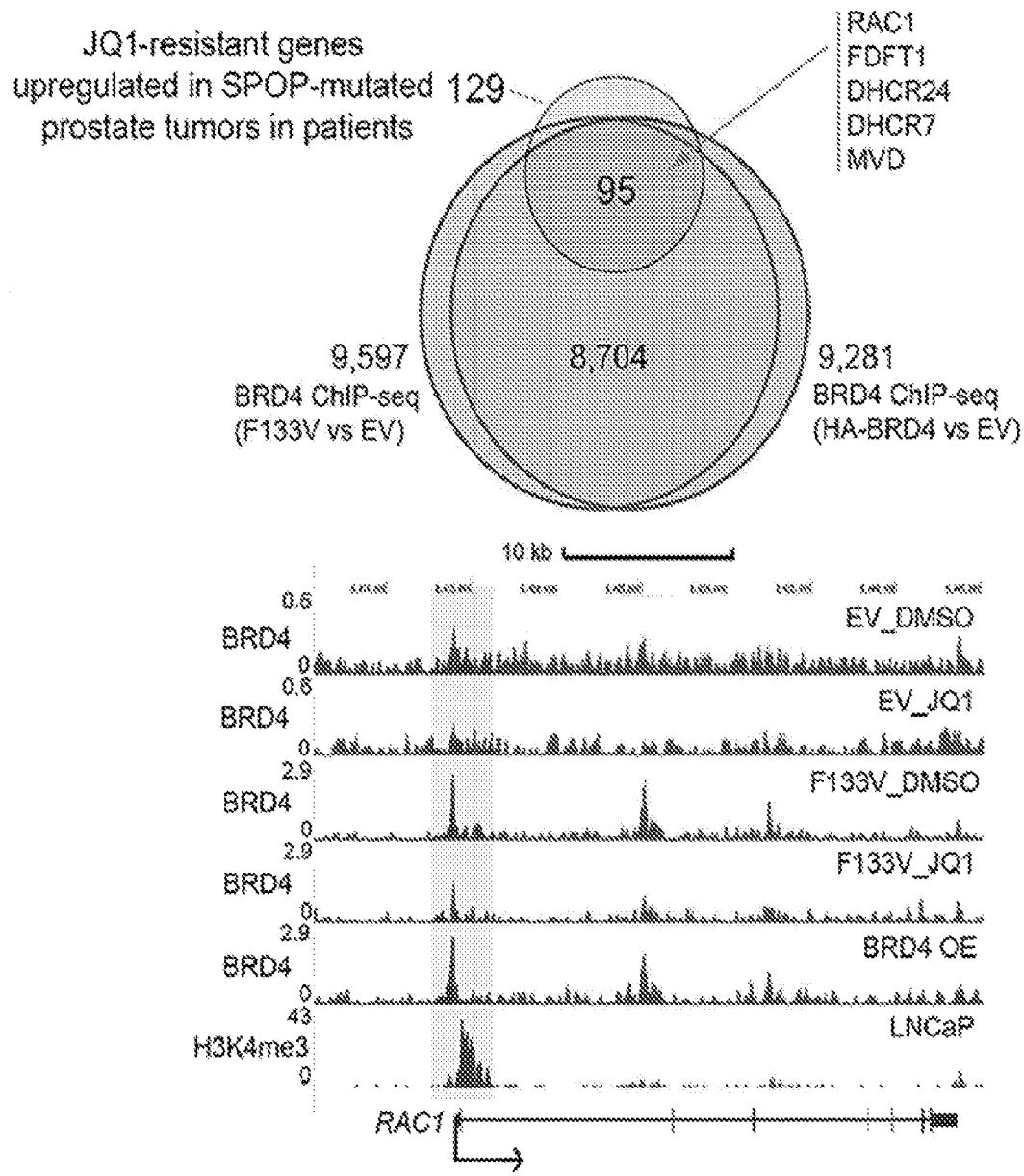
Figure 12D:
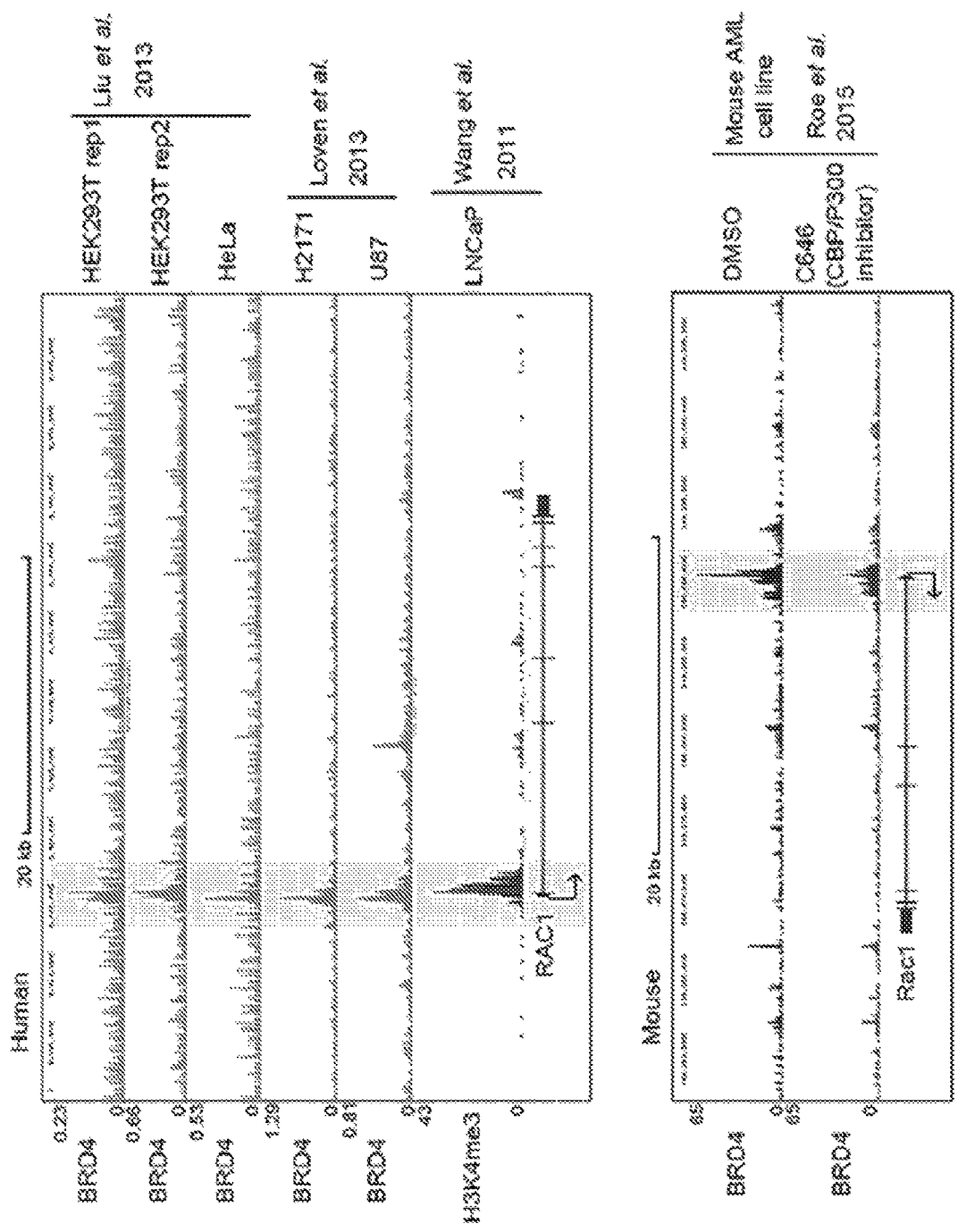
Figure 12E:
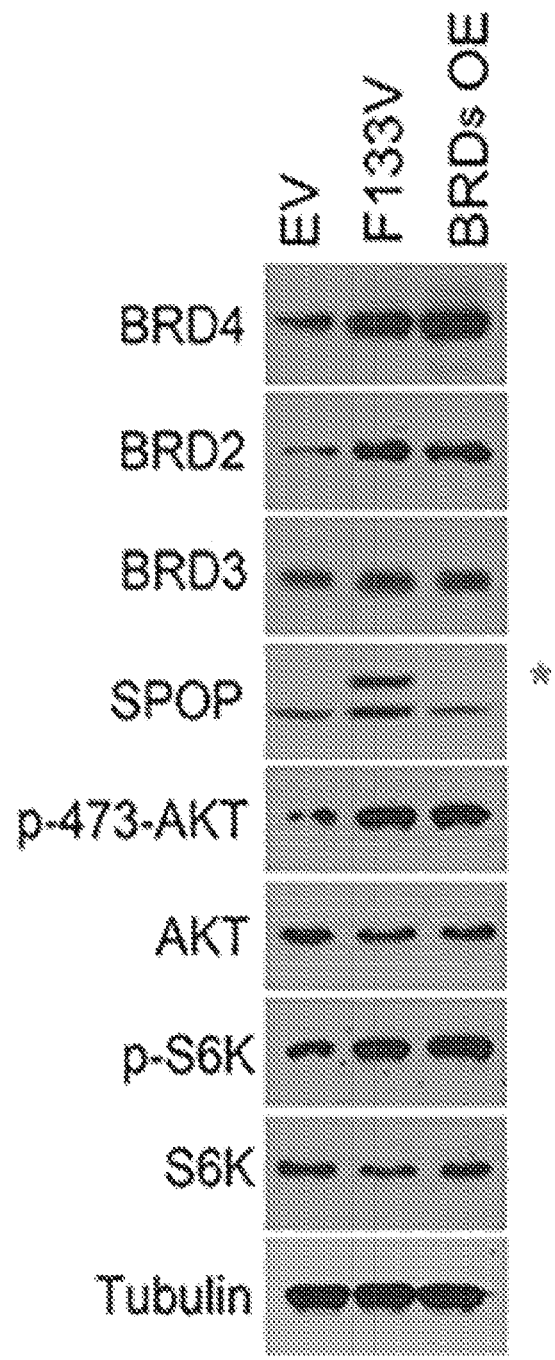
Figure 12F:
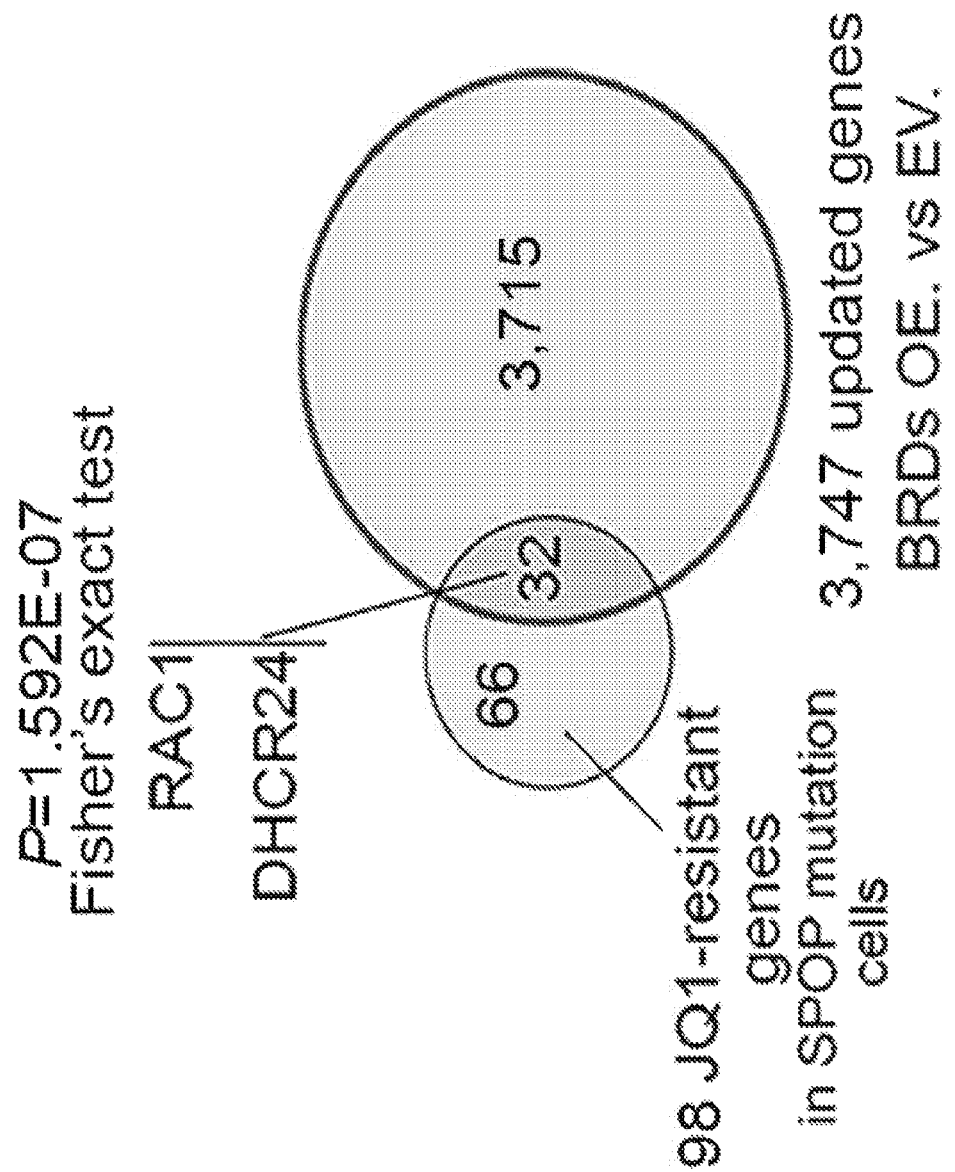
Figure 12G:
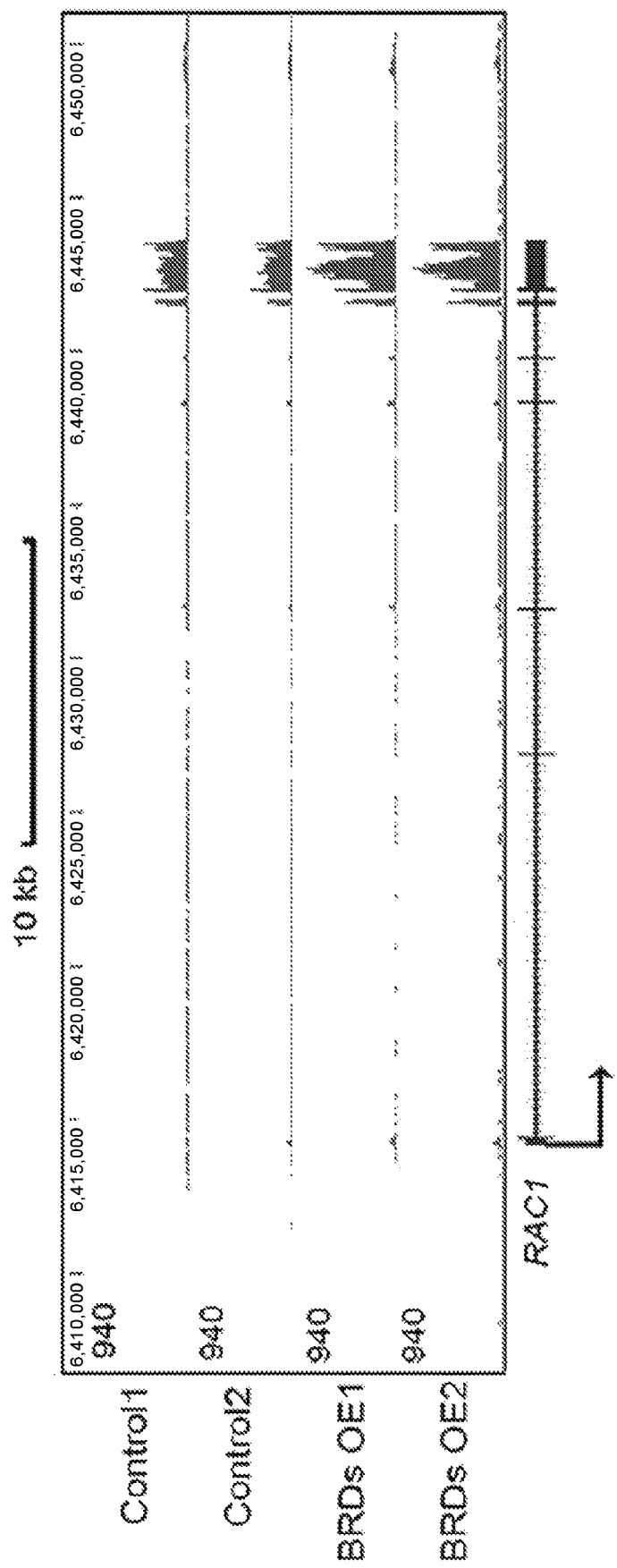
Figure 12H:
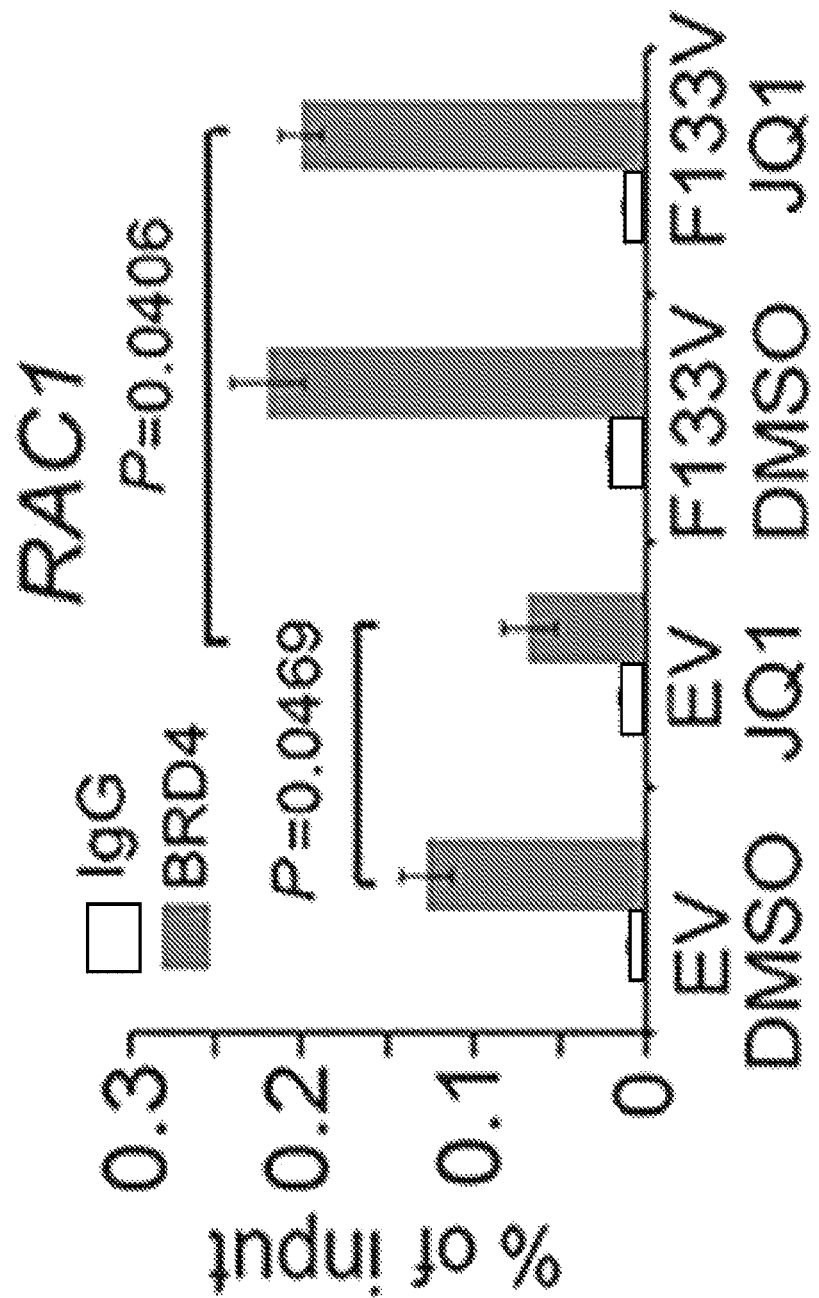
Figure 12I:
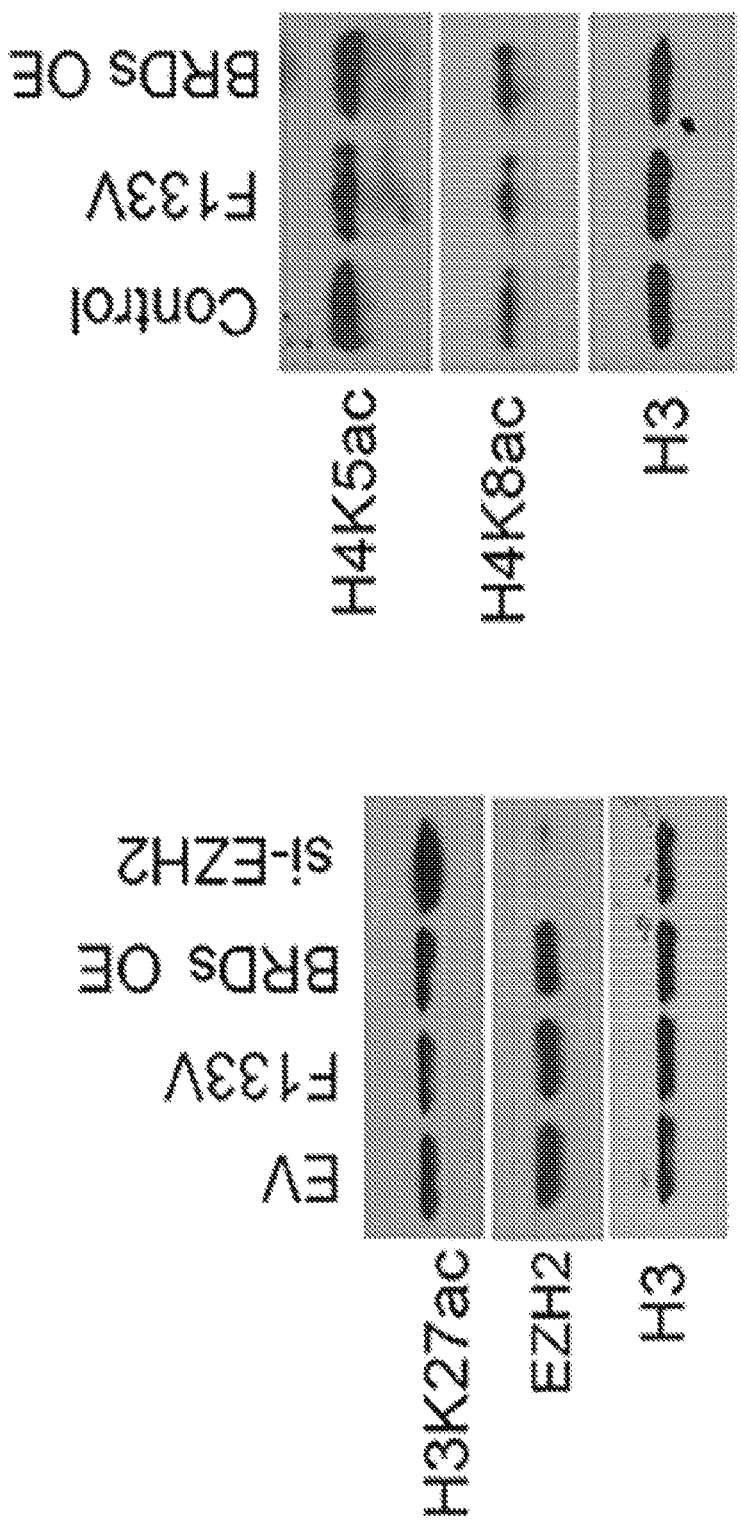
Figure 12J:
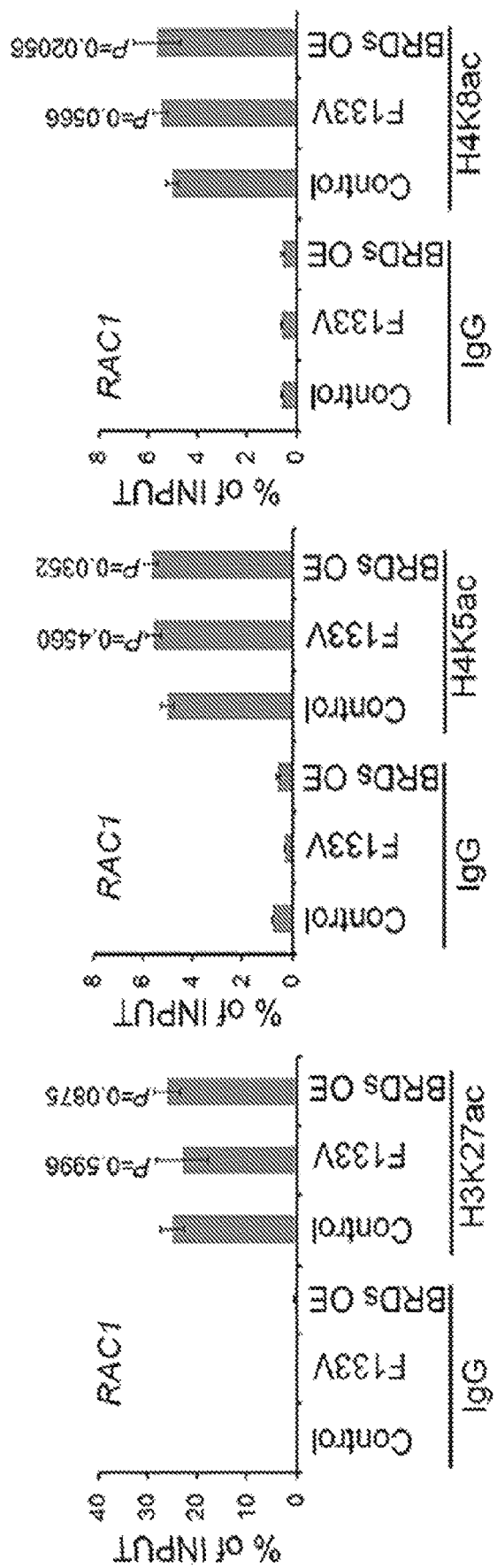
Figure 12K:
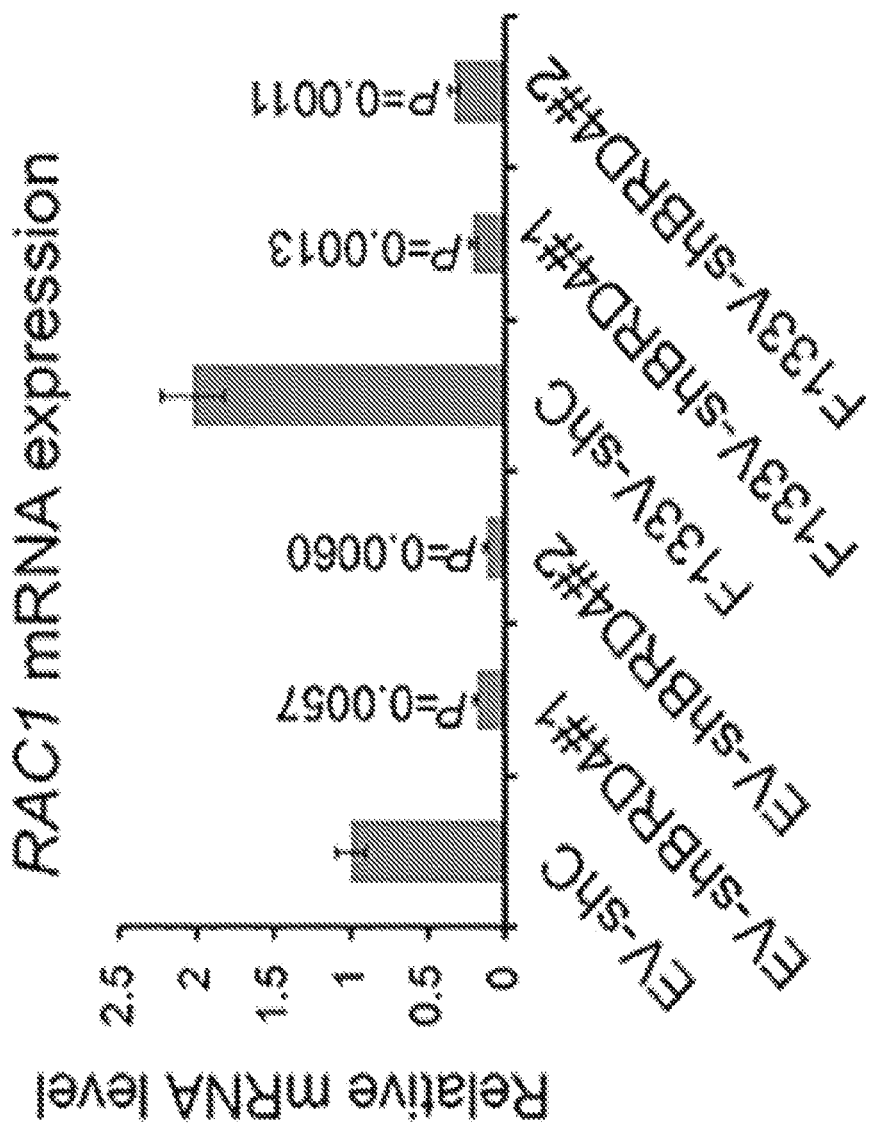
Figure 12L:
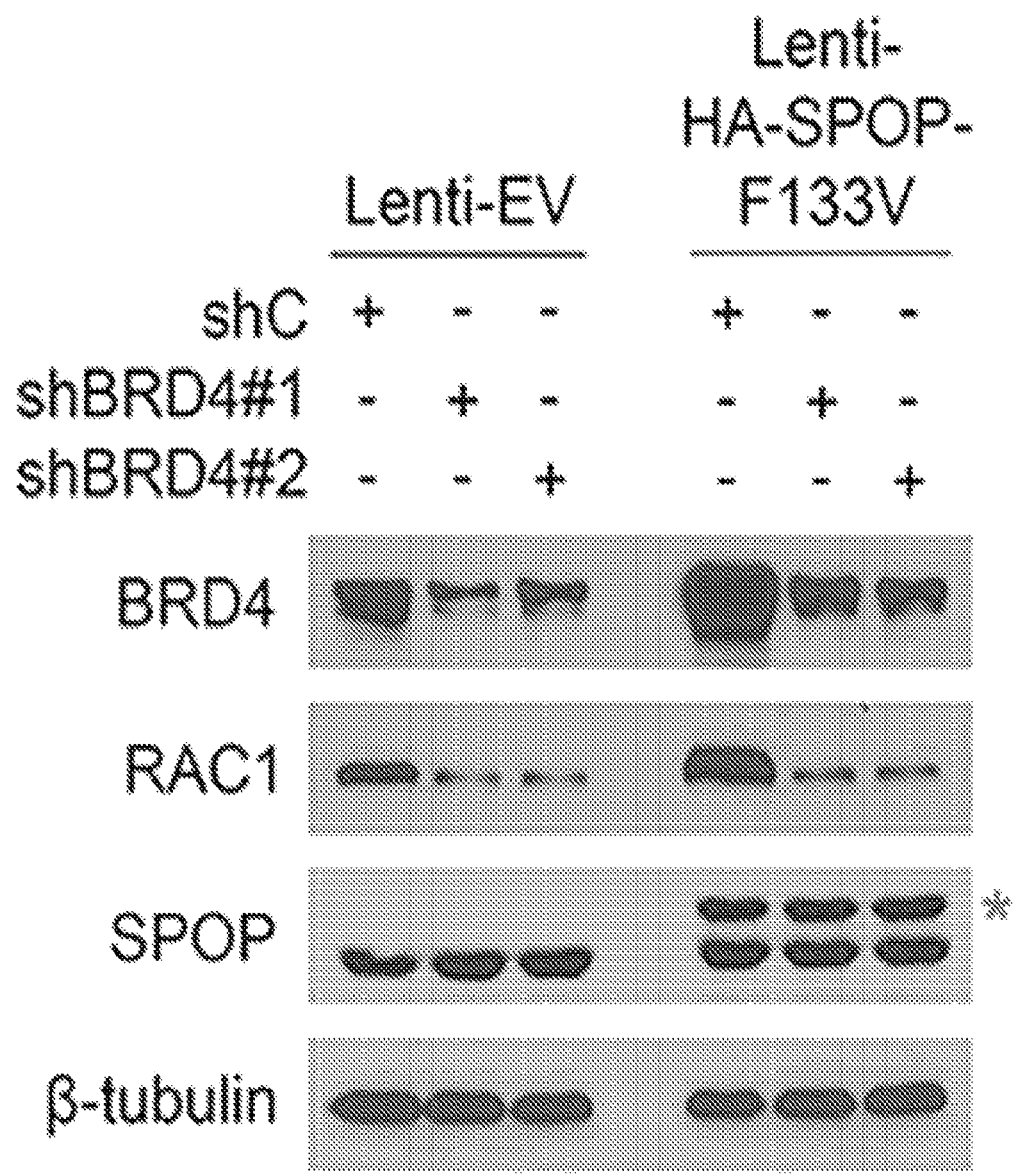
Figure 12M:
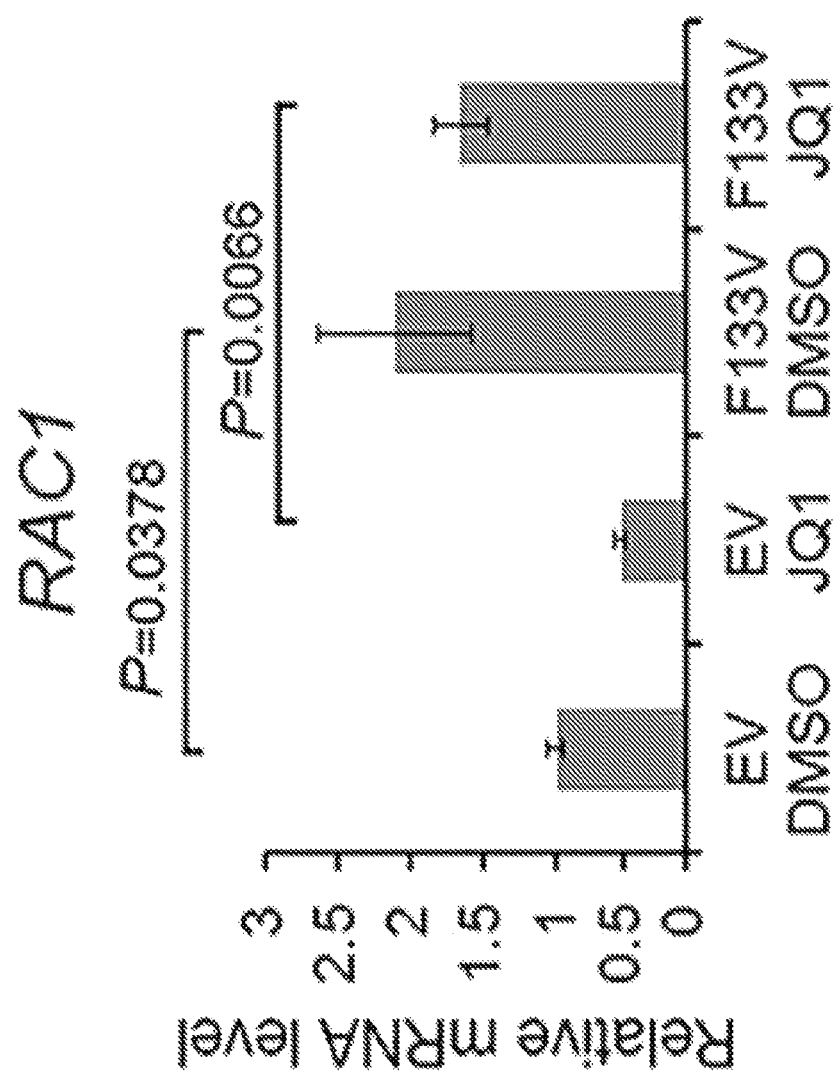
Figure 12N:
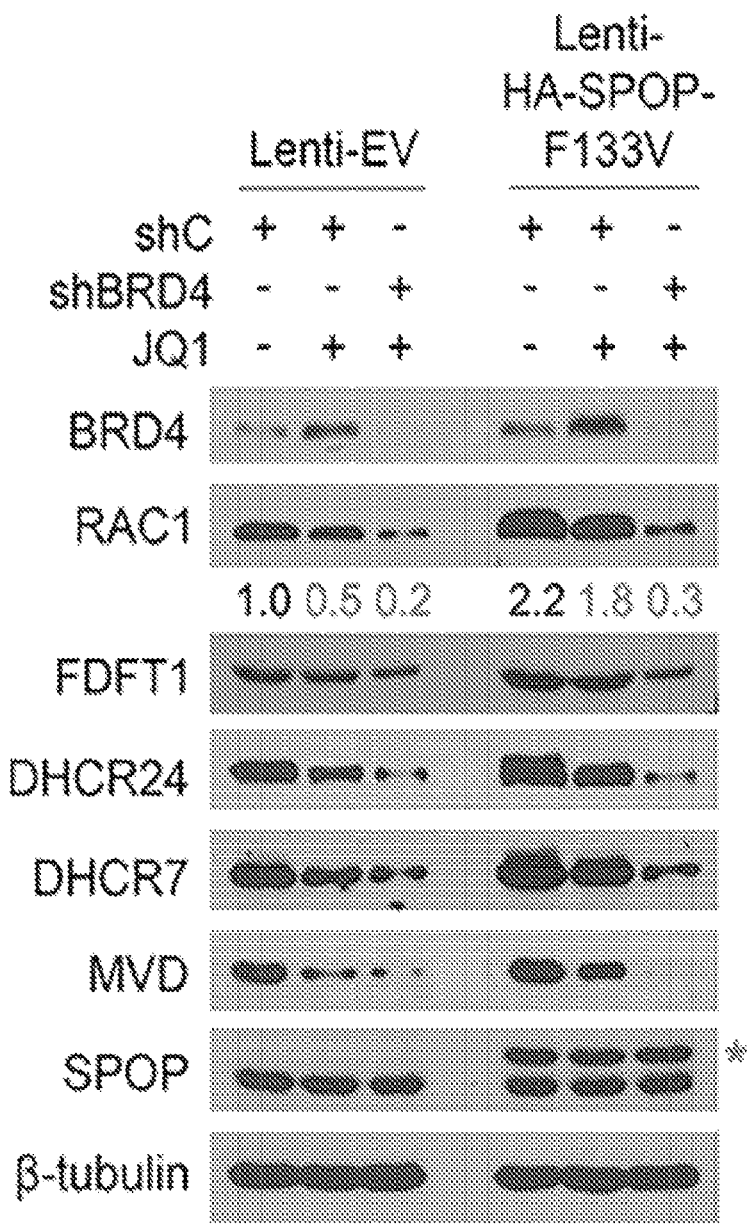
Figure 12O:
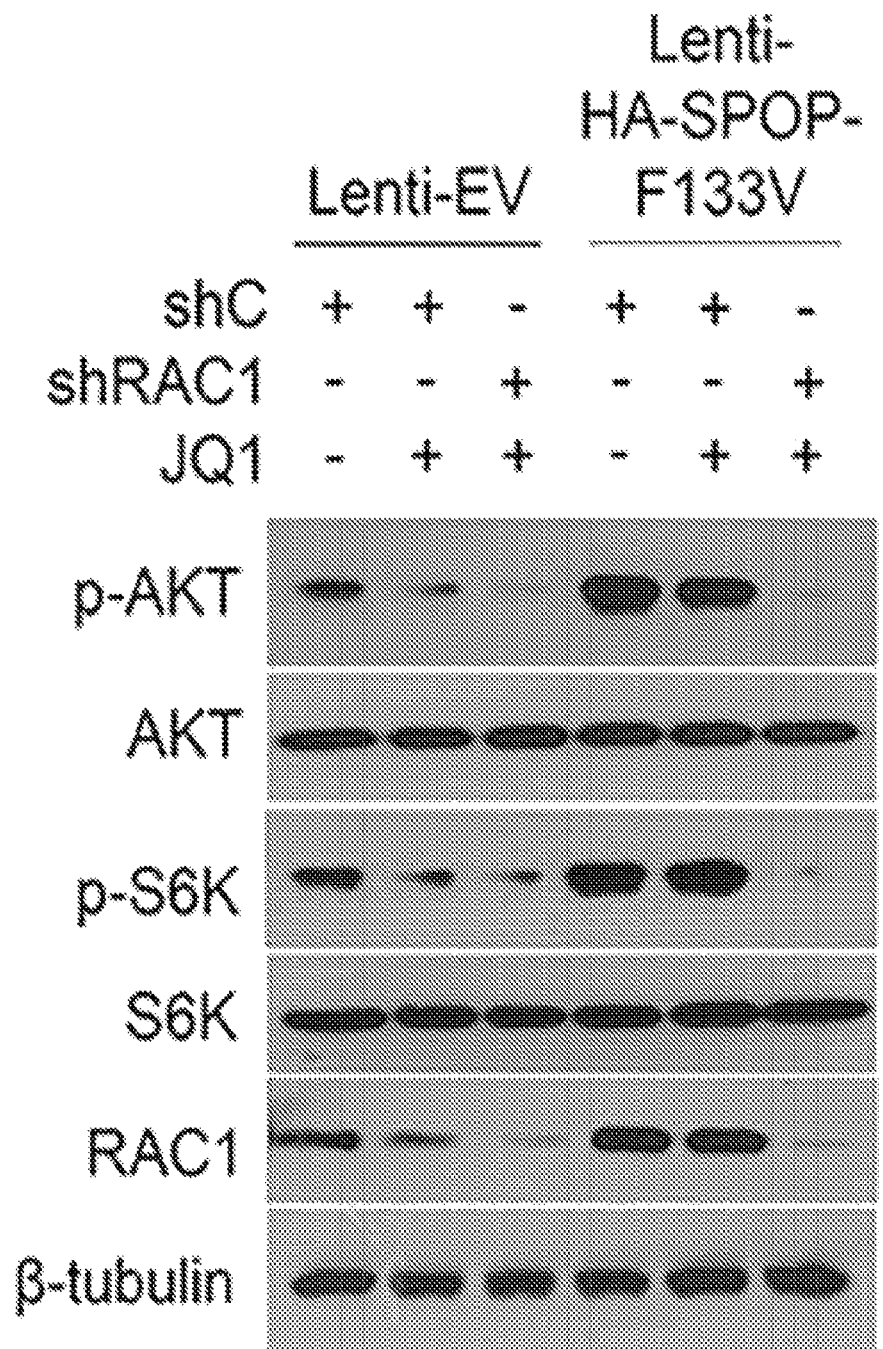
Figure 12P:
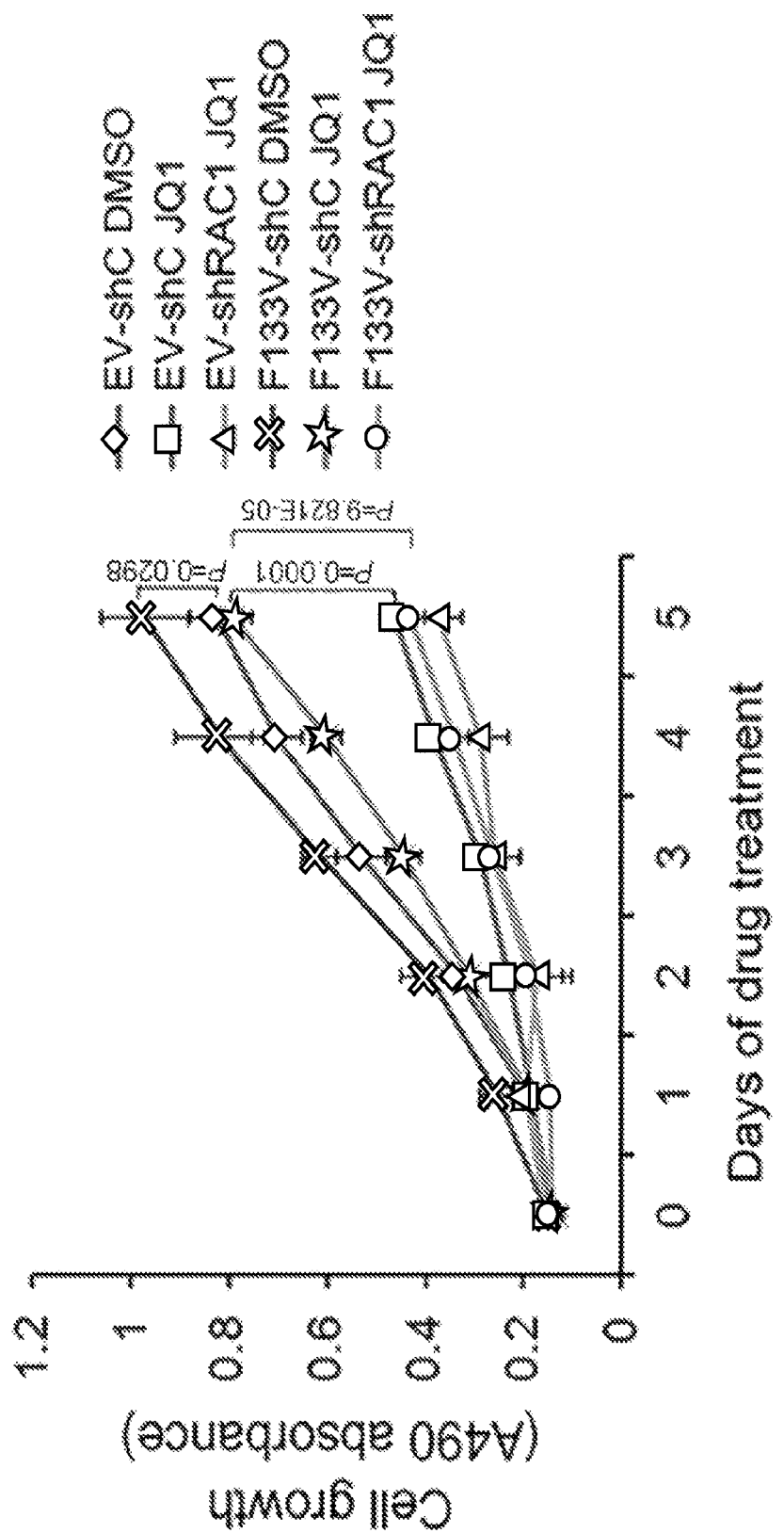

RAC1, a RHO GTPase family member, was upregulated in SPOP-mutated tumors (FIG. 7e). Meta-analysis also showed BRD4 binding at the RAC1 locus in different cell types (FIG. 12d). RNA-seq analysis revealed that global transcriptional changes caused by BRD2/3/4 overexpression in C4-2 cells significantly overlapped with the genes associated with JQ1 resistance in F133V-mutant cells, including RAC1 (FIGS. 12e-g). ChIP-seq and ChIP-qPCR assays revealed that BRD4 readily bound at the RAC1 gene promoter in control cells, but the binding was largely enhanced by expression of SPOP-F133V or HA-BRD4 (FIGS. 7f, 7g, 12c, and 12h). Increased BRD4 binding was unlikely caused by histone acetylation changes since expression of SPOP F133V or BRD proteins had no effect on the level of H3K27ac, H4K5ac, and H4K8ac, both globally and in the RAC1 locus (FIGS. 12i and 12j). BRD4-dependent regulation of RAC1 was confirmed by gene knockdown experiments (FIGS. 12k and 12l), providing further evidence that RAC1 was a bona fide BRD4 target gene. Additionally, increased BRD4 binding and RAC1 mRNA and protein expression correlated with high levels of BRD4 proteins in JQ1-resistant SPOP-F133V cells compared to JQ1-untreated control cells (FIGS. 7g, 12c, 12m, and 12n). Furthermore, SPOP-F133V expression substantially increased phosphorylation of AKT and S6K, a downstream kinase of mTORC1, in both C4-2 and 22Rv1 cells regardless of JQ1 treatment (FIGS. 6m and 12o). Knockdown of RAC1 not only inhibited SPOP-F133V-augmented AKT and S6K phosphorylation, but also abolished SPOP-F133V-mediated JQ1 resistance in C4-2 cells (FIGS. 12o and 12p).

Figure 13A:
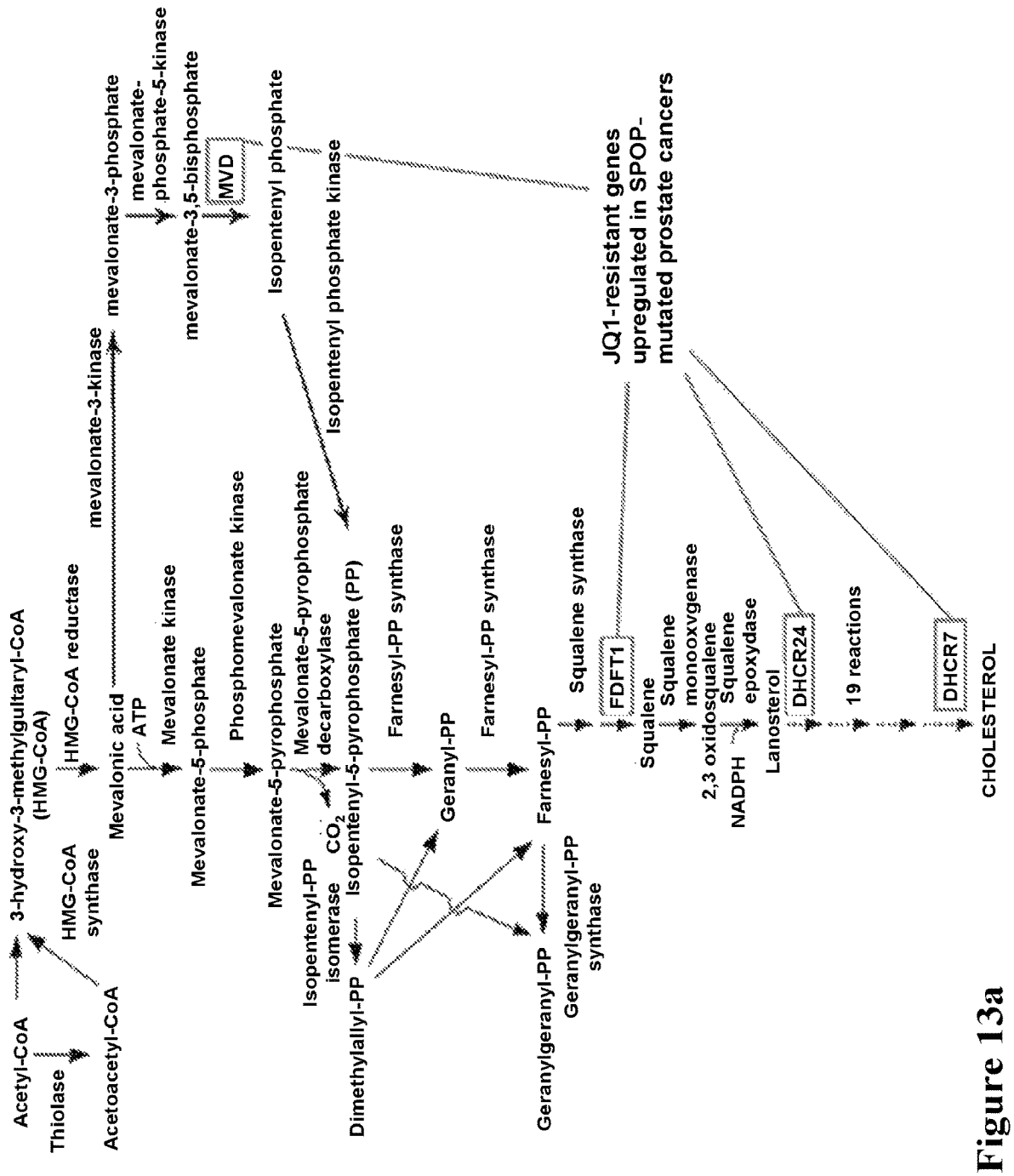
Figure 13B:
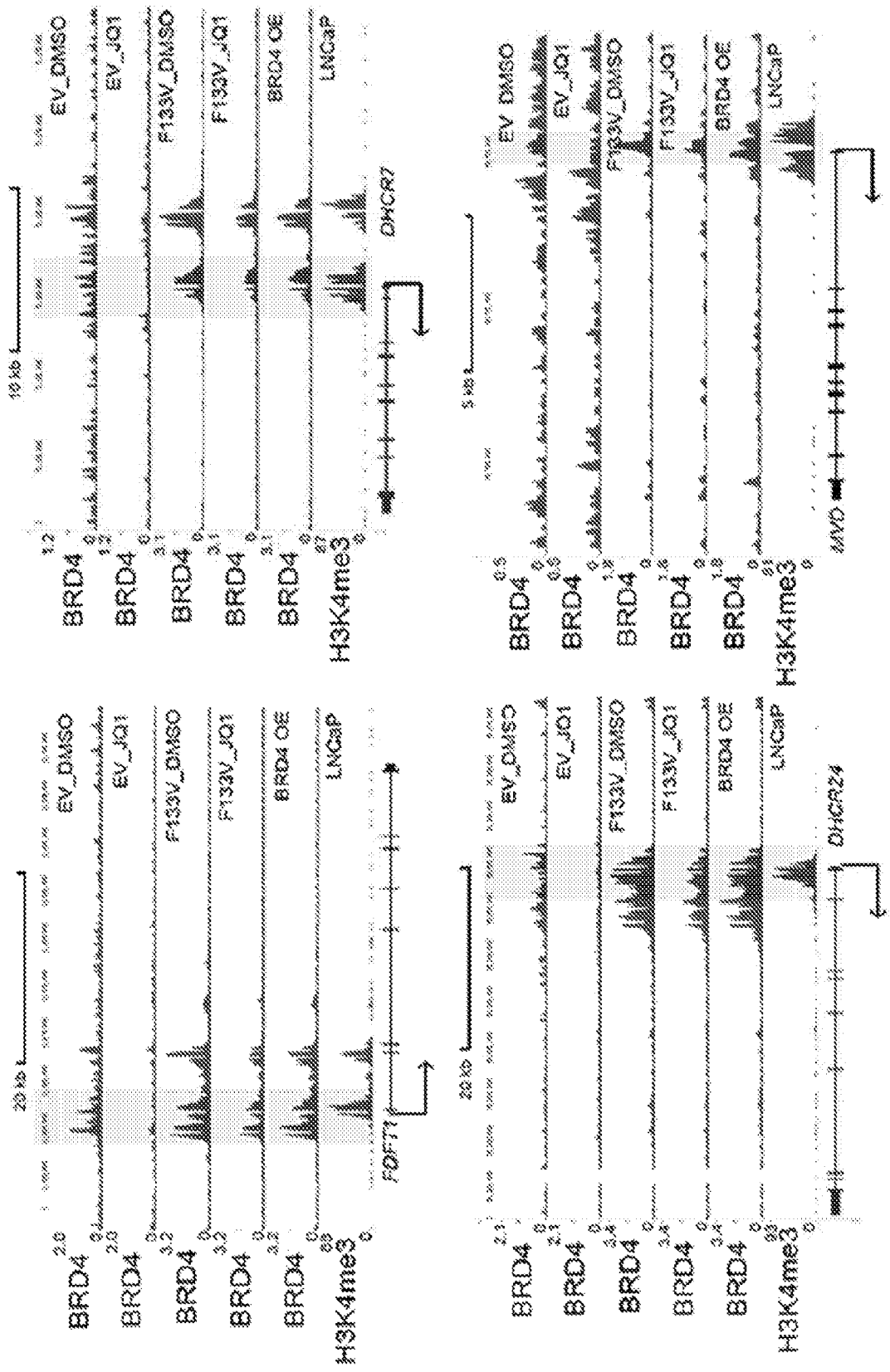
Figure 13C:
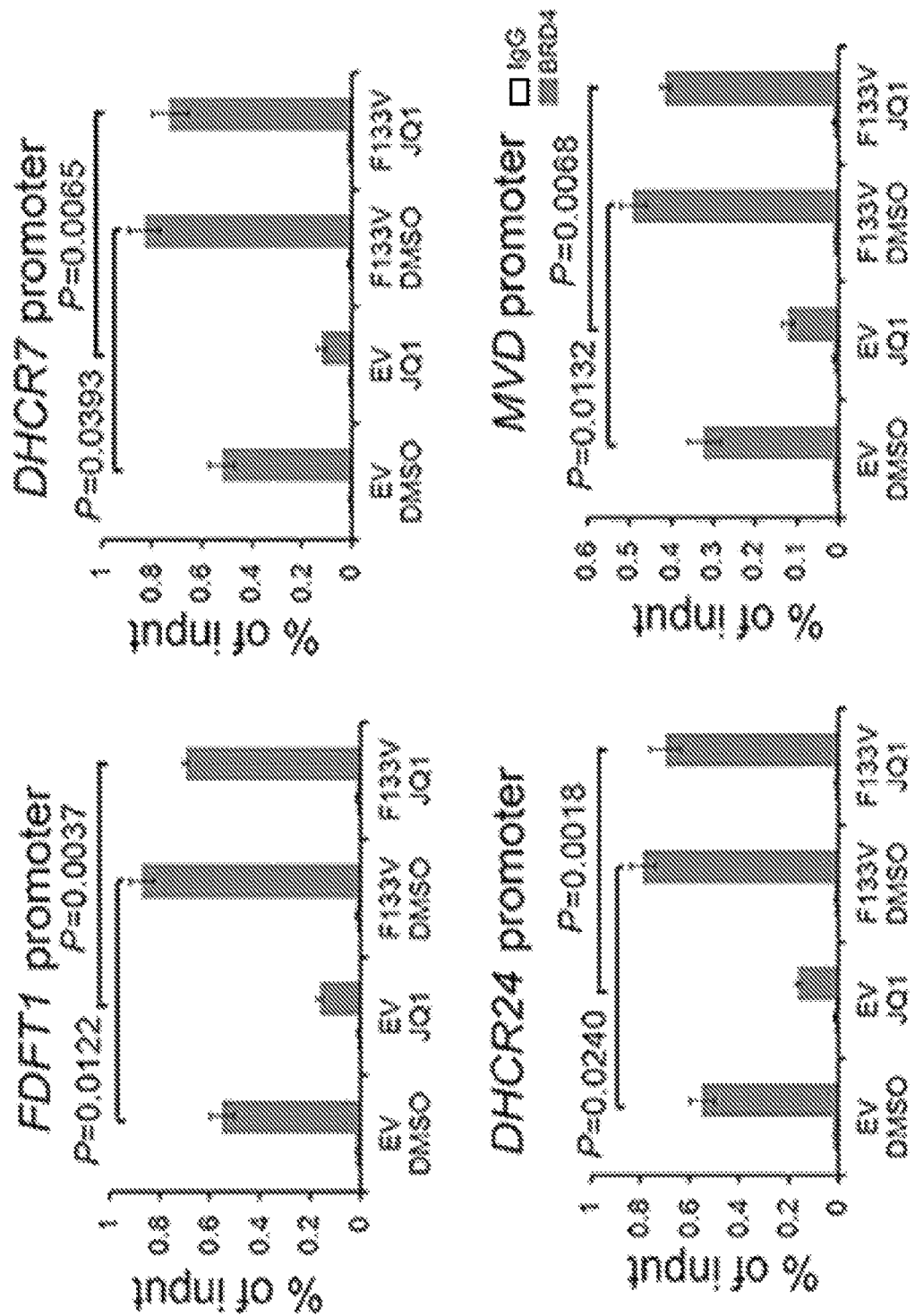
Figure 13D:
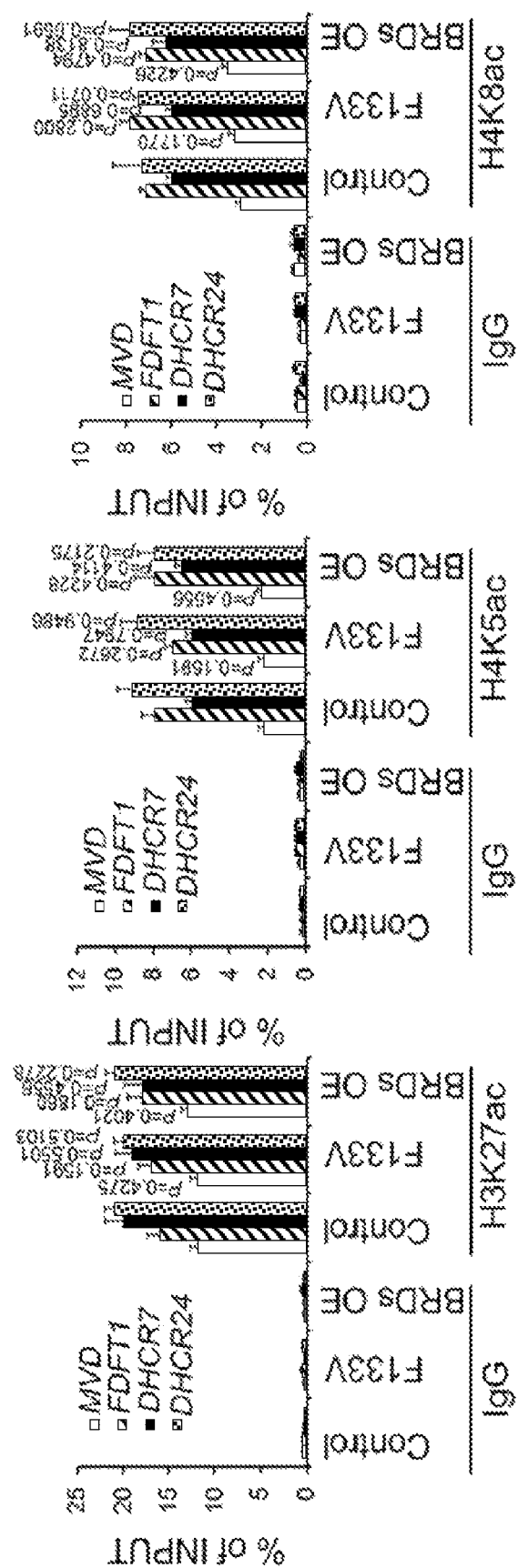
Figure 13E:
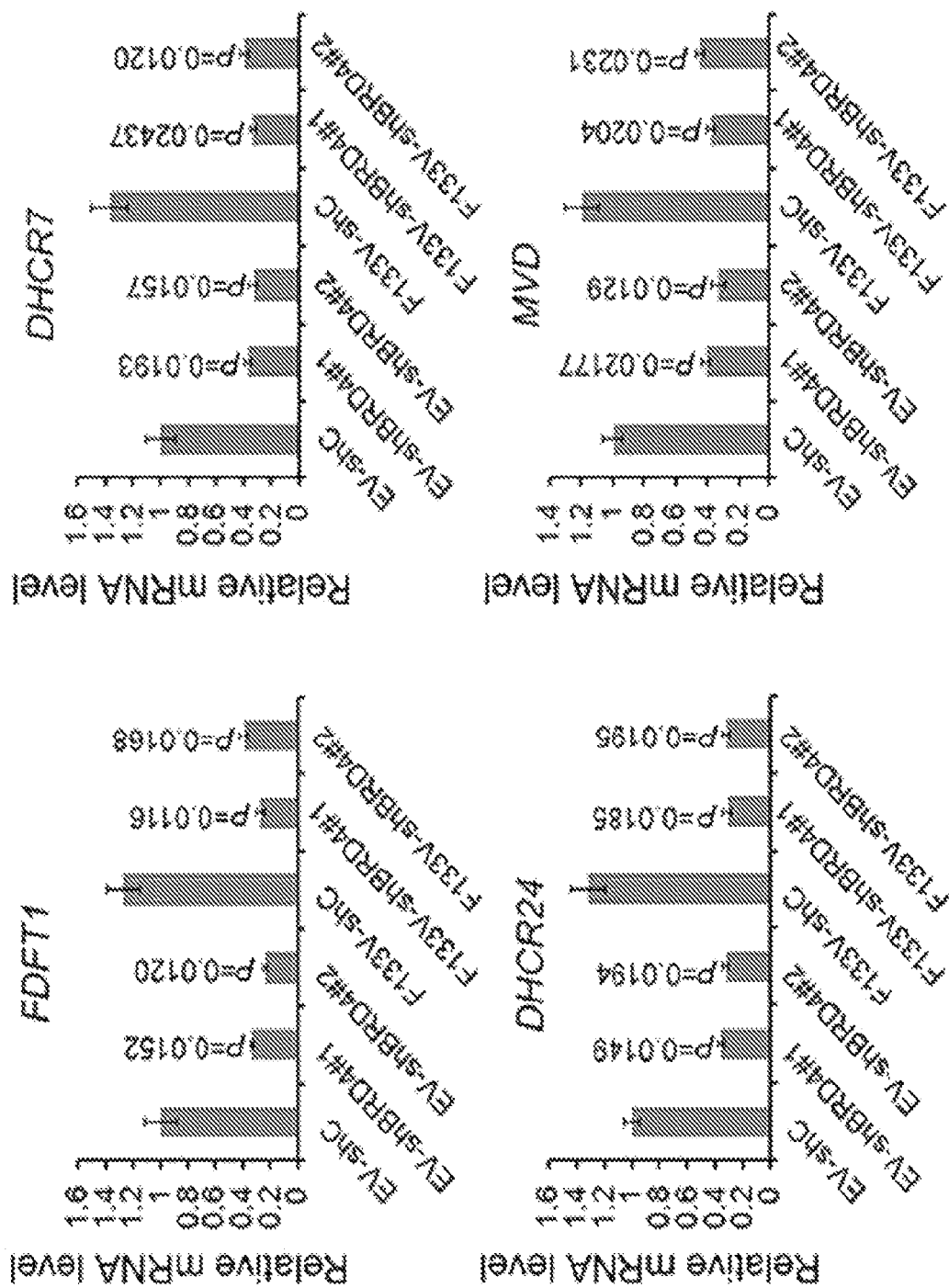
Figure 13F:
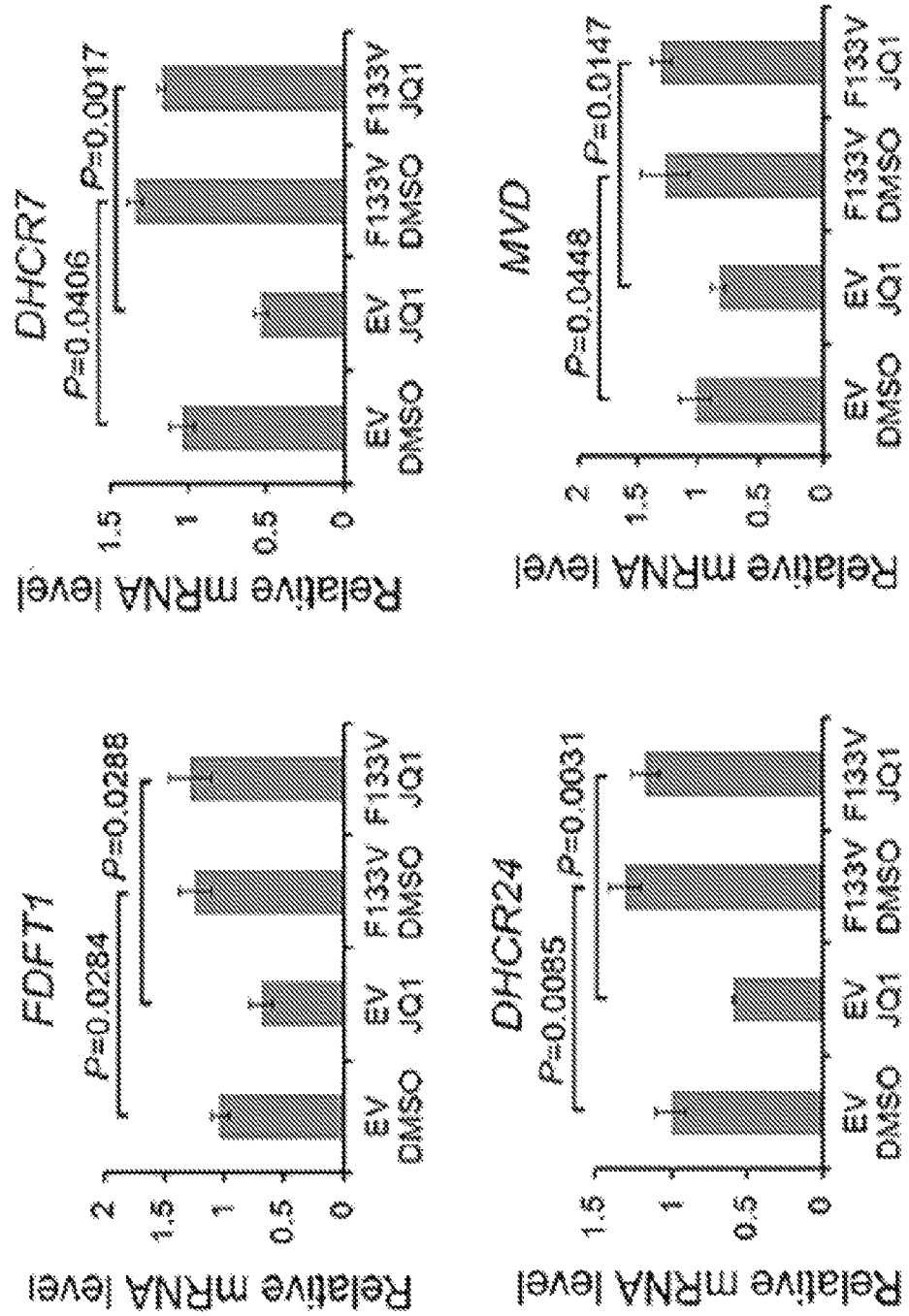
Figure 13G:
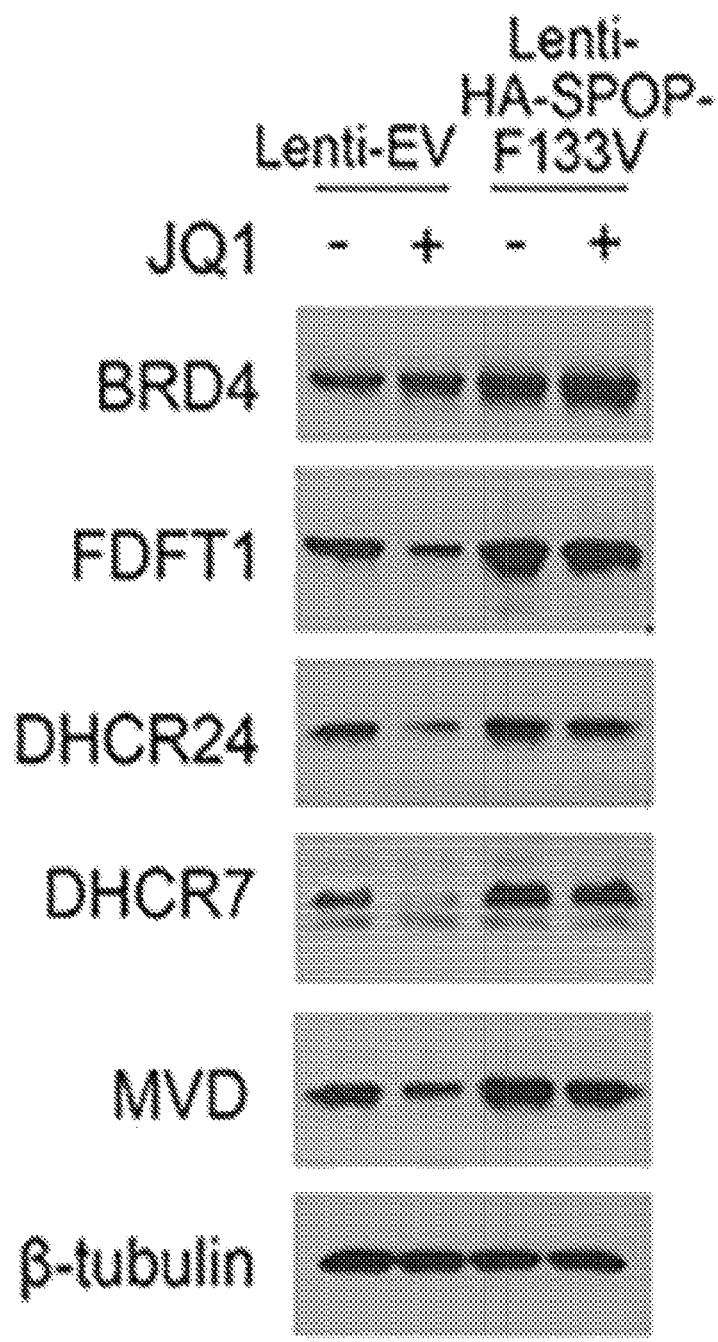
Figure 13H:
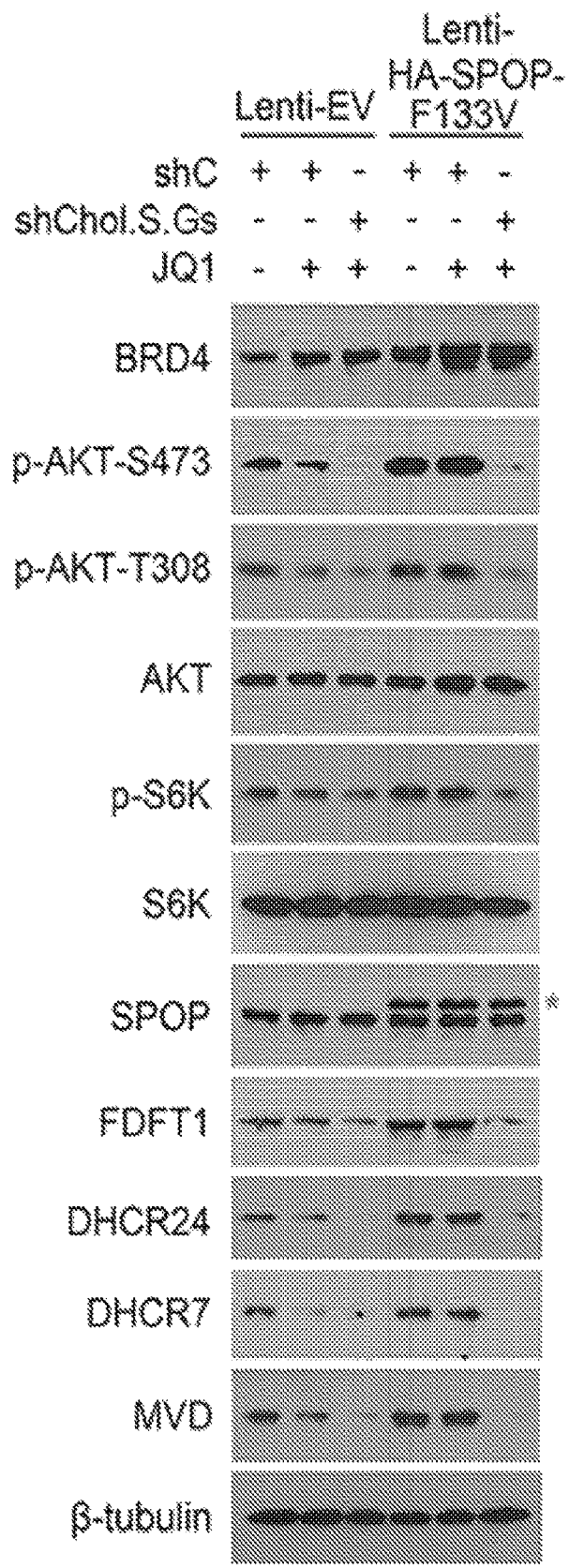
Figure 13I:
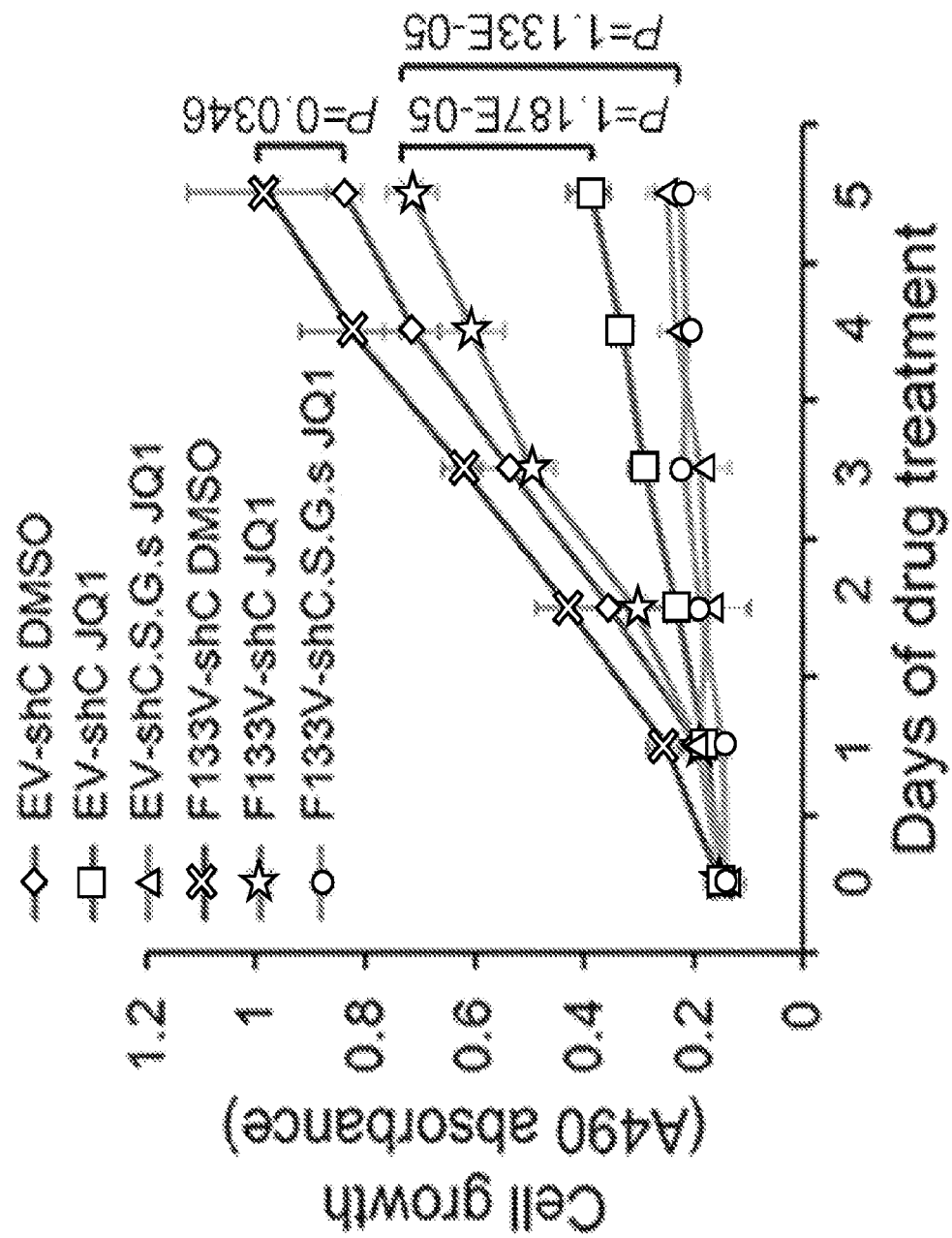
Figure 13J:
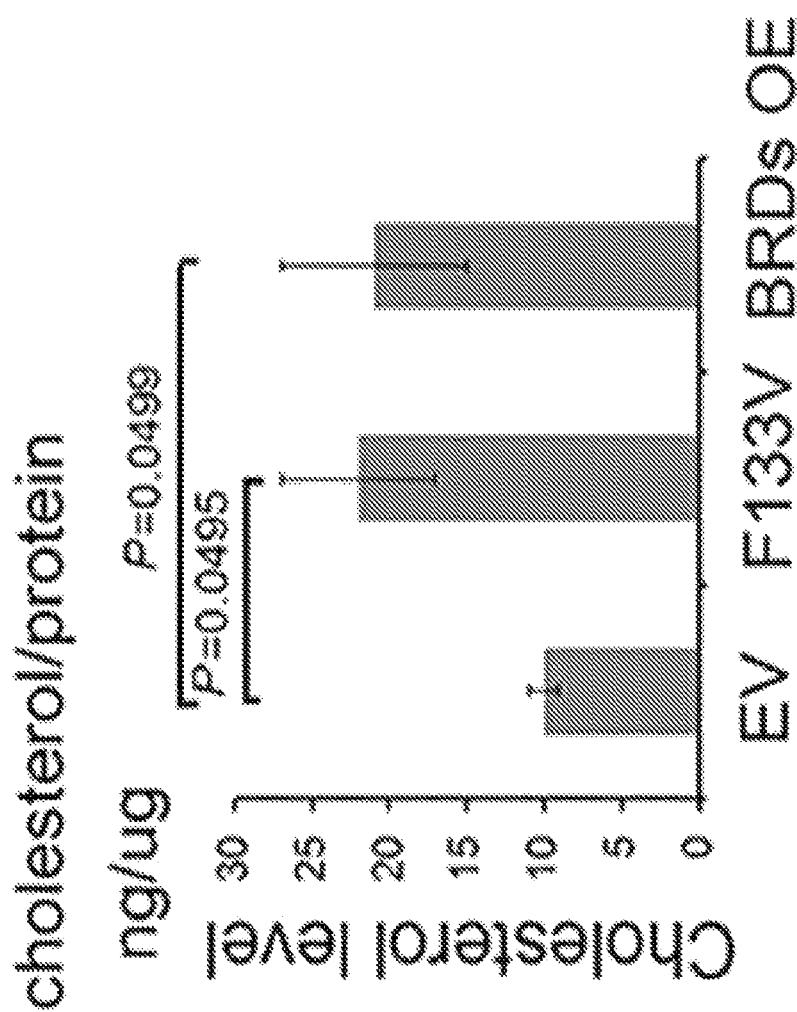
Figure 13K:
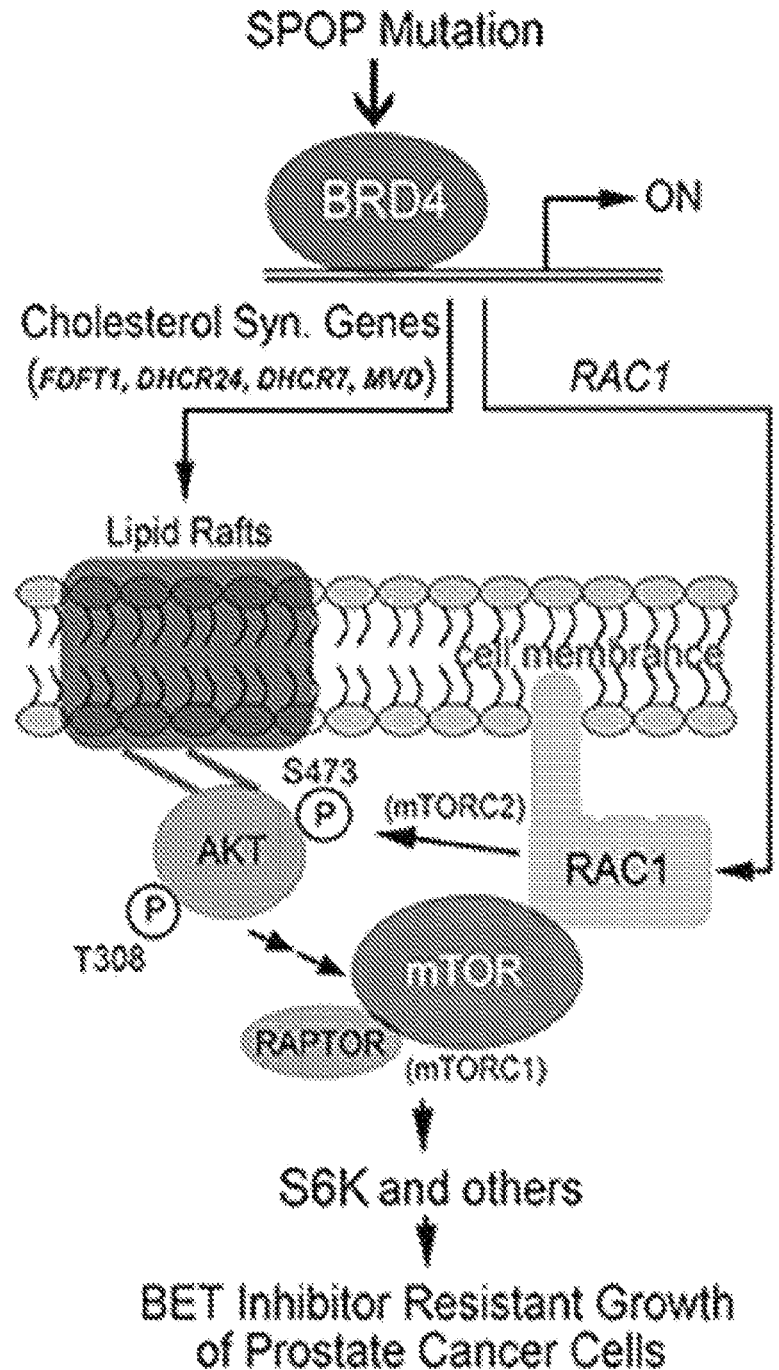
Figure 13I:
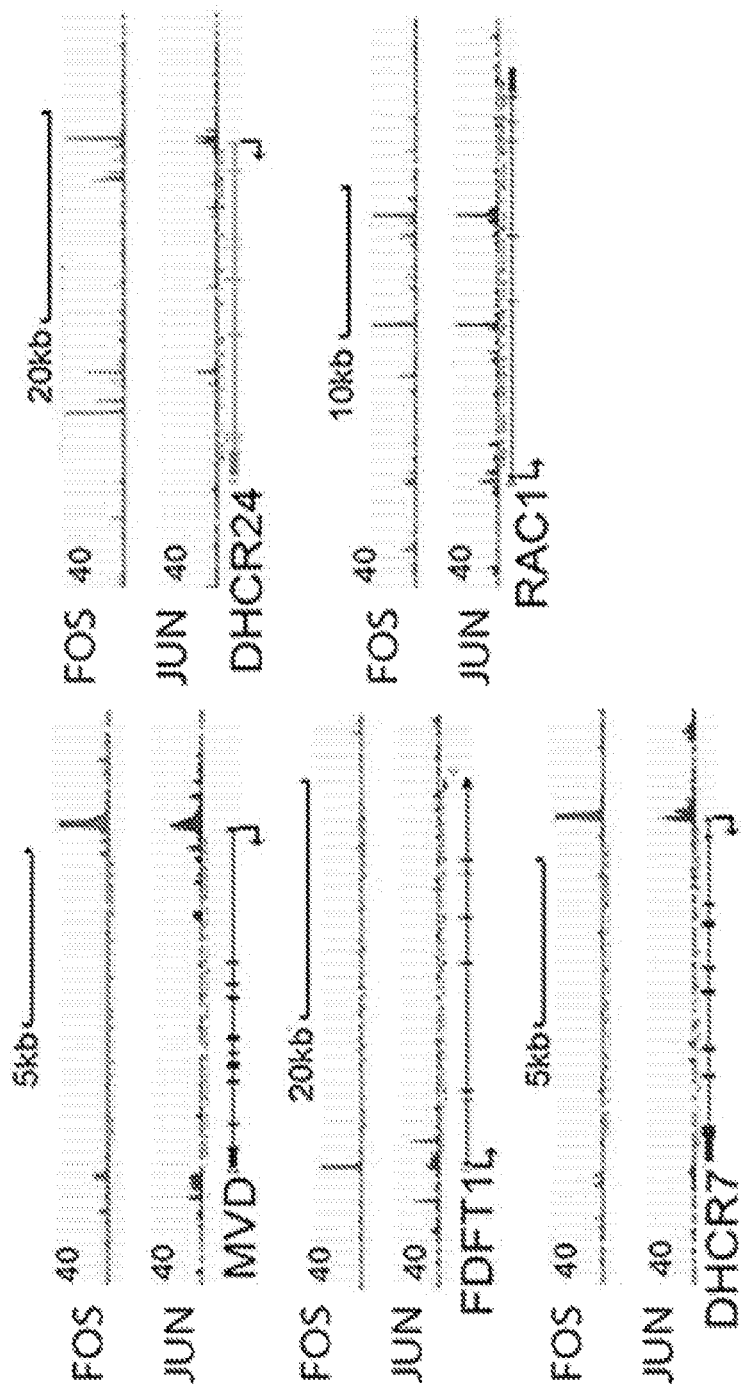

ChIP-seq and ChIP-qPCR assays showed that BRD4 readily bound in the promoters of cholesterol synthesis genes FDFT1, DHCR24, DHCR7 and MVD in control cells and that the binding was enhanced by SPOP-F133V (FIGS. 13a-c). This effect was unlikely caused by global or locus-specific histone acetylation changes (FIGS. 12i and 13d). Knockdown of BRD4 largely decreased expression of these genes at mRNA and protein levels in both control and SPOP-F133V cells (FIGS. 12n and 13e). With concomitant induction of BRD4 protein levels, SPOP-F133V upregulated the expression of cholesterol synthesis genes at both mRNA and protein levels and enhanced BRD4 binding in their promoters (FIGS. 13b, 13c, 13e, and 13f). JQ1 treatment largely inhibited expression of these genes and BRD4 binding at their promoters in control cells, but the effect was not pronounced in SPOP-F133V cells (FIGS. 13b, 13c, 13f, and 13g). Co-depletion of these cholesterol synthesis genes abolished SPOP-F133V-induced activation of the AKT-mTORC1 pathway and JQ1-resistance in C4-2 cells (FIGS. 13h and 13i). Similar to SPOP mutant, moderate overexpression of BRD2/3/4 increased cholesterol biosynthesis and AKT/mTORC1 activation (FIGS. 12e and 13j). These results demonstrate that both RAC1 and cholesterol synthesis pathways are involved in mediating SPOP mutation-induced AKT/mTORC1 activation and JQ1 resistance (FIG. 13k).

Figure 13M:
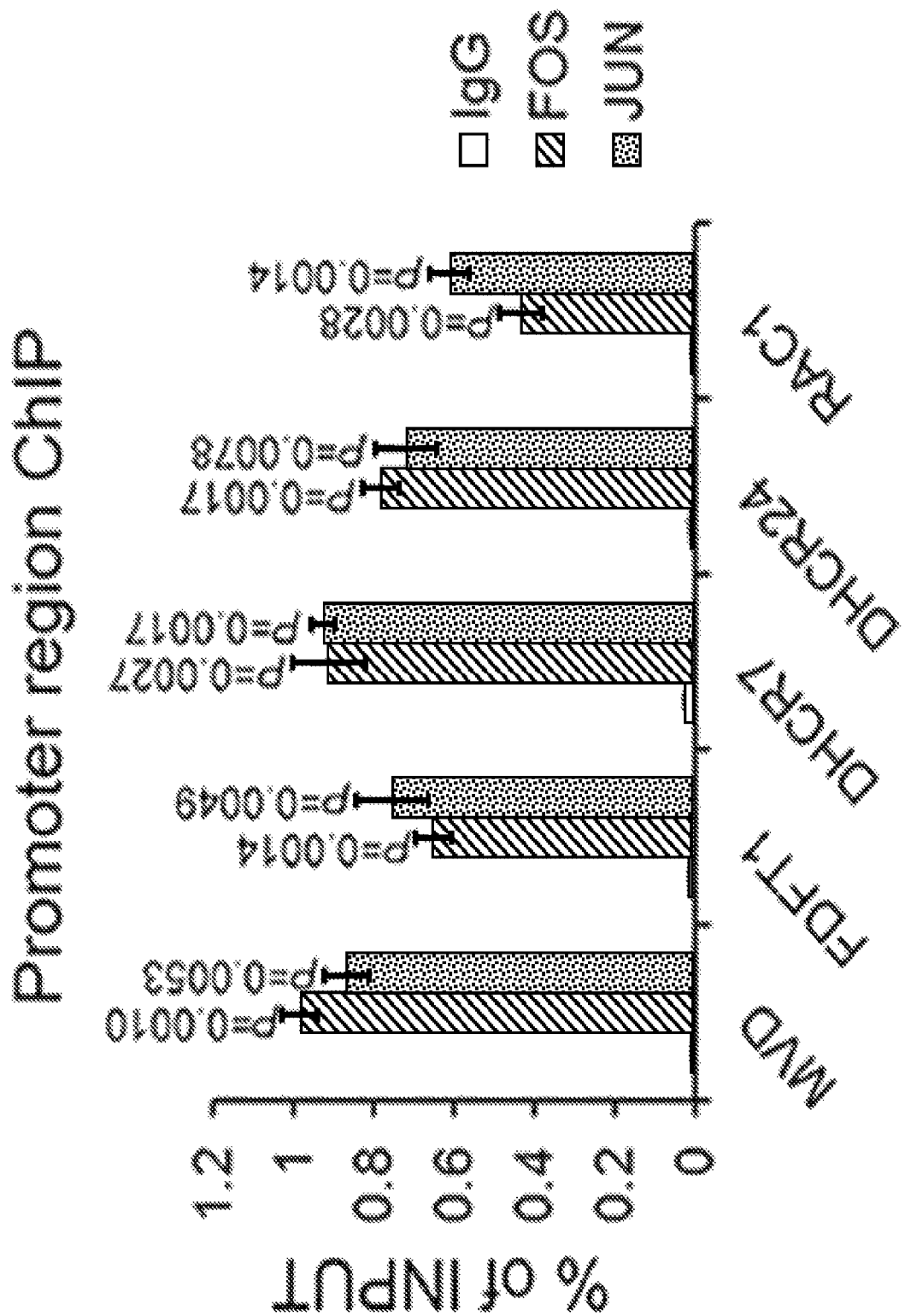
Figure 13N:
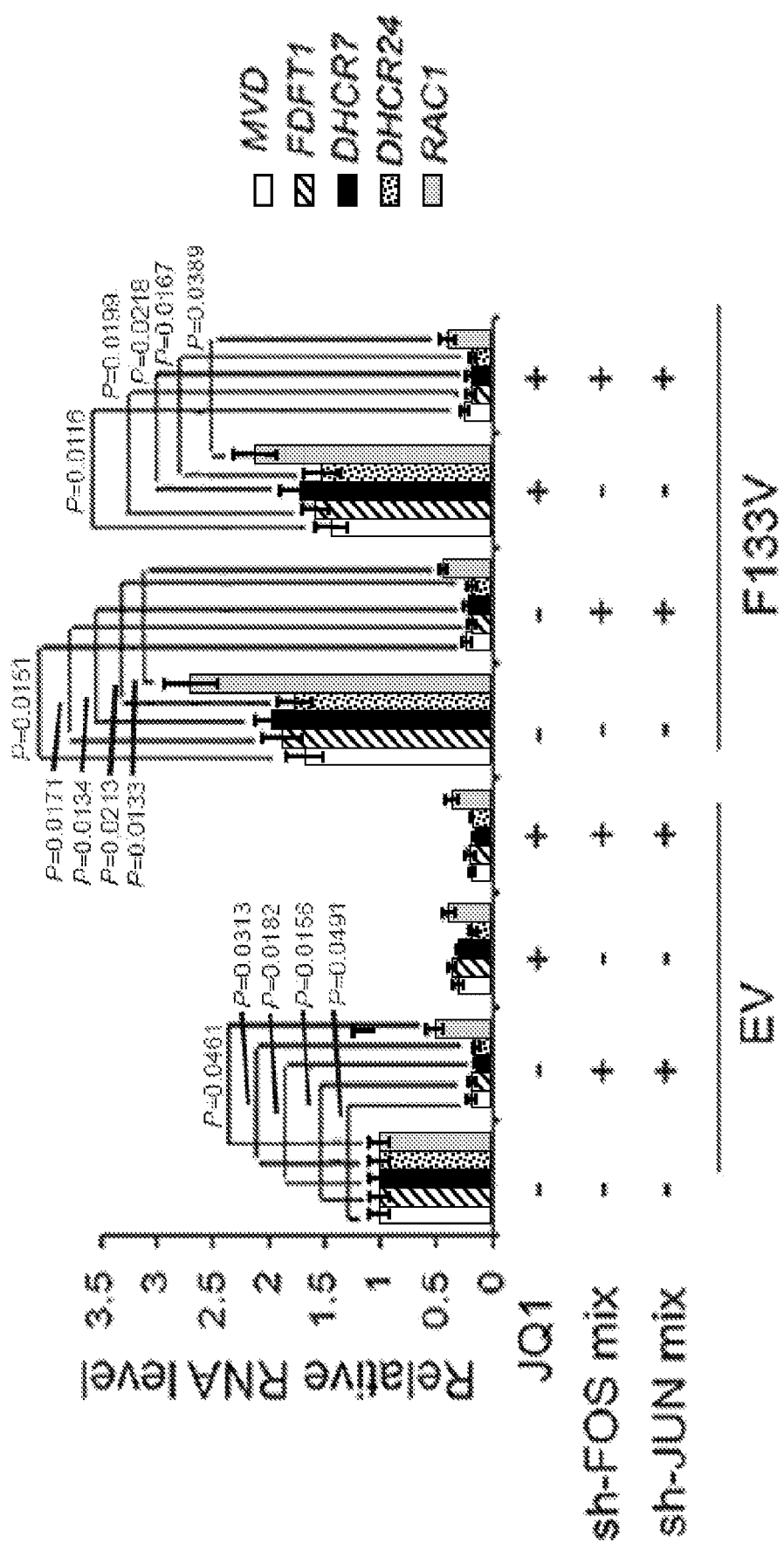
Figure 13O:
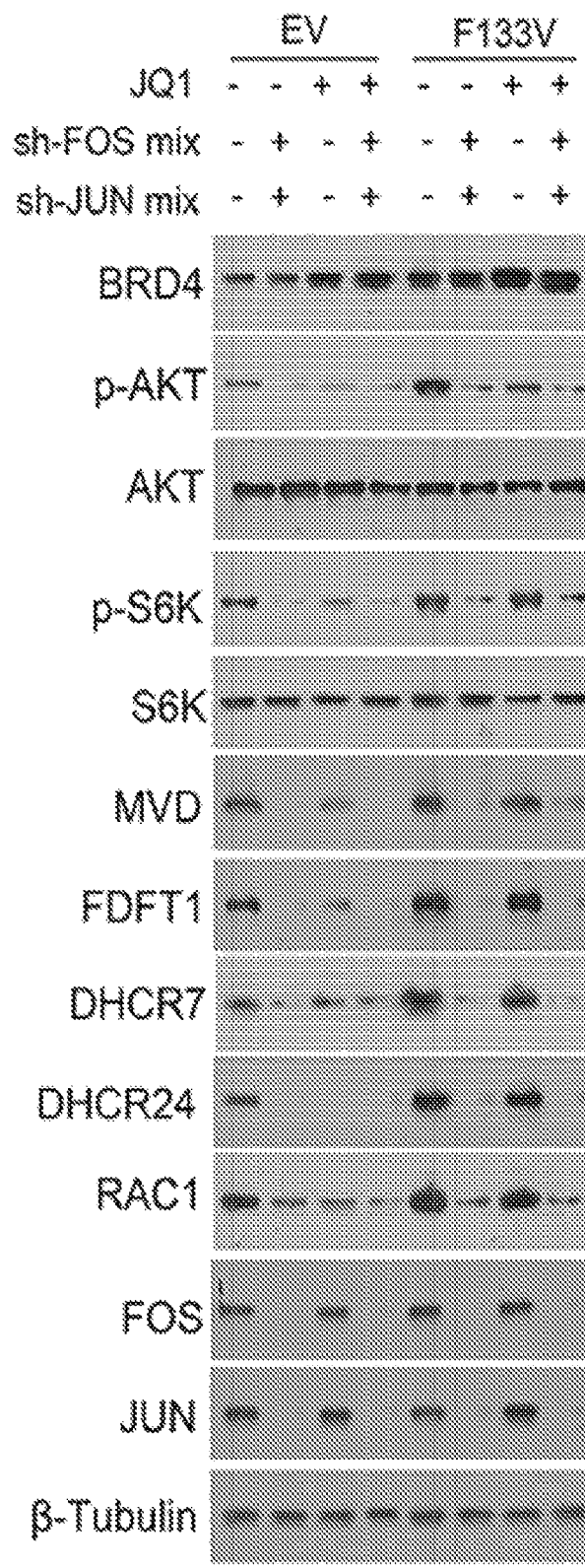
Figure 13P:
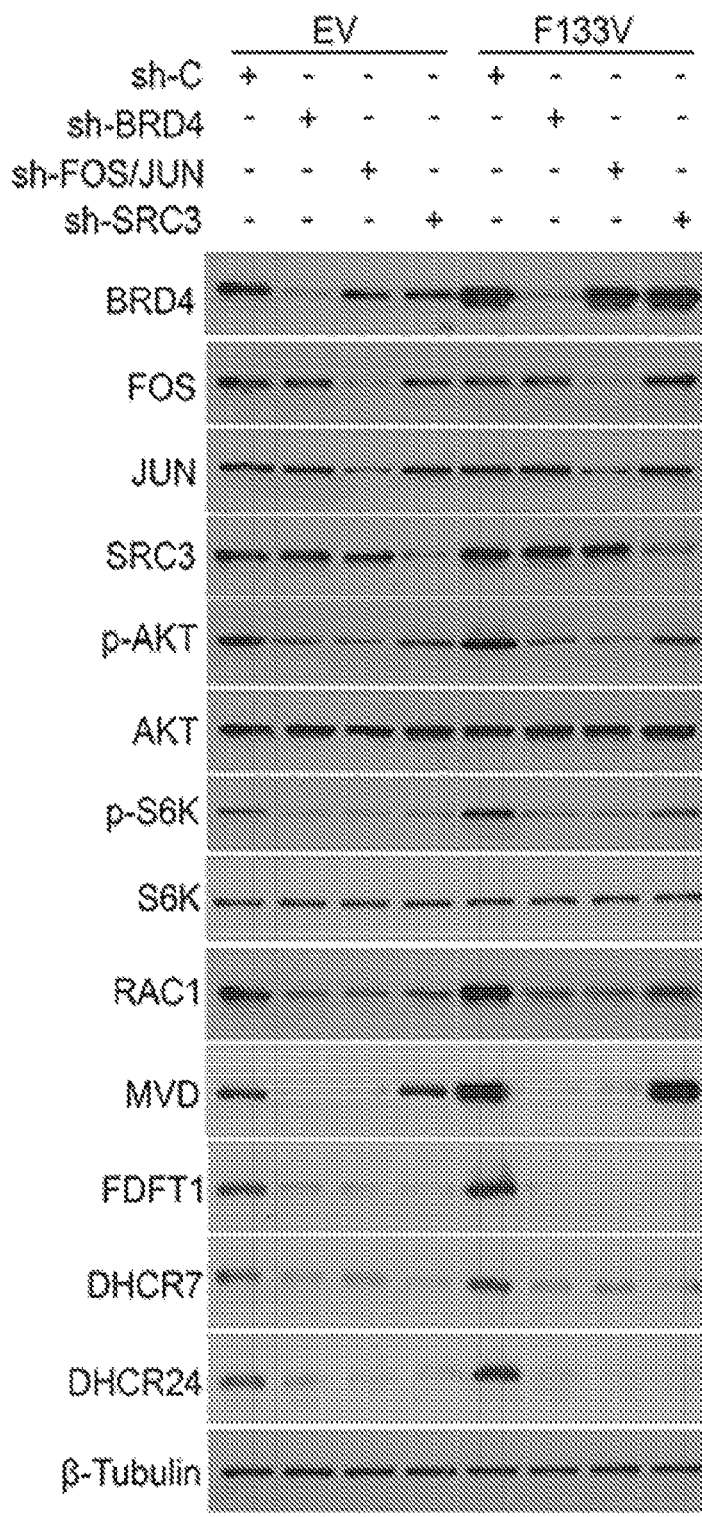

The transcription activator protein 1 (AP-1, a dimer of c-JUN and c-FOS) was demonstrated to bind to RAC1 and cholesterol synthesis gene promoters (FIGS. 13*l* and 13*m*). Although expression of c-JUN and c-FOS was not affected by SPOP mutation, knockdown of both abolished SPOP F133V-induced upregulation of RAC1 and cholesterol synthesis genes and activation of AKT/mTORC1 without disturbing BRD4 expression (FIGS. 13*n-p*). It has been shown that AKT/mTORC1 pathway is activated in the prostate of SPOP F133V knock-in mice and that this effect is mediated partially by increased SRC-3 expression (Blattner et al., *Cancer Cell,* 31:436-451 (2017)). Results provided herein demonstrate that SRC-3 knockdown only partially decreased SPOP F133V-induced AKT/mTORC1 activation by selectively affecting expression of RAC1 and the cholesterol synthesis genes and slightly, but did not significantly, diminish F133V-mediated JQ1 resistance (FIGS. 8*f* and 13*p*), reinforcing a partial, co-activator role of SRC-3 in SPOP F133V-mediated AKT/mTORC1 activation. In contrast, depletion of BET proteins almost completely abolished F133V-induced AKT/mTORC1 activation, upregulation of RAC1 and cholesterol synthesis genes, and BET inhibitor resistance (FIGS. 7*a-c* and 13*p*).

Figure 7H:
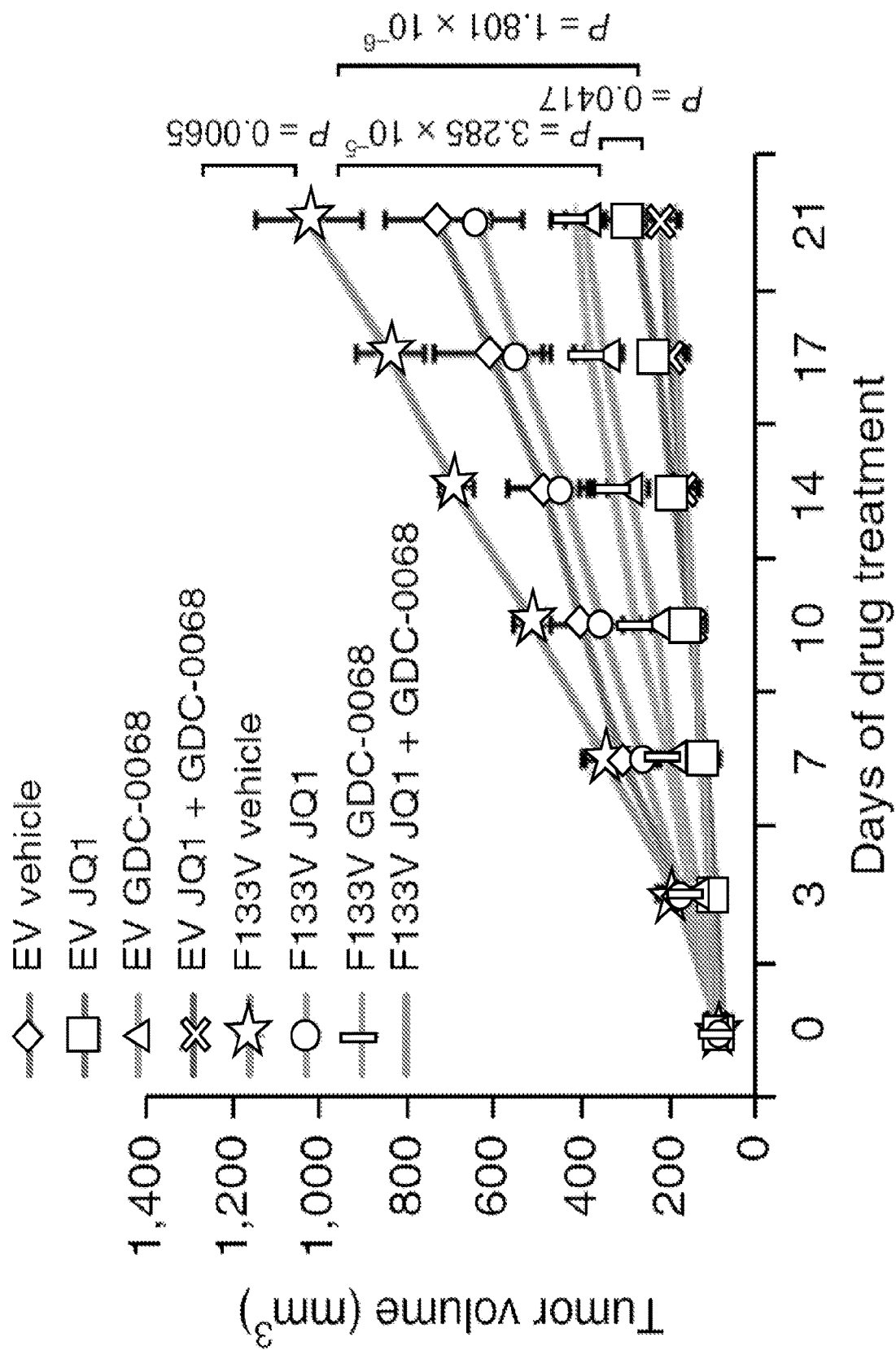
Figure 7I:
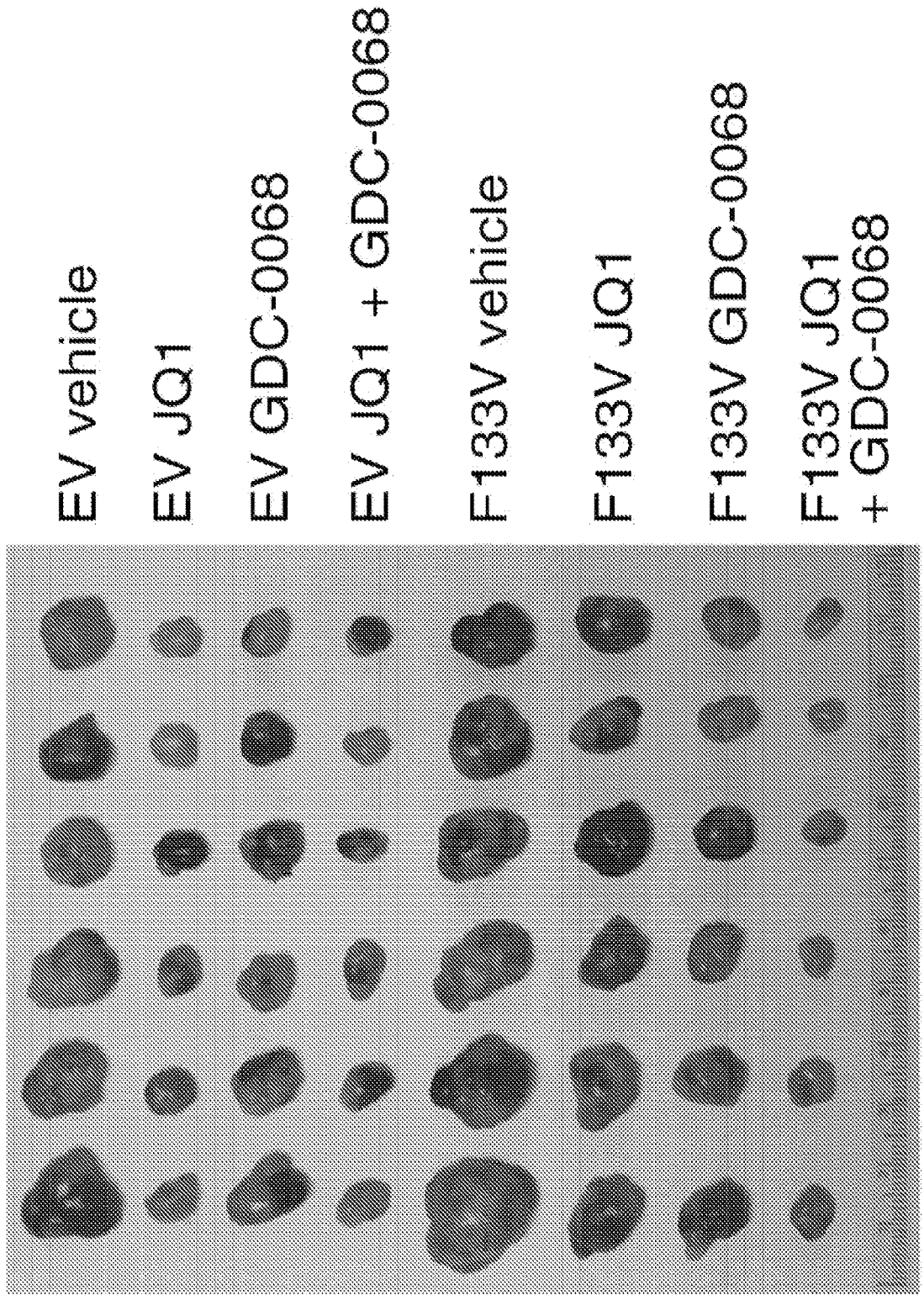
Figure 14A:
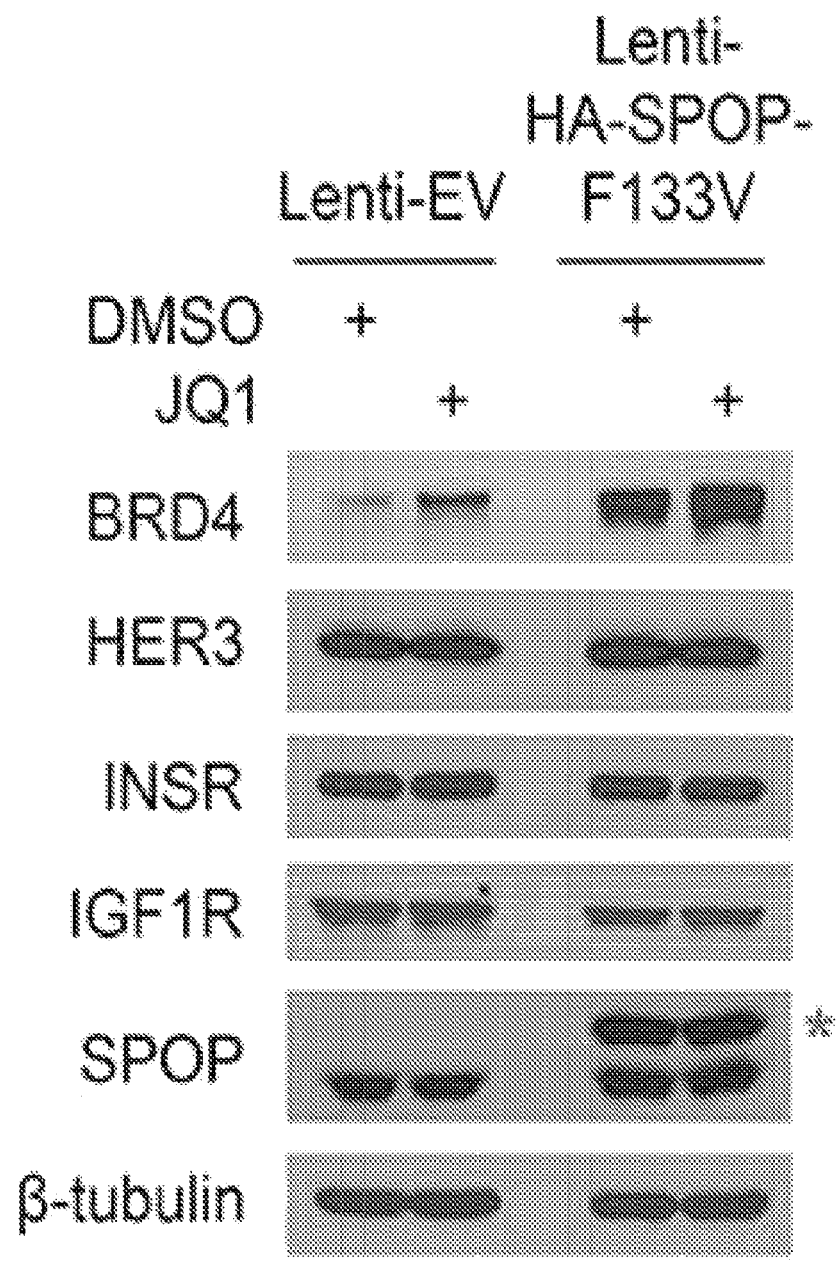
Figure 14B:
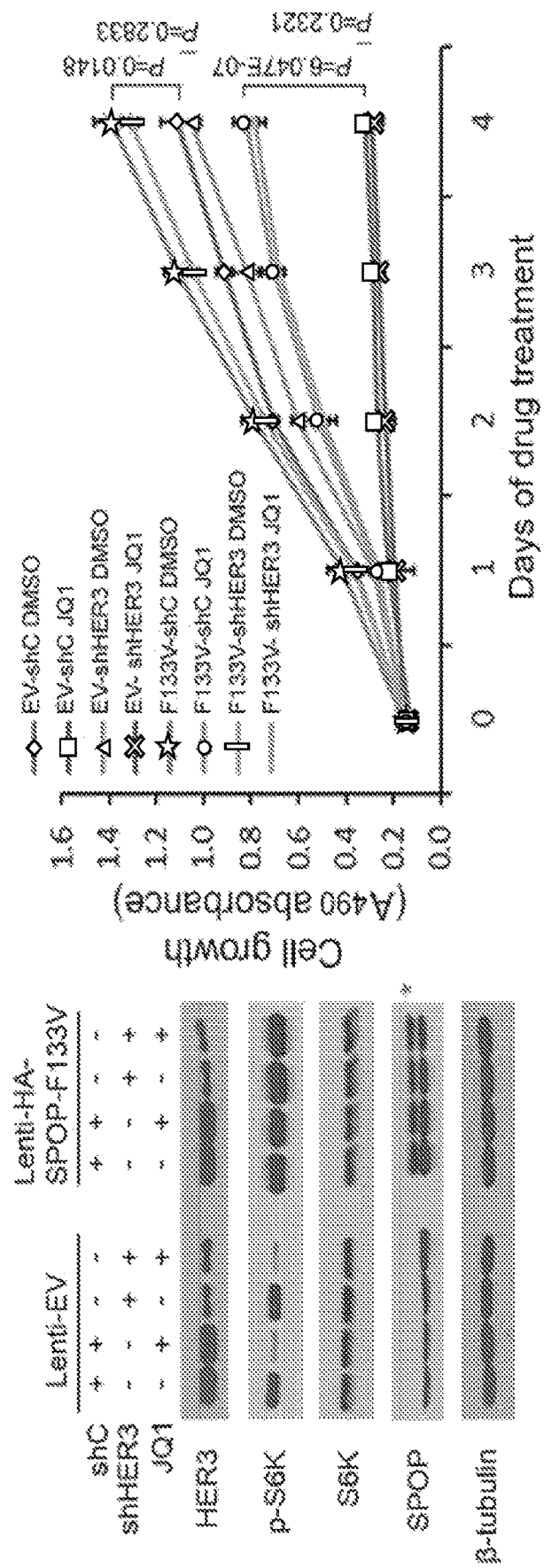
Figure 14C:
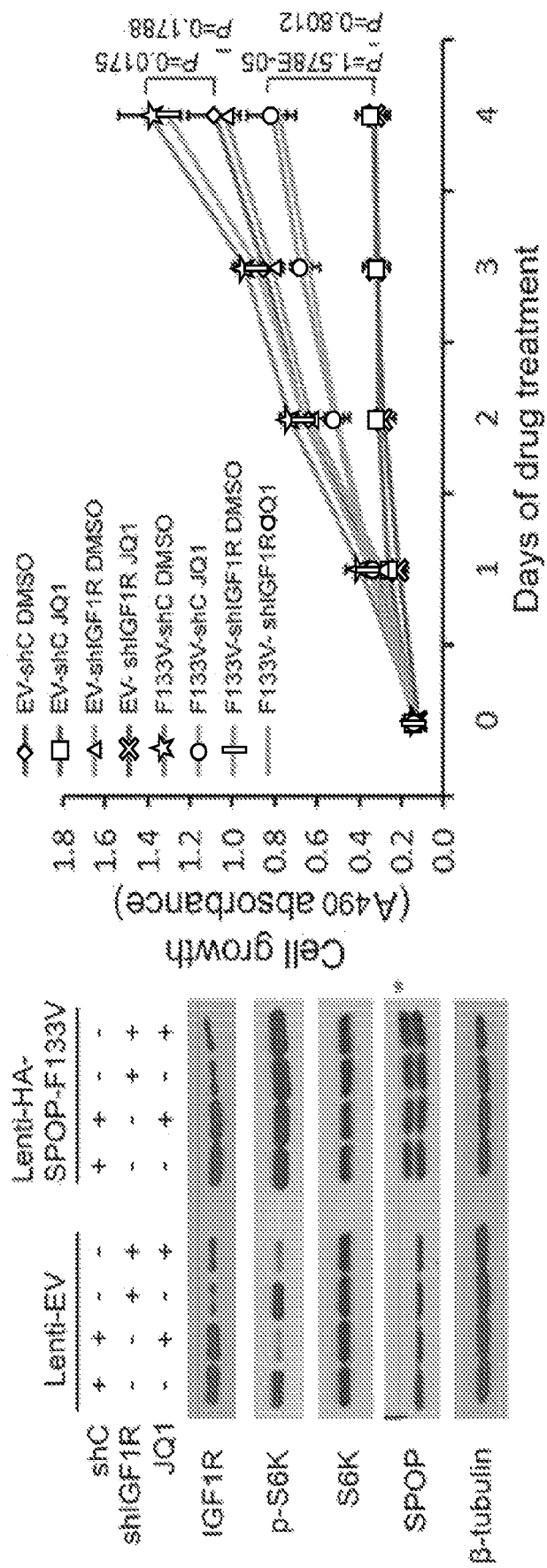
Figure 14D:
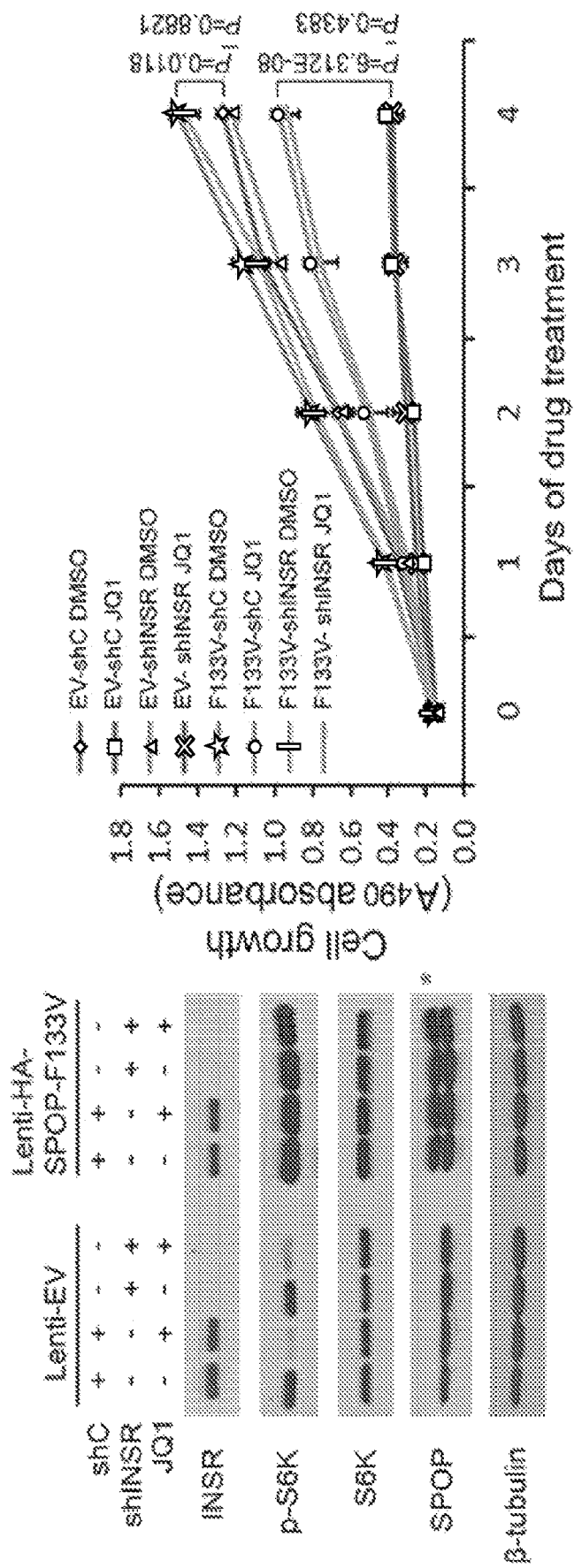
Figure 14E:
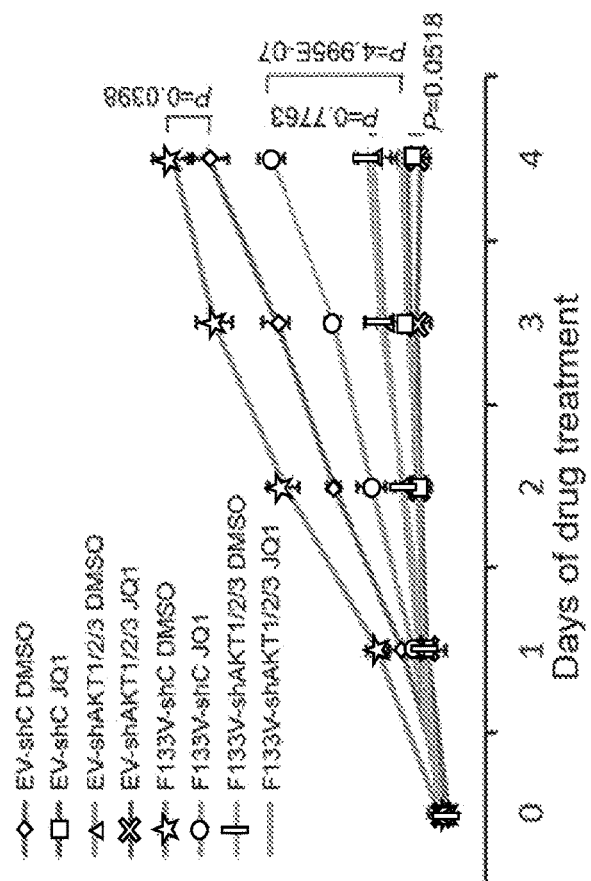
Figure 14E:
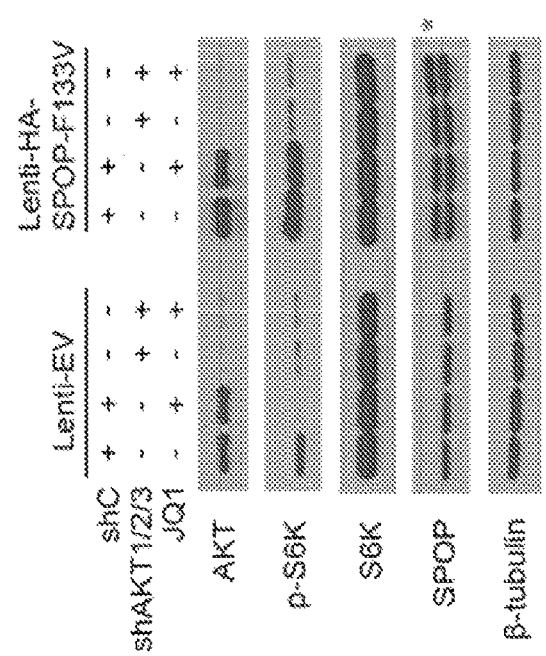
Figure 14F:
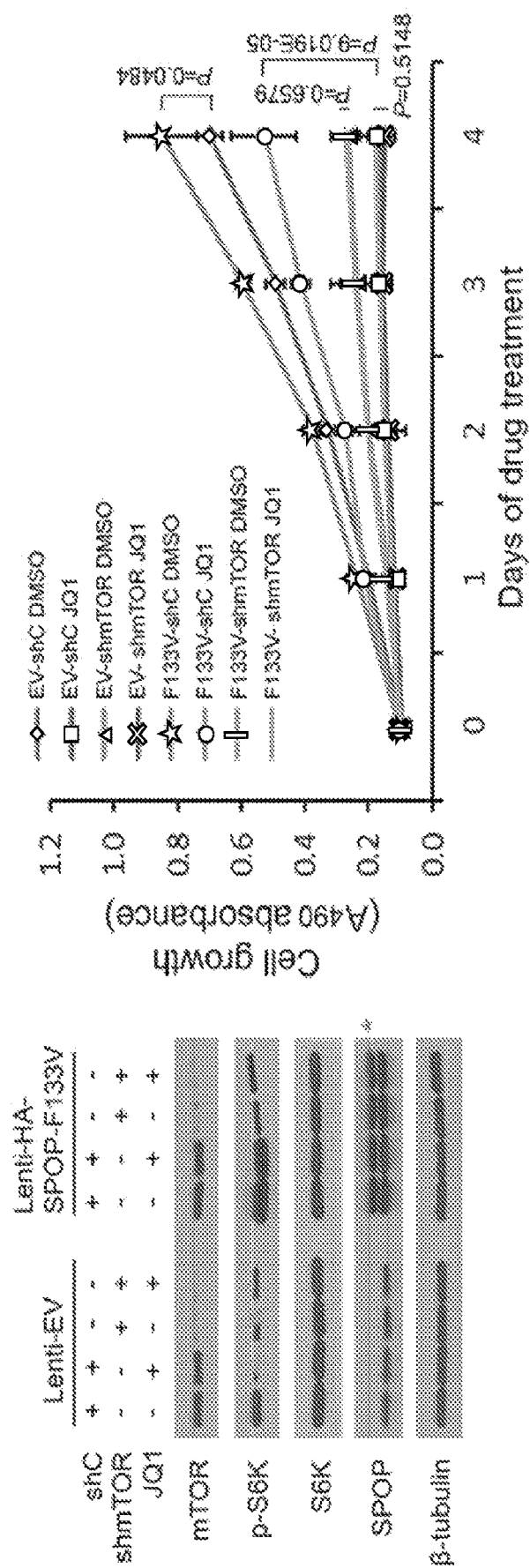
Figure 14G:
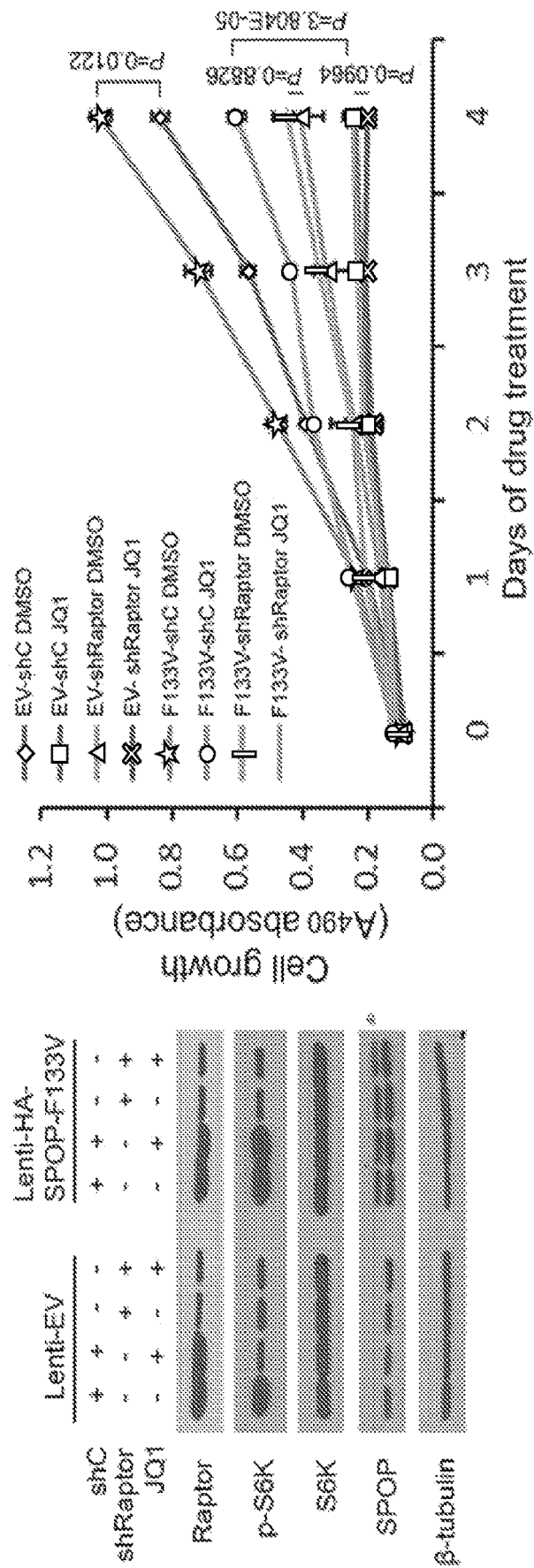
Figure 14H:
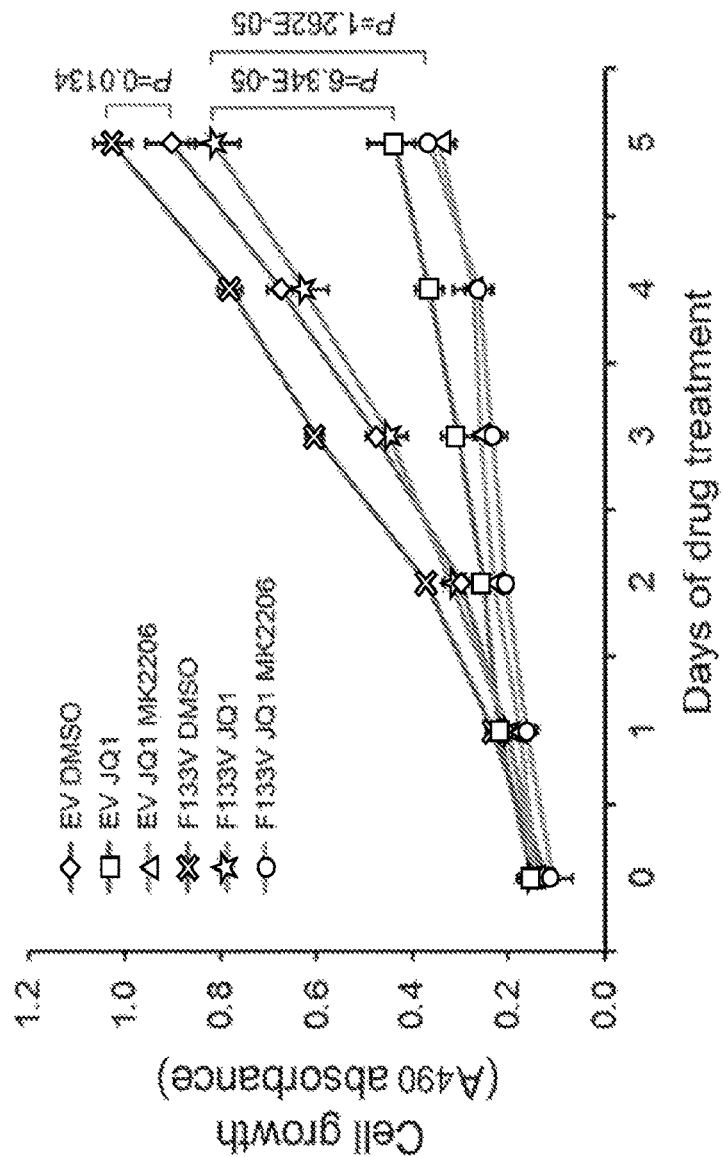
Figure 14H:
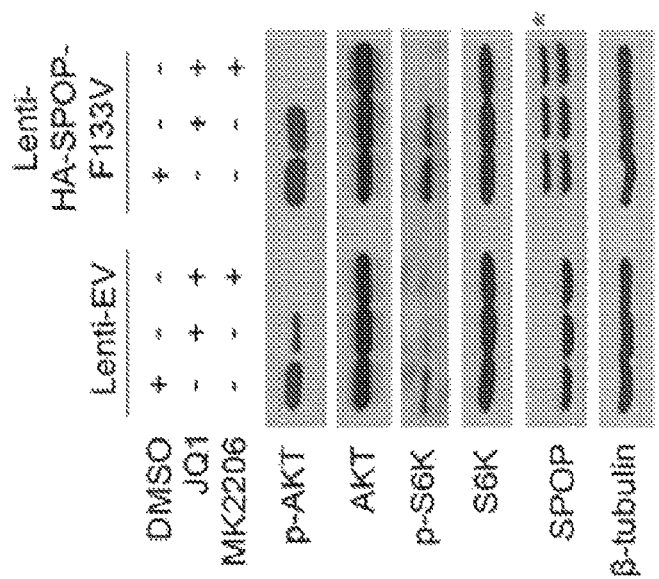
Figure 14I:
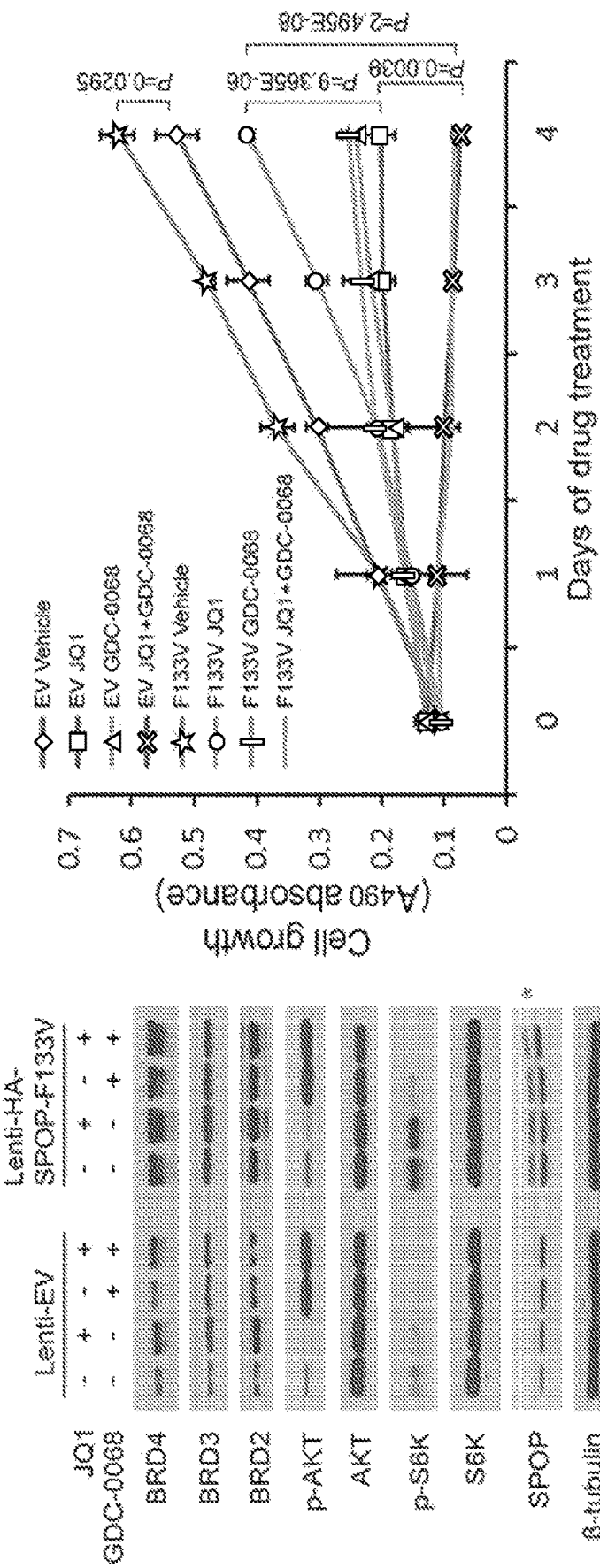
Figure 14J:
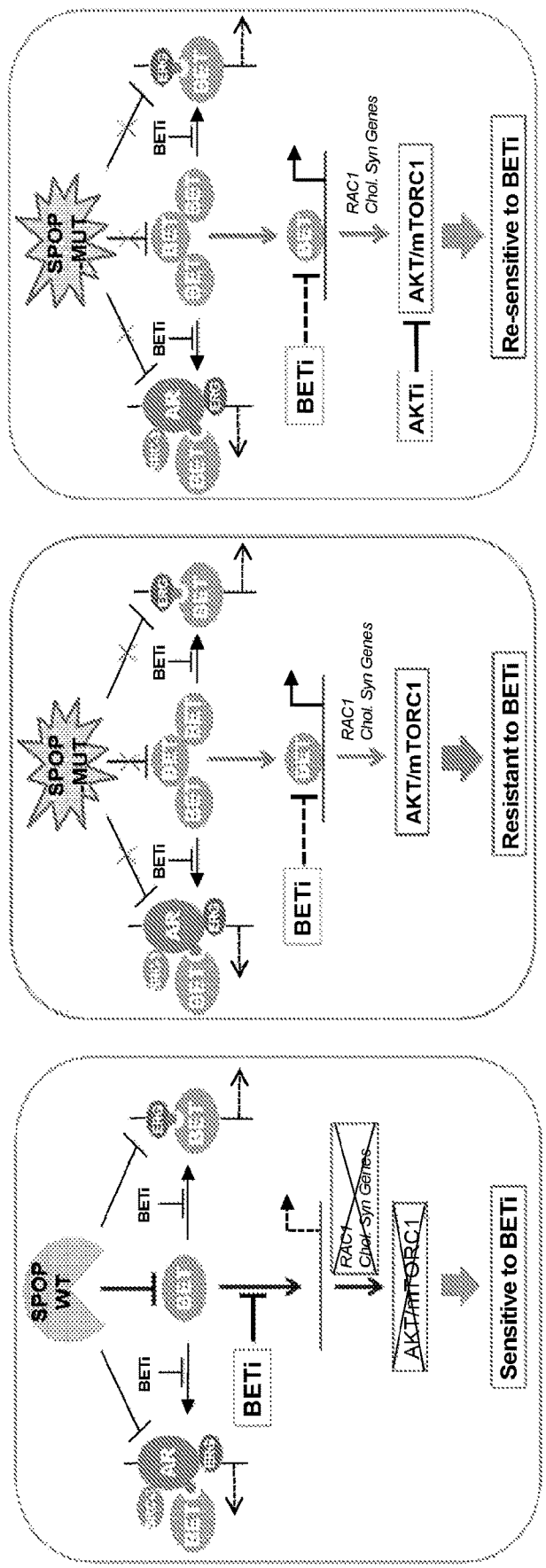

It has been shown that PI3K inhibitor treatment induced expression of receptor tyrosine kinases (RTKs) including HER3, IGF1R and INSR, and the induction was mediated by BRD4, but blocked by BET inhibitor (Stratikopoulos et al., *Cancer Cell,* 27:837-851 (2015)). However, BET inhibitor treatment alone had no effect on RTK expression (Stratikopoulos et al., *Cancer Cell,* 27:837-851 (2015)). Similarly, no effect of JQ1 on expression of these proteins was detected in either JQ1-sensitive (control) or -resistant (SPOP-F133V) C4-2 cells (FIG. 14*a*). In addition, neither mTORC1 activity (S6K phosphorylation) nor JQ1-resistant growth was affected by knockdown of HER3, IGF1R, or INSR individually in SPOP F133V expressing C4-2 cells (FIGS. 14*b-d*). These results ruled out the potential role of these RTKs in F133V-induced AKT activation and JQ1 resistance in these cells. In contrast, knockdown of AKT (AKT1, AKT2 and AKT3), mTOR, or Raptor alone abolished JQ1-resistant growth of SPOP F133V-expressing C4-2 cells (FIGS. 14*e-g*). Similar results were obtained by treating SPOP-F133V cells with the allosteric AKT inhibitor, MK2206 (FIG. 14*h*). Ipatasertib (GDC-0068), an ATP-competitive AKT inhibitor, has been shown to exhibit effective antitumor efficacy in patients with solid tumors (Saura et al., *Cancer Discov.,* 7:102-113 (2017)). GDC-0068 treatment of SPOP mutant expressing cells not only abolished SPOP mutation-induced activation of AKT downstream pathways, but also completely overcame SPOP mutation-conferred resistance to BET inhibitor in C4-2 cells in culture and tumors in mice (FIGS. 7*h*, 7*i*, and 14*i*). These results demonstrate the significance of AKT inhibition in overcoming BET inhibitor resistance in SPOP-mutated prostate cancer (FIG. 14*j*).

Taken together, the results provided herein demonstrate that BRD2/3/4 proteins are degradation substrates of SPOP. SPOP mutation not only induced accumulation of these proteins, but also conferred intrinsic resistance to BET inhibitors in prostate cancer cells, suggesting that besides SPOP mutations, elevation of BET proteins can be a biomarker to predict BET inhibitor resistance in prostate cancer patients.

The results provided herein also demonstrate that (i) expression of mutant SPOP (e.g., an SPOP-F133V mutant) not only increases the basal levels of phosphorylation of AKT-mTORC1 pathway proteins, but also largely impedes JQ1-induced inhibition of their phosphorylation, and (ii) that targeting the AKT pathway using therapeutic agents such as an AKT inhibitor (e.g., Ipatasertib) can be a viable treatment option to overcome BET inhibitor resistance in SPOP-mutated cancer (e.g., SPOP-mutated prostate cancer).

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for increasing the susceptibility of a cancer to treatment with a BET inhibitor, wherein said method comprises:
   (a) identifying a mammal as having a cancer comprising expression of a mutant SPOP polypeptide, and
   (b) administering an AKT inhibitor to said mammal, thereby increasing the susceptibility of said cancer to said treatment with said BET inhibitor.

2. The method of claim 1, wherein said mammal is a human.

3. The method of claim 1, wherein said cancer is a prostate cancer.

4. The method of claim 1, wherein said BET inhibitor is JQ1, I-BET 151 (GSK1210151A), I-BET 762 (GSK525762), OTX-015, TEN-010, CPI-203, CPI-0610, olinone, or RVX-208.

5. The method of claim 1, wherein said AKT inhibitor is VQD-002, MK-2206 2HCl, Perifosine (KRX-0401), GSK690693 Ipatasertib (GDC-0068), AZD5363, Miransertib HCl (ARQ 092 HCl), Deguelin, PF-04691502, AT7867, Triciribine, CCT128930, A-674563, PHT-427, Miltefosine, Honokiol, TIC10 Analogue, Uprosertib (GSK2141795), TIC10, Akti-1/2, Afuresertib (GSK2110183), AT13148, or SC79.

6. A method for increasing the susceptibility of a cancer to treatment with a BET inhibitor, wherein said method comprises administering an AKT inhibitor to a mammal identified as having a cancer comprising expression of a mutant SPOP polypeptide.

7. The method of claim 6, wherein said mammal is a human.

8. The method of claim 6, wherein said cancer is a prostate cancer.

9. The method of claim 6, wherein said BET inhibitor is JQ1, I-BET 151 (GSK1210151A), I-BET 762 (GSK525762), OTX-015, TEN-010, CPI-203, CPI-0610, olinone, or RVX-208.

10. The method of claim 6, wherein said AKT inhibitor is VQD-002, MK-2206 2HCl, Perifosine (KRX-0401), GSK690693 Ipatasertib (GDC-0068), AZD5363, Miransertib HCl (ARQ 092 HCl), Deguelin, PF-04691502, AT7867, Triciribine, CCT128930, A-674563, PHT-427, Miltefosine, Honokiol, TIC10 Analogue, Uprosertib (GSK2141795), TIC10, Akti-1/2, Afuresertib (GSK2110183), AT13148, or SC79.

11. A method for treating cancer, wherein said method comprises administering an AKT inhibitor and a BET inhibitor to a mammal identified as having a cancer comprising expression of a mutant SPOP polypeptide.

12. The method of claim 11, wherein said mammal is a human.

13. The method of claim 11, wherein said cancer is a prostate cancer.

14. The method of claim 11, wherein said BET inhibitor is JQ1, I-BET 151 (GSK1210151A), I-BET 762 (GSK525762), OTX-015, TEN-010, CPI-203, CPI-0610, olinone, or RVX-208.

15. The method of claim 11, wherein said AKT inhibitor is VQD-002, MK-2206 2HCl, Perifosine (KRX-0401), GSK690693 Ipatasertib (GDC-0068), AZD5363, Miransertib HCl (ARQ 092 HCl), Deguelin, PF-04691502, AT7867, Triciribine, CCT128930, A-674563, PHT-427, Miltefosine, Honokiol, TIC10 Analogue, Uprosertib (GSK2141795), TIC10, Akti-1/2, Afuresertib (GSK2110183), AT13148, or SC79.

16. The method of claim 1, wherein said mutant SPOP polypeptide is a SPOP polypeptide having a mutation located in a MATH domain.

17. The method of claim 1, wherein said mutant SPOP polypeptide is a mutant human SPOP polypeptide.

18. The method of claim 17, wherein said mutant SPOP polypeptide is a F133V, F133L, F102C, Y87C, Y87N, S119N, F125V, K129E, W131C, W131G, K134N, or Q165P mutant SPOP polypeptide.

19. The method of claim 6, wherein said mutant SPOP polypeptide is a SPOP polypeptide having a mutation located in a MATH domain.

20. The method of claim 6, wherein said mutant SPOP polypeptide is a mutant human SPOP polypeptide.

21. The method of claim 20, wherein said mutant SPOP polypeptide is a F133V, F133L, F102C, Y87C, Y87N, S119N, F125V, K129E, W131C, W131G, K134N, or Q165P mutant SPOP polypeptide.

22. The method of claim 11, wherein said mutant SPOP polypeptide is a SPOP polypeptide having a mutation located in a MATH domain.

23. The method of claim 11, wherein said mutant SPOP polypeptide is a mutant human SPOP polypeptide.

24. The method of claim 23, wherein said mutant SPOP polypeptide is a F133V, F133L, F102C, Y87C, Y87N, S119N, F125V, K129E, W131C, W131G, K134N, or Q165P mutant SPOP polypeptide.

* * * * *

SEQUENCE LISTING

```
<160> NUMBER OF SEQ ID NOS: 110

<210> SEQ ID NO 1
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 1
acccatagct ttggtttctt ctccc                                           25

<210> SEQ ID NO 2
<211> LENGTH: 25
<212> TYPE: DNA
<213> ORGANISM: Artificial
<220> FEATURE:
<223> OTHER INFORMATION: synthetic oligonucleotide primer

<400> SEQUENCE: 2
tatctgtttt ggacaggtgt ttgcg                                           25
```

```
<210> SEQ ID NO 3
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 3
actcatcaga tctgggaact gc                                              22

<210> SEQ ID NO 4
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 4
agttgtggct ttgatctggt t                                               21

<210> SEQ ID NO 5
<211> LENGTH: 19
<212> TYPE: RNA
<213> ORGANISM: Artificial
<220> FEATURE:
<223> OTHER INFORMATION: synthetic siRNA oligonucleotide

<400> SEQUENCE: 5
ggaugaugua aaugagcaa                                                  19

<210> SEQ ID NO 6
<211> LENGTH: 19
<212> TYPE: DNA
<213> ORGANISM: Artificial
<220> FEATURE:
<223> OTHER INFORMATION: synthetic siRNA oligonucleotide

<400> SEQUENCE: 6
ggacagcgac tctgaatct                                                  19

<210> SEQ ID NO 7
<211> LENGTH: 19
<212> TYPE: RNA
<213> ORGANISM: Artificial
<220> FEATURE:
<223> OTHER INFORMATION: synthetic siRNA oligonucleotide

<400> SEQUENCE: 7
gaaccucccu gauuacuau                                                  19

<210> SEQ ID NO 8
<211> LENGTH: 19
<212> TYPE: RNA
<213> ORGANISM: Artificial
<220> FEATURE:
<223> OTHER INFORMATION: synthetic siRNA oligonucleotide

<400> SEQUENCE: 8
agcugaaccu cccugauua                                                  19

<210> SEQ ID NO 9
<211> LENGTH: 19
<212> TYPE: RNA
<213> ORGANISM: Artificial
<220> FEATURE:
<223> OTHER INFORMATION: synthetic siRNA oligonucleotide
```

<400> SEQUENCE: 9
acagacuucg gaguaccug                                          19

<210> SEQ ID NO 10
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 10
ctacgtaaga aaccccggaa g                                       21

<210> SEQ ID NO 11
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 11 gcttttctc caaagccagt t                                        21

<210> SEQ ID NO 12
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 12
cctcagggag atgctatcca                                         20

<210> SEQ ID NO 13
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 13
atgtcgtggt agtcgtgcag                                         20

<210> SEQ ID NO 14
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 14
agcagcaaca gcaatgtgag                                         20

<210> SEQ ID NO 15
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 15
gcttgcactt gtcctcttcc                                         20

<210> SEQ ID NO 16
<211> LENGTH: 20

```
<212> TYPE: DNA
<213> ORGANISM: Artificial
<220> FEATURE:
<223> OTHER INFORMATION: synthetic oligonucleotide primer

<400> SEQUENCE: 16
tggctaagga gattggtgct                                              20

<210> SEQ ID NO 17
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 17
gcaaagcgta caaaggttcc                                              20

<210> SEQ ID NO 18
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 18
actatgttgc tgggctggtc                                              20

<210> SEQ ID NO 19
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 19
acctgctcca aacctcttga                                              20

<210> SEQ ID NO 20
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 20
caaaggaaat gaggcagagc                                              20

<210> SEQ ID NO 21
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 21
tgtggtacaa ggagccatca                                              20

<210> SEQ ID NO 22
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 22
```
tgacatctgc catgaccact                                              20

<210> SEQ ID NO 23
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 23
acaggtcctt ctggtggttg                                              20

<210> SEQ ID NO 24
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 24
aggacagcaa ccagttccac                                              20

<210> SEQ ID NO 25
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 25
cacacagcag ccacaaactc                                              20

<210> SEQ ID NO 26
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 26
ggcagcattg aaccagagga g                                            21

<210> SEQ ID NO 27
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 27
gcatgaactt ggtcaccttc tg                                           22

<210> SEQ ID NO 28
<211> LENGTH: 19
<212> TYPE: DNA
<213> ORGANISM: Artificial
<220> FEATURE:
<223> OTHER INFORMATION: synthetic oligonucleotide primer

<400> SEQUENCE: 28
cctgcaagga catgggtat                                               19

<210> SEQ ID NO 29
<211> LENGTH: 20
<212> TYPE: DNA
<213> ORGANISM: Artificial

```
<220> FEATURE:
<223> OTHER INFORMATION: synthetic oligonucleotide primer

<400> SEQUENCE: 29
cggcacttgt gttcagtttc                                              20

<210> SEQ ID NO 30
<211> LENGTH: 18
<212> TYPE: DNA
<213> ORGANISM: Artificial
<220> FEATURE:
<223> OTHER INFORMATION: synthetic oligonucleotide primer

<400> SEQUENCE: 30
ggattctctg ctctcctc                                                18

<210> SEQ ID NO 31
<211> LENGTH: 19
<212> TYPE: DNA
<213> ORGANISM: Artificial
<220> FEATURE:
<223> OTHER INFORMATION: synthetic oligonucleotide primer

<400> SEQUENCE: 31
cttgttcctc ctcagagtc                                               19

<210> SEQ ID NO 32
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 32
gacgcttcta ccagctcacc                                              20

<210> SEQ ID NO 33
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 33
gcttcactgg gtgtggaaat                                              20

<210> SEQ ID NO 34
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 34
tgcaccacca actgcttagc                                              20

<210> SEQ ID NO 35
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 35
ggcatggact gtggtcatga g                                            21
```

```
<210> SEQ ID NO 36
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 36
ccaaagtgtt gggattacgg                                              20

<210> SEQ ID NO 37
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 37
cggagtttct ctggacttcg                                              20

<210> SEQ ID NO 38
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 38
acatcacatg aaggccgttt                                              20

<210> SEQ ID NO 39
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 39
gaccttccac caaccaccta                                              20

<210> SEQ ID NO 40
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 40
ccctgagtca gtcacccttt                                              20

<210> SEQ ID NO 41
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 41
acaatggagc tcaccactcc                                              20

<210> SEQ ID NO 42
<211> LENGTH: 20
<212> TYPE: DNA
<213> ORGANISM: Artificial
<220> FEATURE:
<223> OTHER INFORMATION: synthetic oligonucleotide primer
```

```
<400> SEQUENCE: 42
gcacattgat ggagcgtatg                                          20

<210> SEQ ID NO 43
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 43
taataagcag gccacccaga                                          20

<210> SEQ ID NO 44
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 44
cgcattacct ctcagccaat                                          20

<210> SEQ ID NO 45
<211> LENGTH: 19
<212> TYPE: DNA
<213> ORGANISM: Artificial
<220> FEATURE:
<223> OTHER INFORMATION: synthetic oligonucleotide primer

<400> SEQUENCE: 45
agacaggtag cccccacag                                           19

<210> SEQ ID NO 46
<211> LENGTH: 17
<212> TYPE: DNA
<213> ORGANISM: Artificial
<220> FEATURE:
<223> OTHER INFORMATION: synthetic oligonucleotide primer

<400> SEQUENCE: 46
ccctcccctt ccacagc                                             17

<210> SEQ ID NO 47
<211> LENGTH: 26
<212> TYPE: DNA
<213> ORGANISM: Artificial
<220> FEATURE:
<223> OTHER INFORMATION: synthetic oligonucleotide primer

<400> SEQUENCE: 47
gccctataaa accttcattc cccagg                                   26

<210> SEQ ID NO 48
<211> LENGTH: 18
<212> TYPE: DNA
<213> ORGANISM: Artificial
<220> FEATURE:
<223> OTHER INFORMATION: synthetic oligonucleotide primer

<400> SEQUENCE: 48
cgccccagag tcccttat                                            18

<210> SEQ ID NO 49
```

```
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 49
taatctcagg aggcggtgtc                                                20

<210> SEQ ID NO 50
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 50
agggatcgcg ctgagtataa                                                20

<210> SEQ ID NO 51
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 51
tgcctctcgc tggaattact                                                20

<210> SEQ ID NO 52
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 52
gcaggagcta ttcaggaagc                                                20

<210> SEQ ID NO 53
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 53
aggtggagag caaatgcaac                                                20

<210> SEQ ID NO 54
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 54
ctgcccattg cctaaagaag                                                20

<210> SEQ ID NO 55
<211> LENGTH: 18
<212> TYPE: DNA
<213> ORGANISM: Artificial
<220> FEATURE:
<223> OTHER INFORMATION: synthetic oligonucleotide primer

<400> SEQUENCE: 55
```
tgggaagctg tggctgac                                                18

<210> SEQ ID NO 56
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 56
gaccttctgg aggaagtggc                                              20

<210> SEQ ID NO 57
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 57
atcgtaactc atgggcctgc                                              20

<210> SEQ ID NO 58
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 58
tcaaattgaa cctgccggat t                                            21

<210> SEQ ID NO 59
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 59
tgcatacatt cgcttgcact c                                            21

<210> SEQ ID NO 60
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 60
acctccaacc ctaacaagcc                                              20

<210> SEQ ID NO 61
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 61
tttccatagt gtcttgagca cc                                           22

<210> SEQ ID NO 62
<211> LENGTH: 22
<212> TYPE: DNA

<213> ORGANISM: Artificial
<220> FEATURE:
<223> OTHER INFORMATION: synthetic oligonucleotide primer

<400> SEQUENCE: 62
acccgttgaa ccccattcgt ga                                        22

<210> SEQ ID NO 63
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 63
gcctcactaa accatccaat cgg                                       23

<210> SEQ ID NO 64
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 64
ggtgagtgct ggcctccagg                                           20

<210> SEQ ID NO 65
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 65
gcgctaacgc ctgcctagtg                                           20

<210> SEQ ID NO 66
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 66 ctcagcctttt gtctctgatg aag                                      23

<210> SEQ ID NO 67
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 67
tcagatccag gcttgcttac tg                                        22

<210> SEQ ID NO 68
<211> LENGTH: 22
<212> TYPE: DNA
<213> ORGANISM: Artificial
<220> FEATURE:
<223> OTHER INFORMATION: synthetic oligonucleotide primer

<400> SEQUENCE: 68
gtctccctgc accactaact ag                                        22

<210> SEQ ID NO 69
<211> LENGTH: 20
<212> TYPE: DNA
<213> ORGANISM: Artificial
<220> FEATURE:
<223> OTHER INFORMATION: synthetic oligonucleotide primer

<400> SEQUENCE: 69
gcaaacattg aaaagagcct                                           20

<210> SEQ ID NO 70
<211> LENGTH: 23
<212> TYPE: PRT
<213> ORGANISM: Homo sapiens

<400> SEQUENCE: 70

Leu Ala Lys Lys Lys Gly Val Lys Arg Lys Ala Asp Thr Thr Thr Pro
1               5                   10                  15

Thr Pro Thr Ala Ile Leu Ala
            20

<210> SEQ ID NO 71
<211> LENGTH: 23
<212> TYPE: PRT
<213> ORGANISM: Homo sapiens

<400> SEQUENCE: 71

Val Val Lys Lys Lys Gly Val Lys Arg Lys Ala Asp Thr Thr Thr Pro
1               5                   10                  15

Thr Thr Ser Ala Ile Thr Ala
            20

<210> SEQ ID NO 72
<211> LENGTH: 23
<212> TYPE: PRT
<213> ORGANISM: Homo sapiens

<400> SEQUENCE: 72

Val Lys Thr Lys Lys Gly Val Lys Arg Lys Ala Asp Thr Thr Thr Pro
1               5                   10                  15

Thr Thr Ile Asp Pro Ile His
            20

<210> SEQ ID NO 73
<211> LENGTH: 23
<212> TYPE: PRT
<213> ORGANISM: Homo sapiens

<400> SEQUENCE: 73

Lys Gln Gly Glu Val Ser Lys Ala Ala Ser Ala Asp Ser Thr Thr Glu
1               5                   10                  15

Gly Thr Pro Ala Asp Gly Phe
            20

<210> SEQ ID NO 74
<211> LENGTH: 23
<212> TYPE: PRT
<213> ORGANISM: Homo sapiens

<400> SEQUENCE: 74

Lys Ser Val Lys Ser Ala Asn Val Lys Lys Ala Asp Ser Ser Thr Thr
1               5                   10                  15

Lys Lys Asn Gln Asn Ser Ser
            20

<210> SEQ ID NO 75
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 75
agactgggga gtcaagaa                                                 18

<210> SEQ ID NO 76
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 76
tcgggcaaaa tgcaaatt                                                 18

<210> SEQ ID NO 77
<211> LENGTH: 18
<212> TYPE: DNA
<213> ORGANISM: Artificial
<220> FEATURE:
<223> OTHER INFORMATION: synthetic oligonucleotide probe

<400> SEQUENCE: 77
tcgggcaaaa tccaaatt                                                 18

<210> SEQ ID NO 78
<211> LENGTH: 5
<212> TYPE: PRT
<213> ORGANISM: Homo sapiens

<400> SEQUENCE: 78

Ala Asp Thr Thr Thr
1               5

<210> SEQ ID NO 79
<211> LENGTH: 23
<212> TYPE: DNA
<213> ORGANISM: Artificial
<220> FEATURE:
<223> OTHER INFORMATION: synthetic oligonucleotide primer

<400> SEQUENCE: 79
caaaggtgag caacctaggc tta                                           23

<210> SEQ ID NO 80
<211> LENGTH: 21
<212> TYPE: DNA
<213> ORGANISM: Artificial
<220> FEATURE:
<223> OTHER INFORMATION: synthetic oligonucleotide primer

<400> SEQUENCE: 80
atgttcctcc agagtaggtc t                                             21

<210> SEQ ID NO 81
<211> LENGTH: 22
<212> TYPE: DNA

<213> ORGANISM: Artificial
<220> FEATURE:
<223> OTHER INFORMATION: synthetic oligonucleotide primer

<400> SEQUENCE: 81
ggcttacagg ataccccaa ct                                              22

<210> SEQ ID NO 82
<211> LENGTH: 19
<212> TYPE: DNA
<213> ORGANISM: Artificial
<220> FEATURE:
<223> OTHER INFORMATION: synthetic oligonucleotide primer

<400> SEQUENCE: 82
gggctatcac acctcgccc                                                 19

<210> SEQ ID NO 83
<211> LENGTH: 58
<212> TYPE: DNA
<213> ORGANISM: Artificial
<220> FEATURE:
<223> OTHER INFORMATION: synthetic oligonucleotide

<400> SEQUENCE: 83
ccggcaaggt agtgaaattc tcctactcga gtaggagaat ttcactacct tgtttttt      58

<210> SEQ ID NO 84
<211> LENGTH: 58
<212> TYPE: DNA
<213> ORGANISM: Artificial
<220> FEATURE:
<223> OTHER INFORMATION: synthetic oligonucleotide

<400> SEQUENCE: 84
ccggcacaag gctatcttag cagctctcga gagctgctaa gatagccttg tgtttttt      58

<210> SEQ ID NO 85
<211> LENGTH: 57
<212> TYPE: DNA
<213> ORGANISM: Artificial
<220> FEATURE:
<223> OTHER INFORMATION: synthetic oligonucleotide

<400> SEQUENCE: 85
ccggcagtga cagttcgact gatgactcga gtcatcagtc gaactgtcac tgttttt       57

<210> SEQ ID NO 86
<211> LENGTH: 57
<212> TYPE: DNA
<213> ORGANISM: Artificial
<220> FEATURE:
<223> OTHER INFORMATION: synthetic oligonucleotide

<400> SEQUENCE: 86
ccggcctgga gatgacatag tcttactcga gtaagactat gtcatctcca ggttttt       57

<210> SEQ ID NO 87
<211> LENGTH: 57
<212> TYPE: DNA
<213> ORGANISM: Artificial
<220> FEATURE:
<223> OTHER INFORMATION: synthetic oligonucleotide

<400> SEQUENCE: 87
ccggcccaag aggaagttga attatctcga gataattcaa cttcctcttg ggttttt       57

<210> SEQ ID NO 88
<211> LENGTH: 57
<212> TYPE: DNA
<213> ORGANISM: Artificial
<220> FEATURE:
<223> OTHER INFORMATION: synthetic oligonucleotide

<400> SEQUENCE: 88
ccgggctgat gttctcgaat tgctactcga gtagcaattc gagaacatca gctttttt    57

<210> SEQ ID NO 89
<211> LENGTH: 57
<212> TYPE: DNA
<213> ORGANISM: Artificial
<220> FEATURE:
<223> OTHER INFORMATION: synthetic oligonucleotide

<400> SEQUENCE: 89 ccggccctttt gctgtgacac ttcttctcga gaagaagtgt cacagcaaag ggttttt    57

<210> SEQ ID NO 90
<211> LENGTH: 57
<212> TYPE: DNA
<213> ORGANISM: Artificial
<220> FEATURE:
<223> OTHER INFORMATION: synthetic oligonucleotide

<400> SEQUENCE: 90
ccggccctgc ctacaggtta tgattctcga gaatcataac ctgtaggcag ggttttt    57

<210> SEQ ID NO 91
<211> LENGTH: 57
<212> TYPE: DNA
<213> ORGANISM: Artificial
<220> FEATURE:
<223> OTHER INFORMATION: synthetic oligonucleotide

<400> SEQUENCE: 91
ccgggcggag acagaccaac tagaactcga gttctagttg gtctgtctcc gctttttt   57

<210> SEQ ID NO 92
<211> LENGTH: 57
<212> TYPE: DNA
<213> ORGANISM: Artificial
<220> FEATURE:
<223> OTHER INFORMATION: synthetic oligonucleotide

<400> SEQUENCE: 92
ccggtctgct ttgcagaccg agattctcga gaatctcggt ctgcaaagca gattttt    57

<210> SEQ ID NO 93
<211> LENGTH: 58
<212> TYPE: DNA
<213> ORGANISM: Artificial
<220> FEATURE:
<223> OTHER INFORMATION: synthetic oligonucleotide

<400> SEQUENCE: 93
ccggcggacc ttatggctac agtaactcga gttactgtag ccataaggtc cgtttttg   58

<210> SEQ ID NO 94
<211> LENGTH: 58
<212> TYPE: DNA
<213> ORGANISM: Artificial
<220> FEATURE:

<223> OTHER INFORMATION: synthetic oligonucleotide

<400> SEQUENCE: 94
ccggcgcaaa cctcagcaac ttcaactcga gttgaagttg ctgaggtttg cgttttg    58

<210> SEQ ID NO 95
<211> LENGTH: 57
<212> TYPE: DNA
<213> ORGANISM: Artificial
<220> FEATURE:
<223> OTHER INFORMATION: synthetic oligonucleotide

<400> SEQUENCE: 95
ccggcctgct aatcaagtca cacatctcga gatgtgtgac ttgattagca ggttttt    57

<210> SEQ ID NO 96
<211> LENGTH: 57
<212> TYPE: DNA
<213> ORGANISM: Artificial
<220> FEATURE:
<223> OTHER INFORMATION: synthetic oligonucleotide

<400> SEQUENCE: 96
ccggcgcgac tactacaact ttccactcga gtggaaagtt gtagtagtcg cgttttt    57

<210> SEQ ID NO 97
<211> LENGTH: 57
<212> TYPE: DNA
<213> ORGANISM: Artificial
<220> FEATURE:
<223> OTHER INFORMATION: synthetic oligonucleotide

<400> SEQUENCE: 97
ccggccatac atttaattgc cgtatctcga gatacggcaa ttaaatgtat ggttttt    57

<210> SEQ ID NO 98
<211> LENGTH: 57
<212> TYPE: DNA
<213> ORGANISM: Artificial
<220> FEATURE:
<223> OTHER INFORMATION: synthetic oligonucleotide

<400> SEQUENCE: 98
ccgggcagtc tattcgtcct ccatactcga gtatggagga cgaatagact gcttttt    57

<210> SEQ ID NO 99
<211> LENGTH: 57
<212> TYPE: DNA
<213> ORGANISM: Artificial
<220> FEATURE:
<223> OTHER INFORMATION: synthetic oligonucleotide

<400> SEQUENCE: 99
ccgggccagt gctaacttgg aagaactcga gttcttccaa gttagcactg gcttttt    57

<210> SEQ ID NO 100
<211> LENGTH: 57
<212> TYPE: DNA
<213> ORGANISM: Artificial
<220> FEATURE:
<223> OTHER INFORMATION: synthetic oligonucleotide

<400> SEQUENCE: 100
ccggtgaaat tgagaggata catttctcga gaaatgtatc ctctcaattt catttt    57

```
<210> SEQ ID NO 101
<211> LENGTH: 57
<212> TYPE: DNA
<213> ORGANISM: Artificial
<220> FEATURE:
<223> OTHER INFORMATION: synthetic oligonucleotide

<400> SEQUENCE: 101
ccggccctac tgtctttgac aattactcga gtaattgtca aagacagtag ggtttttt        57

<210> SEQ ID NO 102
<211> LENGTH: 57
<212> TYPE: DNA
<213> ORGANISM: Artificial
<220> FEATURE:
<223> OTHER INFORMATION: synthetic oligonucleotide

<400> SEQUENCE: 102
cggggctaag gagattggtg ctgtactcga gtacagcacc aatctcctta gcttttt        57

<210> SEQ ID NO 103
<211> LENGTH: 58
<212> TYPE: DNA
<213> ORGANISM: Artificial
<220> FEATURE:
<223> OTHER INFORMATION: synthetic oligonucleotide

<400> SEQUENCE: 103
ccggtatgcc cagttctctg agaaactcga gtttctcaga gaactgggca tattttttg       58

<210> SEQ ID NO 104
<211> LENGTH: 58
<212> TYPE: DNA
<213> ORGANISM: Artificial
<220> FEATURE:
<223> OTHER INFORMATION: synthetic oligonucleotide

<400> SEQUENCE: 104
ccggtctgca ccaggaccag ttaaactcga gtttaactgg tcctggtgca gatttttg        58

<210> SEQ ID NO 105
<211> LENGTH: 58
<212> TYPE: DNA
<213> ORGANISM: Artificial
<220> FEATURE:
<223> OTHER INFORMATION: synthetic oligonucleotide

<400> SEQUENCE: 105
ccggacttgc tacaagtatc tcaatctcga gattgagata cttgtagcaa gtttttttg       58

<210> SEQ ID NO 106
<211> LENGTH: 58
<212> TYPE: DNA
<213> ORGANISM: Artificial
<220> FEATURE:
<223> OTHER INFORMATION: synthetic oligonucleotide

<400> SEQUENCE: 106
ccggcaacga tctcccttga gtttactcga gtaaactcaa gggagatcgt tgttttttg       58

<210> SEQ ID NO 107
<211> LENGTH: 62
<212> TYPE: DNA
<213> ORGANISM: Artificial
<220> FEATURE:
<223> OTHER INFORMATION: synthetic oligonucleotide
```

```
<400> SEQUENCE: 107
gtaccggact tcaagctgtt cttcaatgct cgagcattga agaacagctt gaagtttttt    60
tg                                                                  62

<210> SEQ ID NO 108
<211> LENGTH: 58
<212> TYPE: DNA
<213> ORGANISM: Artificial
<220> FEATURE:
<223> OTHER INFORMATION: synthetic oligonucleotide

<400> SEQUENCE: 108
ccgggggcca agactccacc tataactcga gttataggtg gagtcttggc ccttttttg    58

<210> SEQ ID NO 109
<211> LENGTH: 58
<212> TYPE: DNA
<213> ORGANISM: Artificial
<220> FEATURE:
<223> OTHER INFORMATION: synthetic oligonucleotide

<400> SEQUENCE: 109
ccggccaaca catctgcact gcttactcga gtaagcagtg cagatgtgtt ggttttttg    58

<210> SEQ ID NO 110
<211> LENGTH: 58
<212> TYPE: DNA
<213> ORGANISM: Artificial
<220> FEATURE:
<223> OTHER INFORMATION: synthetic oligonucleotide

<400> SEQUENCE: 110
ccgggctctc gcttatcttc gatatctcga gatatcgaag ataagcgaga gcttttttg    58
```